US012384777B2

(12) United States Patent
Woodland et al.

(10) Patent No.: US 12,384,777 B2
(45) Date of Patent: Aug. 12, 2025

(54) COMPOUNDS COMPRISING N-METHYL-2-PYRIDONE, AND PHARMACEUTICALLY ACCEPTABLE SALTS

(71) Applicant: Tay Therapeutics Limited, Dundee (GB)

(72) Inventors: Christopher Andrew Woodland, Dundee (GB); Mark Bell, Dundee (GB)

(73) Assignee: Tay Therapeutics Limited, Dundee (GB)

( * ) Notice: Subject to any disclaimer, the term of this patent is extended or adjusted under 35 U.S.C. 154(b) by 922 days.

(21) Appl. No.: 17/594,577

(22) PCT Filed: Apr. 22, 2020

(86) PCT No.: PCT/EP2020/061173
§ 371 (c)(1),
(2) Date: Oct. 22, 2021

(87) PCT Pub. No.: WO2020/216779
PCT Pub. Date: Oct. 29, 2020

(65) Prior Publication Data
US 2022/0204500 A1 Jun. 30, 2022

(30) Foreign Application Priority Data
Apr. 24, 2019 (GB) .................................... 1905721

(51) Int. Cl.
*C07D 471/04* (2006.01)
*C07D 401/04* (2006.01)
*C07D 413/14* (2006.01)

(52) U.S. Cl.
CPC ......... *C07D 471/04* (2013.01); *C07D 401/04* (2013.01); *C07D 413/14* (2013.01)

(58) Field of Classification Search
CPC ............................ C07D 471/04; C07D 401/04
See application file for complete search history.

(56) References Cited

U.S. PATENT DOCUMENTS

| | | | |
|---|---|---|---|
| 4,874,794 A | 10/1989 | Katz | |
| 5,880,066 A | 3/1999 | Wells et al. | |
| 5,910,504 A | 6/1999 | Hutchinson | |
| 8,691,747 B2 | 4/2014 | Kruidenier et al. | |
| 8,828,440 B2 | 9/2014 | Bodick et al. | |
| 9,018,184 B2 | 4/2015 | Lee et al. | |
| 9,296,741 B2 | 3/2016 | Wang et al. | |
| 9,637,456 B2 | 5/2017 | Amans et al. | |
| 9,957,263 B2 | 5/2018 | Dai et al. | |
| 10,064,798 B1 | 9/2018 | De La Serna et al. | |
| 10,150,767 B2 | 12/2018 | Albrecht et al. | |
| 10,292,986 B2 | 5/2019 | Tian et al. | |
| 10,966,961 B2 | 4/2021 | Atkinson et al. | |
| 11,059,821 B2 | 7/2021 | Combs et al. | |
| 2002/0019527 A1 | 2/2002 | Wang et al. | |
| 2005/0070588 A1 | 3/2005 | Weinstein et al. | |
| 2007/0142449 A1 | 6/2007 | Teng et al. | |
| 2008/0194634 A1 | 8/2008 | Arndt et al. | |
| 2008/0207910 A1 | 8/2008 | Podhorez et al. | |
| 2009/0149517 A1 | 6/2009 | Bothe et al. | |
| 2014/0142146 A1 | 5/2014 | Lemieux et al. | |
| 2014/0162971 A1* | 6/2014 | Wang ..................... A61K 45/06 514/228.2 |
| 2015/0148372 A1 | 5/2015 | Yue et al. | |
| 2015/0322076 A1 | 11/2015 | Chen et al. | |
| 2017/0197947 A1 | 7/2017 | Kuehnert et al. | |
| 2017/0340605 A1 | 11/2017 | Albrecht et al. | |
| 2017/0342067 A1 | 11/2017 | Albrecht et al. | |
| 2018/0044335 A1 | 2/2018 | Martin et al. | |
| 2019/0381010 A1 | 12/2019 | Atkinson et al. | |
| 2020/0140459 A1 | 5/2020 | Pham et al. | |
| 2020/0239433 A1 | 7/2020 | Chakravarty et al. | |
| 2020/0385408 A1 | 12/2020 | Xu et al. | |
| 2021/0002293 A1 | 1/2021 | Pham et al. | |
| 2021/0070756 A1 | 3/2021 | Fidanze et al. | |
| 2021/0205284 A1 | 7/2021 | Trzoss et al. | |
| 2021/0261539 A1 | 8/2021 | Xia et al. | |
| 2021/0346336 A1 | 11/2021 | Demont et al. | |
| 2024/0308998 A1 | 9/2024 | Woodland et al. | |

FOREIGN PATENT DOCUMENTS

| | | |
|---|---|---|
| AT | 387966 B | 4/1989 |
| CA | 1145344 A | 4/1983 |
| CA | 2112052 A1 | 6/1994 |
| CN | 102174035 A | 9/2011 |

(Continued)

OTHER PUBLICATIONS

Patani, G. A.; LaVoie, E. J. "Bioisosterism: A Rational Approach in Drug Design" Chem. Rev. 1996, 96, 3147-3176. (Year: 1996).*
Barinotti et al., "Serum Biomarkers of Renal Fibrosis: A Systematic Review," International Journal of Molecular Sciences, 23:14139, 13 pages, 2022.
Moeller et al., "New Aspects of Kidney Fibrosis—From Mechanisms of Injury to Modulation of Disease," Frontiers in Medicine, vol. 8, Article 814497, Jan. 2022.
Rout-Pitt et al., "Epithelial mesenchymal transition (EMT): a universal process in lung diseases with implications for cystic fibrosis pathophysiology," Respiratory Research, 19:136, 2018.
Abbvie, "A Study to Assess Adverse Events and Effectiveness of Upadacitinib Oral Tablets in Adult and Adolescent Participants with Vitiligo (Viti-Up)," NCT06118411, 15 pages, last update posted Mar. 28, 2024. Holla et al., "Repigmentation of Leukotrichia Due to Retrograde Migration of Melanocytes After Noncultured Epidermal Suspension Transplantation," American Society for Dermatologic Surgery, Inc., 40: 169-175, 2013.

(Continued)

*Primary Examiner* — Brandon J Fetterolf
*Assistant Examiner* — John D McAnany
(74) *Attorney, Agent, or Firm* — Fenwick & West LLP; Heidi A. Erlacher; Christine Dunne

(57) ABSTRACT

The present invention concerns compounds comprising N-methyl-2-pyridone, and pharmaceutically-acceptable salts and compositions of such compounds. Such compounds are useful in anti-inflammatory and anti-cancer therapies. Therefore, the present invention also concerns such compounds for use as medicaments, particularly for the treatment of inflammatory diseases and oncology.

51 Claims, No Drawings

(56) References Cited

FOREIGN PATENT DOCUMENTS

| | | |
|---|---|---|
| CN | 102304108 A | 1/2012 |
| CN | 102977090 A | 3/2013 |
| CN | 104136435 A | 11/2014 |
| CN | 105518007 A | 4/2016 |
| CN | 106187854 A | 12/2016 |
| CN | 107108614 A | 8/2017 |
| CN | 107151207 A | 9/2017 |
| CN | 108690020 A | 10/2018 |
| CN | 109384784 A | 2/2019 |
| CN | 109384785 | 2/2019 |
| CN | 109384785 A | 2/2019 |
| CN | 110041253 A | 7/2019 |
| CN | 110143961 A | 8/2019 |
| CN | 110204543 A | 9/2019 |
| CN | 110372693 A | 10/2019 |
| CN | 110577526 A | 12/2019 |
| CN | 111533721 A | 8/2020 |
| CN | 113185404 A | 7/2021 |
| DE | 4217952 A1 | 12/1993 |
| EP | 0 249 236 A1 | 12/1987 |
| EP | 0 353 606 A2 | 2/1990 |
| EP | 0 502 786 A1 | 9/1992 |
| EP | 0 538231 A1 | 4/1993 |
| EP | 0 676 395 A2 | 10/1995 |
| EP | 1 068 866 A1 | 1/2001 |
| EP | 1 092 718 A1 | 4/2001 |
| EP | 1 291 345 A1 | 3/2003 |
| EP | 1 468 990 A1 | 10/2004 |
| EP | 2 792 355 A1 | 10/2014 |
| EP | 2 970 330 A | 1/2016 |
| EP | 2 970 330 A1 | 1/2016 |
| FR | 2889190 A1 | 2/2007 |
| GB | 2 165 537 A | 4/1986 |
| JP | 2000109467 A | 4/2000 |
| JP | 2001192384 A | 7/2001 |
| JP | 2005035983 A | 2/2005 |
| JP | WO 2003/053927 A1 | 4/2005 |
| JP | 2008156311 A | 7/2008 |
| JP | 2013041225 A | 2/2013 |
| JP | 2013041226 A1 | 2/2013 |
| JP | 2015051963 A | 3/2015 |
| JP | 2017137283 A | 8/2017 |
| JP | 2019094290 A | 6/2019 |
| JP | 2021054810 A | 4/2021 |
| WO | WO 92/09580 A1 | 6/1992 |
| WO | WO 94/01433 A1 | 1/1994 |
| WO | WO 94/19326 A1 | 9/1994 |
| WO | WO 94/25436 A1 | 11/1994 |
| WO | WO 96/00218 A1 | 1/1996 |
| WO | WO 96/23788 A1 | 8/1996 |
| WO | WO 97/11065 A1 | 3/1997 |
| WO | WO 98/15278 A1 | 4/1998 |
| WO | WO 98/49162 A1 | 11/1998 |
| WO | WO 99/00359 A1 | 1/1999 |
| WO | WO 00/12498 A1 | 3/2000 |
| WO | WO 00/12499 A1 | 3/2000 |
| WO | WO 00/24739 A1 | 5/2000 |
| WO | WO 00/33836 A1 | 6/2000 |
| WO | WO 00/55155 A2 | 9/2000 |
| WO | WO 01/53257 A2 | 7/2001 |
| WO | WO 01/81316 A2 | 11/2001 |
| WO | WO 02/078706 A1 | 10/2002 |
| WO | WO 2004/000318 A2 | 12/2003 |
| WO | WO 2004/094376 A1 | 11/2004 |
| WO | WO 2005/123731 A2 | 12/2005 |
| WO | WO 2006/074445 A2 | 7/2006 |
| WO | WO 2006/103254 A1 | 10/2006 |
| WO | WO 2007/003389 A2 | 1/2007 |
| WO | WO 2007/068418 A1 | 6/2007 |
| WO | WO 2007/142308 A1 | 12/2007 |
| WO | WO 2008/030266 A2 | 3/2008 |
| WO | WO 2008/038136 A2 | 4/2008 |
| WO | WO 2008/051805 A2 | 5/2008 |
| WO | WO 2008/054605 A2 | 5/2008 |
| WO | WO 2008/064318 A2 | 5/2008 |
| WO | WO 2008/097235 A1 | 8/2008 |
| WO | WO 2008/120759 A1 | 10/2008 |
| WO | WO 2008/138876 A1 | 11/2008 |
| WO | WO 2008/148889 A1 | 12/2008 |
| WO | WO 2009/057784 A1 | 5/2009 |
| WO | WO 2009/067233 A1 | 5/2009 |
| WO | WO 2009/074247 A1 | 6/2009 |
| WO | WO 2009/084693 A1 | 7/2009 |
| WO | WO 2009/088986 A1 | 7/2009 |
| WO | WO 2009/088990 A1 | 7/2009 |
| WO | WO 2009/118567 A2 | 10/2009 |
| WO | WO 2009/156336 A1 | 12/2009 |
| WO | WO 2010/018328 A1 | 2/2010 |
| WO | WO 2010/042925 A2 | 4/2010 |
| WO | WO 2010/048207 A2 | 4/2010 |
| WO | WO 2010/108115 A1 | 9/2010 |
| WO | WO 2011/054553 A1 | 5/2011 |
| WO | WO 2011/054843 A1 | 5/2011 |
| WO | WO 2011/054845 A1 | 5/2011 |
| WO | WO 2011/134925 A1 | 11/2011 |
| WO | WO 2012/028332 A1 | 3/2012 |
| WO | WO2012/055878 A2 | 5/2012 |
| WO | WO2012/055879 A1 | 5/2012 |
| WO | WO 2012/085081 A1 | 6/2012 |
| WO | WO 2013/019548 A1 | 2/2013 |
| WO | WO 2013/033240 A1 | 3/2013 |
| WO | WO 2013/083975 A2 | 6/2013 |
| WO | WO 2013/083991 A1 | 6/2013 |
| WO | WO 2013/097052 | 7/2013 |
| WO | WO 2013/097052 A1 | 7/2013 |
| WO | WO 2013/097601 A1 | 7/2013 |
| WO | WO 2013/123349 A1 | 8/2013 |
| WO | WO 2013/180193 A1 | 12/2013 |
| WO | WO 2013/185284 A1 | 12/2013 |
| WO | WO 2013/188381 A1 | 12/2013 |
| WO | WO 2014/004863 A2 | 1/2014 |
| WO | WO 2014/005129 A1 | 1/2014 |
| WO | WO 2014/010737 A1 | 1/2014 |
| WO | WO 2014/019908 A2 | 2/2014 |
| WO | WO2014/037362 A1 | 3/2014 |
| WO | WO 2014/096381 A1 | 6/2014 |
| WO | WO-2014096965 A2 * | 6/2014 ......... A61K 31/4375 |
| WO | WO 2014/125408 | 8/2014 |
| WO | WO 2014/125408 A2 | 8/2014 |
| WO | WO 2014/144721 A2 | 9/2014 |
| WO | WO 2014/153100 A2 | 9/2014 |
| WO | WO-2014139324 A1 | 9/2014 |
| WO | WO 2014/165127 A1 | 10/2014 |
| WO | WO 2014/170350 A1 | 10/2014 |
| WO | WO 2014/181287 A1 | 11/2014 |
| WO | WO 2014/195697 A1 | 12/2014 |
| WO | WO 2014/195718 A1 | 12/2014 |
| WO | WO 2014/206150 A1 | 12/2014 |
| WO | WO 2014/206345 A1 | 12/2014 |
| WO | WO 2015/048692 A1 | 4/2015 |
| WO | WO2015/054642 A2 | 4/2015 |
| WO | WO 2015/063694 A1 | 5/2015 |
| WO | WO 2015/081203 A1 | 6/2015 |
| WO | WO 2015/081246 A1 | 6/2015 |
| WO | WO 2015/081280 A1 | 6/2015 |
| WO | WO 2015/089075 A1 | 6/2015 |
| WO | WO2015/112809 A2 | 7/2015 |
| WO | WO 2015/148350 A2 | 10/2015 |
| WO | WO2015/153871 A2 | 10/2015 |
| WO | WO 2015/187088 A1 | 12/2015 |
| WO | WO 2016/012485 A1 | 2/2016 |
| WO | WO 2016/016380 A1 | 2/2016 |
| WO | WO 2016/042341 A1 | 3/2016 |
| WO | WO 2016/077378 A1 | 5/2016 |
| WO | WO 2016/077380 A1 | 5/2016 |
| WO | WO 2016/092375 A1 | 6/2016 |
| WO | WO 2016/097031 A1 | 6/2016 |
| WO | WO 2016/097035 A1 | 6/2016 |
| WO | WO 2016/139361 A1 | 9/2016 |
| WO | WO 2016/177703 A1 | 11/2016 |
| WO | WO 2017/043805 A1 | 3/2017 |
| WO | WO 2017/093214 A1 | 6/2017 |
| WO | WO 2017/139526 A1 | 8/2017 |

(56) References Cited

FOREIGN PATENT DOCUMENTS

| WO | WO 2017/177955 | | 10/2017 |
|---|---|---|---|
| WO | WO 2017/177955 | A1 | 10/2017 |
| WO | WO 2018/041947 | A1 | 3/2018 |
| WO | WO 2018/041964 | A1 | 3/2018 |
| WO | WO 2018/086604 | A1 | 5/2018 |
| WO | WO 2018/087160 | A1 | 5/2018 |
| WO | WO 2018/130174 | A1 | 7/2018 |
| WO | WO 2018/158212 | A1 | 9/2018 |
| WO | WO 2018/162312 | A1 | 9/2018 |
| WO | WO 2018/170067 | A1 | 9/2018 |
| WO | WO 2018/177297 | A1 | 10/2018 |
| WO | WO 2018/195155 | A1 | 10/2018 |
| WO | WO 2019/029554 | A1 | 2/2019 |
| WO | WO 2019/043373 | A1 | 3/2019 |
| WO | WO 2019/089442 | A1 | 5/2019 |
| WO | WO 2019/152440 | A1 | 8/2019 |
| WO | WO 2019/154329 | A1 | 8/2019 |
| WO | WO 2019/181939 | A1 | 9/2019 |
| WO | WO 2019/184919 | A1 | 10/2019 |
| WO | WO 2019/229251 | A1 | 12/2019 |
| WO | WO 2020/007322 | A1 | 1/2020 |
| WO | WO 2020/011254 | A1 | 1/2020 |
| WO | WO 2020/012427 | A1 | 1/2020 |
| WO | WO 2020/020288 | A1 | 1/2020 |
| WO | WO 2020/020308 | A1 | 1/2020 |
| WO | WO 2020/022412 | A1 | 1/2020 |
| WO | WO 2020/033413 | A2 | 2/2020 |
| WO | WO 2020/043821 | A1 | 3/2020 |
| WO | WO 2020/056074 | A1 | 3/2020 |
| WO | WO 2020/063976 | A1 | 4/2020 |
| WO | WO 2020/072492 | A1 | 4/2020 |
| WO | WO 2020/092638 | A1 | 5/2020 |
| WO | WO 2020/150681 | A1 | 7/2020 |
| WO | WO2020/169698 | A1 | 8/2020 |
| WO | WO 2020/216779 | A1 | 10/2020 |
| WO | WO 2020/227097 | A1 | 11/2020 |
| WO | WO 2020/237025 | A1 | 11/2020 |
| WO | WO 2020/253711 | A1 | 12/2020 |
| WO | WO 2020/254489 | A1 | 12/2020 |
| WO | WO 2021/016102 | A1 | 1/2021 |
| WO | WO 2021/068755 | A1 | 4/2021 |
| WO | WO 2021/003310 | A1 | 6/2021 |
| WO | WO 2021/156636 | A1 | 8/2021 |
| WO | WO2021/178525 | A1 | 9/2021 |
| WO | WO2021/236685 | A1 | 11/2021 |
| WO | WO2022/046682 | A1 | 3/2022 |
| WO | WO 2022/076831 | A2 | 4/2022 |
| WO | WO 2022/090699 | A1 | 5/2022 |
| WO | WO 2023/275542 | A1 | 1/2023 |
| WO | WO-2023081720 | A1 | 5/2023 |
| WO | WO-2024018423 | A1 | 1/2024 |
| WO | WO-2024138201 | A2 | 6/2024 |
| WO | WO-2024220589 | A2 | 10/2024 |

OTHER PUBLICATIONS

Incyte Corporation, "Topical Ruxolitinib Evaluation in Vitiligo Study 2 (TRuE-V2)," NCT04057573, 25 pages, last update posted Sep. 21, 2022.

Mogawer et al., "New insights into leukotrichia in nonsegmental vitiligo: A cross-sectional study," Indian Journal of Dermatology, Venereology, and Leprology, vol. 85, Issue 4, 374-379, 2019.

Pfizer, "A 104-Week Study of Ritlecitinib Oral Capsules in Adults With Nonsegmental Vitiligo (Active and Stable) Tranquillo 2 (Tranquillo 2)," NCT06072183, 22 pages, last update posted Jun. 26, 2024.

Jin et al., "A BET inhibitor, NHWD-870, can downregulate dendritic cells maturation via the IRF7-mediated signaling pathway to ameliorate imiquimod-induced psoriasis-like murine skin inflammation," European Journal of Pharmacology, 40 pages, 2024.

Chen et al., "Antiinflammatory effects of bromodomain and extraterminal domain inhibition in cystic fibrosis lung inflammation," JCI Insight, 1(11): e87168, 10 pages, 2016.

Harrison et al., "Phase III Manifest-2: pelabresib + ruxolitinib vs placebo + ruxolitinib in JAK inhibitor treatment-naive myelofibrosis," Future Oncol., 18(27): 2987-2997, 2022.

Henderson, Emily, "Insilico Medicine discovers novel preclinical candidate to address idiopathic pulmonary fibrosis," https://www.news-medical.net/news/20210225/Insilico-Medicine-discovers-novel-preclinical-candidate-to-address-idiopathic-pulmonary-fibrosis.aspx, pages, 2021.

Kabala, Pawel A., "Inflammatory Activation of Rheumatoid Arthritis Fibroblast-Like Synoviocytes. The Role of Epigenetic Regulatory Proteins and Endoplasmic Reticulum Stress.," 207 pages. 2018.

Lourdes Rios et al., "Animal Models of Osteoarthritis Part 1—Preclinical Small Animal Models: Challenges and Opportunities for Drug Development," Current Protocols, e596, vol. 2,21 pages, 2022.

Lu et al., "Enriched Populations of Human Megakaryocytic Cells Affect the Behavior of Myelofibrosis CD34+ Cells as Well as Cells Belonging to the MF Supportive Microenvironment," Blood, 132(Supplement 1): 3057, 3 pages, 2018.

Mita et al., "Bromodomain inhibitors a decade later: a promise unfulfilled?," British Journal of Cancer, 123:1713-1714, 2020.

Nadeem et al., "Imiquimod-induced psoriasis-like skin inflammation is suppressed by BET bromodomain inhibitor in mice through RORC/IL-17A pathway modulation," Pharmacological Research, 99: 248-257, 2015.

Park-Min et al., "Inhibition of osteoclastogenesis and inflammatory bone resorption by targeting BET proteins and epigenetic regulation," Nature Communications, 9 pages, 2014.

Perez-Pena et al., "In silico analyses guides selection of BET inhibitors for triple negative breast cancer treatment," Translational Research Unit, Albacete University Hospital, Albacete, Spain; 2 Cancer Research Center, CSIC-University of Salamanca, Spain, 29 pages, no date provided.

Sanders et al., "Brd4-p300 inhibition downregulates Nox4 and accelerates lung fibrosis resolution in aged mice," JCI Insight, 5(14): e137127, 13 pages, 2020.

Sato et al., "Discovery of benzo[f]pyrido[4,3-b][1,4]oxazepin-10-one derivatives as orally available bromodomain and extra-terminal domain (BET) inhibitors with efficacy and an in vivo psoriatic animal model," Bioorganic & Medicinal Chemistry, 34, 12 pages, 2021.

Shorstova et al., "Achieving clinical success with BET inhibitors as anti-cancer agents," British Journal of Cancer, 124: 1478-1490, 2021.

Suzuki et al., "Transcriptomic changes involved in the dedifferentiation of myofibroblasts derived from the lung of a patient with idiopathic pulmonary fibrosis," Molecular Medicine Reports, 22: 1518-1526, 2020.

Tang et al., "BET Bromodomain Proteins Mediate Downstream Signaling Events following Growth Factor Stimulation in Human Lung Fibroblasts and Are Involved in Bleomycin-Induced Pulmonary Fibrosis," Molecular Pharmacology, 83: 283-293, 2013.

Tang et al., "Assessment of Brd4 inhibition in Idiopathic Pulmonary Fibrosis Lung Fibroblasts and in Vivo Models of Lung Fibrosis," The American Journal of Pathology, vol. 183, No. 2, 470-479, 2013.

Tontsch-Grunt et al., "Therapeutic impact of BET inhibitor BI 894999 treatment: backtranslation from the clinic," British Journal of Cancer, 577-586, 2022.

Vichaikul et al., "Inhibition of bromodomain extraterminal histone readers alleviates skin fibrosis in experimental models of scleroderma," JCI Insight, 15 pages, 2022.

Zhang et al., "Targeting bromodomain-containing protein 4 (BRD4) benefits rheumatoid arthritis," Immunology Letters, 166: 103-108, 2015.

PCT International Search Report and Written Opinion mailed Sep. 28, 2020, issued in corresponding International Application No. PCT/EP2020/061173 (17 pgs.).

Keith F. McDaniel et al., Discovery of N-(4-(2,4-Difluorophenoxy)-3-(6-methyl-7-oxo-6,7-dihydro-1H- pyrrolo[2,3-c]pyridin-4-yl)phenyl)ethanesulfonamide (ABBV-075/Mivebresib), a Potent and Orally Available Bromodomain and Extraterminal Domain (BET) Family Bromodomain Inhibitor, J. Med. Chem., 2017, 60, 8369-8384.

(56) References Cited

OTHER PUBLICATIONS

Great Britain Search Report issued for Application No. GB1905721.5 dated Oct. 3, 2019, 5 pages.
Alqahtani et al., "Bromodomain and extra-terminal motif inhibitors: a review of preclinical and clinical advances in cancer therapy," Future Science OA, 5(3) 20 pages, 2019.
Atkinson et al., "Clinical Pharmacokinetics," Ann. Rev. Pharmacol. Toxicol., 19:105-127, 1979.
Bandukwala et al., "Selective inhibition of CD4+ T-cell cytokine production and autoimmunity by BET protein and c-Myc inhibitors," PNAS, 109(36): 14532-14537 (2012).
Belkina et al., "BET Protein Function is Required for Inflammation: Brd2 Genetic Disruption and BET Inhibitor JQ1 Impair Mouse Macrophage Inflammatory Responses," The Journal of Immunology, 190:3670-3678, 2013.
Bourova-Flin et al., "The Role of Bromodomain Testis-Specific Factor, BRDT, in Cancer: A Biomarker and a Possible Therapeutic Target," Cell Journal, vol. 19, Suppl 1, 8 pages, 2017.
Brand et al., "Small Molecule Inhibitors of Bomodomain-Acetyl-lysine Interactions," American Chemical Society, 10:22-39, 2015.
Chan et al., "Advances in Device and Formulation Technologies for Pulmonary Drug Delivery," AAPS PharmSciTech, vol. 15, No. 4, pp. 882-897, 2014.
Chan et al., "BET bromodomain inhibition suppresses transcriptional responses to cytokine-Jak-STAT signaling in a gene-specific manner in human monocytes," Eur. J. Immunol., 45:287-297 2015.
Chen et al., "Discovery, structural insight, and bioactivities of BY27 as a selective inhibitor of the second bromodomains of BET proteins," European Journal of Medicinal Chemistry, 182, 21 pages, 2019.
Choudhary et al. "Lysine Acetylation Targets Protein Complexes and Co-Regulates Major Cellular Functions," Science, 325: 834-840, 2009.
Cook et al., "Lessons learned from the fate of AstraZeneca's drug pipeline: a five-dimensional framework," Nature Reviews Drug Discovery, 13:419-431 (2014).
Coude et al., "BET inhibitor OTX015 targets BRD2 and BRD4 and decreases c-MYC in acute leukemia cells," Oncotarget, 6(19): 17698-17712 (2015).
Ding et al., "BRD4 is a novel therapeutic target for liver fibrosis," PNAS, vol. 112, No. 51, 15713-15718, 2015.
Duan et al., "BET bromodomain inhibition suppresses innate inflammatory and profibrotic transcriptional networks in heart failure," Sci Transl Med, 9(390) 31 pages, 2017.
Endo et al., "Elevation of interleukin-8 (IL-8) levels in joint fluids of patients with rheumatoid arthritis and the induction by IL-8 of leukocyte infiltration and synovitis in rabbit joints," Lymphokine Cytokine Res. 10(4): 245-252, 1991.
Faivre et al., "Selective inhibition of the BD2 bromodomain of BET proteins in prostate cancer," Nature, Vo. 578, p. 306-310, 2020.
Filippakopoulos et al., "Targeting bromodomains: epigenetic readers of lysine acetylation," Nature Review, 13: 337-356, 2014.
George et al., "Pyoderma gangrenosum—a guide to diagnosis and management," Clinical Medicine, 19(3); 224-228, 2019.
Gilan et al., "Selective targeting of BD1 and BD2 of the BET proteins in cancer and immunoinflammation," Science, 368: 387-394, 2020.
Guo et al., "Pharmaceutical strategies to extend pulmonary exposure of inhaled medicines," Acta Pharmaceutica Sinica B, 11(8): 2565-2584, 2021.
Hajmirza et al., "BET Family Protein BRD4: An Emerging Actor in NFκB Signaling in Inflammation in Cancer," Biomedicines, 9 pages, 6(16) 2018.
Huang et al., "Brd4 Coactivates Transcriptional Activation of NF-κB via Specific Binding to Acetylated RelA," Molecular and Cellular Biology, vol. 29, No. 5, pp. 1375-1387, 2009.
International Search Report issued for Application No. PCT/GB2022/051667 dated Aug. 10, 2022, 5 pages.

Ionescu et al., "Pathways of Biotransformation—Phase II Reactions," Chapter 3, Drug Metabolism, Springer, Dordrecht, pp. 129-170, 2005.
Izbicki et al., "Time course of bleomycin-induced lung fibrosis," Int. J. Exp. Path., 83: 111-119, 2002.
Jenkins et al.,"An Official American Thoracic Society Workshop Report: Use of Animal Models for the Preclinical Assessment of Potential Therapies for Pulmonary Fibrosis," Am. J. Respir. Cell Mol. Biol. 56(5): 667-679 (2017).
Johnston et al., "Il-1 and IL-36 are the dominant cytokines in Palmar Plantar Pustulosis," J Dermatol Sci., 84(1): e99 2016.
Johnston et al., "IL-1 and IL-36 are dominant cytokines in generalized pustular psoriasis," J. Allergy Clin Immunol., 140(1): 109-120, 2017.
Jones et al., "Discovery of a Novel Bromodomain and Extra Terminal Domain (BET) Protein Inhibitor, I-BET282E, Suitable for Clinical Progression," J. Med. Chem., 64(16): 12200-12227, 2021.
Junwei et al., "The mechanisms behind the therapeutic activity of BET bromodomain inhibition," Mol Cell, 54(5); 728-736, 2014.
Keck et al., "Bromodomain and extraterminal inhibitors block the Epstein-Barr virus lytic cycle at two distinct steps," J. Biol. Chem., 292(32): 13284-13295, 2017.
Klein et al., "The bromodomain protein inhibitor I-BET151 suppresses expression of inflammatory genes and matrix degrading enzymes in rheumatoid arthritis synovial fibroblasts," Ann Rheum Dis. 75(2): 422-429 2016.
Leroy et al., "The double bromodomain proteins Brd2 and Brd3 couple histone acetylation to transcription," Mol. Cell, 30(1):51-60, 2008.
Ma et al., "Continuously elevated serum matrix metalloproteinase-3 for 3 ~ 6 months predict one-year radiographic progression in rheumatoid arthritis: a prospective cohort study," Arthritis Research & Therapy 17:289 13 pages (2015).
Mele et al., "BET bromodomain inhibition suppresses $T_H17$-mediated pathology," J. Exp. Med., vol. 210, No. 11, pp. 2181-2190, 2013.
Meng et al., "BET Inhibitor JQ1 Blocks Inflammation and Bone Destruction," J. Dent. Res., 93(7); 657-662, 2014.
Mi et al., "Blocking IL-17A Promotes the Resolution of Pulmonary Inflammation and Fibrosis Via TGF-β1-Dependent and -Independent Mechanisms, "J. Immunol., 187(6): 3003-3014, 2011.
Moreno et al., "Phase I study of CC-90010, a reversible, oral BET inhibitor in patients with advanced solid tumors and relapsed/refractory non-Hodgkins lymphoma," Annals of Oncology, 31(6) 780-788, 2020.
Murakami et al., "Patients with palmoplantar pustulosis have increased IL-17 and IL-22 levels both in the lesion and serum," Exp Dermatol., 20(10): 845-847, 2011.
Nickerson et al., "The first bromodomain of Brdt, a testis-specific member of the BET sub-family of double-bromodomain-containing proteins, is essential for male germ cell differentiation," Development; 134(19): 3507-3515, 2007.
Nicodeme et al., "Suppression of inflammation by a synthetic histone mimic," Nature, 468(7327): 1119-1123, 2010.
Otsuka et al., "The interplay between genetic and environmental factors in the pathogenesis of atopic dermatitis," Immunological Reviews, 278:246-262, 2017.
PCT International Search Report and Written Opinion mailed Aug. 10, 2022, issued in corresponding International Application No. PCT/GB2022/051667 (11 pages).
Perez-Salvia et al., "Bomodomain inhibitors and cancer therapy: from structures to applications," Epigenetics, vol. 12, No. 5, 323-339, 2017.
Picaud et al., "RVX-208, an inhibitor of BET transcriptional regulators with selectivity for the second bromodomain," PNAS, 19754-19759, vol. 110, No. 49, 2013.
Preston et al., "Design and Synthesis of a Highly Selective and In Vivo-Capable Inhibitor of the Second Bromodomain of the Bromodomain and Extra Terminal Domain Family of Proteins," J. Med. Chem., 63: 9070-9092, 2020.
Prinjha et al., "Place your BETs: the therapeutic potential of bromodomains," Trends in Pharmacological Sciences, vol. 33, No. 3, pp. 146-153, 2012.

(56) References Cited

OTHER PUBLICATIONS

Regazzetti et al., "Transcriptional Analysis of Vitiligo Skin Reveals the Alteration of WNT Pathway: A Promising Target for Repigmenting Vitiligo Patients," Journal of Investigative Dermatology, 135: 3105-3114, 2015.
Rowland et al., "Clinical Pharmacokinetics. Concepts and Applications", Chapter 11—Elimination, Lippincott Williams & Wilkins, pp. 161-167, 1995.
Seal et al., "The Optimization of a Novel, Weak Bromo and Extra Terminal Domain (BET) Bromodomain Fragment Ligand to a Potent and Selective Second Bromodomain (BD2) Inhibitor," J. Med. Chem., 63:9093-9126, 2020.
Seal et al., "Fragment-based Scaffold Hopping: Identification of Potent, Selective, and Highly Soluble Bromo and Extra Terminal Domain (BET) Second Bromodomain (BD2) Inhibitors," J. Med. Chem., 64: 10772-10805, 2021.
Shah et al., "Regulation of glucocorticoid receptor via a BET-dependent enhancer drive antiandrogen resistance in prostate cancer," eLife, 19 pages, 2017.
Shang et al., "The first bromodomain of Brdt, a testis-specific member of the BET sub-family of double-bromodomain-containing proteins, is essential for male germ cell differentiation," Development, 134: 3507-3515, 2007.
Shapiro et al., "A Phase 1 study of RO6870810, a novel bromodomain and extra-terminal protein inhibitor, in patients with NUT carcinoma, other solid tumours, or diffuse large B-cell lymphoma," British Journal of Cancer, 124: 744-753, 2021.
Sheppard et al., "Discovery of N-Ethyl-4-[2-(4-fluoro-2,6-dimethyl-phenoxy)-5-(1-hydroxy-1-methyl-ethyl)phenyl]-6-methyl-7-oxo-1H-pyrrolo[2,3-c]pyridine-2-carboxamide (ABBV-744), a BET Bromodomain Inhibitor with Selectivity for the Second Bromodomain," J. Med. Chem., 63: 5585-5623, 2020.
Shi et al., "Disrupting the Interaction of BRD4 with Di-acetylated Twist Suppresses Tumorigenesis in Basal-like Breast Cancer," Cancer Cell, 25(2):210-225, 2014.
Shi et al., "The mechanisms behind the therapeutic activity of BET bromodomain inhibition," Mol Cell, 54(5): 728-736, 2014.
Sun et al., "BET bromodomain inhibition suppresses graft-versus-host disease after allogeneic bone marrow transplantation in mice," Blood, 125(17): 2724-2728, 2015.
Tateiwa et al., "Cartilage and Bone Destruction in Arthritis: Pathogenesis and Treatment Strategy: A Literature Review," Cells, 8(818) 31 pages, 2019.
Trivedi et al., "Bromodomain and extra-terminal domain (BET) proteins regulate melanocyte differentiation," Epigenetics & Chromatin, 13:14, 18 pages, 2020.
Tsujikawa et al., "Apabetalone (RVX-208) reduces vascular inflammation in vitro and in CVD patients by a BET-dependent epigenetic mechanism," Clinical Epigenetics, 11:102, 21 pages, 2019.
Urso et al., "A short introduction to pharmacokinetics," European Review for Medical and Pharmacological Sciences, 6: 33-44, 2002.
Wang et al., "Classic Ulcerative Pyoderma Gangrenosum Is a T Cell-Mediated Disease Targeting Follicular Adnexal Structures: A Hypothesis Based on Molecular and Clinicopathologic Studies," Front. Immunol., 8: 8 pages, 2018.
Weidinger et al., "Atopic dermatitis," Lancet, 387:1109-1122, 2016.
Xiao et al., "Bromodomain and extra-terminal domain bromodomain inhibition prevents synovial inflammation via blocking IκB kinase-dependent NF-κB activation in rheumatoid fibroblast-like synoviocytes," Rheumatology, 55:173-184, 2016.
Xue et al., "Endogenous MMP-9 and not MMP-2 promotes rheumatoid synovial fibroblast survival, inflammation and cartilage degradation," Rheumatology, 53: 2270-2279, 2014.
Yang et al., "Brd4 Recruits P-TEFb to Chromosomes at Late Mitosis to Promote $G_1$ Gene Expression and Cell Cycle Progression," Molecular and Cellular Biology, vol. 28, No. 3, pp. 967-976, 2008.
Zhang et al., "The BD2 domain of BRD4 is a determinant in EndoMT and vein graft neointima formation," Cellular Signalling, 61: 20-29, 2019.
Zuber et al., "RNAi screen identifies Brd4 as a therapeutic target in acute myeloid leukaemia," Nature, 478(7370): 524-528, 2011.
Pubchem CID 118863409, "4-(2-anilino-5-methylsulfonylphenyl)-6-methyl-2-(1-methylpyrazol-4-yl)-1H-pyrrolo [2,3-c]pyridine-7-one," National Library of Medicine, 10 pages, 2016.
Business Wire, "Boston Pharmaceuticals Adds Five New Drug Programs to Its Pipeline in Licensing Deal," online press release; https://www.businesswire.com/news/home/20181002006135/en/Boston-Pharmaceuticals-Adds-Five-New-Drug-Programs-to-its-Pipeline-in-Licensing-Deal.
International Search Report issued for Application No. PCT/US22/79171 dated Feb. 28, 2023, 14 pages.
Kohnken et al., "Targeting BRD4 Disables IL-15 Oncogenic Signaling in Cutaneous T-Cell Lymphoma Via Down Regulation of IL-15 Regulator Complex," Blood, 128(22): 1097, 2016.
Office Action issued in corresponding Eurasian Application No. 202192905 on Nov. 28, 2022 (9 pages).
Singh et al., "The Role of IL-17 in Vitiligo: A Review," Autoimmun Rev., 15(4): 397-404, 2016.
Stratton et al., "BRD4 inhibition for the treatment of pathological organ fibrosis," F1000 Research, vol. 6, 7 pages, 2017.
Xiao et al., "BET Bromodomain Inhibition Suppresses HIF-1α-Mediated IL-17 Expression in Peripheral Blood Mononuclear Cells from Patients with Rheumatoid Arthritis," International Journal of Immunology, 6(4): 48-57, 2018.
Zaware et al., "Bromodomain biology and drug discovery," Nature Structural & Molecular Biology, 26: 870-879, 2019.
Bae et al., "Development and validation of the fingertip unit for assessing Facial Vitiligo Area Scoring Index," J. Am. Acad. Dermatol., 86(2): 387-393, Feb. 2022.
Batchelor et al., "Validation of the Vitiligo Noticeability Scale: a patient-reported outcome measure of vitiligo treatment success," British Journal of Dermatology, 174(2):386-394 (2016).
Boukhedouni et al., "Type-1 cytokines regulate MMP-9 production and E-cadherin disruption to promote melanocyte loss in vitiligo," JCI Insight, 16 pages (2020).
Carrington et al., "Use of animal models in IPF research," Pulmonary Pharmacology & Therapeutics, 51:73-78 (2018).
Ezzedine et al., "Vitiligo," Lancet, 386:74-84 (2015).
Furue et al., "Nonsegmental vitiligo update," Dermatologica Sinica, 34:173-176 (2016).
Georgiev et al., "BET Bromodomain Inhibition Suppresses Human T Cell Function," ImmunoHorizons.
Hamzavi et al., "Parametric Modeling of Narrowband UV-β Phototherapy for Vitiligo Using a Novel Quantitative Tool," Arch Dermatol., 140(6):677-683 (2004).
Jahagirdar et al., "RVX-297, a BET Bromodomain Inhibitor, Has Therapeutic Effects in Preclinical Models of Acute Inflammation and Autoimmune Disease," Mol. Pharmacol., 92:694-706, Dec. 2017.
Kaneshita et al., "CG223, a novel BET inhibitor, exerts TGF-B1-mediated antifibrotic effects in a murine model of bleomycin-induced pulmonary fibrosis," Pulmonary Pharmacology & Therapeutics, 70: 10 pages (2021).
Muller et al., "A rationale for determining, testing, and controlling specific impurities in pharmaceuticals that possess potential for genotoxicity," 44(3):198-211 (2006).
Ntranos et al., "Bromodomains: translating the words of lysine acetylation into myelin injury and repair," Neurosci. Lett., 625:4-10 (2016).
Oiso et al., "Nonsegmental Vitiligo and Autoimmune Mechanism," Dermatology Research and Practice, 7 pages (2011).
Shah et al., "Nanoparticle-Encapsulated Bromodomain-Containing Protein 4 Inhibitors for Therapeutics of Inflammatory Bowel Disease," 160(4):S5 (2021).
Sun et al., "Safety and Efficacy of Bromodomain and Extra-Terminal Inhibitors for the Treatment of Hematological Malignancies and Solid Tumors: A Systematic Study of Clinical Trials," Systematic Review, 11:15 pages (2021).
Van Geel et al., "Development and Validation of the Vitiligo Extend Score (VES): an International Collaborative Initiative," Journal of Investigative Dermatology, 136:978-984 (2016).

(56) References Cited

OTHER PUBLICATIONS

Wang et al., "The BET family in immunity and disease," Signal Transduction and Targeted Therapy, 6(23):22 pages (2021).
Wang et al., "(+) -JQ1 attenuated LPS-induced microglial inflammation via MAPK/NFκB signaling," Cell & Bioscience, 8(60):15 pages (2018).
"AbbVie Immunology Strategy and Long-Term Outlook," Corporate Presentation, 2020, 50 pages.
"Dice Therapeutics Corporate Presentation," Mar. 2023, 59 pages.
"Nuvation Bio Driven By Science Focused on Life," Corporate Presentation, Dec. 2022, 33 pages.
"Nuvation Bio Driven By Science Focused on Life," Corporate Presentation, Nov. 2023, 28 pages.
"Opzelura (ruxolitinib) cream 1.5% FDA Approval Call for Vitiligo," Corporate Presentation, Jul. 19, 2022, 37 pages.
"Center for Drug Evaluation and Research Application No. 125504Orig1s000 Summary Review," pharmacology review, CDER, FDA, 14 pages, Dec. 2014.
Abbvie, "Study to Evaluate Adverse Events and Change in Disease Activity With Oral Tablets of Upadacitinib in Adult Participants With Non-Segmental Vitiligo," NCT04927975, 14 pages, last update posted Sep. 11, 2023.
Abdallah et al., "Key Signaling Pathways in Psoriasis: Recent Insights from Antipsoriatic Therapeutics," Psoriasis: Targets and Therapy, 11:83-97, 2021.
Alotaibi, Hend M., "Incidence, Risk Factors, and Prognosis of Hidradenitis Suppurativa Across the Globe: Insights from the Literature," Clinical, Cosmetic and Investigational Dermatology, 545-552, 2023.
Armstrong et al., "Psoriasis Prevalence in Adults in the United States," JAMA Dermatology, 157(8), 940-946, 2021.
Bergqvist et al., "Vitiligo: A Review," Dermatology, 236:571-592, 2020.
Dong, Yuangji et al., "The Role of Decorin in Autoimmune and Inflammatory Diseases," Journal of Immunology Research, vol. 2022, Article ID 1283383, 11 pages, 2022.
Frahm et al., "Incyte Published and distributed by Cowen and Company, LLC," TD Cowen Equity Research, 107 pages, 2023.
Gandhi et al., "Prevalence of Vitiligo Among Adults in the United States," JAMA Dermatology, 158(1):43-50, 2022.
Gerlach et al., "The novel BET bromodomain inhibitor BI 894999 represses super-enhancer-associated transcription and synergizes with CDK9 inhibition in AML," Oncogene, 37:2687-2701, 2018.
Gilan et al.,"Selective targeting of BD1 and BD2 of the BET proteins in cancer and immuno-inflammation," Science, 368(6489):387-394, 2020.
"Incyte 2023 Second Quarter Financial and Corporate Update," Corporate Presentation, Aug. 2023, 31 pages.
Incyte, "Incyte Announces 52-Week Data From the Phase 3 TRuE-V Program Evaluating Ruxolitinib Cream (Opzelura™) in Patients With Vitiligo," 4 pages (2022).
Incyte Corporation, "A Study of INCB018424 Phosphate Cream in Subjects With Vitiligo," NCT03099304, 79 pages, last update posted Nov. 17, 2022.
Incyte Corporation, "A Study to Evaluate the Efficacy and Safety of INCB054707 in Participants With Vitiligo," NCT04818346, 19 pages, last update posted Jul. 5, 2023.
Johnson et al., "Targeting Epigenetic Readers in Hematologic Malignancies: A Good BET?" The Hematologist, 9(2):4 pages, 2012.
Karagaiah et al., "Emerging drugs for the treatment of vitiligo," Expert Opinion on Emerging Drugs, 25:1, 7-24, 2020.
Kruger et al., "A review of the worldwide prevalence of vitiligo in children/adolescents and adults," International Journal of Dermatology, 51:1206-1212, 2012.
Macgearailt et al., "Axial Spondyloarthritis: Clinical Characteristics, Epidemiology, and General Approaches to Management," EMJ Rheumatology, 9(1):105-114, 2021.
Ogdie et al., "Risk of Major Cardiovascular Events in Patients with Psoriatic Arthritis, Psoriasis and Rheumatoid Arthritis: A population-based cohort study," Ann. Rheum. Dis., 74(2):326-332, 2015.
Pandya, "AAD 2023: Povorcitinib Significantly Improved Total Body Repigmentation in Patients with Extensive Nonsegmental Vitilogo," Dermatology (2023).
Pandya et al., "Efficacy and Safety of Povorcitinib for Extensive Vitiligo: Results From a Double Blinded, Placebo Controlled, Dose Ranging Phase 2b Study," Presented at the American Academy of Dermatology (AAD) Annual Meeting, 2023, 12 pages.
Pandya et al., "Treatment-Emergent Adverse Events of Interest for Janus Kinase Inhibitors: Pooled Analysis of the 52-Week TRuE-V Phase 3 Studies of Ruxolitinib Cream Treatment for Vitiligo," (AAD) Annual Meeting, 2023, 5 pages.
Pfizer, "A Phase 2b Study to Evaluate The Efficacy and Safety Profile of PF-06651600 and PF-06700841 In Active Non-segmental Vitiligo Subjects," NCT03715829, 63 pages, last update posted Mar. 25, 2022.
Piper Sandler, "Incyte (INCY) Diversification into Derm Underappreciated; Initiating OW," Insight by Piper Sandler Proprietary Survey, 40 pages, Jan. 31, 2023.
Ran et al., "Structure-based Design of γ-Carboline Analogues as Potent and Specific BET Bromodomain Inhibitors," J. Med. Chem. 58(12):4927-4939, 2015.
Rangu et al., "Therapy Utilization among Children with Vitiligo at an Urban Tertiary Care Center," HSOA Journal of Clinical Dermatology and Therapy, 7:4 pages, 2021.
Ruiz De Morales et al., "Critical role of interleukin (IL)-17 in inflammatory and immune disorders: An updated review of the evidence focusing in controversies," Autoimmunity Reviews, 19:102429, 15 pages, 2020.
Rusinol et al.," Tyk2 Targeting in Immune-Mediated Inflammatory Diseases," International Journal of Molecular Sciences, 24:3391, 17 pages, 2023.
Sosa et al., "Confetti-like depigmentation: A potential sign of rapidly progressing vitiligo," J. Am. Acad. Dermatol., 73(2):272-275, Aug. 2015.
Su et al., "Interleukin-6 Signaling Pathway and Its Role in Kidney Disease: An Update," Frontiers in Immunology, 8(405):10 pages, 2017.
Sugaya, Makoto, "The Role of Th17-Related Cytokines in Atopic Dermatitis," International Journal of Molecular Sciences, 21:12 pages, 2020.
Sun et al., "Inhibition of BRD4 inhibits proliferation and promotes apoptosis of psoriatic keratinocytes," BioMedical Engineering OnLine, 20(107):13 pages, 2021.
Wang et al., "PubChem BioAssay: 2017 update," Nucleic Acids Research, 45(D955-D963):9 pages, 2017.
Xu et al., "Prevalence Trend and Disparities in Rheumatoid Arthritis among US Adults, 2005-2018," Journal of Clinical Medicine, 10(3289):13 pages, 2021.
Yafei et al., "BRD4 has dual effects on the HMGB1 and NF-κB signalling pathways and is a potential therapeutic target for osteoarthritis," BBA—Molecular Basis of Disease, 1863:3001-3015, 2017.
Young et al., "Psoriasis for the primary care practitioner," Journal of the American Association of Nurse Practitioners, 29:157-178, 2017.
Zhang et al., "Severe Hyperhomocysteinemia Promotes Bone Marrow-Derived and Resident Inflammatory Monocyte Differentiation and Atherosclerosis in LDLr/CBS-Deficient Mice," Circulation Research, 111(1):37-49, 2012.
"Recommendations related to contraception and pregnancy testing in clinical trials," Clinical Trials Facilitation and Coordination Group (CTFG), Sep. 21, 2020, 10 pages.
Armstrong et al., "Pathophysiology, Clinical Presentation, and Treatment of Psoriasis," JAMA, 323(19): 1945-1960, 2020.
Balato et al., "Effect of weather and environmental factors on the clinical course of psoriasis," Occup. Environ. Med., 70:600, 2013.
Boehncke et al., "Psoriasis," Lancet, 386:983-994, 2015.
Chen et al., "Adenosine Receptor Neurobiology: Overview," International Review of Neurobiology, 119:49 pagees, 2014.

(56) References Cited

OTHER PUBLICATIONS

"Common Terminology Criteria for Adverse Events (CTCAE) v5.0," U.S. Department of Health and Human Services, National Institutes of Health, National Cancer Institute, Nov. 27, 2017, 147 pages.
Custer et al., "The In Vivo Rodent Micronucleus Assay," Genetic Toxicology Testing, 269-322, 2016.
Dawson et al., "Targeting Epigenetic Readers in Cancer," The New England Journal of Medicine, 367(7):647-657, 2012.
Deng et al., "The Inflammatory Response in Psoriasis: a Comprehensive Review," Clinic Rev. Allerg. Immunol., 50:377-389, 2016.
Ferre, Sergi, "Role of the Central Ascending Neurotransmitter Systems in the Psychostimulant Effects of Caffeine," J. Alzheimers Dis., 20(Suppl 1): S35-S49, 2010.
Harvey et al., "Management of organic impurities in small molecule medicinal products: Deriving safe limits for use in early development," Regulatory Toxicology and Pharmacology, 84:116-123, 2017.
Hawkes et al., "Discovery of the IL-23/IL-17 Signaling Pathway and the Treatment of Psoriasis," J. Immunol., 2018(6):1605-1613, 2018.
Kamiya et al., "Risk Factors for the Development of Psoriasis," International Journal of Molecular Sciences, 20(4347):14 pages, 2019.
Liu et al., "Role of BET Proteins in Inflammation and CNS Diseases," Frontiers in Molecular Biosciences,' 8(748449):9 pages, 2021.
Parisi et al., "Global Epidemiology of Psoriasis: A Systematic Review of Incidence and Prevalence," Journal of Investigative Dermatology, 133:377-385, 2013.
Piha-Paul et al., "First-in-Human Study of Mivebresib (ABBV-075), an Oral Pan-Inhibitor of Bromodomain and Extra Terminal Proteins, in Patients with Relapsed/Refractory Solid Tumors," Clin. Cancer Res., 25:6309-6319, 2019.
Ramanunny et al., "Treatment Strategies Against Psoriasis: Principle, Perspectives and Practices," Current Drug Delivery, 17:52-73, 2020.
Tokuyama et al., "New Treatment Addressing the Pathogenesis of Psoriasis," Int. J. Mol. Sci. 21(7488): 16 pages, 2020.
World Medical Association, "WMA Declaration of Helsinki—Ethical Principles for Medical Research Involving Human Subjects," 4 pages, 2018.
Yang et al., "Datura Metel L. Ameliorates Imiquimod-Induced Psoriasis-Like Dermatitis and Inhibits Inflammatory Cytokines Production through TLR7/8-MyD88-NF-κB-NLRP3 Inflammasome Pathway," Molecules, 24(2157):14 pages, 2019.
Akdis et al., "Type 2 Immunity in the skin and lungs," Allergy, 75:1582-1605 (2020).
Alam, M. et al., "Active ascertainment of recurrence rate after treatment of primary basal cell carcinoma (Bcc)", J Am Acad Dermatol, 2015; 73(2):323-325.
Aletaha, D. and Smolen JS. Diagnosis and Management of Rheumatoid Arthritis: A Review. JAMA, 2018;320(13):1360-1372. doi:10.1001/jama.2018.13103.
Al-Hasani et al., "Phosphoryl exchange is involved in the mechanism of the insulin receptor kinase" FEBS letters, 1994;349(1):17-22.
Alotaibi, Hend M., "Incidence, Risk Factors, and Prognosis of Hidradenitis Suppurativa Across the Globe: Insights from the Literature," Clinical, Cosmetic and Investigational Dermatology, 2023; 16:545-552.
Alperovich et al., "New immunosuppresor strategies in the treatment of murine lupus nephritis", Lupus, 2007;16(1):18-24. doi: 10.1177/0961203306073136.
Ames, Bruce N., et al., "Carcinogens are mutagens: a simple test system combining liver homogenates for activation and bacteria for detection" Proceedings of the National Academy of Sciences, 1973;70(8):2281-2285.
Andugulapati et al. "Biochanin-A ameliorates pulmonary fibrosis by suppressing the TGF-β mediated EMT, myofibroblasts differentiation and collagen deposition in in vitro and in vivo systems," Phytomedicine, 2020;78:153298; 16 pages.
Aoki et al., "The Immunosuppressant Fingolimod (FTY720) for the Treatment of Mechanical Force-Induced Abnormal Scars," Journal of Immunology Research, 2020;2020:7057195, https://doi.org/10.1155/2020/7057195, 11 pages.
Assessment Report for Xeljanz (tofacitinib). Procedure No. EMEA/H/C/004214/0000, Committee for Medicinal Products for Human Use (CHMP), European Medicines Agency, Jan. 26, 2017; 158 pages.
Avena-Woods, "Overview of Atopic Dermatitis," Am J Manag Care, 2017;23:S115-S123.
Azuaga, A.B. et al. "Psoriatic Arthritis: Pathogenesis and Targeted Therapies," Int J Mol Sci, 2023;24:4901, https://doi.org/10.3390/ijms24054901; 23 pages.
Bae et al. "Slower Elimination of Tofacitinib in Acute Renal Failure Rat Models: Contribution of Hepatic Metabolism and Renal Excretion," Pharmaceutics. Jul. 30, 2020;12(8):714, doi: 10.3390/pharmaceutics12080714; 15 pages.
Bahmer, "ADASI Score: Atopic Dermatitis Area and Severity Index," Acta Derm Venereol (Stockh). 1992;176(Suppl.):32-33.
Balestri, R., "Alitretinoin and Darier disease: 'All that glitters is not gold'", J Am Acad Dermatol, vol. 72, No. 2, 2015, 363-364.
Bao et al., "The involvement of the JAK-STAT signaling pathway in chronic inflammatory skin disease atopic dermatitis," JAK-STAT, 2013;2(3):e24137, https://doi.org/10.4161/jkst.24137; 8 pages.
Baron, Bruce M., et al., "[3H] MDL 105,519, a high-affinity radioligand for the N-methyl-D-aspartate receptor-associated glycine recognition site" The Journal of pharmacology and experimental therapeutics, 1996;279(1):62-68.
Basra et al., "The Dermatology Life Quality Index 1994-2007: a comprehensive review of validation data and clinical results" British Journal of Dermatology, 2008;997-1035.
Batalla et al., "Cardiovascular risk factors influence response to biological therapies in psoriasis," J Am Acad Dermatol, 2015;73(2):327-329.
Bayart et al., "Topical Janus kinase inhibitors for the treatment of pediatric alopecia areata," J Am Acad Dermatol, 2017;77(1):167-170. doi: 10.1016/j.jaad.2017.03.024.
Berbert Ferreira et al., "Atopic dermatitis: Tofacitinib, an option for refractory disease," Clin Case Rep, 2020, 8:3243-3246.
Bignon, Eric, et al., "SR146131: a new potent, orally active, and selective nonpeptide cholecystokinin subtype 1 receptor agonist. I: in vitro studies" The Journal of Pharmacology and Experimental Therapeutics, 1999;289(2):742-751.
Bissonnette et al., "Topical tofacitinib for atopic dermatitis: a phase IIa randomized trial," British Journal of Dermatology, 2016, 175:902-911.
Bloom et al., "Private and public coverage policies for rituximab in the treatment of immunobullous disease in the United States," J Am Acad Dermatol, 2015;73(2):337-338.
Bloom et al., "Topical rapamycin combined with pulsed dye laser (PDL) in the treatment of capillary vascular malformations—Anatomical differences in respnose to PDL are relevant to interpretation of study results," J Am Acad Dermatol, 2015;72(1):e71, 1 page.
Blubaugh et al., "The anti-inflammatory effect of topical tofacitinib on immediate and late-phase cutaneous allergic reactions in dogs: a placebo-controlled pilot study," Vet Dermatol, 2018, 29:250-e93.
Blumetti et al., "Optical coherence tomography (OCT) features of nevi and melanomas and their association with intraepidermal or dermal involvement: A pilot study," J Am Acad Dermatol, 2015;73(2):315-317.
Boehm, Marcus F., et al., "Synthesis of high specific activity tritium-labeled [3H]-9-cis-retinoic acid and its application for identifying retinoids with unusual binding properties" Journal of medicinal chemistry, 1994; 137(3):408-414.
Boniface et al. Vitiligo: Focus on Clinical Aspects, Immunopathogenesis, and Therapy. Clin Rev Allergy Immunol. Feb. 2018;54(1):52-67. doi: 10.1007/s12016-017-8622-7.

(56) References Cited

OTHER PUBLICATIONS

Boukhedouni, Nesrine "Mécanismes immunologiques impliqués dans la perte des melanocytes au cours du vitiligo" Diss. Université de Bordeaux, 2018; 247 pages, French with English abstract on p. 1.

Boukhedouni, Nesrine, et al., "Type-1 cytokines regulate MMP-9 production and E-cadherin disruption to promote melanocyte loss in vitiligo" JCI Insight, 2020:5(11):e133772, 17 pages.

Boyd, "Reality in short-term international dermatology missions," J Am Acad Dermatol., 2015;72(2):369, 1 page.

Braun, S. A., "Laser-assisted drug delivery: Enhanced response to ingenol mebutate afer ablative fractional laser treatment," J Am Acad Dermatol., 2015;72(2):364-365.

Bridges et al., "Comments on the safety assessment of decamethylcyclopentasiloxane (D5) published in regulatory toxicology and pharmacology, 2017, 83:117-118," Regulatory Toxicology and Pharmacology, 89:305-306 (2017).

Brinks, A. et al., "Adverse effects of extra-articular corticosteroid injections: a systematic review", BMC Musculoskelet Disord. Sep. 13, 2010;11:206. doi: 10.1186/1471-2474-11-206, 11 pages.

Bronsick et al., "Diet in dermatology. Part I. Atopic dermatitis, acne, and nonmelanoma skin cancer," J Am Acad Dermatol. 2014;71:1039e1-1039e12, with Correction, Aug. 2015;72(2):353.

Brown, George B. "3H-batrachotoxinin-A benzoate binding to voltage-sensitive sodium channels: inhibition by the channel blockers tetrodotoxin and saxitoxin" Journal of Neuroscience, 1986;6(7):2064-2070.

Bryant, Henry U., et al., "A novel class of 5-HT2A receptor antagonists: aryl aminoguanidines" Life sciences, 1996;59(15):1259-1268.

Buchan, Kevin W., et al., "Characterization of three non-peptide endothelin receptor ligands using human cloned ETA and ETB receptors" British journal of pharmacology, 1994;112(4):1251-1257.

Buchanan, Kate, et al., "Guidelines for the treatment of animals in behavioural research and teaching" ASAB Ethical Committee, Animal Behaviour, 2012;83:301-309.

Buhse et al., "Topical drug classification," International Journal of Pharmaceutics, 295:101-112 (2005).

Burns-Naas et al., "Inhalation Toxicology of Decamethylcyclopentasiloxane (D5) Following a 3-Month Nose-Only Exposure in Fischer 344 Rats," Toxicological Sciences, 43:230-240 (1998).

Burns-Naas et al., "Toxicology and Humoral Immunity Assessment of Decamethylcyclopentasiloxane ($D_5$) Following a 1-Month Whole Body Inhalation Exposure in Fischer 344 Rats," Toxicological Sciences, 43:28-38 (1998).

Callis Duffin, K. et al. "A multi-item Physician Global Assessment scale to assess psoriasis disease severity: validation based on four phase III tofacitinib studies," BMC Dermatol, 2019;19:8, https://doi.org/10.1186/s12895-019-0088-2; 9 pages.

Cameron et al., "Review of drug-related causes of oculocutaneous disease," J Am Acad Dermatol, 2015;72(2):361-362.

Canavan et al., "Reply to: 'Diagnosing *Mycoplasma pneumoniae*-induced rash and mucositis (MIRM) in the emergency room,'" J Am Acad Dermatol, 2015;73(2):e69, 1 page.

Carter, Todd A., et al., "Inhibition of drug-resistant mutants of ABL, KIT, and EGF receptor kinases" Proceedings of the National Academy of Sciences, 2005;102(31):11011-11016.

Cesura, A. M., et al., "Characterization of the binding of [3H] Ro 41-1049 to the active site of human monoamine oxidase-A" Molecular pharmacology, 1990;37(3):358-366.

Chapin et al., "Effects of the Janus Kinase Inhibitor, Tofacitinib, on Testicular Leydig Cell Hyperplasia and Adenoma in Rats, and on Prolactin Signaling in Cultured Primary Rat Leydig Cells," Toxicology Sciences, 155(1):148-156, 2017.

Chasset et al., "Influence of smoking on the efficacy of antimalarials in cuataneous lupus: A meta-analysis of the literature," J Am Acad Dermatol., Apr. 2015;72(4):634-639. Corrections to Table I, Aug. 2015;73(2):353.

Chasset et al., "Smoking enhances Toll-like receptor-9 responsiveness and type I interferon production in plasmacytoid dendritic cells in patients with cutaneous lupus erythematosus," J Am Acad Dermatol, 2015;73(2):e81, 1 page.

Chen et al. Mechanisms of melanocyte death in vitiligo. Med Res Rev. Mar. 2021;41(2):1138-1166. doi: 10.1002/med.21754. Epub Nov. 17, 2020.

Chen, Shu Jen, et al., "Studies with synthetic peptide substrates derived from the neuronal protein neurogranin reveal structural determinants of potency and selectivity for protein kinase C" Biochemistry, 1993;32(4):1032-1039.

Chismar et al., "The dermatopathology requisition form: Attitudes and practices of dermatologists," J Am Acad Dermatol, 2015;72(2):353-355.

Choi, Doo-Sup, et al., "The human serotonin 5-HT2B receptor: pharmacological link between 5-HT2 and 5-HT1D receptors" FEBS letters, 1994;352(3):393-399.

Chu et al., "Benefit of different concentrations of intralesional triamcinolone acetonide in alopecia areata: An intrasubject pilot study," J Am Acad Dermatol, 2015;73(2):338-340.

Chun, J. & Hartung, H.-P., "Mechanism of Action of Oral Fingolimod (FTY720) In Multiple Sclerosis," Clin Neuropharmacol. 2010; 33(2):91-101. doi: 10.1097/WNF.0b013e3181cbf825. NIH Public Access Author Manuscript, available in PMC Mar. 1, 2011; 22 pages.

Chung et al., "Biopsies of the acral extremities: Assessing specimen (in)adequacy based on anatomic site," J Am Acad Dermatol, 2015;73(2):313-315.

Cinotti et al., "Sensitivity of handheld reflectance confocal microscopy for the diagnosis of basal cell carcinoma: A series of 344 histologically proven lesions," J Am Acad Dermatol, 2015;73(2):319-320.

Clark, A.F. et al., "Inhibition of dexamethasone-induced cytoskeletal changes in cultured human trabecular meshwork cells by tetrahydrocortisol" Investigative ophthalmology & visual science, 1996;37(5):805-813. Abstract, 1 page.

Clinical Trial, Australian New Zealand Clinical Trials Registry, "A study to evaluate the safety and tolerability of an investigational transdermal patch containing Fingolimod in healthy volunteers," Registration No. ACTRN12618002016213p, Dec. 17, 2018 [last update date] [online]. Retrieved from: https://www.anzctr.org.au/Trial/Registration/TrialReview.aspx?ID=376538, on Dec. 3, 2021; 4 pages.

Clinicaltrials.gov, " A Study to Assess the Safety and Efficacy of Etrasimod in Subjects With Moderate-to-Severe Atopic Dermatitis (ADVISE)", Bethesda (MD): National Library of Medicine (US), Identifier NCT04162769. Last Update Posted: Sep. 16, 2021. Available from: https://clinicaltrials.gov/study/NCT04162769; 7 pages.

ClinicalTrials.gov, "A Dose-Finding Study of GSK2894512 Cream in Subjects With Atopic Dermatitis (AD)", Bethesda (MD): National Library of Medicine (US), Identifier NCT02564055. Last Update Posted: Nov. 20, 2017. Available from: https://clinicaltrials.gov/study/NCT02564055?a=16&tab=results; 66 pages.

Cohen et al., "Long-term safety of tofacitinib up to 9.5 years: a comprehensive integrated analysis of the rheumatoid arthritis clinical development programme," RMD Open, 2020; 6:e001395. doi:10.1136/rmdopen-2020-001395, 15 pages.

Collinge et al., "Immulogic effects of chronic administration of tofacitinib, a Janus kinase inhibitor, in cynomolgus monkeys and rats—Comparison of juvenile and adult responses," Regulatory Toxicology and Pharmacology, 94:306-322 (2018).

Comi et al., "Benefit-Risk Profile of Sphingosine-1-Phosphate Receptor Modulators in Relapsing and Secondary Progressive Multiple Sclerosis," Drugs, 77:1755-1768 (2017).

Constantinescu et al., "Experimental autoimmune encephalomyelitis (EAE) as a model for multiple sclerosis (MS)", Br J Pharmacol. Oct. 2011;164(4):1079-1106. doi: 10.1111/j.1476-5381.2011.01302.x.

Cope et al. Models of osteoarthritis: the good, the bad and the promising. Osteoarthritis Cartilage. Feb. 2019;27(2):230-239.

Crumb Jr, William J., et al., "An evaluation of 30 clinical drugs against the comprehensive in vitro proarrhythmia assay (CiPA)

(56) References Cited

OTHER PUBLICATIONS proposed ion channel panel" Journal of pharmacological and toxicological methods, 2016;81:251-262. doi: 10.1016/j.vascn.2016.03.009.

Curtis et al., "Analysis of non-melanoma skin cancer across the tofacitinib rheumatoid arthritis clinical programme," Clinical and Experimental Rheumatology, 35:614-622 (2017).

Czeloth et al., "Sphingosine-1-Phosphate Mediates Migration of Mature Dendritic Cells," J Immunol, 2005;175:2960-2967.

David et al., "Clinical Pharmacokinetics of Fingolimod," Clin Pharmacokinet, 51(1):15-28 (2012).

Davies, Brian et al., "Physiological parameters in laboratory animals and humans" Pharmaceutical research, 1993; 10(7):1093-1095.

Dekant, W. & Klaunig, J.E., "Toxicology of decamethylcyclopentasiloxane (D5)," Regulatory Toxicology and Pharmacology, 74:S67-S76 (2016).

Delmas, Véronique et al., "Molecular and cellular basis of depigmentation in vitiligo patients" Experimental dermatology, 2019;28(6):662-666.

Devedjian, Jean-Christophe, et al., "Further characterization of human α2-adrenoceptor subtypes: [3H] RX821002 binding and definition of additional selective drugs" European journal of pharmacology, 1994;252(1):43-49.

Dogra et al., "Long-term efficacy and safety of itolizumab in patients with moderate-to-severe chronic plaque psoriasis: A double-blind, randomized-withdrawal, placebo-controlled study," J Am Acad Dermatol., 2015;73(2):331-333.e1. doi: 10.1016/j.jaad.2015.03.040.

Dörje, F., et al., "Antagonist binding profiles of five cloned human muscarinic receptor subtypes" The Journal of pharmacology and experimental therapeutics, 1991;256(2):727-733.

Downes et al., "Oral pharmacokinetic and pharmacodynamic effects of FTY720 in cats," J. Vet Pharmacol. Therap., 30:55-61 (2007).

Dzubow, L., "Wound edge eversion: Tradition or science?" J Am Acad Dermatol, 2015;73(2):e63, 1 page.

Eichenfield et al., "Guidelines of Care for the Management of Atopic Dermatitis: Part 1: Diagnostic and Assessment of Atopic Dermatitis," J Am Acad Dermatol, 2014;70(2):338-351. doi:10.1016/j.jaad.2013.10.010. HHS Public Access Author Manuscript, available in PMC Apr. 27, 2015; 29 pages.

Ellman, George L., et al., "A new and rapid colorimetric determination of acetylcholinesterase activity" Biochemical pharmacology, 1961;7(2):88-95.

European Parliament and the Council of the European Union, "Directive 2010/63/EU of The European Parliament and of the Council of Sep. 22, 2010, on the protection of animals used for scientific purposes." Official Journal of the European Union, Oct. 20, 2010; L 276; pp. 33-79.

European Union Scientific Committee on Consumer Safety (SCCS), "Opinion on decamethylcyclopentasiloxane (cyclopentasiloxane, D5) in cosmetic products", Adopted at 9th Plenary Meeting, Mar. 25, 2015, https://health.ec.europa.eu/index_en, 78 pages.

Fabian, Miles A., et al., "A small molecule-kinase interaction map for clinical kinase inhibitors" Nature biotechnology, 2005;23(3):329-336.

Feldman and Krueger, "Psoriasis assessment tools in clinical trials," Ann Rheum Dis, 2005;64(Suppl II):ii65-ii68.

Fernandes, T., et al., "Characterization of angiotensin-converting enzymes 1 and 2 in the soleus and plantaris muscles of rats" Brazilian Journal of Medical and Biological Research, 2010;43:837-842.

Fernández-Crehuet et al., "Trichoscopic features of frontal fibrosing alopecia: Results in 249 patients," J Am Acad Dermatol, 2015;72(2):357-359.

Ferry, Gilles, et al., "Binding of prostaglandins to human PPARγ: tool assessment and new natural ligands" European journal of pharmacology, 2001;417(1-2):77-89.

Finlay and Khan, "Dermatology Life Quality Index (DLQI)—a simple practical measure for routine clinical use," Clinical and Experimental Dermatology, 1994;19:210-216.

Fiske, Cyrus H., and Yellapragada Subbarow. "The colorimetric determination of phosphorus" J. Biol. Chem, 1925;66(2):375-400.

Fitzpatrick et al., "The Validity and Practicality of Sun-Reactive Skin Types I Through VI," Arch Dermatol., Jun. 1988;124:869-871.

Foley et al., "Efficacy of Guselkumab Compared With Adalimumab and Placebo for Psoriasis in Specific Body Regions A Secondary Analysis of 2 Randomized Clinical Trials," JAMA Dermatol, 2018;154(6):676-689.

Ford, Anthony PDW, et al., "Pharmacological pleiotropism of the human recombinant α1A-adrenoceptor: implications for α1-adrenoceptor classification" British journal of pharmacology, 1997;121(6):1127-1135.

Fowler, E. & Yosipovitch, G., "A New Generation of Treatments for Itch," Acta Derm Venereol, 2020; 100:adv00027. doi:10.2340/00015555-3347, 9 pages.

Franzen et al., "A global human health risk assessment for Decamethylcyclopentasiloxane ($D_5$)," Regulatory Toxicology and Pharmacology, 74:S25-S43 (2016).

Fredriksson and Pettersson "Severe Psoriasis—Oral Therapy with a New Retinoid," Dermatologica, 1978;157:238-244.

Frisoli et al. Vitiligo: Mechanisms of Pathogenesis and Treatment. Annu Rev Immunol. Apr. 26, 2020;38:621-648. doi: 10.1146/annurev-immunol-100919-023531. Epub Feb. 4, 2020.

Fukunaga, Kouichi, et al., "Single nucleotide polymorphism of human platelet-activating factor receptor impairs G-protein activation" Journal of Biological Chemistry, 2001;276(46):43025-43030.

Garrett et al."Induction of a Th17 phenotype in human skin a mimic of dermal inflammatory diseases," Methods and Protocols, 2019;2:45, 14 pages.

Gatehouse, David. "Bacterial mutagenicity assays: test methods" Genetic Toxicology: Principles and Methods, (2012);817:21-34.

Giambrone et al., "The diagnostic accuracy of in vivo confocal microscopy in clinical practice," J Am Acad Dermatol, 2015;73(2):317-319.

Gilbert et al., "Efficacy and safety of etanercept and adalimumab with and without a loading dose for psoriasis: A systematic review," J Am Acad Dermatol., 2015;73(2):329-331.

Gopalakrishnan, Murali, et al., "Stable expression, pharmacologic properties and regulation of the human neuronal nicotinic acetylcholine alpha 4 beta 2 receptor" The Journal of pharmacology and experimental therapeutics, 1996;276(1):289-297.

Gordon et al., "Efficacy and safety of risankizumab in moderate-to-severe plaque psoriasis (UltIMMa-1 and UltIMMa-2): results from two double-blind, randomised, placebo-controlled and ustekinumab-controlled phase 3 trials," Lancet, 2018;392:650-661.

Gottlieb et al., "NMR chemical shifts of common laboratory solvents as trace impurities," J. Org. Chem, 1997;62:7512-7515.

Gould, Robert J., et al., "[3H] nitrendipine-labeled calcium channels discriminate inorganic calcium agonists and antagonists" Proceedings of the National Academy of Sciences, 1982;79(11):3656-3660.

Grandy, David K., et al., "Cloning of the cDNA and gene for a human D2 dopamine receptor" Proceedings of the National Academy of Sciences, 1989;86(24):9762-9766.

Green, Andrew, et al., "Characterization of [3H]-CGP54626A binding to heterodimeric GABAB receptors stably expressed in mammalian cells" British journal of pharmacology, 2000;131(8): 1766-1774.

Guo et al. "Factors affecting wound healing," J Dent Res. Mar. 2010;89(3):219-29. doi: 10.1177/0022034509359125. Epub Feb. 5, 2010.

Gupta et al., "Lack of effect of tofacitinib (CP-690,550) on the pharmacokinetics of the CYP3A4 substrate midazolam in healthy volunteers: confirmation of in vitro data," Br J Clin Pharmacol, 74(1):109-115 (2012).

Hall, David A., and Philip G. Strange. "Evidence that antipsychotic drugs are inverse agonists at D2 dopamine receptors" British journal of pharmacology, 1997;121(4):731-736.

Hamel, Annie, Marise Roy, and Ray Proudlock. "The bacterial reverse mutation test" Genetic Toxicology Testing. Academic Press, 2016;79-138.

(56) References Cited

OTHER PUBLICATIONS

Hanifin et al., "The eczema area and severity index (EASI): assessment of reliability in atopic dermatitis," Exp Dermatol, 10:11-18 (2001).

Hanifin, J. M. & Rajka, G., "Diagnostic Features of Atopic Dermatitis," Acta Dermatovener (Stockholm), Suppl. 92: 44-47, 1980.

Heuillet, E., et al., "Characterization of a human NK1 tachykinin receptor in the astrocytoma cell line U 373 MG" Journal of neurochemistry, 1993;60(3):868-876.

Higgins, H.W. II et al. "Melanoma in situ. Part I. Epidemiology, screening, and clinical features", J Am Acad Dermatol. Aug. 2015;73(2):181-192. doi: 10.1016/j.jaad.2015.04.014.

Ho et al., "Color bar tool for skin type self-identification: A cross-sectional study," J Am Acad Dermatol, Aug. 2015;73(2):312-313.e1.

Hodge et al., "The mechanism of action of tofacitinib—an oral Janus kinase inhibitor for the treatment of rheumatoid arthritis," Clin Exp Rheumatol, 34:318-328 (2016).

Hongbo et al., "Translating the Science of Quality of Life into Practice: What Do Dermatology Life Quality Index Scores Mean?" J Invest Dermatol, 2005;125:659-664.

Hope, Anthony G., et al., "Characterization of a human 5-hydroxytryptamine3 receptor type A (h5-HT3R-AS) subunit stably expressed in HEK 293 cells" British journal of pharmacology, 1996;118(5):1237-1245.

Hoppe et al., "Low-dose total skin electron beam therapy as an effective modality to reduce disease burden in patients with mycosis fungoides: Results of a pooled analysis from 3 phase-II clinical trials," J Am Acad Dermatol, 2015;72:286-292.

Hosking et al., "Topical Janus kinase inhibitors: A review of applications in dermatology," J Am Acad Dermatol, 2018, 79(3):535-544. doi: 10.1016/j.jaad.2018.04.018. Epub Apr. 16, 2018.

Huang, Xi-Ping, et al., "Identification of human Ether-à-go-go related gene modulators by three screening platforms in an academic drug-discovery setting" Assay and drug development technologies, 2010;8(6):727-742.

Hutmacher et al., "Exposure-response modeling using latent variables for the efficacy of a JAK3 inhibitor administered to rheumatoid arthritis," J Pharmacokinetic Pharmacodyn, 35:139-157 (2008).

Incyte Corporation, "Opzelura—ruxolitinib cream," Highlights of Prescribing Information. Initial US Approval 2011, Revised Jul. 2022; 32 pages.

Incyte Corporation, "Incyte Reports 2023 Third Quarter Financial Results and Provides Updates on Key Clinical Programs" Oct. 31, 2023 [online]. Retrieved from: https://investor.incyte.com/node/23411/pdf; 10 pages.

Irvine, A. D. & McLean, W.H.I., "Breaking the (Un)Sound Barrier: Filaggrin Is a Major Gene for Atopic Dermatitis," Journal of Investigative Dermatology, 126:1200-1202 (2006). doi: 10.1038/sj.jid.5700365.

Isquith et al., "Genotoxicity Studies on Selected Organosilicon Compounds: In Vivo Assays," Fd Chem. Toxic., 1988;26(3):263-266.

IUPAC Compendium of Chemical Terminology, Definition of amino acid residue. IUPAC Gold Book, 2nd edition, 1997; doi:10.1351/goldbook.A00279, 1 page.

Japtok et al., "Sphingosine-1-phosphate as signaling molecule in the skin—Relevance in atopic dermatitis," Allergo J Int, 23:54-59, 2014.

Jean et al., "Chronic toxicity and oncogenicity of decamethylcyclopentasiloxane in the Fischer 344 Rat," Regulatory Toxicology and Pharmacology, 74:S57-S66 (2016).

Joseph, Shirin S., et al., "Binding of (−)-[3 H]-CGP12177 at two sites in recombinant human β 1-adrenoceptors and interaction with β-blockers" Naunyn-Schmiedeberg's archives of pharmacology, 2004;369:525-532.

Juneja et al. "Anatomy, joints," StatPearls Publishing; 2022 [online]. Retrieved from: https://www.ncbi.nlm.nih.gov/books/NBK507893/; 8 pages.

Karaman, Mazen W., et al., "A quantitative analysis of kinase inhibitor selectivity" Nature biotechnology, 2008;26(1):127-132.

Kawakami et al., "Mast cells in atopic dermatitis," Curr Opin Immunol., 21(6):666-678 (2009). doi:10.1016/j.coi.2009.09.006. NIH Public Access Author Manuscript, available in PMC Dec. 1, 2010; 20 pages.

Kawakami, T. & Hashimoto, T., "Disease Severity Indexes and Treatment Evaluation Criteria in Vitiligo," Dermatol Res Pract, 2011:750342, 2011, 3 pages.

Kenny, B. A., et al., "Characterization of an α1D-adrenoceptor mediating the contractile response of rat aorta to noradrenaline" British Journal of Pharmacology, 1995;115(6):981-986.

Kim et al., "Correlation between histopathologic findings of psoriasis determined using quantitative computer-aided analysis and elements of the Psoriasis Area and Severity Index," J Am Acad Dermatol, 2015;73(2):325-326.

Kimball et al., "Psychometric properties of the Itch Numeric Rating Scale in patients with moderate-to-severe plaque psoriasis," British Journal of Dermatology, 2016;175:157-162.

Klaunig et al., "Biological relevance of decamethylcyclopentasiloxane (D5) induced rat uterine endometrial adenocarcinoma tumorigenesis: Mode of action and relevance to humans," Regulatory Toxicology and Pharmacology, 74:S44-S56 (2016).

Kostovic et al., "Tofacitinib, an Oral Janus Kinase Inhibitor: Perspectives in Dermatology," Current Medicinal Chemistry, 24:1158-1167 (2017).

Kreuter, A., "Anal cancer screening," J Am Acad Dermatol, 2015;72(2):367-368.

Kubelis-López et al., "Updates and new medical treatments for vitiligo (Review)," Experimental and Therapeutic Medicine, 22:797 (2021), 11 pages.

Kumar et al., "Development and validation of a RP-HPLC method for the quantitation of tofacitinib in rat plasma and its application to a pharmacokinetic study," Biomed. Chromatogr., 29:1325-1329 (2015).

Kwatra, S.G., "Toll-like receptor-9 signaling and decreased efficacy of antimalarial drugs in smokers with cutaneous lupus erythematosus," J Am Acad Dermatol, 73(2):e79 (2015).

Langin, Dominique, et al., "[3H] RX821002: a new tool for the identification of α2A-adrenoceptors" European journal of pharmacology, 1989;167(1):95-104.

Langley et al., "The 5-point Investigator's Global Assessment (IGA) Scale: A modified tool for evaluating plaque psoriasis severity in clinical trials," Journal of Dermatological Treatment, 2015;26(1):23-31, DOI: 10.3109/09546634.2013.865009.

Lattouf et al., "Treatment of alopecia areata with simvastatin/ezetimibe," J Am Acad Dermatol, 72(2):359-361 (2015).

Le, Minh Tam, et al., "Ligand binding and functional properties of human angiotensin AT1 receptors in transiently and stably expressed CHO-K1 cells" European journal of pharmacology, 2005;513(1-2):35-45.

Lee et al., "Efficacy of the long-pulsed 1064-nm neodymium:yttrium-aluminum-garner laser (LPND) (rejuvination mode) in the treatment of papulopustular rosacea (PPR): A pilot study of clinical outcomes and patient satisfaction in 30 cases," J Am Acad Dermatol, 2015;73(2):333-336.

Lee, Y. M., et al., "The human brain cholecystokinin-B/gastrin receptor. Cloning and characterization" Journal of Biological Chemistry, 1993;268(11): 8164-8169.

Leung et al., "Deciphering the Complexities of Atopic Dermatitis: Shifting Paradigms in Treatment Approaches," J Allergy Clin Immunol., 134(4):769-779 (2014). doi: 10.1016/j.jaci.2014.08.008. NIH Public Access Author Manuscript, available in PMC Oct. 1, 2015; 27 pages.

Leurs, Rob, et al., "Pharmacological characterization of the human histamine H2 receptor stably expressed in Chinese hamster ovary cells" British journal of pharmacology, 1994; 112(3): 847-854.

Levenberg, Kenneth. "A method for the solution of certain non-linear problems in least squares" Quarterly of applied mathematics, 1944;2(2):164-168.

Levin et al., "Atopic Dermatitis and the Stratum Corneum. Part 1: The Role of Filaggrin in the Stratum Corneum Barrier and Atopic Skin," J Clin Aesthet Dermatol., 6(10):16-22 (2013).

(56) References Cited

OTHER PUBLICATIONS

Levin, Malin C., et al., "The myocardium-protective Gly-49 variant of the β1-adrenergic receptor exhibits constitutive activity and increased desensitization and down-regulation" Journal of Biological Chemistry, 2002;277(34):30429-30435.
Li et al., "Pharmacokinetics and Cell Trafficking Dynamics of 2-Amino-2-[2(4-octylphenyl)ethyl]propane-1,3-diol Hydrochloride (FTY720) in Cynomolgus Monkeys after Single Oral and Intravenous Doses," The Journal of Pharmacology and Experimental Therapeutics, 301:519-526 (2002).
Lignet, Floriane, et al., "Characterization of pharmacokinetics in the göttingen minipig with reference human drugs: an in vitro and in vivo approach" Pharmaceutical research, 2016;33:2565-2579.
Lin et al., "HEXIM1 as a Robust Pharmacodynamic Marker for Monitoring Target Engagement of BET Family Bromodomain Inhibitors in Tumors and Surrogate Tissues," Mol Cancer Ther, Feb. 2017; 16(2):388-396.
Liszewski et al., "Response to: 'Anal cancer screening,'" J Am Acad Dermatol, 72(2):368 (2015).
Long et al., "The Rule of Hand: 4 Hand Areas-2 FTU-1 g," Arch Dermatol, vol. 128, pp. 1129-1130, 1992.
Longo et al., "Ex vivo fluorescence confocal microscopy in conjunction with Mohs micrographic surgery for cutaneous squamous cell carcinoma," J Am Acad Dermatol, 2015;73(2):321-322.
Lu et al., "A Review of Safety-Related Pregnancy Data Surrounding the Oral Disease-Modifying Drugs for Multiple Sclerosis," CNS Drugs, 28:89-94 (2014).
Lukas, Ronald J. "Characterization of curaremimetic neurotoxin binding sites on membrane fractions derived from the human medulloblastoma clonal line, TE671" Journal of neurochemistry, 1986;46(6):1936-1941.
Luthin, David R., et al., "Characterization of two affinity states of adenosine A2a receptors with a new radioligand, 2-[2-(4-amino-3-[125I] iodophenyl) ethylamino] adenosine" Molecular pharmacology, 1995;47(2):307-313.
Maier, Donna L., et al., "[N-methyl-3H3] AZ10419369 binding to the 5-HT1B receptor: in vitro characterization and in vivo receptor occupancy" The Journal of pharmacology and experimental therapeutics, 2009;330(1):342-351.
Maley, A., "Is a properative tumor diameter of 6 mm or less reliable in excluding a diagnosis of melanoma?" J Am Acad Dermatol., 2015; 73(2): e75, 1 page.
Maley, A., "The ABCDs of melanoma—A complicated morphologic message not intended for the general public," J Am Acad Dermatol, 73(2):e59 (2015), 1 page.
Marks et al. "Assessment of disease progress in psoriasis," Arch Dermatol. Feb. 1989;125(2):235-40.
Marqués et al., "Reply to: 'Topical rapamycin combined with pulsed dye laser (PDL) in the treatment of capillary vascular malformations—Anatomical differences in response to PDL are relevant to interpretation of study results," J Am Acad Dermatol, 73(2):e73-e74 (2015).
Martin et al., "Molecular cloning and functional characterization of murine cysteinyl-leukotriene 1 (CysLT(1)) receptors." Biochem Pharmacol. Nov. 1, 2001;62(9): 1193-200. doi: 10.1016/s0006-2952(01)00774-2.
Marvizón et al., "The glycine receptor: pharmacological studies and mathematical modeling of the allosteric interaction between the glycine- and strychnine-binding sites." Mol Pharmacol. Dec. 1986; 30(6): 590-7.
Mashiko et al., "Human mast cells are major IL-22 producers in patients with psoriasis and atopic dermatitis," J Allergy Clin Immunol, 136:351-9 (2015), and 359e1.
Maurice et al., "Advances in targeting cyclic nucleotide phosphodiesterases." Nat Rev Drug Discov. Apr. 2014; 13(4): 290-314. doi: 10.1038/nrd4228.
Mayer et al., "Reply to: 'Review of drug-related causes of oculocutaneous disease,'" J Am Acad Dermatol, 72(2):362-363 (2015).
McAleer, M. A. & Irvine, A. D., "The multifunctional role of filaggrin in allergic skin disease," J Allergy Clin Immunol, 131:280-291 (2013).

Mesinkovska et al., "The use of oral pioglitazone in the treatment of lichen planopilaris," J Am Acad Dermatol, 72(2):355-356 (2015).
Micali et al., "Reply to: 'Laser assisted drug delivery: Enhanced response to ingenol mebutate after ablative fractional laser treatment,'" J Am Acad Dermatol, 72(2):365-366 (2015).
Monaghan et al., "The distribution of [3H]kainic acid binding sites in rat CNS as determined by autoradiography." Brain Res. Dec. 2, 1982; 252(1): 91-100. doi: 10.1016/0006-8993(82)90981-7.
Moretti et al., "Focus on vitiligo: a generalized skin disorder," Eur J Inflamm., 2006; 4(1): 21-30.
Mori, T. et al., "IL-18 and TNFα-initiated IL-6-STAT3 pathway is critical in mediating inflammatory cytokines and RANKL expression in inflammatory arthritis", International Immunology, 2011;23(11):701-712.
Mortelmans et al., "The Ames Salmonella/microsome mutagenicity assay." Mutat Res. Nov. 20, 2000; 455(1-2): 29-60. doi: 10.1016/s0027-5107(00)00064-6.
Moyakine et al., "Propranolol treatment of infantile hemangiomas does not negatively effect psychomotor development," J Am Acad Dermatol, 73(2):341-342 (2015).
Mulheron et al., "Human 5-HT1A receptor expressed in insect cells activates endogenous G(o)-like G protein(s)." J Biol Chem. Apr. 29, 1994; 269(17): 12954-62.
Munro et al., Molecular characterization of a peripheral receptor for cannabinoids. Nature 365:61-65 (1993). https://doi.org/10.1038/365061a0.
Murase, J. E., "Current problems in dermatology, vol. 45: Human papillomavirus, bench to bedside," J Am Acad Dermatol, Feb. 2015;72(2):e67, 1 page.
Murphy et al., "Characterization of quisqualate recognition sites in rat brain tissue using DL-[3H]alpha-amino-3-hydroxy-5-methylisoxazole-4-propionic acid (AMPA) and a filtration assay." Neurochem Res. Sep. 1987; 12(9): 775-81. doi: 10.1007/BF00971514.
Murzaku et al. "Diet in dermatology. Part II. Melanoma, chronic urticaria, and psoriasis," J Am Acad Dermatol. 2014;71:1053-1068.
Mutel et al., "Characterization of [(3)H]Quisqualate binding to recombinant rat metabotropic glutamate 1a and 5a receptors and to rat and human brain sections." J Neurochem. Dec. 2000; 75(6): 2590-601. doi: 10.1046/j.1471-4159.2000.0752590.x.
Nakagawa et al., "Efficacy and safety of topical JTE-052, a Januse kinase inhibitor, in Japanese adult patients with moderate-to-severe atopic dermatitis: a phase II, multicentre, randomized, vehicle-controlled clinical study," British Journal of Dermatology, 178:424-432 (2018).
Nakagawa et al., "Phase 1 studies to assess the safety, tolerability and pharmacokinetics of JTE-052 (a novel Janus kinase inhibitor) ointment in Japanese healthy volunteers and patients with atopic dermatitis," Journal of Dermatology, 45:701-709 (2018).
Nakajima et al., "Mapping the extended substrate binding site of cathepsin G and human leukocyte elastase. Studies with peptide substrates related to the alpha 1-protease inhibitor reactive site." J Biol Chem. May 25, 1979; 254(10): 4027-32.
Nandakumar et al. "Collagen antibody induced arthritis" Methods Mol Med. 2007;136:215-23.
Neote et al., "Molecular cloning, functional expression, and signaling characteristics of a C-C chemokine receptor." Cell. Feb. 12, 1993; 72(3): 415-25. doi: 10.1016/0092-8674(93)90118-a.
Nicolescu et al., "Psoriasis Management Challenges Regarding Difficult-to-Treat Areas: Therapeutic Decision and Effectiveness," Life, 2022;12:2050, https://doi.org/10.3390/life12122050/, 15 pages.
Nirogi et al., "Incurred sample reanalysis of fingolimod and fingolimod phosphate in blood: stability evaluation and application to a rat pharmacokinetic study," Bioanalysis, 9(7):565-577 (2017).
Norton, "Diagnosing Mycoplasma pneumoniae-induced rash and mucositis (MIRM) in the emergency room," J Am Acad Dermatol, Aug. 2015; 73(2): e67, 1 page.
Nugent et al., "Associations of Pain Numeric Rating Scale Scores Collected during Usual Care with Research Administered Patient Reported Pain Outcomes," Pain Medicine, 2021;22(10):2235-2241.
Obourn et al. "Hormone- and DNA-binding mechanisms of the recombinant human estrogen receptor." Biochemistry. Jun. 22, 1993; 32(24): 6229-36. doi: 10.1021/bi00075a016.

(56) References Cited

OTHER PUBLICATIONS

OECD Test Guideline 432: "OECD Guideline for testing of chemicals: In vitro 3T3 NRU phototoxicity test." OECD (Organisation for Economic Co-operation and Development), Jun. 18, 2019, 20 pages.
Olfert, Ernest D., Brenda M. Cross, and A. Ann McWilliam, eds. Guide to the care and use of experimental animals. vol. 1. $2^{nd}$ Ed. Ottawa: Canadian Council on Animal Care, 1993; revised Feb. 2017; 214 pages [online]. Retrieved from: https://ccac.ca/Documents/Standards/Guidelines/Guide_to_the_Care_and_Use_of_Experimental_Animals_Vol1.pdf.
Pacholczyk et al., "Expression cloning of a cocaine- and antidepressant-sensitive human noradrenaline transporter." Nature. Mar. 28, 1991; 350(6316): 350-4. doi: 10.1038/350350a0.
Paragliola et al. Treatment with Synthetic Glucocorticoids and the Hypothalamus-Pituitary-Adrenal Axis. Int J Mol Sci. Oct. 20, 2017;18(10):2201. doi: 10.3390/ijms18102201; 17 pages.
Park et al., "Homogeneous proximity tyrosine kinase assays: scintillation proximity assay versus homogeneous time-resolved fluorescence." Anal Biochem. Apr. 10, 1999; 269(1): 94-104. doi: 10.1006/abio.1999.4029.
Passeron, T., "Medical and Maintenance Treatments for Vitiligo," Dermatol Clin, 35:163-170 (2017).
Pattaraporn et al., "Inhibition of heme peroxidases by melamine." Enzyme Res. 2012: 2012: 416062. doi: 10.1155/2012/416062. Epub Jul. 18, 2012, 7 pages.
Peralta et al., "Distinct primary structures, ligand-binding properties and tissue-specific expression of four human muscarinic acetylcholine receptors." EMBO J. Dec. 20, 1987; 6(13): 3923-9. doi: 10.1002/j.1460-2075.1987.tb02733.x.
Picardo et al., "Vitiligo." Nat Rev Dis Primers. Jun. 4, 2015: 1: 15011. doi: 10.1038/nrdp.2015.11, 16 pages.
Pristupa et al., "Pharmacological heterogeneity of the cloned and native human dopamine transporter: disassociation of [3H]WIN 35,428 and [3H]GBR 12,935 binding." Mol Pharmacol. Jan. 1994; 45(1): 125-35.
Pruneau et al., "LF 16.0335, a novel potent and selective nonpeptide antagonist of the human bradykinin B2 receptor." Br J Pharmacol. Sep. 1998; 125(2): 365-72. doi: 10.1038/sj.bjp.0702083.
Puar et al., "New treatments in atopic dermatitis," Ann Allergy Asthma Immunol, 126:21-31 (2021).
Purohit et al., "Systemic Tofacitinib Concentrations in Adult Patients With Atopic Dermatitis Treated With 2% Tofacitinib Ointment and Application to Pediatric Study Planning," The Journal of Clinical Pharmacology, 59(6):811-820 (2018).
Rashidghamat et al., "Pityriasis rubra pilaris with histologic features of lichen nitidus," J Am Acad Dermatol, 73(2):336-337 (2015).
Reddy et al., "Modeling of Human Dermal Absorption of Octamethylcyclotetrasiloxane ($D_4$) and Decamethylcyclopentasiloxane ($D_5$)," Toxicological Sciences, 99(2):422-431 (2007). doi: 10.1093/toxics/kfm174.
Reines et al., "Topical Application of Sphingosine-1-Phosphate and FTY720 Attenuate Allergic Contact Dermatitis Reaction through Inhibition of Dendritic Cell Migration," Journal of Investigate Dermatology, 129:1954-1962 (2009). doi:10.1038/jid.2008.454.
Rerknimitr et al., "The etiopathogenesis of atopic dermatitis: barrier disruption, immunological derangement, and pruritus," Inflammation and Regeneration, 2017; 37:14, doi: 10.1186/s41232-017-0044-7, 15 pages.
Reynolds et al., "(−)-[3H] desmethoxyverapamil labels multiple calcium channel modulator receptors in brain and skeletal muscle membranes: differentiation by temperature and dihydropyridines." J Pharmacol Exp Ther. Jun. 1986; 237(3): 731-8.
Richards, J.H., "Solubility and dissolution rate," Chapter 1 in Pharmaceutics: The Science of Dosage Form Design, 1st ed. Aulton, M.E. (Ed.) Churchill Livingstone, 1988; pp. 62-80.
Rinaldi-Carmona et al., "Characterization of two cloned human CB1 cannabinoid receptor isoforms." J Pharmacol Exp Ther. Aug. 1996; 278(2): 871-8.

Robinson et al., "A strategy for skin irritation testing." Am J Contact Dermat. Mar. 2002; 13(1): 21-9. doi: 10.1053/ajcd.2002.30471.
Saluja et al., "Role of Sphingosine-1-Phosphate in Mast Cell Functions and Asthma and Its Regulation by Non-Coding RNA," Front Immunol., May 2017;8:587, doi:10.3389/fimmu.2017.00587, 6 pages.
Sarup et al., "Resolution of high and low affinity progesterone receptors from human breast carcinoma T47D cells." J Biol Chem. Apr. 25, 1988; 263(12): 5624-33.
Schioth et al., "Characterization of the binding of MSH-B, HB-228, GHRP-6 and 153N-6 to the human melanocortin receptor subtypes." Neuropeptides. Dec. 1997; 31(6): 565-71. doi: 10.1016/s0143-4179(97)90002-0.
Schoemaker et al., "[3H]diltiazem binding to calcium channel antagonists recognition sites in rat cerebral cortex." Eur J Pharmacol. May 8, 1985; 111(2): 273-7. doi: 10.1016/0014-2999(85)90768-x.
Schwartz et al., "Inhibition of the GABA receptor-gated chloride ion channel in brain by noncompetitive inhibitors of the nicotinic receptor-gated cation channel." J Pharmacol Exp Ther. Mar. 1988; 244(3): 963-70.
Schwinn et al., "Molecular cloning and expression of the cDNA for a novel alpha 1-adrenergic receptor subtype." J Biol Chem. May 15, 1990; 265(14): 8183-9.
Seneschal et al., "An update on Vitiligo pathogenesis," Pigment Cell Melanoma Res. Mar. 2021;34(2):236-243. doi: 10.1111/pcmr.12949. Epub Dec. 15, 2020.
Serpero et al., "Fingolimod Modulates Peripheral Effector and Regulatory T Cells in MS Patients," J Neuroimmune Pharmacol, 8:1106-1113 (2013).
Shank et al., "Ion and temperature effects on the binding of gamma-aminobutyrate to its receptors and the high-affinity transport system." J Neurochem. Jun. 1990; 54(6): 2007-15. doi: 10.1111/j.1471-4159.1990.tb04905.x.
Sheth, V.M., A pilot study to determine vitiligo target size using a computer-based image analysis program. J Am Acad Dermatol, 2015;73(2):342-345.
Sica et al., "Fingolimod Immune Effects Beyond Its Sequestration Ability," Neurol Ther, 8:231-240 (2019).
Siddiqui et al., "A two-generation reproductive toxicity study of decamethylcyclopentasiloxane ($D_5$) in rats exposed by whole-body vapor inhalation," Reproductive Toxicology, 23:216-225 (2007).
Sideris et al., "Under Development JAK Inhibitors for Dermatologic Diseases," Mediterr J Rheumatol, 31(Suppl):137-44 (2020). https//:doi.org/10.31138/mjr.31.1.137.
Siedlikowski et al., "Treatment of Atopic Dermatitis Using JAK Inhibitors: A Systematic Review," EMJ Dermatol., 7(1):89-100 (2019).
Siegrist et al., "Radioreceptor assay for alpha-MSH using mouse B16 melanoma cells+." J Recept Res. 1988; 8(1-4): 323-43. doi: 10.3109/10799898809048996.
Siiskonen, H. & Harvima, I., "Mast Cells and Sensory Nerves Contribute to Neurogenic Inflammation and Pruritus in Chronic Skin Inflammation," Front. Cell. Neurosci., Sep. 2019;13:422, 11 pages. doi:10.3389/fncel.2019.00422.
Sills et al., "[3H]CGP 39653: a new N-methyl-D-aspartate antagonist radioligand with low nanomolar affinity in rat brain." Eur J Pharmacol. Jan. 3, 1991; 192(1): 19-24. doi: 10.1016/0014-2999(91)90063-v.
Silman and Pearson, "Supplement Review: Epidemiology and genetics of rheumatoid arthritis," Arthritis Res., 2002;4(suppl 3):S265-S272.
Simonin et al., "kappa-Opioid receptor in humans: cDNA and genomic cloning, chromosomal assignment, functional expression, pharmacology, and expression pattern in the central nervous system." Proc Natl Acad Sci USA. Jul. 18, 1995; 92(15): 7006-10. doi: 10.1073/pnas.92.15.7006.
Simonin et al., "The human delta-opioid receptor: genomic organization, cDNA cloning, functional expression, and distribution in human brain." Mol Pharmacol. Dec. 1994; 46(6): 1015-21.
Smit et al., "Regulation of the human histamine H1 receptor stably expressed in Chinese hamster ovary cells." Br J Pharmacol. Mar. 1996; 117(6): 1071-80. doi: 10.1111/j.1476-5381.1996.tb16699.x.

(56) References Cited

OTHER PUBLICATIONS

Smith et al., "Development of a Topical Treatment for Psoriasis Targeting RORγ: From Bench to Skin." PLoS One. Feb. 12, 2016; 11(2): e0147979. doi: 10.1371/journal.pone.0147979. eCollection 2016. 18 pages.

Smolen et al., "Rheumatoid arthritis," Nature Reviews Disease Primers, 2018;4:18001, doi:10.1038/nrdp.2018.1, Published online Feb. 8, 2018, 23 pages.

Solimani et al., "Emerging Topical and Systemic JAK Inhibitors in Dermatology," Front. Immunol., Dec. 3, 2019; 10:2847, 19 pages. doi: 10.3389/fimmu.2019.02847.

Soltani-Arabshahi, R., "Reply to: 'Is a preoperative tumor diameter of 6 mm or less reliable in excluding a diagnosis of melanoma?'" J Am Acad Dermatol, 73(2):e77, 2015, 1 page.

Sonthalia, S. & Aggarwal, P., "Oral tofacitinib: Contemporary appraisal of its role in dermatology," Indian Dermatol Online J, Sep.-Oct. 2019;10:503-518.

Sorensen et al., "Rat brain dendrotoxin receptors associated with voltage-gated potassium channels: dendrotoxin binding and receptor solubilization." Mol Pharmacol. Nov. 1989; 36(5): 689-98.

Speth et al., "Benzodiazepine receptors: temperature dependence of [3H]flunitrazepam binding." Life Sci. Jan. 22, 1979; 24(4): 351-7. doi: 10.1016/0024-3205(79)90331-x.

Stam et al., "Genomic organisation and functional expression of the gene encoding the human serotonin 5-HT2C receptor." Eur J Pharmacol. Nov. 15, 1994; 269(3): 339-48. doi: 10.1016/0922-4106(94)90042-6.

Stein, E.M. et al., "Results from phase 1 of the Manifest clinical trial to evaluate the safety and tolerability of pelabresib in patients with myeloid malignancies," Leukemia & Lymphoma, 2024;65(4):503-510, DOI: 10.1080/10428194.2023.2300710.

Stoff et al., "Expanding the reality of short-term international volunteerism in dermatology," J Am Acad Dermatol., 2015;72(2):369-370.

Subei, A. M. & Cohen, J. A., "Sphingosine 1-Phosphate Receptor Modulators in Multiple Sclerosis," CNS Drugs, 29(7):565-575 (2015). HHS Public Access Author Manuscript, available in PMC Jul. 1, 2016; 18 pages.

Sufficool et al., "T-cell clonality assessment by next-generation sequencing improves detection sensitivity in mycosis fungoides," J Am Acad Dermatol, 73(2):228-236.e2 (2015).

Sun et al., "Topical Application of Fingolimod Perturbs Cutaneous Inflammation," J Immunol, 196:3854-3864 (2016).

Tahara et al., "Pharmacological characterization of the human vasopressin receptor subtypes stably expressed in Chinese hamster ovary cells." Br J Pharmacol. Dec. 1998; 125(7): 1463-70. doi: 10.1038/sj.bjp.0702220.

Taieb et al., "The definition and assessment of vitiligo: a consensus report of the Vitiligo European Task Force," Pigment Cell Res., 20:27-35 (2007).

Tamakuwala, M. & Stagni, G., "Fingolimod Hydrochloride Gel for Dermatological Applications: Optimization of Formulation Strength and Effect of Colloidal Oatmeal (Aveeno®) as Penetration Enhancer," AAPS PharmSciTech, 17(4):907-914 (2016).

Tan et al. "Steroid Phobia: Is There a Basis? A Review of Topical Steroid Safety, Addiction and Withdrawal," Clin Drug Investig. Oct. 2021;41(10):835-842. doi: 10.1007/s40261-021-01072-z. Epub Aug. 18, 2021.

Tatsumi et al., "Pharmacological profile of neuroleptics at human monoamine transporters." Eur J Pharmacol. Mar. 5, 1999; 368(2-3): 277-83. doi: 10.1016/s0014-2999(99)00005-9.

Taylor, P.C., "Clinical Efficacy of launched JAK inhibitors in rheumatoid arthritis," Rheumatology, 58i117-i26 (2019).

Thaci et al., "Calcipotriol Solution for the Treatment of Scalp Psoriasis: Evaluation of Efficacy, Safety and Acceptance in 3,396 Patients", Dermatology, 2001;203:153-156.

Torres et al., "Update on Atomic Dermatitis," Acta Med Port, Sep. 2019;32(9):606-613.

Townsend-Nicholson and Schofield, "A threonine residue in the seventh transmembrane domain of the human A1 adenosine receptor mediates specific agonist binding." J Biol Chem. Jan. 28, 1994; 269(4): 2373-6.

Troncoso, P. & Kahan, B. D., "Preclinical Evaluation of a New Immunosuppressive Agent, FTY720," Clinical Biochemistry, 31(5):369-373 (1998).

Tsao et al., "Reply to: The ABCDs of melanoma-A complicated morphologic message not intended for the general public," J Am Acad Dermatol, 73(2):e61, 2015, 1 page.

Tsugeno et al., "Regions of the molecule responsible for substrate specificity of monoamine oxidase A and B: a chimeric enzyme analysis." J Biochem. Nov. 1995; 118(5): 974-80. doi: 10.1093/jb/118.5.974.

Tsuji et al., "Therapeutic approach to mite-induced intractable dermatitis using novel immunomodulator FTY720 ointment (fingolimod) in NC/Nga mice," Allergology International, 65:172-179 (2016).

Tsuji et al., "Therapeutic Approach to Steroid-Resistant Dermatitis Using Novel Immunomodulator FTY720 (Fingolimod) in Combination with Betamethasone Ointment in NC/Nga Mice," Biol. Pharm. Bull, 35(8):1314-1319 (2012).

U.S. Department of Health and Human Services, Food and Drug Administration, Center for Drug Evaluation and Research (CDER), Guidance for Industry, In Vitro Cytochrome P450 Enzyme- and Transporter-Mediated Drug Interactions, Jan. 2020. 46 pages.

Väkevä et al., "Allergen specific IgE responses are found in pre-Sézary syndrome patients and in erythrodermic atopic patients but no in true Sézary syndrome patients," J Am Acad Dermatol, vol. 72, No. 2, 2015, 352-353.

Van Leent et al., "Effectiveness of the Ascomycin Macrolactam SDZ ASM 981 in the Topical Treatment of Atopic Dermatitis," Arch Dermatol., 134:805-809 (1998).

Vaughan et al., "Effect of recent Ebola outbreaks on estimating the global burden of diseases with skin manifestations," J Am Acad Dermatol, 2015;72(2):366-367.

Verma et al., "Nitrobenzylthioinosine binding in brain: an interspecies study." Life Sci. Jan. 21, 1985; 36(3): 283-90. doi: 10.1016/0024-3205(85)90071-2.

Vignon et al., "[3H]thienyl-phencyclidine ([3H]TCP) binds to two different sites in rat brain. Localization by autoradiographic and biochemical techniques." Brain Res. Jul. 16, 1986; 378(1): 133-41. doi: 10.1016/0006-8993(86)90294-5.

Vitiligo Calculator [online]. Retrieved from: https://www.vitiligo-calculator.com, 2025. Retrieved on Feb. 26, 2025; 3 printed pages.

Wagner et al., "Omega-conotoxin GVIA binding to a high-affinity receptor in brain: characterization, calcium sensitivity, and solubilization." J Neurosci. Sep. 1988; 8(9): 3354-9. doi: 10.1523/JNEUROSCI.08-09-03354.1988.

Wang et al. "Corticosteroids and wound healing: clinical considerations in the perioperative period," Am J Surg. Sep. 2013;206(3):410-7. doi: 10.1016/j.amjsurg.2012.11.018. Epub Jun. 4, 2013.

Wang et al., "Human mu opiate receptor. cDNA and genomic clones, pharmacologic characterization and chromosomal assignment." FEBS Lett. Jan. 31, 1994; 338(2): 217-22. doi: 10.1016/0014-5793(94)80368-4.

Wang et al., "Insight into the conformational polymorph transformation of a block-buster multiple sclerosis drug fingolimod hydrochloride (FTY 720)," Journal of Pharmaceutical and Biomedical Analysis, 109:45-51 (2015).

Wang, "Pharmacological study on recombinant human GABA-A receptor complex containing alpha5 (leucine155 to valine) combined with beta3gamma2s subunits." Acta Pharmacol Sin. Jun. 2001; 22(6): 521-3.

Wang, A. S., "Reply to: Wound edge eversion: Tradition or science?" J Am Acad Dermatol, 73(2): e65 (2015), 1 page.

Wells, J.I. and M.E. Aulton, "Preformulation," Chapter 13 in Pharmaceutics: The Science of Dosage Form Design, 1st ed. Aulton, M.E. (Ed.) Churchill Livingstone, 1988; pp. 223-253.

Welss et al., "In vitro skin irritation: facts and future. State of the art review of mechanisms and models." Toxicol In Vitro. Jun. 2004; 18(3): 231-43. doi: 10.1016/j.tiv.2003.09.009.

(56) References Cited

OTHER PUBLICATIONS

White et al., "Identification of a potent, selective non-peptide CXCR2 antagonist that inhibits interleukin-8-induced neutrophil migration." J Biol Chem. Apr. 24, 1998; 273(17): 10095-8. doi: 10.1074/jbc.273.17.10095.

Wieland et al., "Subtype selectivity and antagonistic profile of the nonpeptide Y1 receptor antagonist BIBP 3226." J Pharmacol Exp Ther. Oct. 1995; 275(1): 143-9.

Xiao et al., "Adverse Effect Profile of Topical Ocular Administration of Fingolimod for Treatment of Dry Eye Disease," Basic & Clinical Pharmacology & Toxicology, 120:398-406 (2017).

Yang et al., "Grand Rounds quiz: Multiple papules on the hands of a woman with common variable immunodeficiency," J Am Acad Dermatol. Aug. 2015;73(2):350-352. doi: 10.1016/j.jaad.2012.09.057.

Yang et al., "Skin Barrier Abnormalities and Immune Dysfunction in Atopic Dermatitis," Int. J. Mol. Sci, 21:2867 (2020); doi:10.3390/ijms21082867, 14 pages.

York, P. The design of dosage forms, Chapter 1 in Pharmaceutics: The Science of Dosage Form Design, 1st ed. Aulton, M.E. (Ed.) Churchill Livingstone, 1988; pp. 1-13.

Yu et al. Transcriptome analysis reveals markers of aberrantly activated innate immunity in vitiligo lesional and non-lesional skin. PloS One. 2012;7(12): e51040; 12 pages.

Zava et al., "Androgen receptor assay with [3H]methyltrienolone (R1881) in the presence of progesterone receptors." Endocrinology. Apr. 1979; 104(4): 1007-12. doi: 10.1210/endo-104-4-1007.

Zhou et al., "Cloning and expression of human and rat D1 dopamine receptors." Nature. Sep. 6, 1990; 347(6288):76-80. doi: 10.1038/347076a0.

\* cited by examiner

COMPOUNDS COMPRISING N-METHYL-2-PYRIDONE, AND PHARMACEUTICALLY ACCEPTABLE SALTS

RELATED APPLICATIONS

This application is a U.S. National Stage Application under 35 U.S.C. § 371 of International Application No. PCT/EP2020/061173, filed Apr. 22, 2020, which claims priority to, and the benefit of, GB Application No. 1905721.5, filed Apr. 24, 2019, the contents of each of which are incorporated herein by reference in their entireties for all purposes.

FIELD OF THE INVENTION

The present invention concerns compounds comprising N-methyl-2-pyridone, and pharmaceutically-acceptable salts and compositions of such compounds. The compounds of the invention are useful as anti-inflammatory and anti-cancer therapies. Therefore, the present invention also concerns compounds comprising N-methyl-2-pyridone for use as medicaments, particularly for the treatment of inflammatory diseases and oncology.

BACKGROUND OF THE INVENTION

Bromodomain and Extra-Terminal (BET) proteins are a family of four bromodomain-containing (BRD) proteins (BRD2, BRD3, BRD4 and BRDT). All four members contain two BRDs (located next to each other toward the N-terminal of the proteins) and an extra-terminal domain (Shi, J. et al. Cancer Cell 25(2):210-225 (2014)). The two BRDs in each BET protein are designated binding domain I (BDI) and binding domain 11 (BDII). The BRD is a functional protein domain that contains a defined and predominantly hydrophobic pocket that binds to acetylated lysine residues, typically those found on transcription factors (Shi, J. et al. Cancer Cell 25(2):210-225 (2014)) or on the N-terminal tails of histone proteins. BRDs function as epigenetic regulators, i.e. they functionally alter gene activity and expression without altering the DNA sequence. For example, BRD4 recruits the transcription factor P-TEFb to promoters leading to altered expression of genes involved in the cell cycle (Yang et al., Mol. Cell Biol. 28: 967-976 (2008)). BRD2 and BRD3 also regulate growth promoting genes (LeRoy et al., Mol Cell 30:51-60 (2008)). Therefore, BRDs are responsible for transducing the signals carried by acetylated lysine residues into various phenotypes. BETs are considered in the art to be ubiquitously expressed in humans except for BRDT, which is normally expressed in the testes but is also expressed by some cancers (Ekaterina B. F. et al. Cell J. 19(Suppl 1): 1-8 (2017)).

BET proteins have roles in the regulation of a number of pathways such as MYC, BCL2, FOSL1, P-TEFb, NFkB, Glucocorticoid signalling and others (Shi J. et al. Mol Cell. June 5; 54(5):728-36 (2014)), (Hajmirza A. Biomedicines. February 6; 6(1). pii: E16 (2018)), (Shan N. Elife. September 11; 6. pii: e27861. (2017)), (Huang B. Mol Cell Biol. March; 29(5):1375-87 (2009)). As such, BET inhibitors are considered to have potential uses in a range of inflammatory diseases, cancers, infections, metabolic diseases, CNS disorders, fibrotic diseases and cardiac diseases (Deanna A. M. et al. J Exp Med. October 21; 210(11): 2181-2190 (2013)), (Rab K. P. et al. Trends Pharmacol. Sci. March; 33(3):146-53 (2012)), (Anna C. B. et al. J Immunol. April 1; 190(7): 3670-3678 (2013)), (Zuber J. et al. Nature. August 3; 478(7370):524-8. (2011)), (Montserrat P. S. et al. Epigenetics.; 12(5): 323-339 (2017)), (Qiming D. et al. Sci Transl Med. May 17; 9(390): eaah5084. (2017)), (Kristin M. K et al. J Biol Chem. August 11; 292(32): 13284-13295 (2017)), (Ning D. et al. PNAS December 22, 112 (51) 15713-15718 (2015)).

Compounds that can inhibit or affect the function of BET proteins have the potential to modulate gene expression and treat diseases that are at least in part caused by abnormal regulation of BET protein activity. Several small molecules have been reported to be effective in BET inhibition, including diazepine-, 3,5-dimethylisoxazole-, thiazol-2-one-, diazobenzene-, and 4-acylpyrrole-based compounds (see M. Brand et al, ACS Chem. Biol. 2015, 10, 22-39, WO2011054553, WO2011054845). Compounds that can selectively inhibit the function of BDII over BDI have the potential to modulate gene expression and treat diseases that are at least in part caused by abnormal regulation of BET protein activity while offering the potential of an improved therapeutic index. Improved therapeutic index and pre-clinical safety of BDII selective BET inhibitors verses pan-BET inhibitors has been demonstrated (E. Faivre et al. Nature 578, 306-310 (2020)).

Compounds comprising 6-methyl-1,6-dihydro-7H-pyrrolo[2,3-c]pyridin-7-one moieties, substituted at the 4- and/or 2-positions are described in patent applications WO 2017177955, WO 2016077378, WO 2015081280, WO 2014206150, WO 2014206345, WO 2013097601, WO 2013097052 and WO 2018130174 as useful for the inhibition of BET proteins.

The present invention provides alternative BET protein inhibitors useful in the treatment or prophylaxis of the conditions described herein.

SUMMARY OF THE INVENTION

It has been found that the compounds and compositions of this teaching are surprisingly active in inhibiting all four BET BRDs, with effective potency at nanomolar concentrations. The compounds and compositions are highly soluble in a range of solvents and formulations suitable for topical and/or oral application. Advantageously, many of the compounds and compositions of the invention are stable in human skin and under hydrolytic conditions at a range of pH values. Furthermore, formulations of the compounds and compositions may deliver practicable concentrations of the compound into the epidermis of the skin and the compounds are not toxic to skin cells. Some of the compounds and compositions exhibit surprisingly effective clearance by the liver, offering potential use as medicaments with a lower risk of side-effects. Other compounds and compositions are surprisingly stable, offering potential use as medicaments for oral administration. Some of the compounds are surprisingly selective for BDII over BDI offering the potential of an improved therapeutic index and a lower risk of side-effects.

The skilled person is aware that any reference to an aspect of the current disclosure includes every embodiment of that aspect. For example, any reference to the first aspect includes the first aspect and all embodiments of the first aspect.

Viewed from a first aspect, there is provided a compound of formula (I):

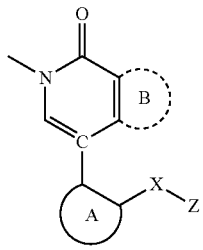

(I)

wherein ring structure A is a 5- or 6-membered aromatic or heteroaromatic ring, optionally substituted at one or more carbon and/or heteroatoms with a first substituent;
wherein each first substituent is independently selected from the group consisting of hydroxy, oxo, $C_1$-$C_6$alkyl, $C_3$-$C_6$cycloalkyl, $C_1$-$C_6$alkylol, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $SO_2C_1$-$C_4$alkylol, $NHSO_2C_1$-$C_4$alkylol, $C_1$-$C_5$alkyloxy, $C_1$-$C_5$alkylamino, $SO_2NH_2$, $CONH_2$, $CONHC_1$-$C_4$alkyl, $NHCOC_1$-$C_4$alkyl, $NHSO_2N(C_1$-$C_4alkyl)_2$, $C_1$-$C_6$fluoroalkyl, $SO_2C_1$-$C_4$fluoroalkyl, $NHSO_2C_1$-$C_4$fluoroalkyl, $C_1$-$C_5$fluoroalkyloxy, and $C_1$-$C_5$fluoroalkylamino;
X is O, $CR_2$, NR' or S, wherein R is individually selected from the group consisting of H, $C_1$-$C_4$alkyl and halo, and R' is selected from the group consisting of $C_1$-$C_4$alkyl and H;
Z is a 5- or 6-membered aromatic or heteroaromatic ring, $C_1$-$C_6$alkyl, $C_3$-$C_6$cycloalkyl, $CR^AR^BR^C$, $C_2$-$C_5$oxacycloalkyl, $C_2$-$C_5$azacycloalkyl or morpholinyl, optionally substituted at one or more carbon and/or heteroatoms with a second substituent;
wherein $R^A$ is a $C_3$-$C_5$cycloalkyl, $R^B$ is a $C_3$-$C_5$cycloalkyl, methyl or ethyl, and $R^C$ is OH; and
each second substituent is independently selected from the group consisting of hydroxy, $C_1$-$C_6$alkyl, $C_3$-$C_6$cycloalkyl, halo, $C_1$-$C_5$alkyloxy, $C_1$-$C_5$alkylamino, oxo, cyano, $C_1$-$C_6$fluoroalkyl, $C_1$-$C_5$fluoroalkyloxy, and $C_1$-$C_5$fluoroalkylamino;
ring structure B is optionally present; wherein when ring structure B is present, it is an optionally substituted pyrrole bonded such that C is in the 4 position relative to NH; wherein the pyrrole is optionally substituted at position 2 with a third substituent;
wherein the third substituent is selected from the group consisting of $CONHC_1$-$C_4$alkyl, $CONH_2$, $CONHC_1$-$C_6$fluoroalkyl, $CONHC_3$-$C_6$cycloalkyl optionally substituted at one or more carbon atoms with a methyl or ethyl; $CONHC_3$-$C_5$cyclofluoroalkyl optionally substituted at one or more carbon atoms with a methyl or ethyl, $NHCOC_1$-$C_4$alkyl and $NHCOC_1$-$C_4$fluoroalkyl;
with the proviso that when A is 6-membered, it is substituted at least once with a hydroxy or oxo group.

Viewed from a second aspect, there is provided a pharmaceutical composition comprising any one or a combination of the compounds defined in the first aspect, in combination with one or more pharmaceutically acceptable excipients.

Viewed from a third aspect, there is provided a compound as defined in the first aspect or a pharmaceutical composition as defined in the second aspect, for use as a medicament.

Viewed from a fourth aspect, there is provided a compound as defined in the first aspect, or a pharmaceutical composition as defined in the second aspect, for use in a method of treatment or prophylaxis of inflammatory skin disorders, respiratory diseases, gastrointestinal diseases, eye diseases, cancers, rheumatic diseases, demyelinating diseases and fibrotic diseases.

Viewed from a fifth aspect, there is provided a compound as defined in the second aspect, or a pharmaceutical composition as defined in the second aspect, for use in the inhibition of Bromodomain and Extra-Terminal proteins.

Viewed from a sixth aspect, there is provided a method for the treatment or prophylaxis of inflammatory skin disorders, respiratory diseases, gastrointestinal diseases eye diseases cancers, rheumatic diseases, demyelinating diseases and fibrotic diseases, said method comprising administering to a subject, an effective amount of a compound as defined in the first aspect, or a pharmaceutical composition as defined in the second aspect.

Viewed from a seventh aspect, there is provided a method of inhibiting Bromodomain and Extra-Terminal protein activity in a subject, said method comprising administering to a subject an effective amount of a compound as defined in the first aspect, or a pharmaceutical composition as defined in the second aspect.

DETAILED DESCRIPTION OF THE INVENTION

Structurally novel derivatives of N-methyl-2-pyridone have been found to be surprisingly effective in inhibiting all four BET BRDs to at least a similar degree as the inhibitors known in the art. In some cases, known BET protein inhibitors are outperformed by the compounds described herein. The compounds are now described in detail.

In the discussion that follows, reference is made to a number of terms, which have the meanings provided below, unless a context indicates to the contrary. The nomenclature used herein for defining compounds, in particular the compounds according to the invention, is in general based on the rules of the IUPAC organisation for chemical compounds, specifically the "IUPAC Compendium of Chemical Terminology (Gold Book)". For the avoidance of doubt, if a rule of the IUPAC organisation is contrary to a definition provided herein, the definition herein is to prevail. Furthermore, if a compound structure is contrary to the name provided for the structure, the structure is to prevail.

The term "therapeutic index", also known as the "therapeutic window" or "safety window" defines the relative safety of a drug. The therapeutic index may be calculated as the ratio of the area under the curve (AUC) in blood, at a concentration of drug that results in no toxicity (No Observed Adverse Effect Level—NOAEL), to the concentration of drug that produces the desired efficacy, typically the dose that has a 50% effect—the Effective dose 50 or ED50. TI=AUC(NOAEL)/AUC(ED50). A drug with a higher therapeutic index is preferable, since administration of the drug is less likely to lead to unwanted side effects, and more drug may be administered to treat a subject more effectively. The efficacy of BET inhibitors is driven by their inhibition of the function of BDII, whereas inhibition of the function of BDI leads to unwanted side effects. Thus, drugs that selectively inhibit the function of BDII over BDI have the potential to modulate gene expression and treat diseases that are at least in part caused by abnormal regulation of BET and are less likely to give rise to unwanted side effects with respect to pan inhibitors administered at the same dose.

A higher dose of drugs that selectively inhibit BDII over BDI may be administered with respect to pan inhibitors, thus such selective drugs may be more efficacious.

The term "aromatic" defines a cyclically conjugated molecular entity with a stability (due to delocalisation) significantly greater than that of a hypothetical localised structure. The Hückel rule is often used in the art to assess aromatic character; monocyclic planar (or almost planar) systems of trigonally (or sometimes diagonally) hybridised atoms that contain (4n+2) π-electrons (where n is a non-negative integer) will exhibit aromatic character. The rule is generally limited to n=0 to 5.

The term "heteroaromatic" defines a cyclically conjugated molecular entity comprising heteroatoms, with a stability (due to delocalisation) significantly greater than that of a hypothetical localised structure.

The term "cyclic" or variants thereof defines a compound in which one or more series of atoms in the compound is connected to form a ring. Whereas, the term "acyclic" defines a compound containing no rings of atoms.

The term "conjugated" or variants thereof defines a molecular entity whose structure may be represented as a system of alternating single and multiple bonds. In such systems, conjugation is the interaction of one p-orbital with another across an intervening π-bond in such structures. In appropriate molecular entities d-orbitals may be involved. The term is also extended to the analogous interaction involving a p-orbital containing an unshared electron pair.

The term "delocalised" defines the π-bonding in a conjugated system where the bonding is not localised between two atoms, but instead each link has a fractional double bond character, or bond order.

The term "comprising" or variants thereof will be understood to imply the inclusion of a stated element, integer or step, or group of elements, integers or steps, but not the exclusion of any other element, integer or step, or group of elements, integers or steps.

The term "consisting" or variants thereof will be understood to imply the inclusion of a stated element, integer or step, or group of elements, integers or steps, and the exclusion of any other element, integer or step or group of elements, integers or steps.

The term "alkyl" is well known in the art and defines univalent groups derived from alkanes by removal of a hydrogen atom from any carbon atom, wherein the term "alkane" is intended to define cyclic or acyclic branched or unbranched hydrocarbons having the general formula $C_nH_{2n+2}$, wherein n is an integer ≥1.

The term "cycloalkyl" defines all univalent groups derived from cycloalkanes by removal of a hydrogen atom from a ring carbon atom. The term "cycloalkane" defines saturated monocyclic and polycyclic hydrocarbons.

The term "alkylol" defines a hydroxy derivative of an alkyl radical, i.e. a hydroxy-alkyl.

The term "halo" is well known in the art and defines a halogen radical that, when bonded to a carbon radical makes a fluoride, chloride, bromide or iodide compound.

The term "alkyloxy" is synonymous with "alkoxy" and when used herein defines a univalent group comprising an alkyl singly bonded to an oxygen atom, derived from the corresponding alcohol by removal of the hydrogen atom bonded to the oxygen atom.

The term "alkylamino" is synonymous with "alkamino" and when used herein defines a univalent group comprising an alkyl singly bonded to an amino group, derived from the corresponding amine by removal of a hydrogen atom bonded to the nitrogen atom.

The term "oxacycloalkyl" defines a univalent group comprising a cycloalkyl, in which one of the $CH_2$ moieties is replaced with an oxide. Similarly, the term "azacycloalkyl" defines a univalent group comprising a cycloalkyl, in which one of the $CH_2$ moieties is replaced with an NH moiety.

The term "treatment" defines the therapeutic treatment of a human or non-human animal, in order to impede or reduce or halt the rate of the progress of the condition, or to ameliorate or cure the condition. Prophylaxis of the condition as a result of treatment is also included. References to prophylaxis are intended herein not to require complete prevention of a condition: its development may instead be hindered through treatment in accordance with the invention. Typically, treatment is not prophylactic, and the compound or composition is administered to a patient having a diagnosed or suspected condition. By an "effective amount" herein defines an amount of the compound or composition of the invention that is sufficient to impede the noted diseases and thus produces the desired therapeutic or inhibitory effect.

The term "stereoisomer" is used herein to refer to isomers that possess identical molecular formulae and sequence of bonded atoms, but which differ in the arrangement of their atoms in space.

The term "enantiomer" defines one of a pair of molecular entities that are mirror images of each other and non-superimposable, i.e. cannot be brought into coincidence by translation and rigid rotation transformations. Enantiomers are chiral molecules, i.e. are distinguishable from their mirror image.

The term "racemic" is used herein to pertain to a racemate. A racemate defines a substantially equimolar mixture of a pair of enantiomers.

The term "diastereoisomers" (also known as diastereomers) defines stereoisomers that are not related as mirror images.

The term "solvate" is used herein to refer to a complex comprising a solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

The term "isotope" is used herein to define a variant of a particular chemical element, in which the nucleus necessarily has the same atomic number but has a different mass number owing to it possessing a different number of neutrons.

The term "prodrug" is used herein to refer to a compound which acts as a drug precursor and which, upon administration to a subject, undergoes conversion by metabolic or other chemical processes to yield a compound of formula (I).

The term "pharmaceutically acceptable excipient" defines substances other than a pharmacologically active drug or prodrug, which are included in a pharmaceutical product.

The term "topical" when used with respect to compounds or compositions of the invention is used to refer to the ability to apply the compound or composition to body surfaces, for example skin or mucous membranes. Topical compounds or compositions may be applied in the form of creams, foams, gels, lotions or ointments.

The term "oral" when used with respect to compounds or compositions of the invention is used to refer to the ability to administer the compound or composition through the mouth. Typically, oral compounds exhibit a systemic effect rather than a topical effect, i.e. they affect multiple organ systems, rather than a local area.

The terms "transduce" or "transducing", when used with respect to a signal, are synonymous with "transfer" or "transferring", i.e. "signal transduction" is the process of transferring a signal throughout an organism, for example through a cell.

The term "pan" is used herein to refer to "all". For example, pan inhibition of the BET family means that all of the members of the BET family (BRD2, BRD3, BRD4 and BRDT) are inhibited.

The term "T-cell" (also known as a T lymphocyte) is known in the art to refer to a lymphocyte with a T-cell receptor on the cell surface (a molecule that is responsible for recognising fragments of antigen peptides).

The term "cytokine" is used herein to refer to a small protein (~5 to 20 kDa) that is important in cell signalling, such as autocrine, paracrine and endocrine signalling, as immunomodulating agents.

The term "chemokine" is used herein to refer to a family of cytokines that are able to induce directed chemotaxis in responsive cells, i.e. they act as a chemoattractant to guide the migration of cells.

The term "intrinsic clearance" is well known in the art and refers to the ability of the liver to remove a drug in the absence of flow limitations and binding to cells or proteins in the blood. Intrinsic clearance is herein expressed as a percentage of liver blood flow, i.e.:

$$\text{Intrinsic clearence}(\%) = \frac{\text{rate of drug clearance}}{\text{rate of liver blood flow}} \times 100$$

The term "soft drug" refers to compounds that are rapidly metabolised on reaching the blood or liver. Highly cleared compounds are considered to have clearance rates of >70% of liver blood flow, most often clearance rates of >75%, with intermediate rates being 30-70%, most often 50-75%, and low rates being <30%, most often <50%. Soft drugs are often characterised by a predictable and controllable in vivo metabolism to non-toxic products after they have achieved their therapeutic role. Soft drugs have lower systemic exposure and may lead to a lower risk of side effects.

The systemic inhibition of drug targets is often associated with dose limiting side-effects and there is an unmet need for efficacious agents, which are well tolerated in patients. Compounds that are rapidly cleared upon entering the blood stream have lower systemic exposure and may lead to a lower risk of side effects (see Atkinson AJ Jr. and Kushner W., Annu. Rev. Pharmacol. Toxicol., 1979, 19, 105-127 and Rowland M. and Tozer T. N., Clinical Pharmacokinetics. Concepts and Applications. Lippincott Williams & Wilkins, 1995, 161-167).

It is unpredictable which groups within a drug structure will lead to rapid systemic clearance of a drug. Phenol groups, in some cases, are observed to be cleared via phase II conjugative clearance mechanisms such as glucuronidation and sulfation (see *Pathways of Biotransformation—Phase II Reactions*. In: Ionescu C., Caira M. R. (eds) *Drug Metabolism*. Springer, Dordrecht, 2005).

As alluded to above, the first aspect provides a compound of formula (I):

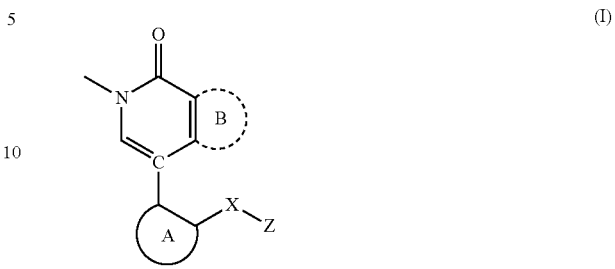

wherein ring structure A is a 5- or 6-membered aromatic or heteroaromatic ring, optionally substituted at one or more carbon and/or heteroatoms with a first substituent;

wherein each first substituent is independently selected from the group consisting of hydroxy, oxo, $C_1$-$C_6$alkyl, $C_3$-$C_6$cycloalkyl, $C_1$-$C_6$alkylol, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $SO_2C_1$-$C_4$alkylol, $NHSO_2C_1$-$C_4$alkylol, $C_1$-$C_5$alkyloxy, $C_1$-$C_5$alkylamino, $SO_2NH_2$, $CONH_2$, $CONHC_1$-$C_4$alkyl, $NHCOC_1$-$C_4$alkyl, $NHSO_2N(C_1$-$C_4$alkyl$)_2$, $C_1$-$C_6$fluoroalkyl, $SO_2C_1$-$C_4$fluoroalkyl, $NHSO_2C_1$-$C_4$fluoroalkyl, $C_1$-$C_5$fluoroalkyloxy, and $C_1$-$C_5$fluoroalkylamino;

X is O, $CR_2$, NR' or S, wherein R is individually selected from the group consisting of H, $C_1$-$C_4$alkyl and halo, and R' is selected from the group consisting of $C_1$-$C_4$alkyl and H;

Z is a 5- or 6-membered aromatic or heteroaromatic ring, $C_1$-$C_6$alkyl, $C_3$-$C_6$cycloalkyl, $CR^AR^BR^C$, $C_2$-$C_5$oxacycloalkyl, $C_2$-$C_5$azacycloalkyl or morpholinyl, optionally substituted at one or more carbon and/or heteroatoms with a second substituent;

wherein $R^A$ is a $C_3$-$C_5$cycloalkyl, $R^B$ is a $C_3$-$C_5$cycloalkyl, methyl or ethyl, and $R^C$ is OH; and each second substituent is independently selected from the group consisting of hydroxy, $C_1$-$C_6$alkyl, $C_3$-$C_6$cycloalkyl, halo, $C_1$-$C_5$alkyloxy, $C_1$-$C_5$alkylamino, oxo, cyano, $C_1$-$C_6$fluoroalkyl, $C_1$-$C_5$fluoroalkyloxy, and $C_1$-$C_5$fluoroalkylamino;

ring structure B is optionally present; wherein when ring structure B is present, it is an optionally substituted pyrrole bonded such that C is in the 4 position relative to NH; wherein the pyrrole is optionally substituted at position 2 with a third substituent;

wherein the third substituent is selected from the group consisting of $CONHC_1$-$C_4$alkyl, $CONH_2$, $CONHC_1$-$C_6$fluoroalkyl, $CONHC_3$-$C_6$cycloalkyl optionally substituted at one or more carbon atoms with a methyl or ethyl; $CONHC_3$-$C_5$cyclofluoroalkyl optionally substituted at one or more carbon atoms with a methyl or ethyl, $NHCOC_1$-$C_4$alkyl and $NHCOC_1$-$C_4$fluoroalkyl;

with the proviso that when A is 6-membered, it is substituted at least once with a hydroxy or oxo group.

B is optionally present. When absent, the carbon atoms positioned ortho and meta to C are each bound to H. When present, ring structure B is an optionally substituted pyrrole; C is in the 4 position relative to NH, thereby forming a 6-methyl-1,6-dihydro-7H-pyrrolo[2,3-c]pyridin-7-one derivative.

The pyrrole is optionally substituted at position 2 with a third substituent, which is selected from the group consisting of $CONHC_1$-$C_4$alkyl, $CONH_2$, $CONHC_1$-$C_6$fluoroalkyl, $CONHC_3$-$C_6$cycloalkyl optionally substituted at one or more carbon atoms with a methyl or ethyl; $CONHC_3$-

C$_5$cyclofluoroalkyl optionally substituted at one or more carbon atoms with a methyl or ethyl, NHCOC$_1$-C$_4$alkyl and NHCOC$_1$-C$_4$fluoroalkyl. The CONHC$_3$-C$_6$cycloalkyl may be unsubstituted. Often, the third substituent is selected from the group consisting of CONHC$_1$-C$_4$alkyl, CONHC$_1$-C$_6$fluoroalkyl, CONHC$_3$-C$_6$cycloalkyl optionally substituted at one or more carbon atoms with a methyl or ethyl, and CONHC$_3$-C$_5$cyclofluoroalkyl optionally substituted at one or more carbon atoms with a methyl or ethyl. The third substituent may be selected from the group consisting of CONHC$_1$-C$_4$alkyl, CONHC$_1$-C$_6$fluoroalkyl, CONHC$_3$-C$_6$cycloalkyl and CONHC$_3$-C$_5$cyclofluoroalkyl optionally substituted at one or more carbon atoms with a methyl or ethyl. The third substituent may be selected from the group consisting of CONHC$_1$-C$_4$alkyl, CONH$_2$, CONHC$_1$-C$_6$fluoroalkyl, CONHC$_3$-C$_5$cycloalkyl; CONHC$_3$-C$_5$cyclofluoroalkyl, NHCOC$_1$-C$_4$alkyl and NHCOC$_1$-C$_4$fluoroalkyl. Often, the third substituent is CONHC$_1$-C$_4$alkyl, typically CONHethyl. Typically the pyrrole is unsubstituted. Most typically, the pyrrole is unsubstituted or is substituted at position 2 with CONHethyl.

Typically, B is present and is sometimes a pyrrole optionally substituted at position 2 with a third substituent that is a CONHC$_1$-C$_4$alkyl. Often the third substituent is CONH-ethyl. Typically, B is present and is an unsubstituted pyrrole. Most typically, B is present and is an unsubstituted pyrrole or a pyrrole substituted at position 2 with CONHethyl. Therefore, the compound of the invention is typically represented by formula (II) or (III):

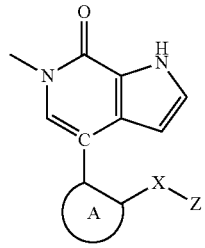

(II)

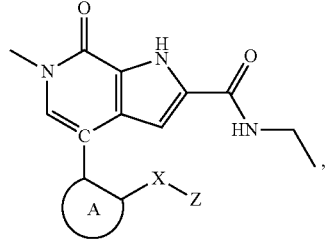

(III)

wherein A, X and Z are as defined for formula (I), with the proviso that when A is 6-membered, it is substituted at least once with a hydroxy or oxo group.

Often, when A is 6-membered, it is substituted at least once with a hydroxy group positioned ortho or meta to X, or an oxo group.

A connects C to X and may be any 5-membered aromatic or heteroaromatic ring, or any 6-membered aromatic or heteroaromatic ring that is substituted at least once with a hydroxy or oxo group. 5-membered aromatic or heteroaromatic rings include thiazole, oxazole, imidazole, isoxazole, pyrazole, thiophene, pyrrole, furan and cyclopentadienyl. 5-membered heteroaromatic rings also include triazole, such as 1,2,4-triazole. 6-membered aromatic or heteroaromatic rings include benzene, pyridine, pyridone, pyrazine, pyrimidine, pyridazine, 1,2,3-triazine, 1,2,4-triazine and 1,3,5-triazine. The 5-membered or 6-membered aromatic or heteroaromatic rings may be substituted at one or more carbon and/or heteroatoms with the first substituent. For example, when A is a pyridine ring, it may be substituted with the first substituent at any of the one, two or three carbon atoms that are not bound to C or X and/or at the nitrogen atom.

When A is 5-membered, it is often unsubstituted or substituted at one position. Typically, when A is 5-membered, it is unsubstituted.

Often, A is selected from the group consisting of benzene, pyridine, thiazole, pyridone, pyrazole, imidazole and triazole, optionally substituted at one or more carbon and/or heteroatoms with the first substituent. Typically, A is selected from the group consisting of benzene, pyridine, thiazole and pyridone, optionally substituted at one or more carbon and/or heteroatoms with the first substituent. When A is a pyridone, it may be a 2-, 3- or 4-pyridone. Commonly, when A is a pyridone, it is a 2-pyridone, i.e. A is commonly selected from the group consisting of benzene, pyridine, thiazole and 2-pyridone, optionally substituted at one or more carbon or heteroatoms with the first substituent.

When A is a thiazole, it is commonly bound to C via the thiazole carbon atom at position 5, and bound to X via the thiazole carbon at position 4. The resulting C-A-X moiety is represented by:

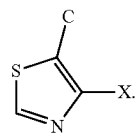

The thiazole may be substituted at one or more carbon and/or nitrogen atoms with the first substituent. Often, the thiazole is substituted at position 2 with the first substituent.

When A is a 2-pyridone, it is typically either: bound to C via the carbon atom at position 4, and bound to X via the carbon atom at position 3, or bound to C via the carbon atom at position 4 and bound to X via the carbon atom at position 5. The resulting C-A-X moieties are represented by:

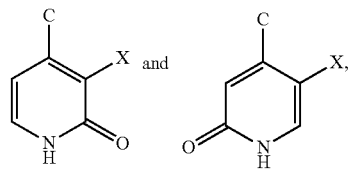

respectively.

The 2-pyridone may be substituted at one or more carbon and/or nitrogen atoms with the first substituent. Often, the 2-pyridone is substituted at one or more carbon and/or nitrogen atoms with a C$_1$-C$_6$alkyl. Commonly, the C$_1$-C$_6$alkyl is a C$_1$-C$_4$alkyl selected from the group consisting of methyl, ethyl, n-propyl, isopropyl, n-butyl, sec-butyl, isobutyl and tert-butyl. Typically, the C$_1$-C$_6$alkyl is a methyl. Often, the 2-pyridone is substituted at the nitrogen atom with a methyl.

When A is a pyrazole, it is commonly bound to C via the pyrazole carbon atom at position 5, and bound to X by the nitrogen atom at position 1. The resulting C-A-X moiety is represented by:

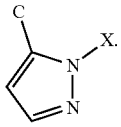

The pyrazole may be substituted at one or more carbon and/or nitrogen atoms with the first substituent. Often, the pyrazole is substituted at position 3 or 4 with the first substituent.

When A is an imidazole, it is commonly bound to C via the imidazole carbon atom at position 2, and bound to X by the nitrogen atom at position 1. The resulting C-A-X moiety is represented by:

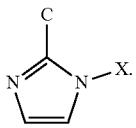

The imidazole may be substituted at one or more carbon and/or nitrogen atoms with the first substituent. Often, the imidazole is substituted at position 4 or 5 with the first substituent.

When A is a triazole, it is typically a 1,2,4-triazole. When A is a 1,2,4-triazole it is commonly bound to C via the imidazole carbon atom at position 5, and bound to X by the nitrogen atom at position 1. The resulting C-A-X moiety is represented by:

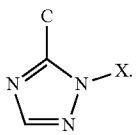

The 1,2,4-triazole may be substituted at one or more carbon and/or nitrogen atoms with the first substituent. Often, the 1,2,4-triazole is substituted at position 3 with the first substituent.

The first substituent may be hydroxy, oxo, $C_1$-$C_6$alkyl, $C_3$-$C_6$cycloalkyl, $C_1$-$C_6$alkylol, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $SO_2C_1$-$C_4$alkylol, $NHSO_2C_1$-$C_4$alkylol, $C_1$-$C_5$alkyloxy, $C_1$-$C_5$alkylamino, $SO_2NH_2$, $CONH_2$, $CONHC_1$-$C_4$alkyl, $NHCOC_1$-$C_4$alkyl, $NHSO_2N(C_1$-$C_4$alkyl), $C_1$-$C_6$fluoroalkyl, $SO_2C_1$-$C_4$fluoroalkyl, $NHSO_2C_1$-$C_4$fluoroalkyl, $C_1$-$C_5$fluoroalkyloxy, and/or $C_1$-$C_5$fluoroalkylamino. When the first substituent is selected from $SO_2C_1$-$C_4$alkyl, $NHSO_2C_1$-$C_4$alkyl, $SO_2C_1$-$C_4$fluoroalkyl and $NHSO_2C_1$-$C_4$fluoroalkyl, it is often $SO_2CH_3$, $NHSO_2CH_3$, $SO_2CF_3$ and/or $NHSO_2CF_3$, i.e. methanesulfonyl, methanesulfonamido, trifluoromethanesulfonyl and/or trifluoromethanesulfonamido. When the first substituent is selected from $SO_2C_3$-$C_6$cycloalkyl and $NHSO_2C_3$-$C_6$cycloalkyl, it is often $SO_2C_3H_5$, $S0_2C_5H_9$, $SO_2C_6H_{11}$, $NHSO_2C_3H_5$, $NHSO_2C_5H_9$ and/or $NHSO_2C_6H_{11}$, i.e. cyclopropanesulfonyl, cyclopentanesulfonyl, cyclohexanesulfonyl, cyclopropanesulfonamido, cyclopentanesulfonamido and/or cyclohexanesulfonamido. When the first substituent is selected from $SO_2C_1$-$C_4$alkylol and $NHSO_2C_1$-$C_4$alkylol, it is often $SO_2C$ $(CH_3)_2OH$ and/or $NHSO_2C(CH_3)_2OH$, i.e. tert-butanolsulfonyl and/or tert-butanolsulfonamido.

Therefore, each first substituent is often independently selected from the group consisting of hydroxy, oxo, $C_1$-$C_6$alkyl, $C_3$-$C_6$cycloalkyl, $C_1$-$C_6$alkylol, halo, $SO_2CH_3$, $NHSO_2CH_3$, $SO_2{}^tBu$, $NHSO_2{}^tBu$, $SO_2C_3H_5$, $SO_2C_5H_9$, $SO_2C_6H_{11}$, $NHSO_2C_3H_5$, $NHSO_2C_5H_9$, $NHSO_2C_6H_{11}$, $C_1$-$C_5$alkyloxy, $C_1$-$C_5$alkylamino, $SO_2NH_2$, $CONH_2$, $CONHC_1$-$C_4$alkyl, $NHCOC_1$-$C_4$alkyl, $NHSO_2N(C_1$-$C_4$alkyl), $C_1$-$C_6$fluoroalkyl, $SO_2CF_3$, $NHSO_2CF_3$, $C_1$-$C_5$fluoroalkyloxy, and/or $C_1$-$C_5$fluoroalkylamino.

Typically, each first substituent is independently selected from the group consisting of hydroxy, oxo, $C_1$-$C_6$alkyl, $C_1$-$C_6$alkylol, $C_3$-$C_6$cycloalkyl, halo, $SO_2CH_3$, $NHSO_2CH_3$, $SO_2C_3H_5$, $SO_2C_5H_9$, $SO_2C_6H_{11}$, $NHSO_2C_3H_5$, $NHSO_2C_5H_9$ and $NHSO_2C_6H_{11}$. Often, each first substituent is independently selected from the group consisting of hydroxy, oxo, $C_1$-$C_6$alkyl, $C_3$-$C_6$cycloalkyl, halo, $SO_2CH_3$ and $NHSO_2CH_3$.

Commonly, each first substituent is independently selected from the group consisting of hydroxy, oxo, $C_1$-$C_6$alkyl, $C_3$-$C_6$cycloalkyl, $C_1$-$C_6$alkylol, and halo. Typically, the $C_1$-$C_6$alkyl is a $C_1$-$C_4$alkyl selected from the group consisting of methyl, ethyl, n-propyl, isopropyl, n-butyl, sec-butyl, isobutyl and tert-butyl, and the $C_3$-$C_6$cycloalkyl is selected from the group consisting of cyclopropyl, cyclopentyl and cyclohexyl. Typically, the $C_1$-$C_6$alkylol is hydroxymethyl, hydroxyethyl, hydroxy-n-propyl, hydroxy-isopropyl, hydroxy-n-butyl, hydroxy-sec-butyl, hydroxy-isobutyl and hydroxy-tert-butyl. Typically, the halo is fluoro or chloro. Therefore, each first substituent is commonly independently selected from the group consisting of hydroxy, oxo, methyl, ethyl, n-propyl, isopropyl, n-butyl, sec-butyl, isobutyl, tert-butyl, cyclopropyl, cyclopentyl, cyclohexyl, hydroxymethyl, hydroxyethyl, hydroxy-n-propyl, hydroxy-isopropyl, hydroxy-n-butyl, hydroxy-sec-butyl, hydroxy-isobutyl and hydroxy-tert-butyl, fluoro and chloro.

Most typically, each first substituent is independently selected from the group consisting of hydroxy, oxo, methyl, ethyl, isopropyl, tert-butyl, cyclopropyl, hydroxy-tert-butyl, fluoro and chloro.

Often, each first substituent is independently selected from the group consisting of hydroxy, oxo, methyl and halo.

When A is benzene or pyridine, it is substituted at least once with a hydroxy group. Sometimes, it is substituted with a hydroxy group and a further first substituent, selected from the group consisting of methyl, ethyl, n-propyl, isopropyl, n-butyl, sec-butyl, isobutyl, tert-butyl, cyclopropyl, cyclopentyl, cyclohexyl, fluoro and chloro. Typically, it is substituted with a hydroxy group and a further first substituent, selected from the group consisting of methyl, fluoro and chloro. Often, the at least one hydroxy group is positioned ortho or meta to X.

X is O, $CR_2$ or NR', wherein R is individually selected from the group consisting of H, $C_1$-$C_4$alkyl and halo, and R' is selected from the group consisting of $C_1$-$C_4$alkyl and H.

When X is $CR_2$, halo is typically chloro or fluoro. Therefore, R is typically individually selected from the group consisting of H, $C_1$-$C_4$alkyl, fluoro and chloro.

When X is $CR_2$ or NR', $C_1$-$C_4$alkyl may be methyl, ethyl, n-propyl, isopropyl, n-butyl, sec-butyl, isobutyl or tert-butyl. Therefore, R is typically individually selected from the group consisting of H, methyl, ethyl, n-propyl, isopropyl, n-butyl, sec-butyl, isobutyl or tert-butyl, fluoro and chloro, and R' is selected from the group consisting of H, methyl, ethyl, n-propyl, isopropyl, n-butyl, sec-butyl, isobutyl or tert-butyl and H. Sometimes, R is individually selected from the group consisting of H, methyl and halo, and R' is selected from the group consisting of methyl and H. Often, R is individually selected from the group consisting of H, methyl and fluoro, and R' is methyl.

Typically, X is O, i.e. A is bound to Z via an oxide.

Z is a 5- or 6-membered aromatic or heteroaromatic ring, $C_1$-$C_6$alkyl, $C_3$-$C_6$cycloalkyl, $CR^AR^BR^C$, $C_2$-$C_5$oxacycloalkyl, $C_2$-$C_5$azacycloalkyl or morpholinyl, optionally substituted at one or more carbon and/or heteroatoms with a second substituent, each selected independently from the group consisting of hydroxy, $C_1$-$C_6$alkyl, $C_3$-$C_6$cycloalkyl, halo, $C_1$-$C_5$alkyloxy, $C_1$-$C_5$alkylamino, oxo, cyano, $C_1$-$C_6$fluoroalkyl, $C_1$-$C_5$fluoroalkyloxy, and $C_1$-$C_5$fluoroalkylamino;

wherein $R^A$ is a $C_3$-$C_5$cycloalkyl, $R^B$ is a $C_3$-$C_5$cycloalkyl, methyl or ethyl, and $R^C$ is OH.

Z may be any optionally substituted 5-membered aromatic or heteroaromatic ring, for example Z may be thiazole, oxazole, imidazole, isoxazole, pyrazole, thiophene, pyrrole, furan or cyclopentadienyl.

Alternatively, Z may be any optionally substituted 6-membered aromatic or heteroaromatic ring, for example Z may be benzene, pyridine, pyridone, pyrazine, pyrimidine, pyridazine, 1,2,3-triazine, 1,2,4-triazine or 1,3,5-triazine.

Otherwise, Z may be an optionally substituted $C_1$-$C_6$alkyl, $C_3$-$C_6$cycloalkyl, $CR^AR^BR^C$, $C_2$-$C_5$oxacycloalkyl, $C_2$-$C_5$azacycloalkyl or morpholinyl. Typically, the $C_1$-$C_6$alkyl is a $C_1$-$C_4$alkyl selected from the group consisting of methyl, ethyl, n-propyl, isopropyl, n-butyl, sec-butyl, isobutyl and tert-butyl; the $C_3$-$C_6$cycloalkyl is selected from the group consisting of cyclopropyl, cyclopentyl and cyclohexyl; $R^A$ is cyclopropyl, cyclobutyl or cyclopentyl, $R^B$ is cyclopropyl, cyclobutyl, cyclopentyl, methyl or ethyl; the $C_2$-$C_5$oxacycloalkyl is selected from the group consisting of oxacyclopropyl, oxacyclopentyl and oxacyclohexyl; and the $C_2$-$C_5$azacycloalkyl is selected from the group consisting of azacyclopropyl, azacyclopentyl and azacyclohexyl.

Often, Z is selected from the group consisting of benzene, pyridine, thiazole, pyridone, methyl, ethyl, n-propyl, isopropyl, n-butyl, tert-butyl, cyclopropyl, cyclopentyl, cyclohexyl, oxacyclopentyl, oxacyclohexyl, azacyclopentyl, azacyclohexyl and morpholinyl, optionally substituted at one or more carbon and/or heteroatoms with a second substituent. Sometimes, Z is selected from the group consisting of benzene, pyridine, pyridone, n-propyl, isopropyl, n-butyl, tert-butyl, cyclopropyl, cyclopentyl and cyclohexyl, optionally substituted at one or more carbon and/or nitrogen atoms with a second substituent.

Z is commonly an optionally substituted 6-membered aromatic or heteroaromatic ring, a $C_1$-$C_6$alkyl, or a $C_3$-$C_6$cycloalkyl.

Typically, Z is a phenyl or pyridyl ring, a $C_1$-$C_6$alkyl, or a $C_3$-$C_6$cycloalkyl optionally substituted at one or more carbon and/or nitrogen atoms with a second substituent.

Each second substituent is independently selected from the group consisting of hydroxy, $C_1$-$C_6$alkyl, $C_3$-$C_6$cycloalkyl, halo, $C_1$-$C_5$alkyloxy, $C_1$-$C_5$alkylamino, oxo, cyano, $C_1$-$C_6$fluoroalkyl, $C_1$-$C_5$fluoroalkyloxy, and $C_1$-$C_5$fluoroalkylamino.

Often, each second substituent is independently selected from the group consisting of hydroxy, $C_1$-$C_6$alkyl, $C_3$-$C_6$cycloalkyl, and halo. Typically, the $C_1$-$C_6$alkyl is a $C_1$-$C_4$alkyl selected from the group consisting of methyl, ethyl, n-propyl, isopropyl, n-butyl, sec-butyl, isobutyl and tert-butyl, and the $C_3$-$C_6$cycloalkyl is selected from the group consisting of cyclopropyl, cyclopentyl and cyclohexyl. Often, the halo is fluoro, chloro or bromo. Therefore, each second substituent is often independently selected from the group consisting of hydroxy, methyl, ethyl, n-propyl, isopropyl, n-butyl, sec-butyl, isobutyl, tert-butyl, cyclopropyl, cyclopentyl, cyclohexyl, fluoro, chloro and bromo. Typically, the halo is fluoro or chloro. Therefore, each second substituent is commonly independently selected from the group consisting of hydroxy, methyl, ethyl, n-propyl, isopropyl, n-butyl, sec-butyl, isobutyl, tert-butyl, cyclopropyl, cyclopentyl, cyclohexyl, fluoro and chloro.

Sometimes, each second substituent is independently selected from the group consisting of hydroxy, methyl, ethyl, isopropyl, tert-butyl, fluoro, chloro and bromo. Often, each second substituent is independently selected from the group consisting of hydroxy, methyl, ethyl, isopropyl, tert-butyl, fluoro and chloro. Typically, each second substituent is independently selected from the group consisting of hydroxy, methyl, fluoro and chloro. For example, Z may be a phenyl ring substituted by two methyl groups positioned ortho to X, and further substituted by a fluoro positioned para to X. Typically, each second substituent is selected from any one or a combination of hydroxy, methyl or fluoro. Most typically, each second substituent is hydroxy.

Z is often a phenyl ring optionally substituted at one to three carbon atoms with a second substituent, each second substituent independently selected from the group consisting of hydroxy, methyl, ethyl, isopropyl, tert-butyl, fluoro and chloro; a pyridyl ring optionally substituted at one carbon atom with a hydroxy; a $C_1$-$C_6$alkyl; or a $C_3$-$C_6$cycloalkyl.

Sometimes, C-A-X of formula (I) is any one of formulae (Ia), (Ib), (Ic), (Id) or (Id'):

(Ia)

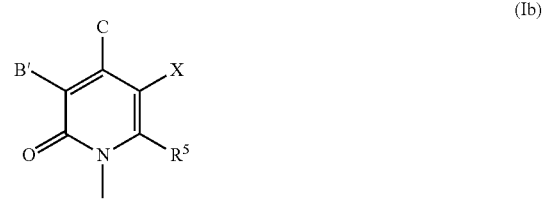

(Ib)

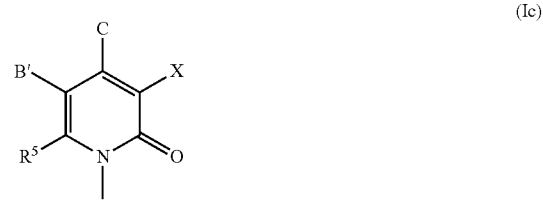

(Ic)

(Id)

-continued (Id')

wherein $A_1$ is $CR^1$ or N, $A_2$ is $CR^2$ or N, $A_3$ is $CR^3$ or N, $A_4$ is $CR^4$, $A_5$ is $CR^5$ or N and $A_6$ is $CR^5$ or N;

$R^1$ is H or hydroxy;

$R^2$ is H, hydroxy, $C_3$-$C_6$cycloalkyl, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $C_1$-$C_5$alkyloxy or $C_1$-$C_5$alkylamino;

$R^3$ and $R^4$ are independently selected from the group consisting of H, hydroxy, $C_3$-$C_6$cycloalkyl, halo, $C_1$-$C_5$alkyloxy or $C_1$-$C_5$alkylamino;

with the proviso that at least one of $R^1$, $R^2$, $R^3$ or $R^4$ is hydroxy;

B' is H or hydroxy; and $R^5$ is either H or the first substituent, defined above.

Sometimes, C-A-X of formula (I) is any one of formulae (Ia), (Ib), (Ic) or (Id):

(Ia)

(Ib)

(Ic)

(Id)

wherein $A_1$ is $CR^1$ or N, $A_2$ is $CR^2$ or N, $A_3$ is $CR^3$ or N and $A_4$ is $CR^4$;

$R^1$ is H or hydroxy;

$R^2$ is H, $C_1$-$C_6$alkyl, $C_3$-$C_6$cycloalkyl, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $C_1$-$C_5$alkyloxy or $C_1$-$C_5$alkylamino;

$R^3$ and $R^4$ are independently selected from the group consisting of H, hydroxy, $C_3$-$C_6$cycloalkyl, halo, $C_1$-$C_5$alkyloxy or $C_1$-$C_5$alkylamino;

with the proviso that at least one of $R^1$, $R^3$ or $R^4$ is hydroxy;

B' is H or hydroxy; and $R^5$ is either H or the first substituent, defined above.

Typically, $R^2$ is H, $C_1$-$C_3$alkyl, halo, $SO_2C_1$-$C_4$alkyl or $NHSO_2C_1$-$C_4$alkyl; and $R^3$ and $R^4$ are independently selected from the group consisting of H, hydroxy, $C_1$-$C_3$alkyl and halo. Often, $R^2$ is H, fluoro, chloro, $SO_2CH_3$ or $NHSO_2CH_3$; and $R^3$ and $R^4$ are independently selected from the group consisting of H, hydroxy, $C_1$-$C_3$alkyl and fluoro or chloro.

Typically, $R^5$ is H.

Often, when CAX is represented by formula (Ia), Z is a phenyl ring, optionally substituted at one or more carbon atoms with the second substituent; a $C_1$-$C_6$alkyl; or a $C_3$-$C_6$cycloalkyl; and when CAX is represented by any one of formulae (Ib), (Ic) and (Id), Z is a phenyl or pyridyl ring, optionally substituted at one or more carbon and/or nitrogen atoms with the second substituent; a $C_1$-$C_6$alkyl; or a $C_3$-$C_6$cycloalkyl.

Often, when CAX is represented by formula (Ia), Z is a phenyl ring, optionally substituted at one or more carbon atoms with the second substituent; a $C_1$-$C_6$alkyl; or a $C_3$-$C_6$cycloalkyl; and when CAX is represented by any one of formulae (Ib), (Ic), (Id) and (Id'), Z is a phenyl or pyridyl ring, optionally substituted at one or more carbon and/or nitrogen atoms with the second substituent; a $C_1$-$C_6$alkyl; or a $C_3$-$C_6$cycloalkyl.

Typically, when CAX is represented by formula (Ia), Z is an unsubstituted phenyl ring; and when CAX is represented by any one of formulae (Ib), (Ic) and (Id), Z is a phenyl or pyridyl ring, optionally substituted at one or more carbon and/or nitrogen atoms with the second substituent, each second substituent independently selected from the group consisting of hydroxy, methyl, fluoro and chloro.

Typically, when CAX is represented by formula (Ia), Z is an unsubstituted phenyl ring; and when CAX is represented by any one of formulae (Ib), (Ic), (Id) and (Id'), Z is a phenyl or pyridyl ring, optionally substituted at one or more carbon and/or nitrogen atoms with the second substituent, each second substituent independently selected from the group consisting of hydroxy, methyl, fluoro and chloro. Often, the compound is any one of formulae (Ie) to (Ili):

(Ie)

(If)
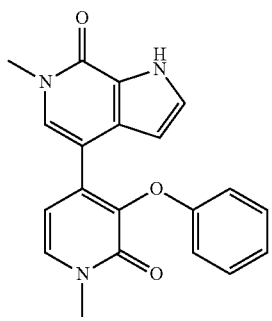
(Ig)
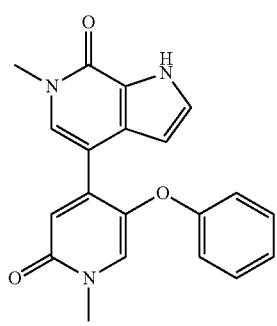
(Ih)
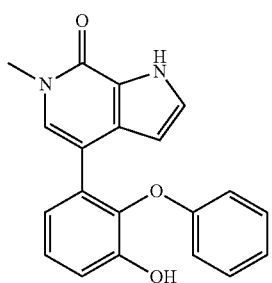
(Ii)
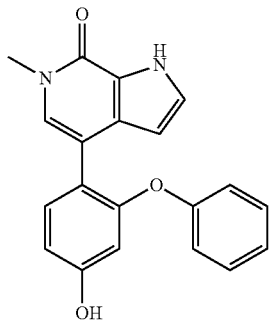
(Ij)
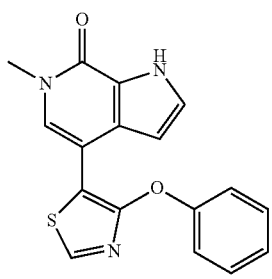
(Ik)
(Il)
(Im)
(In)
(Io)

19
-continued
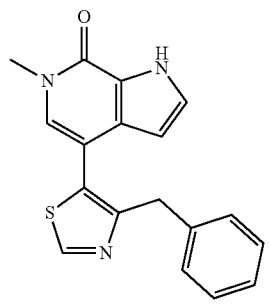
(Ip)
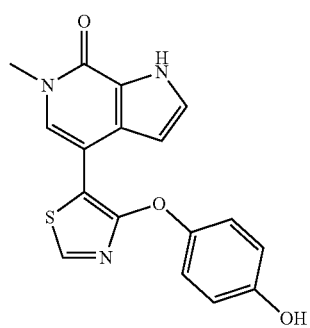
(Iq)
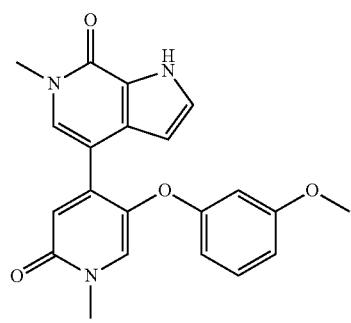
(Ir)
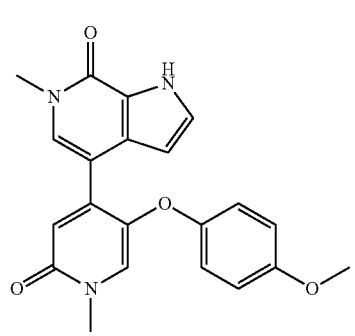
(Is)
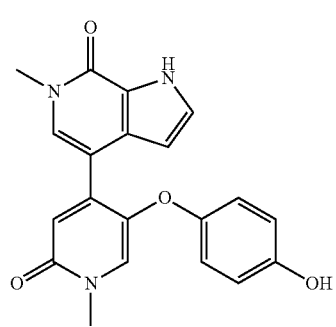
(It)
20
-continued
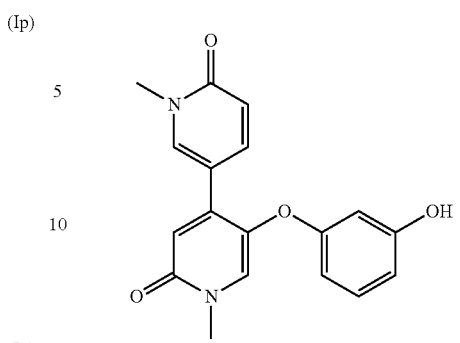
(Iu)
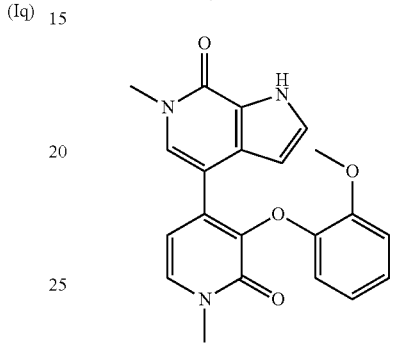
(Iv)
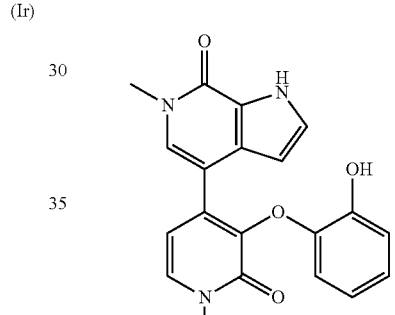
(Iw)
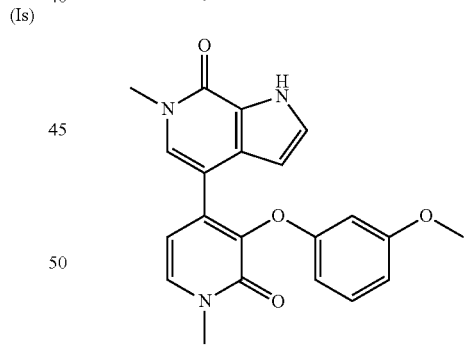
(Ix)
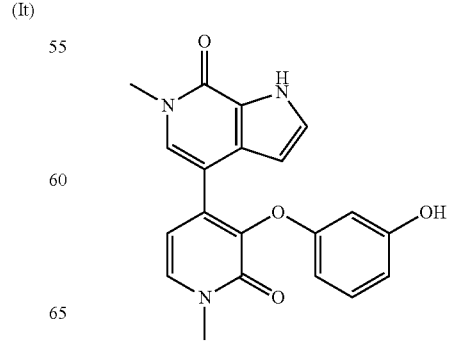
(Iy)

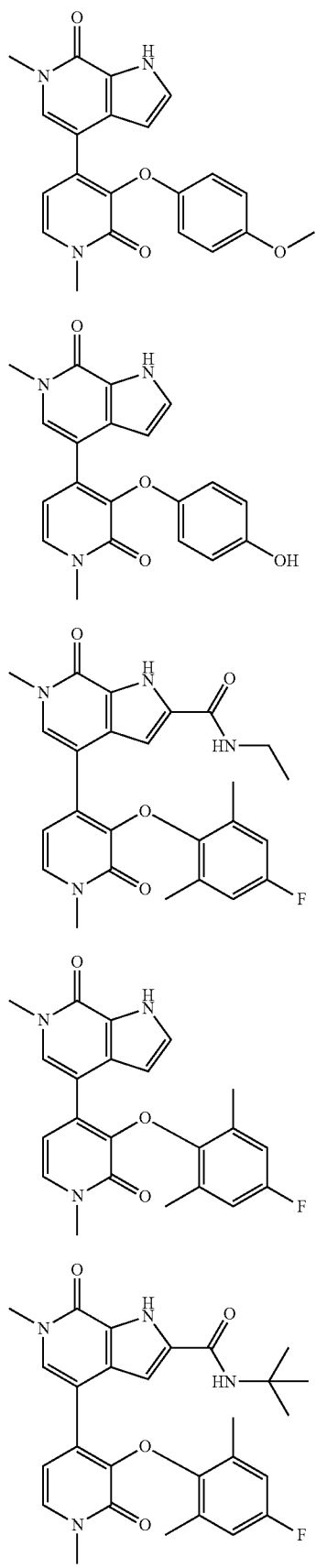
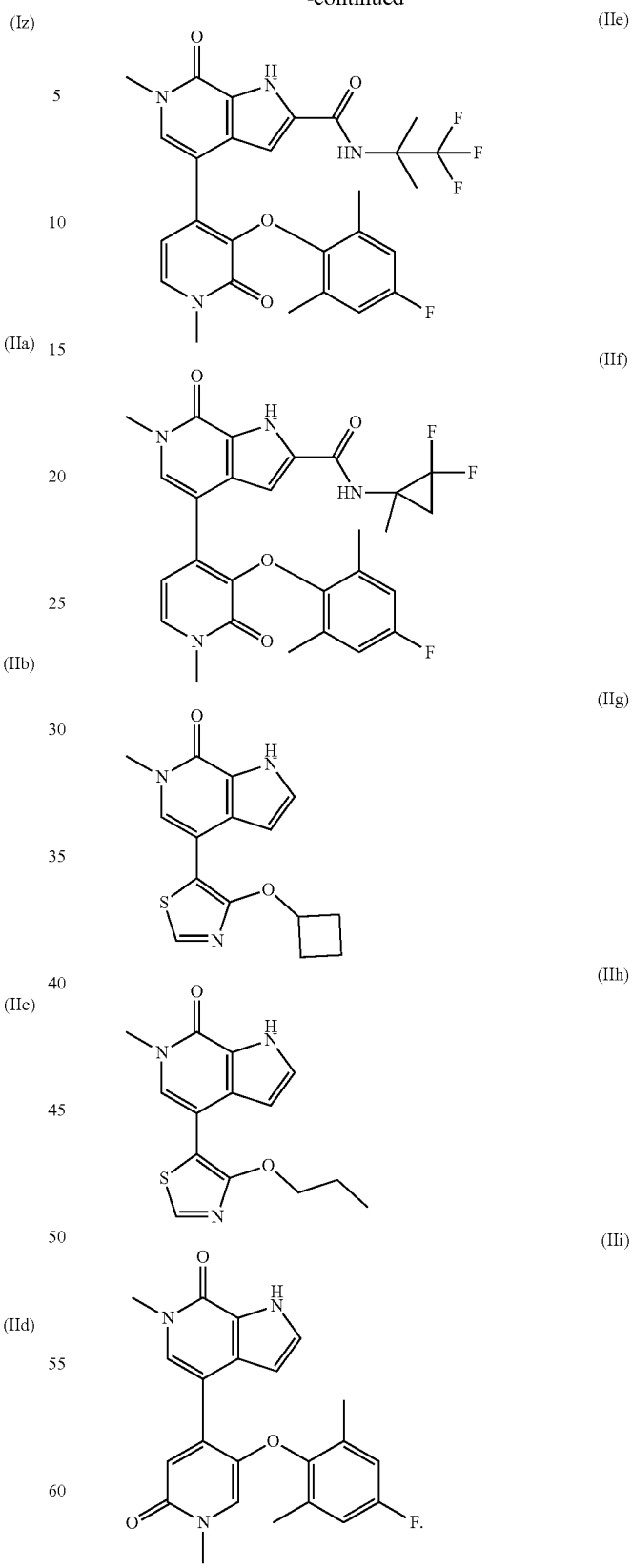
Commonly, the compound is any one of formulae (Ie), (If), (Ig), (Ih), (Ii), (Ij) or (Ik). Typically, the compound is of formula (Ih) or (IIb).

The compounds described herein may be in the form of a pharmaceutically acceptable salt. The term "pharmaceutically acceptable salt" is intended to define organic and/or inorganic salts that are pharmaceutically useful. The compounds of the invention may be isolated from reaction mixtures as pharmaceutically acceptable salts. Alternatively, the pharmaceutically acceptable salt may be prepared in situ during the final isolation and purification of compounds of the invention by reacting a carboxylic acid-containing moiety with a suitable base such as a hydroxide, carbonate or bicarbonate of a pharmaceutically acceptable metal cation, or with ammonia or a primary, secondary or tertiary amine. Pharmaceutically acceptable salts include cations based on alkali metals or alkaline earth metals such as lithium, sodium, potassium, calcium, magnesium and aluminium salts and nontoxic quaternary ammonia and amine cations including ammonium, tetramethylammonium, tetraethylammonium, methylamine, dimethylamine, trimethylamine, triethylamine, diethylamine, and ethylamine. Other examples of organic amines useful for the formation of base addition salts include ethylenediamine, ethanolamine, diethanolamine, piperidine, and piperazine.

The pharmaceutically acceptable salt may also be prepared by treatment of the compound of the invention with a suitable acid, for example, hydrogen chloride, hydrogen bromide, hydrogen iodide, sulfuric acid, phosphoric acid, acetic acid, trifluoroacetic acid, propionic acid, glycolic acid, maleic acid, malonic acid, methanesulfonic acid, fumaric acid, succinic acid, tartaric acid, citric acid, benzoic acid and ascorbic acid.

The compounds of the invention may exist in different stereoisomeric forms. All stereoisomeric forms and mixtures thereof, including enantiomers and racemic mixtures, are included within the scope of the invention. Such stereoisomeric forms include enantiomers and diastereoisomers. Individual stereoisomers of compounds of the invention, i.e., associated with less than 5%, preferably less than 2% and in particular less than 1% of the other stereoisomer, are included. Mixtures of stereoisomers in any proportion, for example a racemic mixture comprising substantially equal amounts of two enantiomers are also included within the invention.

Also included are solvates and isotopically-labelled compounds of the invention. Isotopically-labelled compounds are identical to those recited herein, but for the fact that one or more atoms are replaced by an atom having an atomic mass or mass number different from the atomic mass or mass number predominantly found in nature. Examples of isotopes that can be incorporated into compounds of the invention include isotopes of hydrogen, carbon, nitrogen, oxygen, sulfur, fluorine and chlorine, such as $^{2}H$, $^{3}H$, $^{13}O$, $^{14}O$, $^{15}N$, $^{18}O$, $^{17}O$, $^{35}S$, $^{18}F$, and $^{36}Cl$, respectively.

In a further aspect, intermediates suitable for production of compounds of the invention are included. Specifically, intermediates of formulae (ia) to (ip) are included.

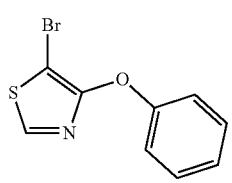

(ia)

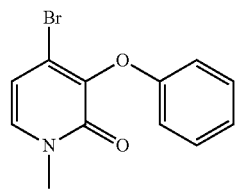

(ib)

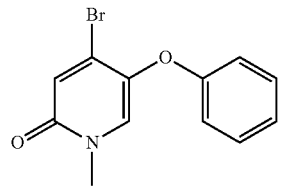

(ic)

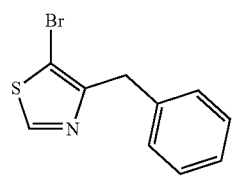

(id)

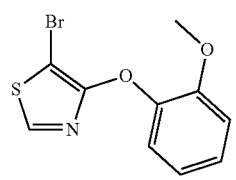

(ie)

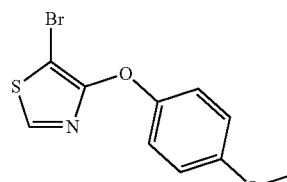

(ig)

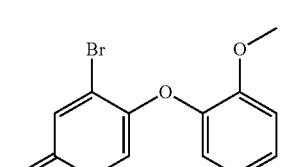

(ig)

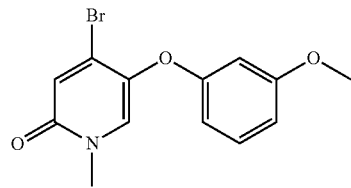

(ih)

(ii)

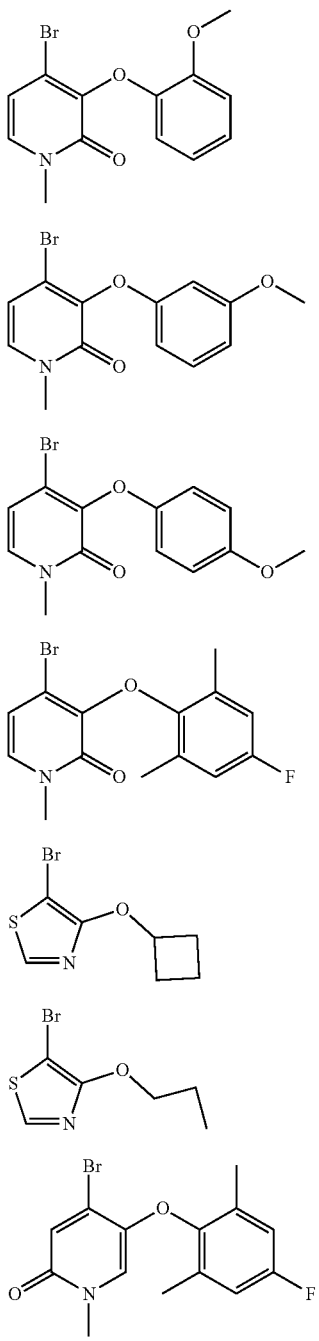

Intermediates may be of formula (ig), (ii), (ij), (ik), or (if). Often, intermediates are of formula (ia) to (id), (if), or (ih) to (ip). Typically, intermediates are of formula (im).

Prodrugs of the compounds and compositions of the invention are also within the scope of the invention. Upon administration to a subject, a prodrug undergoes conversion by metabolic or other chemical processes to yield a compound of the invention.

All amorphous and crystalline forms of the compounds of the invention are included.

Whilst it is possible for the compounds to be administered alone, it is typical to use a pharmaceutical composition. The second aspect provides a pharmaceutical composition comprising any one or a combination of the compounds defined in the first aspect, in combination with one or more pharmaceutically acceptable excipients. The excipient may aid transport of a compound to the site in the body where it is intended to act, for example by increasing the rate of dissolution of the compound into the blood stream or by increasing the stability of the compound in order to delay its release, in order to increase its efficiency and prevent damage to tender tissues. Alternatively, the excipient may be for identification purposes, or to make the compound more appealing to the patient, for example by improving its taste, smell and/or appearance. Typically, the excipient makes up the bulk of the pharmaceutical composition.

Excipients include diluents or fillers, binders, disintegrants, lubricants, colouring agents and preservatives. Diluents or fillers are inert ingredients that may affect the chemical and physical properties of the final composition. If the dosage of the compound of the invention is small then more diluents will be required to produce a composition suitable for practical use. If the dosage of the compound of the invention is high then fewer diluents will be required.

Binders add cohesiveness to powders in order to form granules, which may form a tablet. The binder must also allow the tablet to disintegrate upon ingestion so that the compound of the invention dissolves. Disintegration of the composition after administration may be facilitated through the use of a disintegrant.

An extensive overview of pharmaceutically acceptable excipients is described in the *Handbook of Pharmaceutical Excipients*, 6$^{th}$ Edition; Editors R. C. Rowe, P. J. Sheskey and M. E. Quinn, The Pharmaceutical Press, London, American Pharmacists Association, Washington, 2009. Any suitable pharmaceutically acceptable excipient is within the scope of the invention.

Pharmaceutical compositions include those suitable for oral, nasal, topical (including buccal, sublingual and transdermal), parenteral (including subcutaneous, intravenous and intramuscular) or rectal administration. In some embodiments, the pharmaceutical composition is suitable for topical or oral administration, i.e. the pharmaceutical composition is a topical or oral formulation.

The pharmaceutical compositions may be compressed into solid dosage units, such as tablets, or be processed into capsules or suppositories. The pharmaceutical compositions may also be injected and may be prepared in the form of a solution, suspension or emulsion for such an application. Alternatively, the pharmaceutical compositions may be administered as a spray, including a nasal or buccal spray. Otherwise, the pharmaceutical compositions may be processed into a gel, cream, patch, implant or any other preparation for immediate and/or sustained release. Typically, the pharmaceutical compositions are processed into a gel, cream, lotion, foam or ointment for topical administration; or a tablet, capsule or buccal spray for oral administration.

The third aspect of the invention provides a compound of the first aspect or a pharmaceutical composition of the second aspect for use as a medicament. Specifically, the compounds are useful in the treatment of diseases or conditions associated with the activity of Bromodomain and Extra-Terminal proteins. In the fifth aspect, there is provided a compound of the first aspect or a pharmaceutical composition of the second aspect for use in the inhibition of Bromodomain and Extra-Terminal proteins. Diseases or conditions associated with the activity of Bromodomain and Extra-Terminal proteins include inflammatory skin disorders, respiratory diseases, gastrointestinal diseases, eye diseases, cancers, rheumatic diseases, demyelinating diseases and fibrotic diseases. Therefore, in the fourth aspect, the invention provides a compound of the invention or a pharmaceutical composition of the invention for use in a method of treatment or prophylaxis of inflammatory skin disorders, respiratory diseases, gastrointestinal diseases, eye diseases, cancers, rheumatic diseases, demyelinating diseases and fibrotic diseases and in the sixth aspect, the invention provides a method for the treatment or prophylaxis of skin disorders, respiratory diseases, gastrointestinal diseases, eye diseases, cancers, rheumatic diseases, demyelinating diseases and fibrotic diseases, said method comprising administering to a subject, an effective amount of a compound of the first aspect, or a pharmaceutical composition of the second aspect.

Inflammatory diseases rely on T helper cells $Th_1$, $Th_2$ and $Th_{17}$ for innate and adaptive immunity responses which affect either or both of the acute or chronic stages of the disease. Many cytokine and chemokines are upregulated in an inflammatory disease and the ability to reduce the levels of these inflammatory markers is evidence of the ability of a drug to ameliorate a disease. Such cytokine and chemokines include but are not limited to granulocyte-macrophage colony-stimulating factor (GM-CSF); interleukins IL-1, IL-2, IL-4, IL-6, IL-8, IL-13, IL-17, IL-22; chemokine (c-c motif) ligands CCL2, CCL27 and CCL20; tumour necrosis factor alpha (TNF-α); thymic stromal lymphopoietin (TSLP); and chemokine (c-x-c motif) ligand 9 (CXCL9).

Pan-BET inhibitors may be of value in the treatment of inflammatory disorders. These include skin disorders such as alopecia areata, Atopic dermatitis, bullous diseases, dermatitis, dermatitis herpetiformis, dermatomyositis, vitiligo, contact dermatitis, psoriasis, rosacea, scleroderma, xerosis, urticarial and chronic idiopathic pruritus and vitiligo; respiratory diseases such as asthma, chronic obstructive pulmonary disease, pulmonary fibrosis, cystic fibrosis, rhinitis, bronchiolitis, byssinosis, pneumoconiosis, bronchiectasis, hypersensitivity pneumonitis, mesothelioma, sarcoidosis; gastrointestinal diseases such as inflammatory bowel disease, ulcerative colitis, Crohn's disease, retroperitoneal fibrosis, celiac disease and gastrointestinal cancers; eye diseases such as myasthenia gravis, Sjögran's syndrome, conjunctivitis, scleritis, uveitis, dry eye syndrome, keratitis and iritis; systemic indications like Addison's disease, acute gout, ankylosing spondylitis, atherosclerosis, Behcet's disease, giant cell arthritis, glomerulonephritis, hepatitis, hypophysitis, lupus nephritis, Kawasaki disease, multiple sclerosis, myocarditis, myositis, nephritis, osteoarthritis, pancreatitis, pericarditis, polyarteritis nodosa, pneumonitis, primary biliary cirrhosis, psoriatic arthritis, rheumatoid arthritis, scleroderma (cutaneous or systemic), scleritis, sclerosing cholangitis, sepsis, systemic lupus erythematosus, Takayasu's arteritis, toxic shock, thyroiditis, type 1 diabetes and complications from diabetes, uvenitis, vasculitis and Wegener's granulomatosis; as well as other autoimmune diseases and indications where immunosuppression would be desirable for instance in organ transplantation. BET inhibitors are also known to affect the growth or survival of a range of cancers, specifically skin and systemic cancers, and may be useful for the treatment of acoustic neuroma, acute leukaemia, acute lymphocytic leukaemia, acute myelocytic leukaemia (monocyctic, myeloblastic, adenocarcinoma, angiosarcoma, astrocytoma, myelomonocytic and promyelocytic), acute t-cell leukaemia, basal cell carcinoma, bile duct carcinoma, bladder cancer, brain cancer, breast cancer, bronchogenic carcinoma, cervical cancer, chondrosarcoma, chordoma, choriocarcinoma, chronic leukaemia, chronic lymphocytic leukemia, chronic myelocytic (granulocytic) leukaemia, chronic myelogenous leukaemia, colon cancer, colorectal cancer, craniopharyngioma, cystadenocarcinoma, cutaneous T-cell lymphoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukaemia, liposarcoma, lung cancer, lymphagioendotheliosarcoma, lymphangiosarcoma, lymphoblastic leukaemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukaemia, lymphoma, medullary carcinoma, medulloblastoma, melanoma, meningioma, mesothelioma, multiple myeloma, myelogenous leukaemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumours, uterine cancer, and Wilms' tumor.

BET inhibitors may also be of use in the treatment of obesity, dyslipidaemia, hypercholesterolemia, Alzheimer's disease, metabolic syndrome, hepatic steatosis, type II diabetes, insulin resistance, diabetic retinopathy or diabetic neuropathy.

The seventh aspect provides a method of inhibiting Bromodomain and Extra-Terminal protein activity in a subject, said method comprising administering to a subject an effective amount of a compound of the first aspect, or a pharmaceutical composition of the second aspect.

An effective amount of the compound may be administered to a subject topically, parenterally or enterally. The compound may be administered parenterally, sometimes by direct injection, which is typically intramuscular, subcutaneous or intravenous. Typically, however, the compound is administered topically to the skin or mucous membranes via a cream, gel, foam, lotion or ointment, or enterally via a tablet, capsule or buccal spray.

The subject may, and typically is, a human, and may be suffering from or liable to suffer from inflammatory skin disorders, respiratory diseases, gastrointestinal diseases and eye diseases. Treatment of said subject may comprise administering an effective amount of a compound of the invention. The term "effective amount" denotes an amount of the compound that ameliorates the above-noted diseases and thus produces the desired therapeutic or inhibitory effect.

The skilled person is aware that an effective amount is likely to vary with the particular compound of the invention, the subject and the administration procedure used. It is within the means and capacity of the skilled person to identify the effective amount of the compounds and compositions of the invention via routine work and experimentation.

Any discussion herein of documents, acts, materials, devices, articles or the like is not to be taken as an admission that any or all of these matters form part of the prior art base or were common general knowledge in the field relevant to the present disclosure as it existed before the priority date of each claim of this application.

It will be appreciated by those skilled in the art that numerous variations and/or modifications may be made to the invention as described herein without departing from the scope of the invention as described. The present embodiments are therefore to be considered for descriptive purposes and are not restrictive, and are not limited to the extent of that described in the embodiment. The person skilled in the art is to understand that the present embodiments may be read alone, or in combination, and may be combined with any one or a combination of the features described herein. The subject-matter of each patent and non-patent literature reference cited herein is hereby incorporated by reference in its entirety.

The aspects and embodiments of this disclosure are further described in the following clauses:

1. A compound of formula (I):

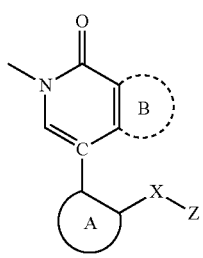

(I)

wherein ring structure A is a 5- or 6-membered aromatic or heteroaromatic ring, optionally substituted at one or more carbon and/or heteroatoms with a first substituent;
wherein each first substituent is independently selected from the group consisting of hydroxy, oxo, $C_1$-$C_6$alkyl, $C_3$-$C_6$cycloalkyl, $C_1$-$C_6$alkylol, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $SO_2C_1$-$C_4$alkylol, $NHSO_2C_1$-$C_4$alkylol, $C_1$-$C_5$alkyloxy, $C_1$-$C_5$alkylamino, $SO_2NH_2$, $CONH_2$, $CONHC_1$-$C_4$alkyl, $NHCOC_1$-$C_4$alkyl, $NHSO_2N(C_1$-$C_4$alkyl$)_2$, $C_1$-$C_6$fluoroalkyl, $SO_2C_1$-$C_4$fluoroalkyl, $NHSO_2C_1$-$C_4$fluoroalkyl, $C_1$-$C_5$fluoroalkyloxy, and $C_1$-$C_5$fluoroalkylamino;
X is O, $CR_2$, NR' or S, wherein R is individually selected from the group consisting of H, $C_1$-$C_4$alkyl and halo, and R' is selected from the group consisting of $C_1$-$C_4$alkyl and H;
Z is a 5- or 6-membered aromatic or heteroaromatic ring, $C_1$-$C_6$alkyl, $C_3$-$C_6$cycloalkyl, $CR^AR^BR^C$, $C_2$-$C_5$oxacycloalkyl, $C_2$-$C_5$azacycloalkyl or morpholinyl, optionally substituted at one or more carbon and/or heteroatoms with a second substituent;
wherein $R^A$ is a $C_3$-$C_5$cycloalkyl, $R^B$ is a $C_3$-$C_5$cycloalkyl, methyl or ethyl, and $R^C$ is OH; and
each second substituent is independently selected from the group consisting of hydroxy, $C_1$-$C_6$alkyl, $C_3$-$C_6$cycloalkyl, halo, $C_1$-$C_5$alkyloxy, $C_1$-$C_5$alkylamino, oxo, cyano, $C_1$-$C_6$fluoroalkyl, $C_1$-$C_5$fluoroalkyloxy, and $C_1$-$C_5$fluoroalkylamino;
ring structure B is optionally present; wherein when ring structure B is present, it is an optionally substituted pyrrole bonded such that C is in the 4 position relative to NH; wherein the pyrrole is optionally substituted at position 2 with a third substituent;
wherein the third substituent is selected from the group consisting of $CONHC_1$-$C_4$alkyl, $CONH_2$, $CONHC_1$-$C_6$fluoroalkyl, $CONHC_3$-$C_6$cycloalkyl optionally substituted at one or more carbon atoms with a methyl or ethyl; $CONHC_3$-$C_5$cyclofluoroalkyl optionally substituted at one or more carbon atoms with a methyl or ethyl, $NHCOC_1$-$C_4$alkyl and $NHCOC_1$-$C_4$fluoroalkyl;
with the proviso that when A is 6-membered, it is substituted at least once with a hydroxy or oxo group.

2. The compound of clause 1, wherein the third substituent is selected from the group consisting of $CONHC_1$-$C_4$alkyl, $CONH_2$, $CONHC_1$-$C_6$fluoroalkyl, $CONHC_3$-$C_5$cycloalkyl; $CONHC_3$-$C_5$cyclofluoroalkyl, $NHCOC_1$-$C_4$alkyl and $NHCOC_1$-$C_4$fluoroalkyl.

3. The compound of clause 1 or clause 2, wherein when A is 6-membered, it is substituted at least once with a hydroxy group positioned ortho or meta to X, or an oxo group.

4. The compound of any one preceding clause, wherein the third substituent is $CONHC_1$-$C_4$alkyl.

5. The compound of any one preceding clause, wherein the third substituent is CONHethyl.

6. The compound of any one of clauses 1 to 3, wherein the compound is of formula (II):

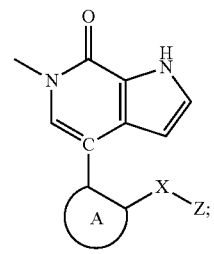

(II)

wherein A, X and Z are as defined for formula (I).

7. The compound of any preceding clause wherein A is selected from the group consisting of benzene, pyridine, thiazole, pyridone, pyrazole, imidazole and 1,2,4-triazole, optionally substituted at one or more carbon and/or heteroatoms with the first substituent.

8. The compound of clause 7 wherein the pyrazole carbon at position 5 is bound to C and the pyrazole nitrogen at position 1 is bound to X.

9. The compound of clause 7 or clause 8 wherein the imidazole carbon at position 2 is bound to C and the nitrogen at position 1 is bound to X.

10. The compound of any one of clauses 7 to 9 wherein the 1,2,4-triazole carbon at position 5 is bound to C and the nitrogen at position 1 is bound to X.

11. The compound of any one of clauses 1 to 6 wherein A is selected from the group consisting of benzene, pyridine, thiazole and pyridone, optionally substituted at one or more carbon and/or heteroatoms with the first substituent.

12. The compound of any one of clauses 7 to 11 wherein the pyridone is a 2-pyridone.

13. The compound of clause 12 wherein the 2-pyridone carbon at position 3 is bound to X and the 2-pyridone carbon at position 4 is bound to C; or the 2-pyridone carbon at position 5 is bound to X and the 2-pyridone carbon at position 4 is bound to C.

14. The compound of any one of clauses 7 to 13 wherein the thiazole carbon at position 4 is bound to C and the thiazole carbon at position 5 is bound to X.

15. The compound of any one preceding clause wherein each first substituent is independently selected from the group consisting of hydroxy, oxo, $C_1$-$C_6$alkyl, $C_3$-$C_6$cycloalkyl, $C_1$-$C_6$alkylol, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $SO_2C_1$-$C_4$alkylol, $NHSO_2C_1$-$C_4$alkylol, $C_1$-$C_5$alkyloxy and $C_1$-$C_5$alkylamino.

16. The compound of any one preceding clause wherein each first substituent is independently selected from the group consisting of hydroxy, oxo, $C_1$-$C_6$alkyl, $C_3$-$C_6$cycloalkyl, $C_1$-$C_6$alkylol and halo.

17. The compound of any one preceding clause wherein each first substituent is independently selected from the group consisting of hydroxy, oxo, methyl and halo.

18. The compound of any one preceding clause wherein R is individually selected from the group consisting of H, methyl and halo, and R' is selected from the group consisting of methyl and H.

19. The compound of any one preceding clause wherein halo is fluoro or chloro.

20. The compound of any one preceding clause wherein R is individually selected from the group consisting of H, methyl and fluoro, and R' is methyl.

21. The compound of any one preceding clause wherein X is O.

22. The compound of any one preceding clause wherein Z is a 5- or 6-membered aromatic or heteroaromatic ring, $C_1$-$C_6$alkyl, or $C_3$-$C_6$cycloalkyl, optionally substituted on one or more carbon or heteroatoms with a second substituent.

23. The compound of any one preceding clause wherein Z is a 6-membered aromatic or heteroaromatic ring, $C_1$-$C_6$alkyl, or $C_3$-$C_6$cycloalkyl, optionally substituted on one or more carbon or heteroatoms with a second substituent.

24. The compound of any one preceding clause, wherein Z is a 5- or 6-membered aromatic or heteroaromatic ring, optionally substituted on one or more carbon or heteroatoms with a second substituent 25. The compound of any one preceding clause, wherein Z is a 6-membered aromatic or heteroaromatic ring, optionally substituted on one or more carbon or heteroatoms with a second substituent 26. The compound of any one preceding clause wherein Z is a phenyl or pyridyl ring, optionally substituted at one or more carbon and/or nitrogen atoms with a second substituent.

27. The compound of any one preceding claim wherein Z is a phenyl ring, optionally substituted at one or more carbon and/or nitrogen atoms with a second substituent.

28. The compound of any one preceding clause wherein each second substituent is independently selected from the group consisting of hydroxy, $C_1$-$C_6$alkyl, $C_3$-$C_6$cycloalkyl, halo, $C_1$-$C_5$alkyloxy, $C_1$-$C_5$alkylamino, oxo and cyano.

29. The compound of any one preceding clause wherein each second substituent is independently selected from the group consisting of hydroxy, $C_1$-$C_4$alkyl and halo.

30. The compound of any one preceding clause wherein the second substituent is hydroxy.

31. The compound of clause 27 wherein each second substituent is independently selected from the group consisting of methyl and fluoro.

32. The compound of clause 27 wherein Z is a phenyl ring substituted with two methyl groups positioned ortho to X and one fluoro positioned para to X.

33. The compound of any one preceding clause, wherein C-A-X of formula (I) is any one of formulae (Ia), (Ib), (Ic), (Id) or (Id'):

(Ia)

(Ib)

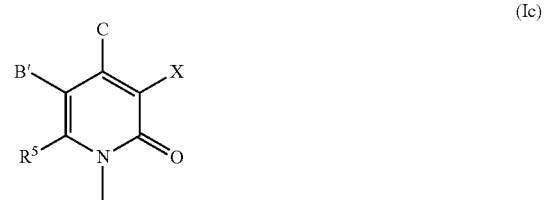

(Ic)

(Id)

(Id')

wherein $A_1$ is $CR^1$ or N, $A_2$ is $CR^2$ or N, $A_3$ is $CR^3$ or N, $A_4$ is $CR^4$, $A_5$ is $CR^5$ or N and $A_6$ is $CR^5$ or N;

$R^1$ is H or hydroxy;

$R^2$ is H, hydroxy, $C_1$-$C_6$alkyl, $C_3$-$C_6$cycloalkyl, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $C_1$-$C_5$alkyloxy or $C_1$-$C_5$alkylamino;

$R^3$ and $R^4$ are independently selected from the group consisting of H, hydroxy, $C_1$-$C_6$alkyl, $C_3$-$C_6$cycloalkyl, halo, $C_1$-$C_5$alkyloxy or $C_1$-$C_5$alkylamino;

with the proviso that at least one of $R^1$, $R^2$, $R^3$ or $R^4$ is hydroxy;

B' is H or hydroxy; and $R^5$ is either H or the first substituent, defined above.

34. The compound of any one preceding clause wherein C-A-X is any one of formulae (Ia), (Ib), (Ic) or (Id):

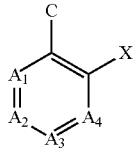

(Ia)

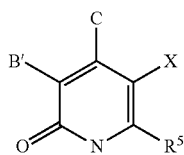

(Ib)

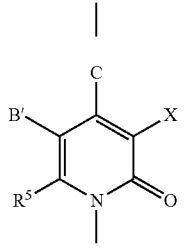

(Ic)

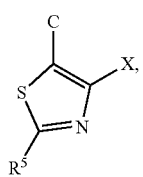

(Id)

wherein $A_1$ is $CR^1$ or N, $A_2$ is $CR^2$ or N, $A_3$ is $CR^3$ or N and $A_4$ is $CR^4$;

$R^1$ is H or hydroxy;

$R^2$ is H, $C_3$-$C_6$cycloalkyl, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $C_1$-$C_5$alkyloxy or $C_1$-$C_5$alkylamino;

$R^3$ and $R^4$ are independently selected from the group consisting of H, hydroxy, $C_3$-$C_6$cycloalkyl, halo, $C_1$-$C_5$alkyloxy or $C_1$-$C_5$alkylamino;

with the proviso that at least one of $R^1$, $R^3$ or $R^4$ is hydroxy;

B' is H or hydroxy; and $R^5$ is either H or the first substituent.

35. The compound of clause 33 or 34 wherein $R^2$ is H, $C_1$-$C_3$alkyl, halo, $SO_2C_1$-$C_4$alkyl or $NHSO_2C_1$-$C_4$alkyl; and $R^3$ and $R^4$ are independently selected from the group consisting of H, hydroxy, $C_1$-$C_3$alkyl and halo.

36. The compound of any one of clauses 33 to 35 wherein when CAX is represented by formula (Ia), Z is a phenyl ring, optionally substituted at one or more carbon atoms with a second substituent; and when CAX is represented by any one of formulae (Ib), (Ic), (Id) and (Id'), Z is a phenyl or pyridyl ring, optionally substituted at one or more carbon and/or nitrogen atoms with a second substituent.

37. The compound of any one of clauses 33 to 35 wherein when CAX is represented by formula (Ia), Z is an unsubstituted phenyl ring; and when CAX is represented by any one of formulae (Ib), (Ic), (Id) and (Id'), Z is a phenyl or pyridyl ring, optionally substituted at one or more carbon and/or nitrogen atoms with a second substituent selected from the group consisting of hydroxy, methyl, fluoro and chloro.

38. The compound of any one of clauses 33 to 37, wherein the compound is any one of:
(i) formula (Ia), (Id) or (Id'); or
(ii) formula (Ib) or (Ic).

39. The compound of any one of clauses 33 to 37, wherein the compound is any one of:
(i) formula (Ia) or (Id); or
(ii) formula (Ib) or (Ic).

40. The compound of clause 1, wherein the compound is any one of formulae (Ie) to (IIe):

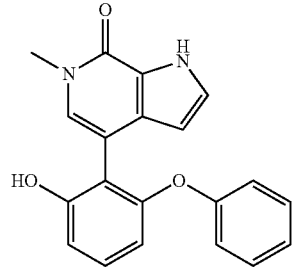

(Ie)

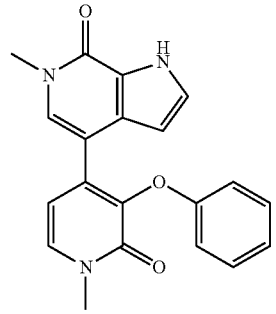

(If)

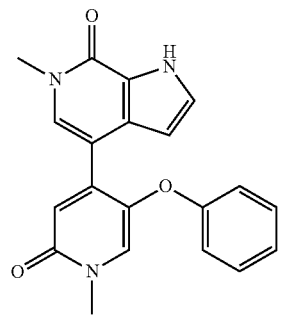

(Ig)

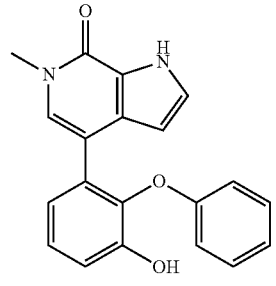

(Ih)

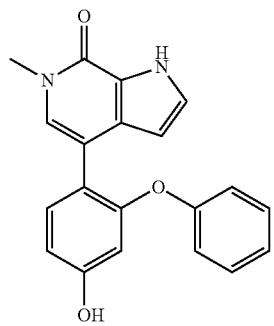
(Ii)
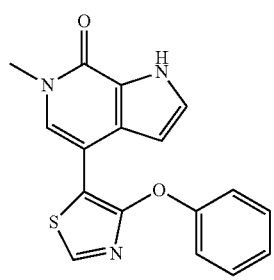
(Ij)
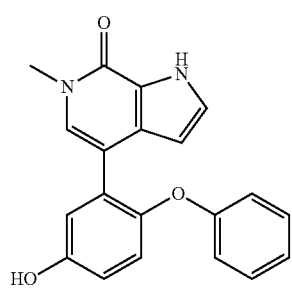
(Ik)
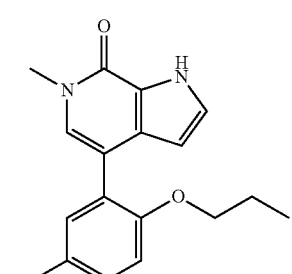
(Il)
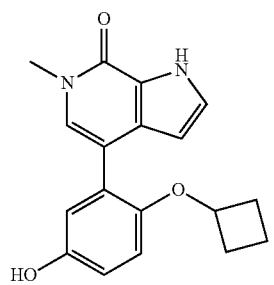
(Im)
(In)
(Io)
(Ip)
(Iq)
(Ir)

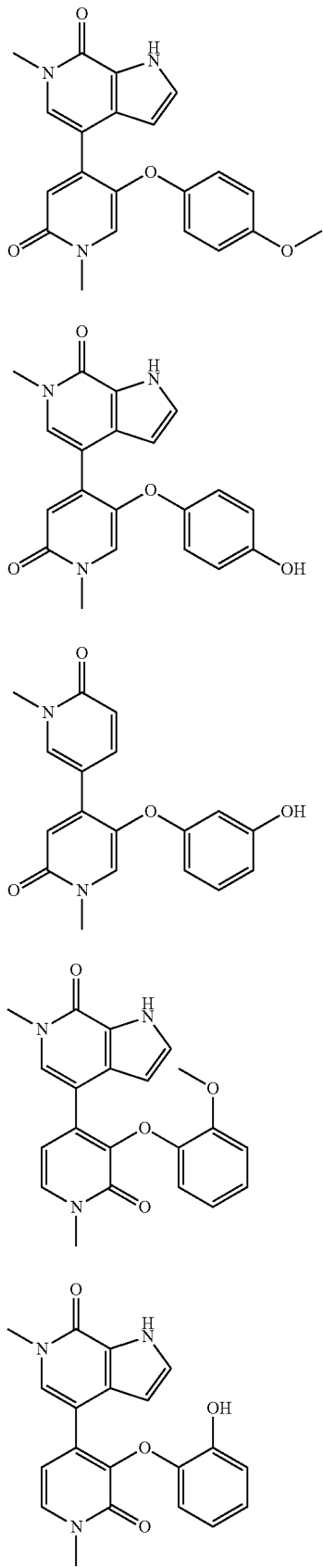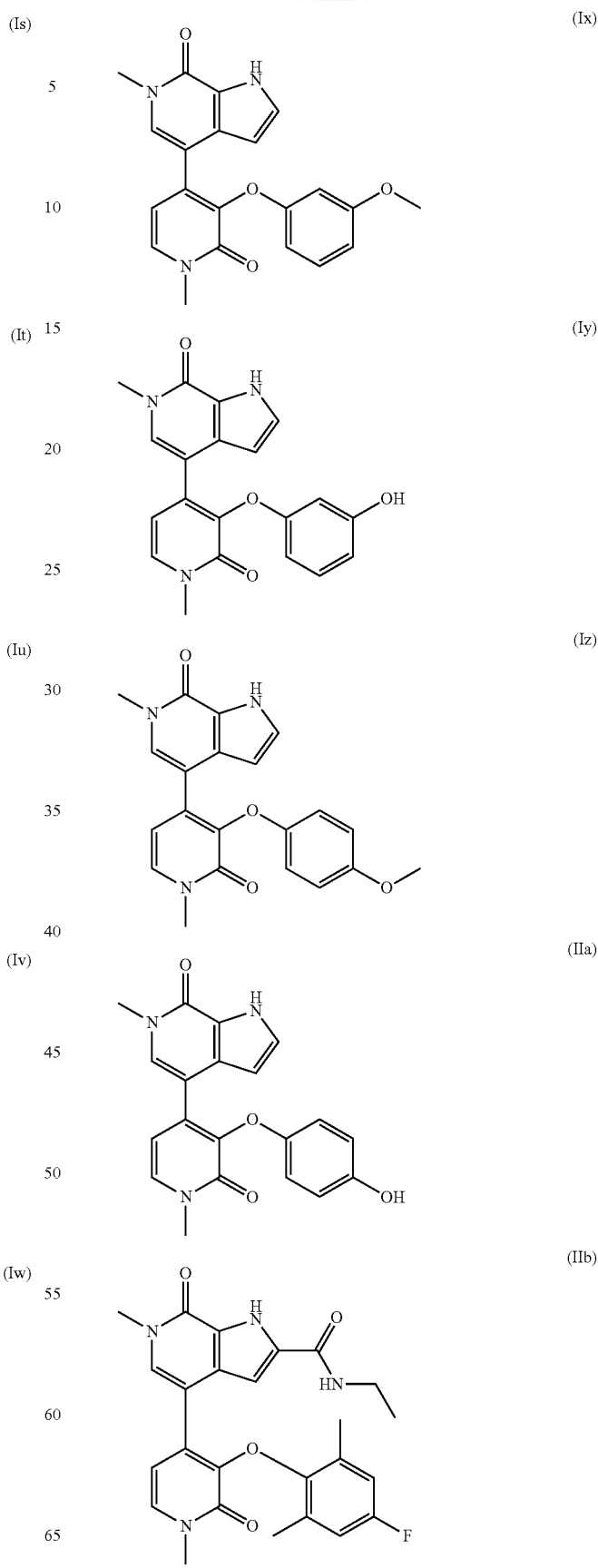

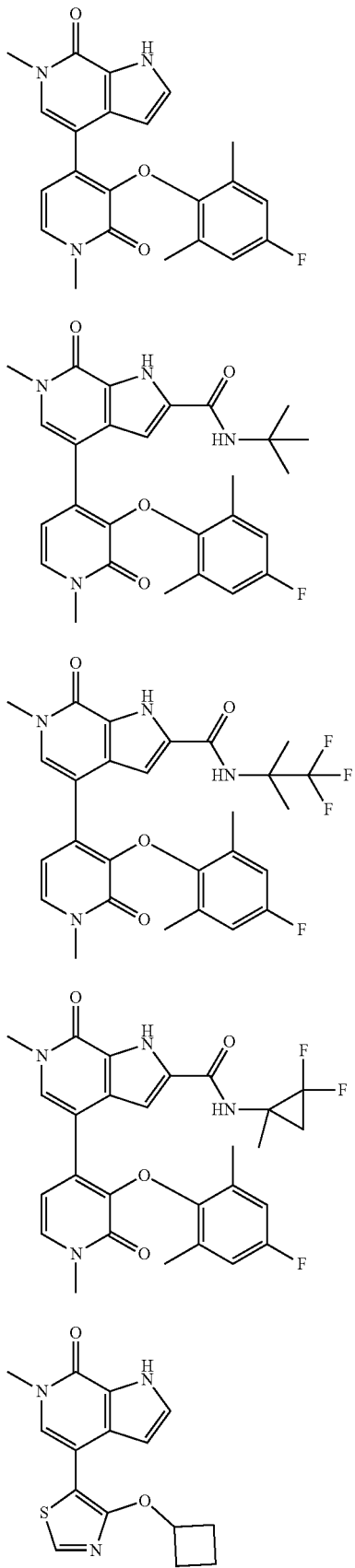

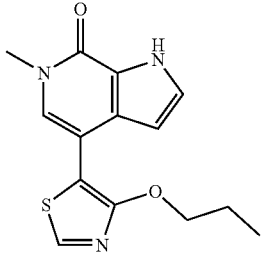

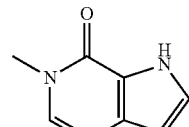

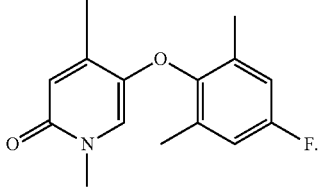

41. The compound of clause 40 wherein the compound is any one of formulae (Ie), (If), (Ig), (Ih), (Ii), (Ij) or (Ik).
42. The compound of any one preceding clause, in the form of a pharmaceutically acceptable salt.
43. The compound of formula (Ib) or (Ic), as defined in any one of clauses 33 to 41, in the form of a pharmaceutically acceptable salt.
44. The compound of formula (Ia), (Id) or (Id'), as defined in any one of clauses 33 to 41, in the form of a pharmaceutically acceptable salt.
44. The compound of formula (Ia) or (Id), as defined in any one of clauses 33 to 41, in the form of a pharmaceutically acceptable salt.
45. A pharmaceutical composition comprising any one or a combination of the compounds defined in any one of clauses 1 to 41, in combination with one or more pharmaceutically acceptable excipients.
46. The pharmaceutical composition of clause 45, wherein the pharmaceutical composition is a topical formulation.
47. A pharmaceutical composition comprising any one or a combination of the compounds of formula (Ia), (Id) or (Id'), as defined in any one of clauses 33 to 41, in combination with one or more pharmaceutically acceptable excipients.
48. A pharmaceutical composition comprising any one or a combination of the compounds of formula (Ia) or (Id), as defined in any one of clauses 33 to 41, in combination with one or more pharmaceutically acceptable excipients.
49. The pharmaceutical composition of clause 45, wherein the pharmaceutical composition is an oral formulation.
50. A pharmaceutical composition comprising any one or a combination of the compounds of formula (Ib) or (Ic), as defined in any one of clauses 33 to 41, in combination with one or more pharmaceutically acceptable excipients.
51. A compound as defined in any one of clauses 1 to 44, or a pharmaceutical composition as defined in any one of clauses 45 to 50, for use as a medicament.

52. A compound as defined in any one of clauses 1 to 44, or a pharmaceutical composition as defined in any one of clauses 45 to 50, for use in a method of treatment or prophylaxis of inflammatory skin disorders, respiratory diseases, gastrointestinal diseases, eye diseases, cancers, rheumatic diseases, demyelinating diseases and fibrotic diseases.

53. The compound or composition for the use of clause 52, wherein the use is in a method of treatment or prophylaxis of inflammation or cancer of the gut, skin or lung.

54. A compound as defined in any one of clauses 1 to 44, or a pharmaceutical composition as defined in any one of clauses 45 to 50, for use in the inhibition of Bromodomain and Extra-Terminal proteins.

55. A method for the treatment or prophylaxis of inflammatory skin disorders, respiratory diseases, gastrointestinal diseases, eye diseases, cancers, rheumatic diseases, demyelinating diseases and fibrotic diseases, said method comprising administering to a subject, an effective amount of a compound as defined in any one of clauses 1 to 44, or a pharmaceutical composition as defined in any one of clauses 45 to 50.

56. The method according to clause 55, wherein the method is for the treatment or prophylaxis of fibrosis of inflammation or cancer of the gut, skin or lung.

57. A method of inhibiting Bromodomain and Extra-Terminal protein activity in a subject, said method comprising administering to a subject an effective amount of a compound as defined in any one of clauses 1 to 44, or a pharmaceutical composition as defined any one of clauses 45 to 50.

The following are presented as non-limiting examples.

EXAMPLES

It has been found that the compounds described herein are surprisingly effective as pan-inhibitors of BET BRDs. The examples disclosed herein exhibit nanomolar potency in inhibiting GM-CSF, IL-1a, IL-6, IL-8, CCL2, TNF-α, TSLP, CCL27, CCL20 and CXCL9 from stimulated keratinocytes. They also exhibit surprisingly effective clearance by human hepatocytes and solubility in formulations suitable for topical application. Advantageously for topical administration, the exemplified compounds are stable in human skin S9 fractions and under hydrolytic conditions at a range of pHs. Furthermore, exemplified topical formulations deliver practicable concentrations of the compound into the epidermis of the skin and the exemplified compounds are not toxic to primary keratinocytes.

Abbreviations

| | |
|---|---|
| APCI | atmospheric pressure chemical ionisation mass spectrum |
| BD | binding domain |
| br | broad |
| c | centi |
| CCL | chemokine (C-C motif) ligand |
| CXCL | chemokine (C-X-C motif) ligand |
| δ | chemical shift |
| d | doublet |
| dd | double doublet |
| DCM | dichloromethane |
| DMF | dimethylformamide |
| DMA | dimethylacetamide |
| DMSO | dimethyl sulfoxide |
| EC | effective concentration |
| ES | electrospray |
| ESI | electrospray ionization |
| g | gram |
| GM-CSF | granulocyte-macrophage colony-stimulating factor |
| hr | hour |
| HPLC | high performance liquid chromatography |
| HRMS | high resolution mass spectrum |
| IL | interleukin |
| J | coupling constant |
| $K_d$ | dissociation constant |
| L | litre |
| LC | liquid chromatography |
| LG | leaving group |
| m | multiplet |
| m | milli |
| m | meter |
| M | molar |
| M+ | molecular ion |
| MHz | megahertz |
| min | minutes |
| mol | mole |
| MS | mass spectrometry |
| m/z | mass/charge |
| n | nano |
| NMR | nuclear magnetic resonance |
| p | para |
| PTSA | p-Toluenesulfonic acid |
| q | quartet |
| Rf | retardation factor |
| rpm | revolutions per minute |
| RT | room temperature |
| s | singlet |
| SM | starting material |
| $S_NAr$ | nucleophilic aromatic substitution (addition-elimination) |
| t | triplet |
| THF | tetrahydrofuran |
| TLC | thin layer chromatography |
| TLR | toll-like receptors |
| TBME | methyl tert-butyl ether |
| $t_R$ | retention time |
| TSLP | thymic stromal lymphopoietin |
| TNF | tumor necrosis factor |
| XPhos | 2-dicyclohexylphosphino-2',4',6'-triisopropylbiphenyl |
| Ts or Tosyl | toluenesulfonyl |
| DTT | dithioreitol |
| BSA | bovine serum albumin |
| PBS | phosphate-buffered saline |
| MEG | monoethylene glycol |
| NADPH | nicotinamide adenine dinucleotide phosphate |
| μ | micro |
| UDPGA | uridine diphosphate glucuronic acid |
| UPLC | ultra performance liquid chromatography |
| UV | ultraviolet |
| vis | visable |
| w/w | weight by weight |
| ° C. | degree Celsius |
| % | per cent |

Equipment

Reactions using microwave irradiation were carried out in a Biotage Initiator microwave.

Normal phase TLCs were carried out on pre-coated silica plates (Kieselgel 60 $F_{254}$, BDH) with visualisation via U.V. light (UV254/365 nm) and/or ninhydrin solution.

Flash chromatography was performed using Combiflash Companion Rf (Teledyne ISCO) and prepacked silica gel columns purchased from Grace Davison Discovery Science or SiliCycle.

Mass-directed preparative HPLC separations were performed using a Waters HPLC (2545 binary gradient pumps, 515 HPLC make up pump, 2767 sample manager) connected to a Waters 2998 photodiode array and a Waters 3100 mass detector.

Preparative HPLC separations were performed with a Gilson HPLC (321 pumps, 819 injection module, 215 liquid handler/injector) connected to a Gilson 155 UV/vis detector.

On both instruments, HPLC chromatographic separations were conducted using Waters XBridge C18 columns, 19×100 mm, 5 um particle size; using 0.1% ammonia in water (solvent A) and acetonitrile (solvent B) as mobile phase.

$^1$H NMR and $^{19}$F NMR spectra were recorded on a Bruker Avance DPX 500 spectrometer ($^1$H at 500.1 MHz, $^{13}$C at 125 MHz $^{19}$F at 470.5 MHz), or a Bruker Avance DPX 300 ($^1$H at 300 MHz). Chemical shifts (δ) are expressed in ppm recorded using the residual solvent as the internal reference in all cases. Signal splitting patterns are described as singlet (s), doublet (d), triplet (t), quartet (q), multiplet (m), broad (br), or a combination thereof. Coupling constants (J) are quoted to the nearest 0.5 Hz. Low resolution electrospray (ES) mass spectra were recorded on a Bruker MicroTof mass spectrometer, run in positive mode. High resolution mass spectroscopy (HRMS) was performed using a Bruker Micro-Tof mass spectrometer.

LC-MS analysis and chromatographic separation were conducted with an Agilent Technologies 1200 series HPLC connected to an Agilent Technologies 6130 quadrupole LC/MS, connected to an Agilent diode array detector. The column used was a Waters XBridge column (50 mm×2.1 mm, 3.5 μm particle size) and the compounds were eluted with a gradient of 5 to 95% acetonitrile/water+0.1% formic acid or a Shimadzu HPLC connected to a LCMS-2020 quadrupole LC/MS, connected to a Shimadzu diode array detector. The column used was a Kinetex EVO C18 column (30 mm×1.8 mm, 5.0 μm particle size) and the compounds were eluted with a gradient of 5 to 95% acetonitrile/water+ 0.0375% trifluoroacetic acid.

Unless otherwise stated herein, reactions have not been optimised. Solvents and reagents were purchased from commercial suppliers and used without further purification. Dry solvents were purchased in sure sealed bottles stored over molecular sieves.

Preparations and compounds have been named using the ChemDraw Professional 15.0 naming application.

Process for Preparation

The following schemes illustrate methods of synthesising the compounds of the invention. Scheme 1 illustrates a general route for the preparation of compounds of the invention via Suzuki coupling of intermediates (II) and (VIII) followed by deprotection. The 6-methyl-1,6-dihydro-7H-pyrrolo[2,3-c]pyridin-7-one boronic ester intermediate (II) is prepared as follows:

5-bromo-2-methoxy-4-methyl-3-nitropyridine is reacted with DMF-DMA to give intermediate (VII). An iron catalysed reduction of the 3-nitro group to the corresponding amine initiates ring closure to give intermediate (VI). Tosyl protection followed by acid hydrolysis with HBr gives intermediate (IV). The pyridone group is then N-methylated with methyl iodide and sodium hydride to give intermediate (III). Intermediate (II) is then formed from the 4-bromoaryl compound (III) via treatment with 4,4,4',4',5,5,5',5'-Octamethyl-2,2'-bi-1,3,2-dioxaborolane in a palladium-catalysed coupling reaction. Suzuki coupling of (II) and (VIII), followed by deprotection, produces compound (I). Deprotection involves removal of the tosyl group of intermediate (II) using, for example, sodium hydroxide. Often, deprotection also involves conversion of a methoxy substituent on A and/or Z to a hydroxy group using, for example, boron tribromide.

Alternatively, the compound may be functionalised at position 2 of the pyrrole with a third substituent, typically CONHethyl. This may be carried out by using an alternative synthetic pathway, shown in Scheme 2, in which intermediate (III) is reacted with ethylchloroformate and a strong base, such as lithium diisopropylamide (LDA) to form intermediate (III'). Intermediate (II') is then formed from compound (III') via treatment with 4,4,4',4',5,5,5',5'-Octamethyl-2,2'-bi-1,3,2-dioxaborolane in a palladium-catalysed coupling reaction. Suzuki coupling of (II') and (VIII), followed by deprotection, produces compound (I'). Deprotection involves removal of the tosyl group using, for example, sodium hydroxide. This also converts the ethoxy substituent of the ethyl formyl to a hydroxy group. Finally, the carboxylic acid at position 2 of the pyrrole of intermediate (I') is reacted with a suitable amine to produce the desired third substituent. Oxalyl chloride is typically used to catalyse this reaction step by first converting the carboxylic acid to an acyl chloride, which is more susceptible to nucleophilic substitution with an amine. The skilled person is able to assess which amines and reaction conditions are suitable to functionalise the carboxylic acid of intermediate (I') to produce compound (I").

Scheme 1: general synthetic pathway for the synthesis of compounds of the invention.

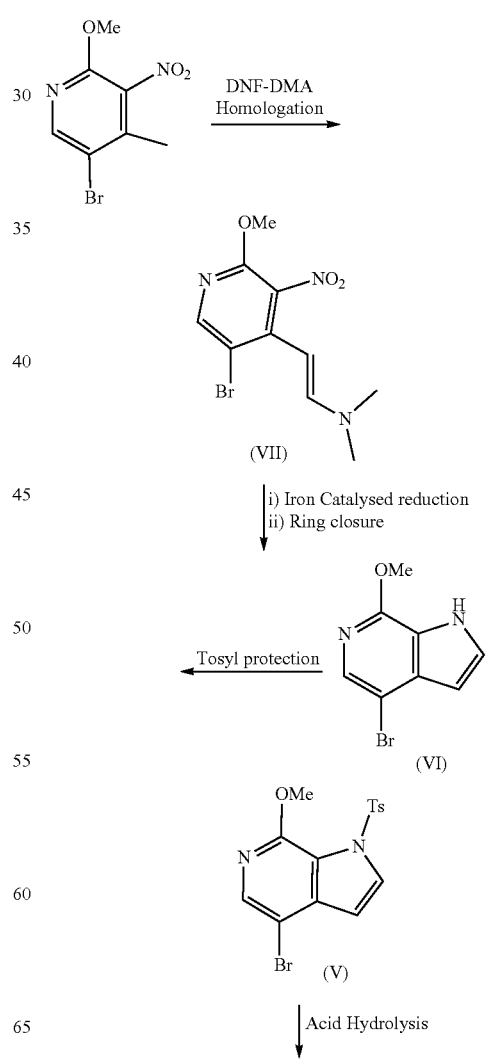

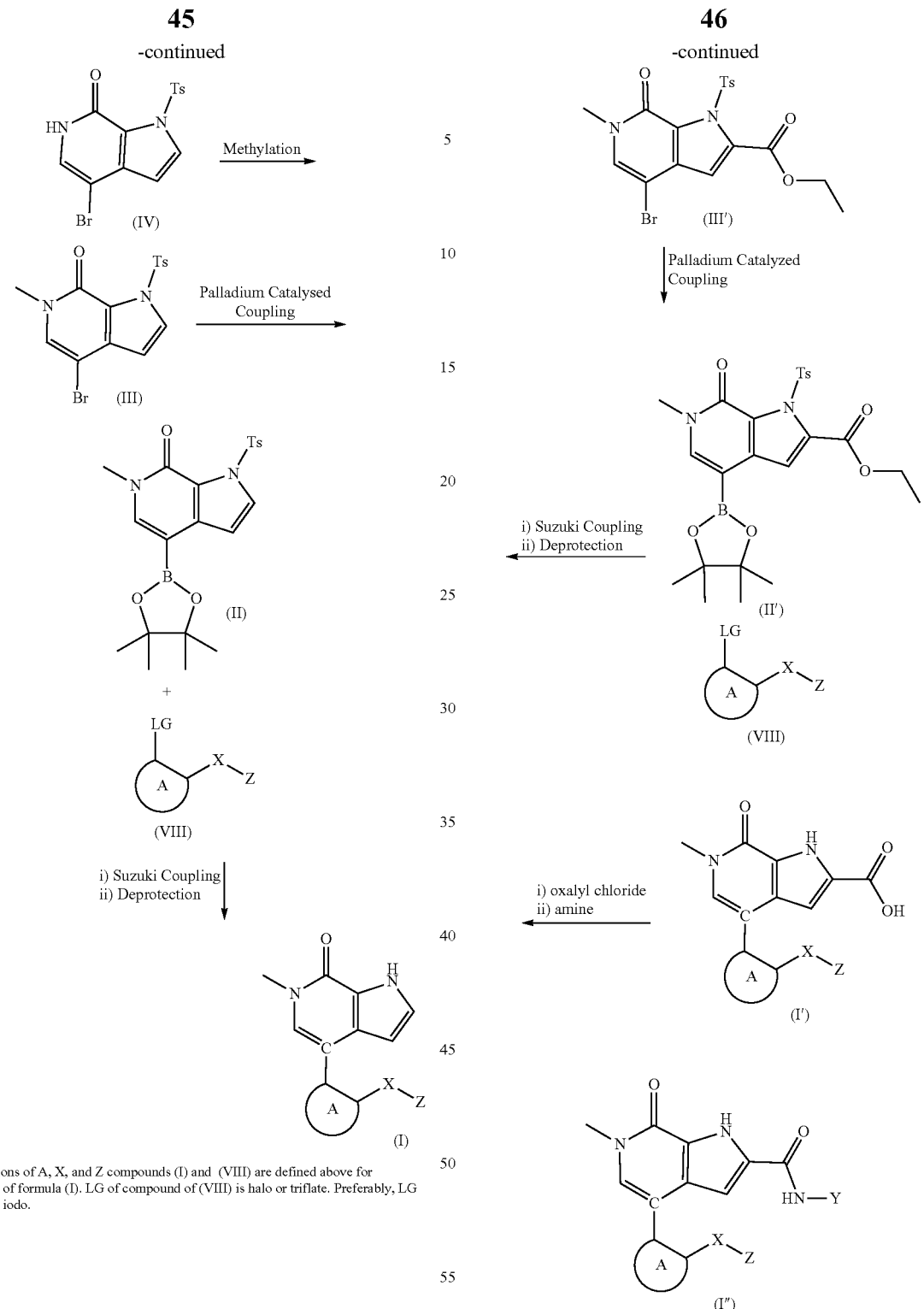
Scheme 2: general synthetic pathway for the synthesis of compounds of the invention.
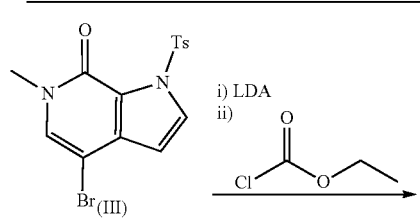
The use of Scheme 2 to synthesise compounds described herein wherein A is 2-pyridone, X is oxide and Z is 2,6-dimethyl-4-fluoro-phenyl, such as Example 41, is shown in Scheme 3.

Scheme 3: Exemplification of general Scheme 2 wherein A is a 2-pyridone, X is an oxide, Z is 2,6-dimethyl-4-fluoro-phenyl, and LG is bromo.

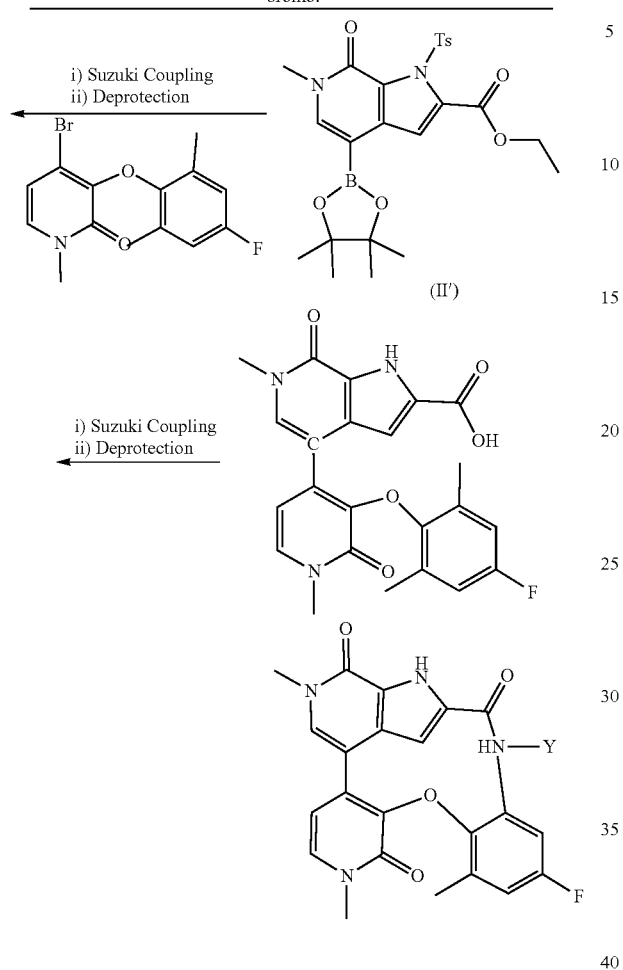

The synthetic pathways suitable for the synthesis of intermediates of formula (VIII) of Schemes 1 and 2 depend on the identity of A. Suitable pathways to synthesise intermediates of formula (VIII) are shown in Schemes 4, 5 and 6, in which: A is a 6-membered aromatic or heteroaromatic ring optionally substituted at one or more carbon and/or heteroatoms with the first substituent and substituted at a minimum of one carbon atom with a hydroxy or oxo group; A is an N-methyl-2-pyridone optionally substituted with a hydroxy group; and A is a thiazole.

Iodo-intermediate (IX) is prepared via a Sandmeyer reaction of the corresponding aniline (X), which is in turn formed through an iron catalysed reduction of the nitro-containing compound (XI). (XI) is formed via a $S_NAr$ reaction of the ortho-fluoro nitroaryl compound (XII).

N-methyl-2-pyrone-intermediates (XIII) are prepared via methylation and iron-catalysed oxidation of the corresponding pyridines (XIV), which are in turn formed via reduction of the corresponding pyridine oxides (XV) using phosphorus tribromide. Bromo-intermediates (XV) are prepared via reaction of the corresponding nitro intermediates (XVI) with acetyl bromide, and compounds (XVI) are in turn produced via $S_NAr$ reaction of the corresponding ortho-fluoro nitro pyridine oxide compounds (XVII).

5-bromothiazole intermediate (XVIII) is prepared via bromination of the corresponding thiazole intermediate (XIX), which is in turn prepared via the copper-catalysed Ullmann-type reaction of the corresponding bromo compound (XX).

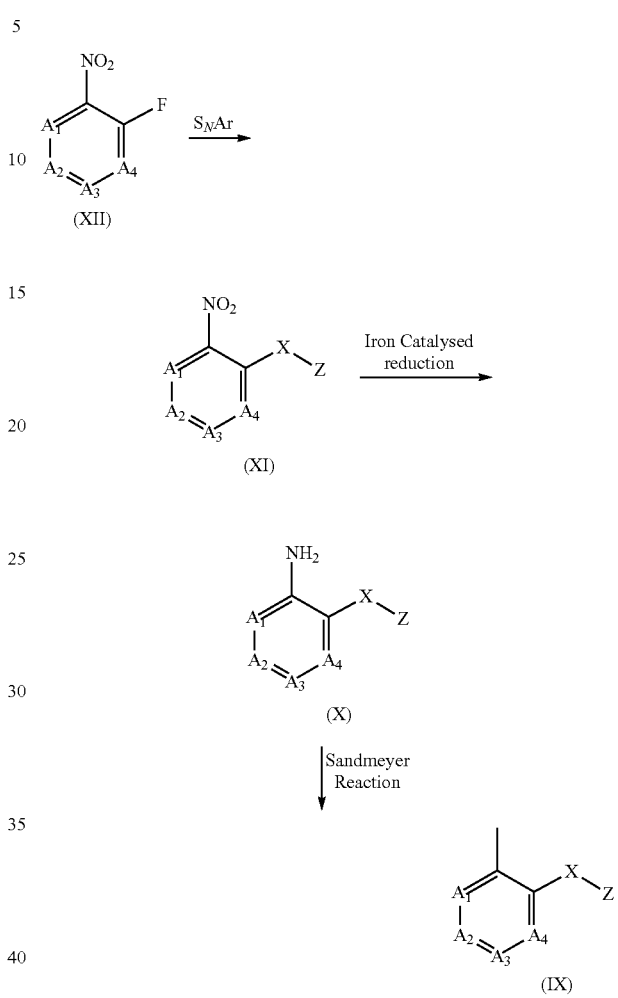

Scheme 5: general synthetic pathway for the synthesis of compounds of the invention wherein A is a 2-pyridone.

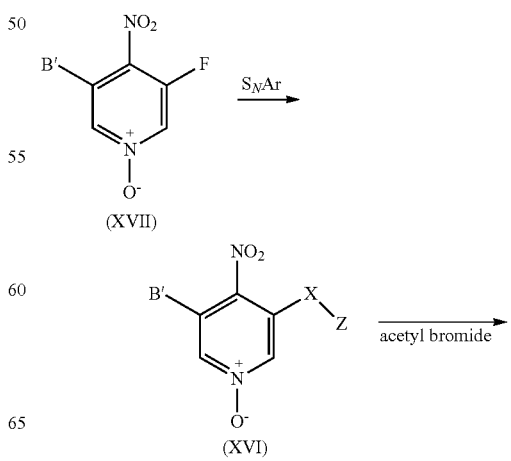

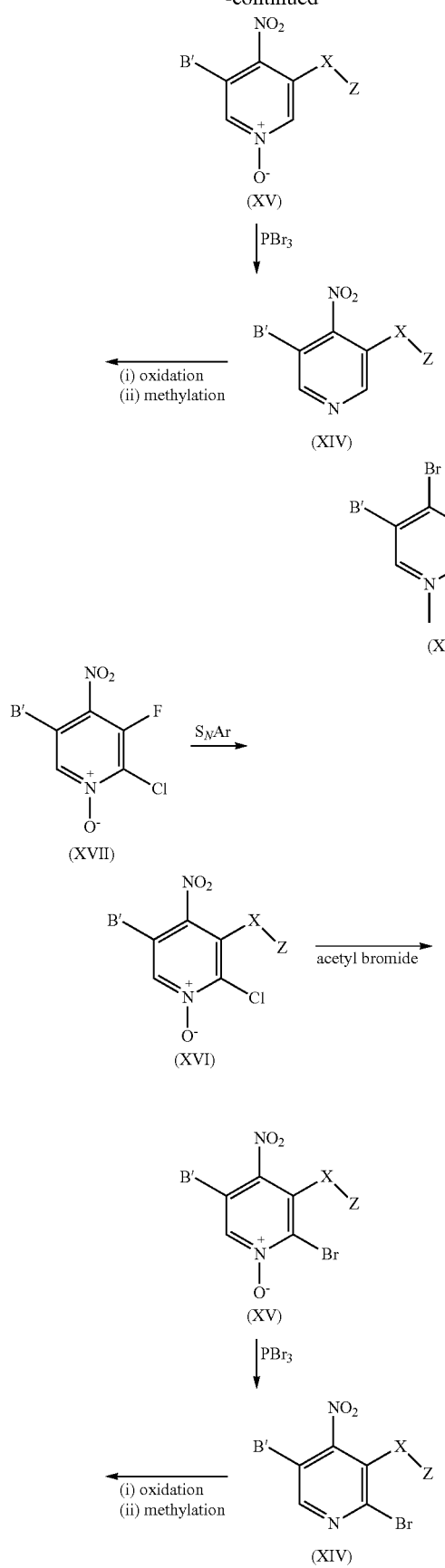
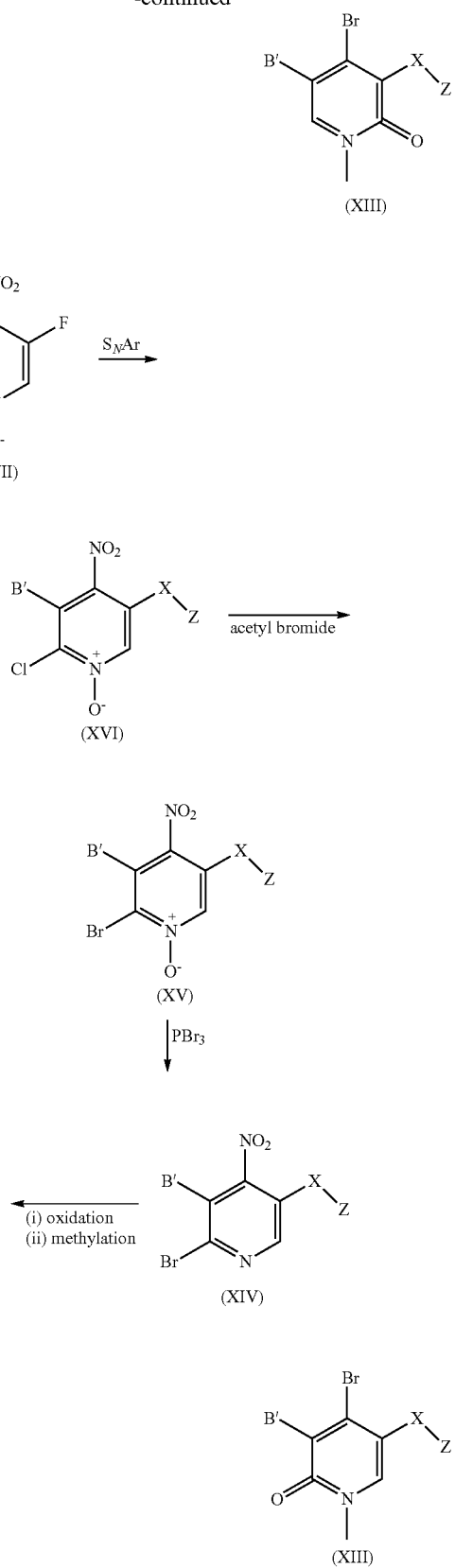
The definitions of X, Z, B' are as defined above for compounds of formula (I), (Ib) and (Ic)

Scheme 6: general synthetic pathway for the synthesis of the compounds of the invention wherein A is a thiazole.

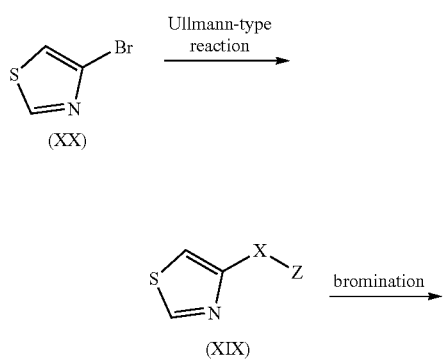

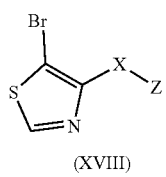

(XVIII)

The definitions of X and Z are as defined above for compounds of formula (I), and (Id).

Typically, X is O (an oxide). Scheme 7 illustrates suitable reagents and reaction conditions for the preparation of the compound of Example 1. The skilled person is aware that the reagents and conditions employed in the chemical transformations of Scheme 7 may be utilised, modified and/or substituted for alternatives as necessary in order to furnish various alternative compounds via the general processes in Schemes 1 and 2.

Synthetic 7: synthetic pathway for the synthesis of the compound of Example 1.

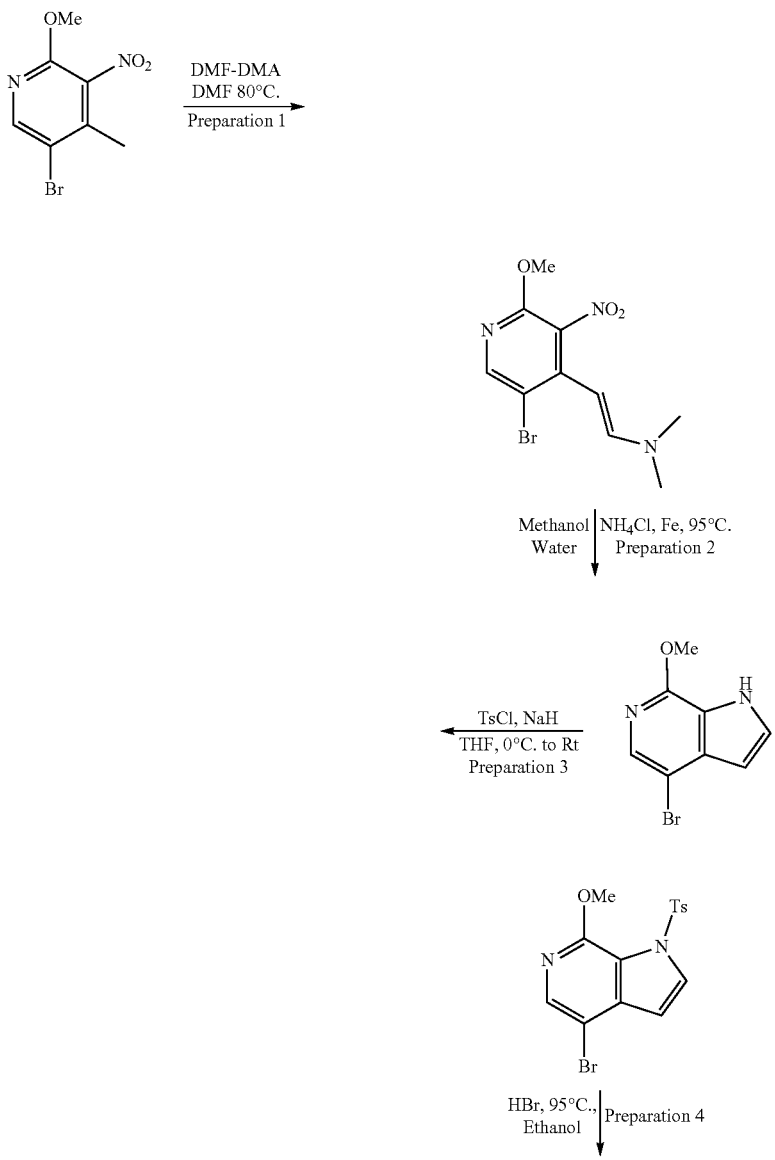

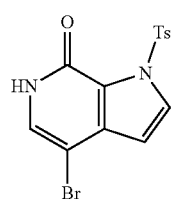 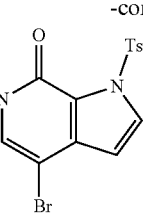 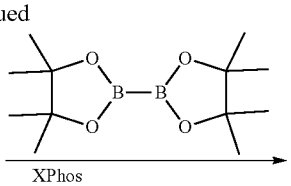 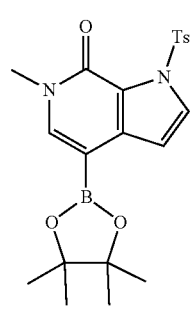
-continued
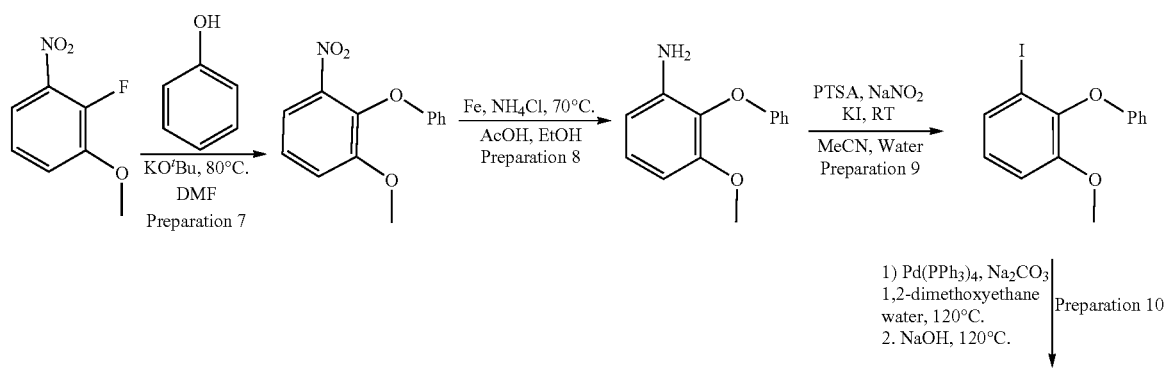
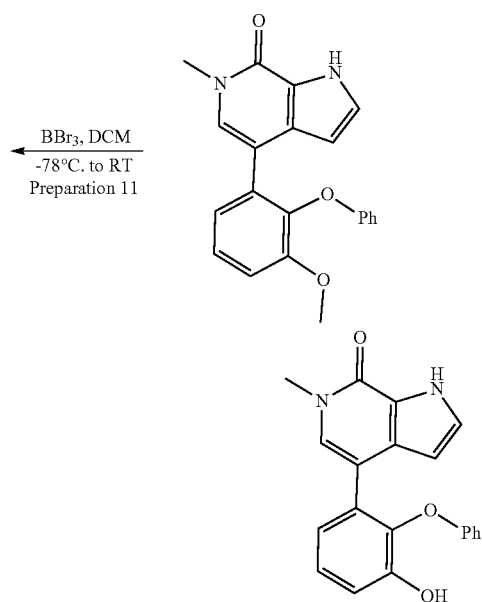
Example 1

Example 1: 4-(3-hydroxy-2-phenoxyphenyl)-6-methyl-1,6-dihydro-7H-pyrrolo[2,3-c]pyridin-7-one

Preparation 1: (E)-2-(5-bromo-2-methoxy-3-nitropyridin-4-yl)-N,N-dimethylethen-1-amine

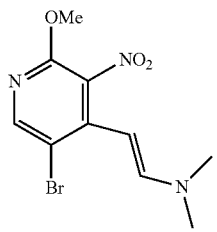

5-bromo-2-methoxy-4-methyl-3-nitropyridine (50 g, 202 mmol) was dissolved in DMF (410 mL) under nitrogen and heated to 80° C. DMF-DMA (224 mL, 1.686 mol) was added over a period of 20 min. The resulting dark solution was heated at 95° C. TLC (4:1 heptane/EA) after 5 hr showed no SM remaining. The mixture was cooled to RT and poured into ice water (1100 mL). The resulting suspension was stirred for 15 min then filtered. The collected red solid was washed with water and dried overnight under vacuum at 50° C. (56.6 g, 61%). The material was used directly in preparation 2 without further purification.

$^1$H NMR (400 MHz, CDCl$_3$) δ 8.14 (s, 1H), 7.02 (d, J=13.7 Hz, 1H), 4.94 (d, J=13.7 Hz, 1H), 3.97 (s, 3H), 2.94 (s, 6H).

Preparation 2: 4-bromo-7-methoxy-1H-pyrrolo[2,3-c]pyridine

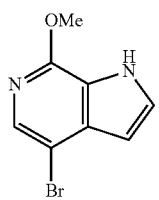

(E)-2-(5-bromo-2-methoxy-3-nitropyridin-4-yl)-N,N-dimethylethen-1-amine (23.3 g, 77.1 mmol) was partially dissolved in methanol (1100 mL) and ammonium chloride (23.3 g, 436 mmol), followed by water (140 mL). Iron powder (23.3 g, 417 mmol) was added and the mixture heated at reflux. The reaction mixture was stirred using an overhead stirrer. After 5 hr a further aliquot of iron powder (23.3 g, 417 mmol) was added and heating continued overnight. The mixture was cooled and solid Na$_2$CO$_3$ was added. The mixture was filtered through a pad of celite. The filtrate was filtered and the residue triturated with 4:1 heptane/Ethyl acetate. The mixture was filtered through a pad of silica. The filtrate was evaporated. The residue was purified on silica, eluting with 100:0 to 80:20 heptane/ethyl acetate. Solvent reduction gave an off-white solid (3.7 g, 21%).

HPLC t$_R$ (Agilent, acidic, 3.5 min): 1.46 min, MS: m/z 229.0 [M+2H]$^+$.

Preparation 3: 4-bromo-7-methoxy-1-tosyl-1H-pyrrolo[2,3-c]pyridine

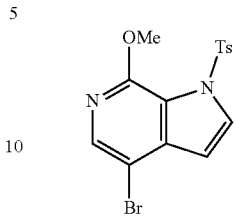

Sodium hydride (60% w/w, 7.90 g, 198 mmol) was suspended in THF (290 mL) under nitrogen and was cooled to below 4° C. in an ice bath. 4-bromo-7-methoxy-1H-pyrrolo[2,3-c]pyridine (14.0 g, 61.7 mmol) was dissolved in THF (290 mL) and added dropwise over a period of 30 min (evolution of gas was observed and formation of an exotherm raised the reaction temperature to 5° C.). The maroon mixture was stirred at RT for 45 min before cooling to 3° C. 4-Methylbenzenesulfonyl chloride (15.7 g, 82.1 mmol) was dissolved in THF (290 mL) and added dropwise. The resulting grey suspension was stirred 1.5 hr with cooling, and then 1 hr at RT. TLC (3:2 heptane/ethyl acetate) showed no remaining SM. The reaction mixture was quenched by dropwise addition of sat NH$_4$Cl (300 mL). The mixture was stirred 5 min before separating the phases. The aqueous phase was extracted with ethyl acetate (2×300 mL). The combined organics were washed (brine), dried (MgSO$_4$), filtered and evaporated to an oil that crystallized on cooling to give a light tan solid (26.2 g 99%). The material was used directly in preparation 4 without further purification.

HPLC t$_R$ (Agilent, acidic, 3.5 min): 1.94 min, m/z=383.1 [M+2H]$^+$.

Preparation 4: 4-bromo-1-tosyl-1,6-dihydro-7H-pyrrolo[2,3-c]pyridin-7-one

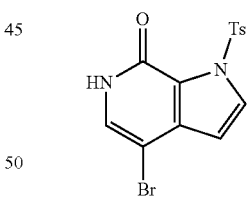

4-bromo-7-methoxy-1-tosyl-1H-pyrrolo[2,3-c]pyridine (26.2 g, 65.3 mmol) was suspended in ethanol (50 mL) and hydrogen bromide (48% w/w, 280 mL) was added in a steady stream. The resulting mixture was heated at 90° C. TLC (3:2 heptane/ethyl acetate) after 2 hr showed no remaining SM. The reaction mixture was cooled to RT and then cooled in an ice bath with stirring for 30 min. The mixture was filtered and the cream coloured solid was collected and washed with water. The solid was dried overnight under vacuum at 50° C. (22.5 g, 94%). The material was used directly in preparation 5 without further purification.

HPLC t$_R$ (Agilent, acidic, 3.5 min): 1.59 min, m/z=369.0 [M+2H]$^+$.

Preparation 5: 4-bromo-6-methyl-1-tosyl-1,6-dihydro-7H-pyrrolo[2,3-c]pyridin-7-one

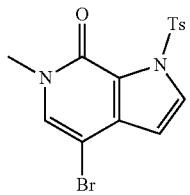 [SMILES: Cc1ccc(S(=O)(=O)n2ccc3c(Br)cn(C)c(=O)c32)cc1]

4-bromo-1-tosyl-1,6-dihydro-7H-pyrrolo[2,3-c]pyridin-7-one (22.5 g, 61.3 mmol) was dissolved in DMF (225 mL) under nitrogen. The mixture was cooled to 3° C. and sodium hydride (60% w/w, 3.06 g, 76.6 mmol) added in small portions, producing an evolution of gas and exotherm to 5° C. The mixture was stirred for 20 min with cooling where after the evolution of gas had ceased, iodomethane (7.63 mL, 123 mmol) was added dropwise, producing an exotherm which raised the reaction temperature to 10° C. The mixture was stirred for 15 min with cooling, then for 15 min at RT. LCMS after 2 hr showed no SM remaining. The reaction mixture was quenched by dropwise addition of water (100 mL, evolution of gas and exotherm to 39° C.). The mixture was extracted with ethyl acetate (3×300 mL). The combined organics were washed (brine), dried (Na$_2$SO$_4$), filtered and evaporated. The crude product was triturated with TBME and filtered. The collected off-white solid was washed with TBME and dried under vacuum (15 g, 64%).

HPLC $t_R$ (Agilent, basic, 6.0 min): 4.0 min, m/z=382.9 [M+H]$^+$.

Preparation 6: 6-methyl-4-(4,4,5,5-tetramethyl-1,3,2-dioxaborolan-2-yl)-1-tosyl-1,6-dihydro-7H-pyrrolo[2,3-c]pyridin-7-one

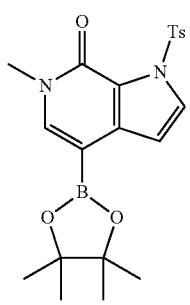 [SMILES: Cc1ccc(S(=O)(=O)n2ccc3c(B4OC(C)(C)C(C)(C)O4)cn(C)c(=O)c32)cc1]

To a flask containing XPhos (625.22 mg, 1.31 mmol), 4-bromo-6-methyl-1-tosyl-1,6-dihydro-7H-pyrrolo[2,3-c]pyridin-7-one (5 g, 13.1 mmol), 4,4,5,5-tetramethyl-2-(4,4,5,5-tetramethyl-1,3,2-dioxaborolan-2-yl)-1,3,2-dioxaborolane (6.66 g, 26.23 mmol) and potassium acetate (2.83 g, 28.85 mmol) was added 1,4-Dioxane (100 mL) and the suspension was degassed for 10 min. Pd$_2$(dba)$_3$ (300 mg, 0.32 mmol) was added and the mixture degassed for 1 min more. The reaction was heated at 80° C. overnight. The reaction was diluted with ethyl acetate and washed with 50% brine. The organics were dried, filtered and concentrated to a yellow/brown oil. The product was purified by flash chromatography on silica gel (80 g) eluting with ethyl acetate/heptane gradient (0-80%). Fractions corresponding to product were combined and concentrated to give a yellow solid (3.4 g, 55%).

HPLC $t_R$ (Agilent, acidic, 3.5 min): 1.93 min, m/z=429.2 [M+H]$^+$.

Preparation 7: 1-methoxy-3-nitro-2-phenoxybenzene

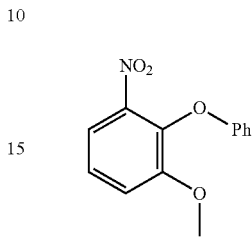

Phenol (2.3 g, 24.10 mmol) and potassium tert-butoxide (2.7 g, 24.10 mmol) were dissolved in DMF (40 mL) and stirred for 30 min at RT before the addition of 2-fluoro-1-methoxy-3-nitro-benzene (3.75 g, 21.91 mmol). The reaction mixture was heated to 80° C. and allowed to stir overnight. The reaction mixture was concentrated under vacuum, then re-dissolved in ethyl acetate and washed with water. The organic phase was dried over MgSO$_4$ and evaporated in vacuo. The crude material was purified by column chromatography (0-100% ethyl acetate in heptane) to afford 1-methoxy-3-nitro-2-phenoxy-benzene (5.4 g, 90%) as a yellow solid.

$^1$H NMR (500 MHz, CDCl$_3$) δ 7.55 (dd, J=1.4, 8.3 Hz, 1H), 7.35-7.30 (m, 3H), 7.24 (dd, J=1.4, 8.4 Hz, 1H), 7.11-7.05 (m, 1H), 6.89-6.87 (m, 2H), 3.93 (s, 3H).

Preparation 8: 3-methoxy-2-phenoxyaniline

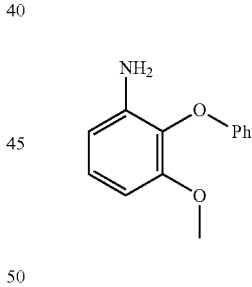

A solution of iron (7.37 g, 132.12 mmol) in acetic acid (12 mL)/ethanol (30 mL), was degassed with nitrogen for 5 min. 1-methoxy-3-nitro-2-phenoxy-benzene (5.4 g, 22.02 mmol) was added and the reaction heated to 70° C. The orange solution went black after 5 min. After 4 hrs the reaction was allowed to cool and the solvent removed. DCM was added and the organic layer was washed with sodium bicarbonate, passed through a hydrophobic frit and concentrated. The product was purified by column chromatography (ethyl acetate/heptane gradient 0-100%). Fractions corresponding to product were combined and concentrated to provide 3-methoxy-2-phenoxyaniline (830 mg, 15%) as a brown solid.

HPLC $t_R$ (Agilent, acidic, 3.5 min): 1.53 min, m/z=216.2 [M+H]$^+$.

Preparation 9: 1-iodo-3-methoxy-2-phenoxybenzene

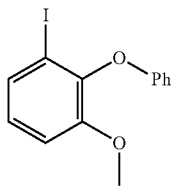 [SMILES: COc1cccc(I)c1Oc1ccccc1]

To a solution of 3-methoxy-2-phenoxyaniline (770 mg, 3.57 mmol) in MeCN (21 mL), and water (12 mL), p-toluenesulfonic acid monohydrate (2.0 g, 10.72 mmol) was added and the reaction mixture was stirred vigorously. A solution of potassium iodide (1.48 g, 8.93 mmol) and sodium nitrite (0.49 g, 7.13 mmol) in water (12 mL) was added dropwise over 10 min. The solution turned brown, and was stirred for 1 hr. Saturated sodium bicarbonate solution was then added to the solution until a pH of 8 was achieved. 1M sodium thiosulphate solution was then added. The product was extracted into DCM and the organics collected via phase separator and concentrated. The product was purified by flash chromatography on silica gel (12 g) eluting with an ethyl acetate/heptane gradient (0-40%). Fractions corresponding to product were combined and concentrated to provide 1-iodo-3-methoxy-2-phenoxybenzene (740 mg, 57%).

$^1$H NMR (500 MHz, CDCl$_3$) δ 7.43 (dd, J=1.4, 8.3 Hz, 1H), 7.34-7.28 (m, 3H), 7.10-7.04 (m, 1H), 6.99 (dd, J=1.4, 8.4 Hz, 1H), 6.88-6.85 (m, 2H), 3.93 (s, 3H).

Preparation 10: 4-(3-methoxy-2-phenoxyphenyl)-6-methyl-1,6-dihydro-7H-pyrrolo[2,3-c]pyridin-7-one

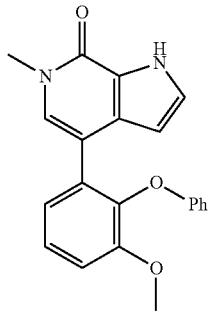 [SMILES: COc1cccc(-c2cn(C)c(=O)c3[nH]ccc23)c1Oc1ccccc1]

In a microwave tube, 1-iodo-3-methoxy-2-phenoxybenzene (83.7 mg, 0.25 mmol), sodium carbonate (81.6 mg, 0.77 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (110 mg, 0.25 mmol) in 1,2-Dimethoxyethane (2 mL) and Water (1 mL) was degassed by bubbling nitrogen for 10 min. Pd(PPh$_3$)$_4$ (14.83 mg, 0.013 mmol) was added, the tube sealed and the reaction heated at 120° C. for 30 min. NaOH (53 mg, 1.25 mmol) was added and the reaction heated at 120° C. for 1 h. Ethyl acetate (50 ml) was added and the organics washed with 2×50 ml water then 1×50 ml saturated brine solution. The organics were then separated and dried (MgSO$_4$) before concentration to dryness. The crude was then purified by flash column chromatography eluting with ethyl acetate/heptane gradient (0-100%). The desired fractions were combined and dried to afford 4-(3-methoxy-2-phenoxyphenyl)-6-methyl-1,6-dihydro-7H-pyrrolo[2,3-c]pyridin-7-one (22 mg, 26%) as a white solid.

HPLC t$_R$ (Agilent, acidic, 3.5 min): 1.62 min, m/z=347.5 [M+H]$^+$.

Preparation 11: 4-(3-hydroxy-2-phenoxyphenyl)-6-methyl-1,6-dihydro-7H-pyrrolo[2,3-c]pyridin-7-one

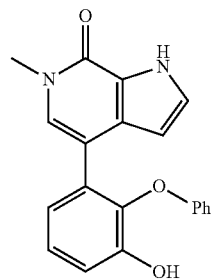 [SMILES: Cn1cc(-c2cccc(O)c2Oc2ccccc2)c2cc[nH]c2c1=O]

4-(3-methoxy-2-phenoxyphenyl)-6-methyl-1,6-dihydro-7H-pyrrolo[2,3-c]pyridin-7-one (21 mg, 0.06 mmol) was dissolved in DCM (2 mL) and cooled to −78° C. before the addition of BBr$_3$ (74 mg, 0.29 mmol). The reaction temperature was maintained for 1 hr and then allowed to warm to 0° C. and stirred for a further 1 hr. The reaction mixture was quenched with water and the pH was adjusted to 8 with saturated aqueous NaHCO$_3$. The reaction mixture was extracted with ethyl acetate. The combined organic layers were separated, passed through a phase separator and concentrated under vacuum. The crude material was purified by column chromatography (0-50% 20% MeOH/DCM in DCM) followed by reverse phase preparative HPLC (Gilson acidic 60-90% gradient). Fractions were concentrated on the genevac overnight to afford 4-(3-hydroxy-2-phenoxyphenyl)-6-methyl-1,6-dihydro-7H-pyrrolo[2,3-c]pyridin-7-one (17 mg, 85%) as a white solid.

HPLC t$_R$ (Agilent, acidic, 3.5 min): 1.43 min, m/z=333.2 [M+H]$^+$.

$^1$H NMR (500 MHz, CDCl$_3$) δ 10.36-10.30 (m, 1H), 7.26-7.20 (m, 2H), 7.15-7.06 (m, 4H), 6.89-6.85 (m, 2H), 6.68-6.64 (m, 2H), 6.39 (dd, J=2.4, 2.4 Hz, 1H), 6.29 (s, 1H), 3.53 (s, 3H).

Example 2: 4-(4-hydroxy-2-phenoxyphenyl)-6-methyl-1,6-dihydro-7H-pyrrolo[2,3-c]pyridin-7-one Preparation 12: 4-methoxy-1-nitro-2-phenoxybenzene

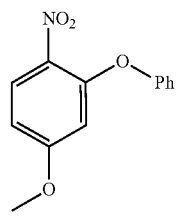 [SMILES: COc1ccc([N+](=O)[O-])c(Oc2ccccc2)c1]

Following the procedure in preparation 7,2-fluoro-4-methoxy-1-nitrobenzene (400 mg, 2.34 mmol) was reacted to give the title compound (541 mg, 85%).

¹H NMR (500 MHz, CDCl₃) δ 8.10 (d, J=9.2 Hz, 1H), 7.43-7.39 (m, 2H), 7.21 (t, J=7.4 Hz, 1H), 7.09-7.07 (m, 2H), 6.70 (dd, J=2.7, 9.2 Hz, 1H), 6.46 (d, J=2.6 Hz, 1H), 3.81 (s, 3H).

Preparation 13: 4-methoxy-2-phenoxyaniline

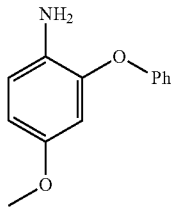

Following the procedure in preparation 8, 4-methoxy-1-nitro-2-phenoxybenzene (525 mg, 2.14 mmol) was reacted to give the title compound (366 mg, 71%).
¹H NMR (500 MHz, CDCl₃) δ 7.35-7.31 (m, 2H), 7.08 (t, J=7.4 Hz, 1H), 7.02-7.00 (m, 2H), 6.71-6.69 (m, 2H), 6.60 (dd, J=2.5, 6.9 Hz, 1H), 3.92 (s, 3H), 3.90 (bs, 2H).

Preparation 14: 1-iodo-4-methoxy-2-phenoxybenzene

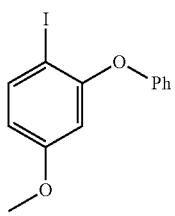 [SMILES: COc1ccc(I)c(Oc2ccccc2)c1]

Following the procedure in preparation 9, 4-methoxy-2-phenoxyaniline (366 mg, 1.70 mmol) was reacted to give the title compound (197 mg, 35%).
¹H NMR (400 MHz, CDCl₃) δ 7.38-7.34 (m, 2H), 7.29-7.23 (m, 1H), 7.14 (t, J=7.4 Hz, 1H), 7.01 (d, J=7.7 Hz, 2H), 6.63 (d, J=8.3 Hz, 1H), 6.55 (d, J=8.3 Hz, 1H), 3.96 (s, 3H).

Preparation 15: 4-(4-methoxy-2-phenoxyphenyl)-6-methyl-1,6-dihydro-7H-pyrrolo[2,3-c]pyridin-7-one

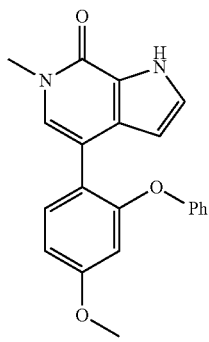 [SMILES: COc1ccc(-c2cn(C)c(=O)c3[nH]ccc23)c(Oc2ccccc2)c1]

Following the procedure in preparation 10, 1-iodo-4-methoxy-2-phenoxybenzene (198 mg, 0.61 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (260 mg, 0.61 mmol) was reacted to give the title compound (182 mg, 86%).
HPLC $t_R$ (Agilent, acidic, 3.5 min): 1.59 min, m/z=347.2 [M+H]⁺.

Preparation 16: 4-(4-hydroxy-2-phenoxyphenyl)-6-methyl-1,6-dihydro-7H-pyrrolo[2,3-c]pyridin-7-one

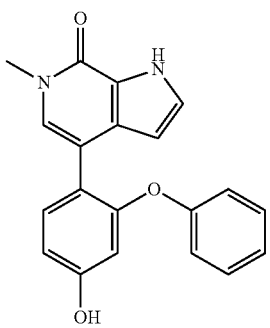 [SMILES: Cn1cc(-c2ccc(O)cc2Oc2ccccc2)c2cc[nH]c2c1=O]

Following the procedure in preparation 11, 4-(4-methoxy-2-phenoxyphenyl)-6-methyl-1,6-dihydro-7H-pyrrolo[2,3-c]pyridin-7-one (94 mg, 0.27 mmol) was reacted to give the title compound (41 mg, 43%).
HPLC $t_R$ (Agilent, acidic, 3.5 min): 1.48 min, m/z=333.2 [M+H]⁺.
¹H NMR (500 MHz, DMSO-d6) δ 11.82 (s, 1H), 9.89 (bs, 1H), 7.25 (dd, J=7.4, 8.6 Hz, 2H), 7.18-7.12 (m, 2H), 7.00 (s, 2H), 6.84 (d, J=7.6 Hz, 2H), 6.75 (d, J=7.8 Hz, 1H), 6.35 (d, J=8.1 Hz, 1H), 6.00 (d, J=2.6 Hz, 1H), 3.46 (s, 3H).

Example 3: 4-(2-hydroxy-6-phenoxyphenyl)-6-methyl-1,6-dihydro-7H-pyrrolo[2,3-c]pyridin-7-one Preparation 17: 1-fluoro-3-methoxy-2-nitrobenzene

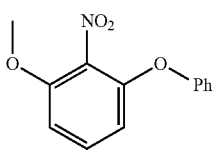 [SMILES: COc1cccc(Oc2ccccc2)c1[N+](=O)[O-]]

Following the procedure in preparation 7, 1-fluoro-3-methoxy-2-nitrobenzene (400 mg, 2.34 mmol) was reacted to give the title compound (565 mg, 89%).
¹H NMR (500 MHz, CDCl₃) δ 7.41-7.37 (m, 2H), 7.30 (dd, J=7.4, 7.4 Hz, 1H), 7.21 (dd, J=7.4, 7.4 Hz, 1H), 7.11-7.09 (m, 2H), 6.76 (d, J=7.8 Hz, 1H), 6.53 (d, J=8.5 Hz, 1H), 3.95 (s, 3H).

Preparation 18: 2-methoxy-6-phenoxyaniline

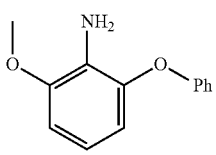 [SMILES: COc1cccc(Oc2ccccc2)c1N]

Following the procedure in preparation 8, 1-methoxy-2-nitro-3-phenoxybenzene (565 mg, 2.30 mmol) was reacted to give the title compound (350 mg, 64%).

¹H NMR (500 MHz, CDCl₃) δ 7.36-7.32 (m, 2H), 7.09 (dd, J=7.3, 7.3 Hz, 1H), 7.02-7.00 (m, 2H), 6.80 (d, J=8.7 Hz, 1H), 6.62 (dd, J=2.7, 8.7 Hz, 1H), 6.52 (d, J=2.7 Hz, 1H), 3.72 (s, 3H), 3.61-3.51 (m, 2H).

Preparation 19:
2-iodo-1-methoxy-3-phenoxybenzene

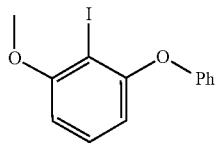 [SMILES: COc1cccc(Oc2ccccc2)c1I]

Following the procedure in preparation 9, 2-methoxy-6-phenoxyaniline (350 mg, 1.63 mmol) was reacted to give the title compound (324 mg, 55%).

¹H NMR (400 MHz, CDCl₃) δ 7.63 (d, J=8.6 Hz, 1H), 7.29-7.25 (m, 2H), 7.05 (dd, J=7.4, 7.4 Hz, 1H), 6.91 (d, J=7.6 Hz, 2H) 6.45-6.39, (m, 2H), 3.64 (s, 3H).

Preparation 20: 4-(2-methoxy-6-phenoxyphenyl)-6-methyl-1,6-dihydro-7H-pyrrolo[2,3-c]pyridin-7-one

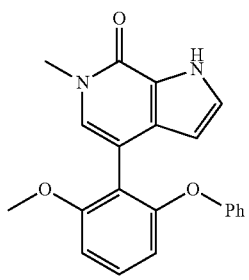 [SMILES: COc1cccc(Oc2ccccc2)c1-c1cn(C)c(=O)c2[nH]ccc12]

Following the procedure in preparation 10, 2-iodo-1-methoxy-3-phenoxybenzene (320 mg, 0.98 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (420 mg, 0.98 mmol) was reacted to give the title compound (143 mg, 42%).

HPLC t_R (Agilent, acidic, 3.5 min): 1.65 min, m/z=347.2 [M+H]⁺.

Preparation 21: 4-(2-hydroxy-6-phenoxyphenyl)-6-methyl-1,6-dihydro-7H-pyrrolo[2,3-c]pyridin-7-one

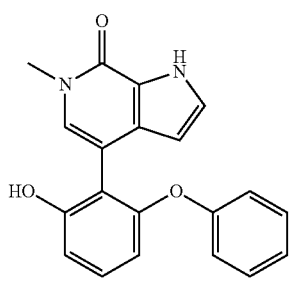 [SMILES: Cn1cc(-c2c(O)cccc2Oc2ccccc2)c2cc[nH]c2c1=O]

Following the procedure in preparation 12, 4-(2-methoxy-6-phenoxyphenyl)-6-methyl-1,6-dihydro-7H-pyrrolo[2,3-c]pyridin-7-one (190 mg, 0.55 mmol) was reacted to give the title compound (32 mg, 16%).

HPLC t_R (Agilent, acidic, 3.5 min): 1.40 min, m/z=333.2 [M+H]⁺.

¹H NMR (500 MHz, DMSO-d6) δ 11.93 (d, J=0.9 Hz, 1H), 9.64 (s, 1H), 7.33-7.22 (m, 4H), 7.13 (s, 1H), 7.06 (t, J=7.4 Hz, 1H), 6.93 (d, J=7.8 Hz, 2H), 6.64 (dd, J=2.4, 8.3 Hz, 1H), 6.35 (d, J=2.4 Hz, 1H), 6.22-6.21 (m, 1H), 3.49 (s, 3H).

Example 4: 6-methyl-4-(4-phenoxythiazol-5-yl)-1,6-dihydro-7H-pyrrolo[2,3-c]pyridin-7-one Preparation 22: 4-phenoxythiazole

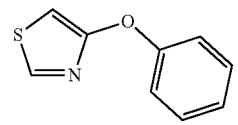 [SMILES: c1ccc(Oc2cscn2)cc1]

To an oven dried microwave vial was added CuI (58.0 mg, 0.30 mmol), picolinic acid (75.0 mg, 0.61 mmol), phenol (0.31 mL, 3.66 mmol) and potassium phosphate tribasic (1.3 g, 6.1 mmol). The tube was then evacuated and backfilled with N2 twice. 4-bromo-thiazole (500 mg, 3.0 mmol) in DMSO (10 mL) was added and the mixture heated at 150° C. for 1 hr. DMSO was removed using a Genevac EZ-2. To the residue was added ethyl acetate (50 mL) and the organics washed with 2×50 mL water then 1×50 mL saturated brine solution. The organics were then separated and dried (MgSO₄) before concentration to dryness. The crude product was purified by flash chromatography on silica gel eluting with ethyl acetate/heptane gradient (0-100%). Fractions corresponding to product were combined and concentrated to give the title compound, a yellow solid (93 mg, 17%).

HPLC t_R (Agilent, acidic, 3.5 min): 1.54 min, m/z=177.9 [M+H]⁺.

Preparation 23: 5-bromo-4-phenoxythiazole

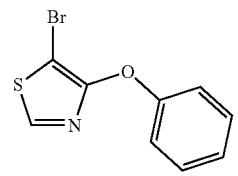 [SMILES: Brc1scnc1Oc1ccccc1]

4-phenoxythiazole (60 mg, 0.34 mmol) in MeCN (2 mL) was cooled to 0° C. 1-bromopyrrolidine-2,5-dione (72 mg, 0.41 mmol) in MeCN (2 mL) was added dropwise. The reaction was warmed to RT and left for 3 h. Ethyl acetate (50 ml) was added and the organics washed with 2×50 ml saturated sodium carbonate then 1×50 ml saturated brine solution. The organics were then separated and dried (MgSO₄) before concentration to dryness to give the title compound (75 mg, 87%). The material was used directly in preparation 27 without further purification. HPLC t_R (Agilent, acidic, 3.5 min): 1.71 min, m/z=257.7 [M+H]⁺.

Preparation 24: 6-methyl-4-(4-phenoxythiazol-5-yl)-1,6-dihydro-7H-pyrrolo[2,3-c]pyridin-7-one

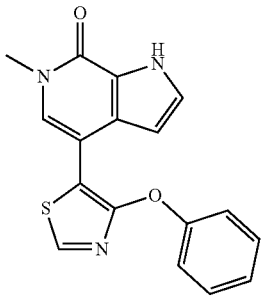 [SMILES: Cn1cc(-c2scnc2Oc2ccccc2)c2cc[nH]c2c1=O]

Following the procedure in preparation 10, 5-bromo-4-phenoxythiazole (72 mg, 0.28 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (110 mg, 0.26 mmol) was reacted to give the title compound (10 mg, 12%).

HPLC $t_R$ (Agilent, acidic, 3.5 min): 1.43 min, m/z=324.2 [M+H]$^+$.

$^1$H NMR (500 MHz, DMSO-d6) δ 12.20 (bs, 1H), 9.02 (s, 1H), 7.52 (s, 1H), 7.36-7.31 (m, 3H), 7.09 (t, J=7.4 Hz, 1H), 7.00 (d, J=7.9 Hz, 2H), 6.44 (s, 1H), 3.53 (s, 3H).

Example 5: 6-methyl-4-(1-methyl-2-oxo-3-phenoxy-1,2-dihydropyridin-4-yl)-1,6-dihydro-7H-pyrrolo[2,3-c]pyridin-7-one

Preparation 25: 4-nitro-3-phenoxypyridine 1-oxide

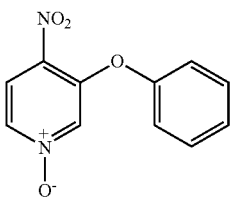

Sodium hydride (278 mg, 6.96 mmol) in DMF (5 mL) was cooled to 0° C. Phenol (0.58 mL, 6.96 mmol) in DMF (5 mL) was added and the mixture stirred for 10 min at this temperature before 3-fluoro-4-nitro-pyridine 1-oxide (1.0 g, 6.3 mmol) in DMF (5 mL) was added. The reaction was warmed to RT over 30 min. The reaction mixture was stirred with ice-water and extracted with DCM. The organic extract was washed with water and saturated sodium chloride solution, dried (MgSO$_4$), filtered and concentrated to give 4-nitro-3-phenoxy-pyridine 1-oxide (1.1 g, 74.9%), as a waxy solid. The material was used directly in preparation 29 without further purification.

HPLC $t_R$ (Agilent, acidic, 3.5 min): 1.72 min, m/z=233.4 [M+H]$^+$.

Preparation 26: 4-bromo-3-phenoxypyridine 1-oxide

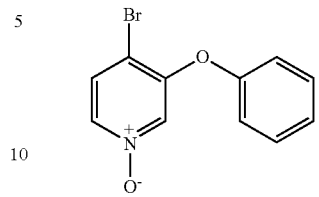

4-nitro-3-phenoxy-pyridine 1-oxide (1.1 g, 4.74 mmol) in acetyl bromide (3.51 mL, 47.4 mmol) was stirred at reflux for 2 hr. After cooling to ambient temperature the mixture was poured onto crushed ice and stirred vigorously. The solution was brought to pH 10 with careful addition of saturated sodium carbonate. The organic extract was washed with water and saturated sodium chloride solution, dried (MgSO$_4$), filtered and concentrated. Purification was performed by silica gel chromatography, eluting with ethyl acetate/heptane gradient (0-100%) to give the title product 4-bromo-3-phenoxy-pyridine 1-oxide (870 mg, 62%).

HPLC $t_R$ (Agilent, acidic, 3.5 min): 1.55 min, m/z=267.9 [M+H]$^+$.

Preparation 27: 4-bromo-3-phenoxypyridine

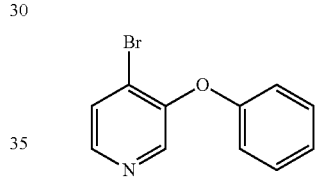

4-bromo-3-phenoxy-pyridine 1-oxide (715 mg, 2.69 mmol) in chloroform (20 mL) was cooled to 0° C. PBr$_3$ (1.2 g, 3.23 mmol) in chloroform (20 mL) was added dropwise and then warmed to 50° C. for 1 hr. The reaction was concentrated to dryness and the residue was taken up in ethyl acetate (50 mL) and the organics washed with 2×50 mL water then 1×50 mL saturated brine solution. The organics were then separated and dried (MgSO$_4$) before concentration to dryness. The crude mixture was then purified by flash column chromatography eluting with ethyl acetate/heptane gradient (0-100%). The desired fractions were concentrated to dryness in vacuo to give 4-bromo-3-phenoxy-pyridine (500 mg, 74%).

HPLC $t_R$ (Agilent, acidic, 3.5 min): 1.61 min, m/z=249.8 [M]$^+$.

Preparation 28: 4-bromo-1-methyl-3-phenoxypyridin-2(1H)-one

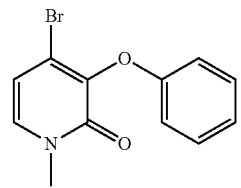 [SMILES: Cn1ccc(Br)c(Oc2ccccc2)c1=O]

In a sealable tube, to 4-bromo-3-phenoxy-pyridine (528 mg, 2.11 mmol) in MeCN (10 mL) was added dimethyl sulfate (2.0 mL, 21.1 mmol) and the mixture heated at 80° C. for 30 min. Additional dimethyl sulfate (7.0 mL, 73.9 mmol) was added and the mixture heated at 80° C. for 16 hr. The mixture was cooled on ice to 0° C. and potassium ferricyanide (1.74 g, 5.28 mmol) in water (5 mL) was added followed by dropwise addition of potassium hydroxide (948 mg, 16.9 mmol) in water (5 mL) and stirred at 80° C. for 16 hr. DCM and water were added and passed through a phase separator. The organic layer was dried and the residue purified by column chromatography, eluting with ethyl acetate/heptane gradient (0-100%). The desired fractions were concentrated to dryness in vacuo to give 4-bromo-1-methyl-5-phenoxypyridin-2(1H)-one (45 mg, 7.6%).

HPLC $t_R$ (Agilent, acidic, 3.5 min): 1.42 min, m/z=281.0 [M+H]$^+$.

Preparation 29: 6-methyl-4-(1-methyl-2-oxo-3-phenoxy-1,2-dihydropyridin-4-yl)-1,6-dihydro-7H-pyrrolo[2,3-c]pyridin-7-one

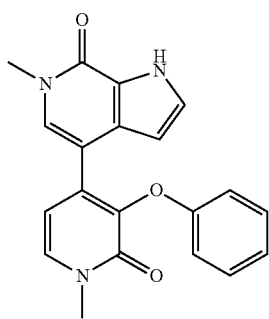 [SMILES: Cn1ccc(-c2cn(C)c(=O)c3[nH]ccc23)c(Oc2ccccc2)c1=O]

Following the procedure in preparation 10, 4-bromo-1-methyl-5-phenoxypyridin-2(1H)-one (45 mg, 0.16 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (65 mg, 0.15 mmol) was reacted to give the title compound (6 mg, 11%).

HPLC $t_R$ (Agilent, acidic, 3.5 min): 1.17 min, m/z=348.1 [M+H]$^+$.

$^1$H NMR (500 MHz, DMSO-d6) δ 12.08 (bs, 1H), 7.71 (d, J=7.0 Hz, 1H), 7.36-7.30 (m, 2H), 7.18 (dd, J=7.9, 7.9 Hz, 2H), 6.90 (dd, J=7.4, 7.4 Hz, 1H), 6.71 (d, J=7.8 Hz, 2H), 6.41 (d, J=7.0 Hz, 1H), 6.31 (dd, J=2.3, 2.3 Hz, 1H), 3.53 (s, 3H), 3.47 (s, 3H).

Example 6: 4-(5-hydroxy-2-phenoxyphenyl)-6-methyl-1,6-dihydro-7H-pyrrolo[2,3-c]pyridin-7-one Preparation 30: 4-methoxy-2-nitro-1-phenoxybenzene

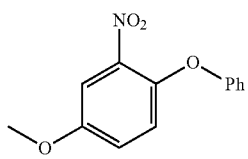

Following the procedure in preparation 7, 1-fluoro-4-methoxy-2-nitrobenzene (1.2 g, 7.01 mmol) was reacted to give the title compound (1.50 mg, 87%).

HPLC $t_R$ (Agilent, acidic, 3.5 min): 1.79 min, m/z=246.1 [M+H]$^+$.

Preparation 31: 5-methoxy-2-phenoxyaniline

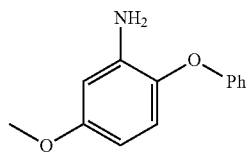 [SMILES: COc1ccc(Oc2ccccc2)c([N+](=O)[O-])c1]

Following the procedure in preparation 8, 4-methoxy-2-nitro-1-phenoxybenzene (1.80 mg, 5.38 mmol) was reacted to give the title compound (1.23 g, 64%).

HPLC $t_R$ (Agilent, acidic, 3.5 min): 1.64 min, m/z=216.1 [M+H]$^+$.

Preparation 32: 2-iodo-4-methoxy-1-phenoxybenzene

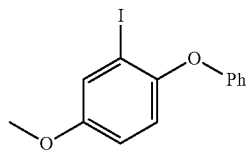 [SMILES: COc1ccc(Oc2ccccc2)c(I)c1]

Following the procedure in preparation 9, 5-methoxy-2-phenoxyaniline (1.23 g, 5.71 mmol) was reacted to give the title compound (180 mg, 10%).

$^1$H NMR (500 MHz, CDCl$_3$) 7.41 (d, J=2.9 Hz, 1H), 7.35-7.31 (m, 2H), 7.10-7.03 (m, 1H), 6.96-6.91 (m, 4H), 3.83 (s, 3H).

Preparation 33: 4-(5-methoxy-2-phenoxyphenyl)-6-methyl-1,6-dihydro-7H-pyrrolo[2,3-c]pyridin-7-one

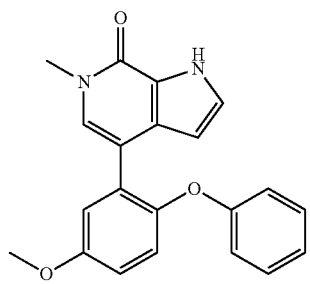 [SMILES: COc1ccc(Oc2ccccc2)c(-c2cn(C)c(=O)c3[nH]ccc23)c1]

Following the procedure in preparation 10, 2-iodo-4-methoxy-1-phenoxybenzene (152 mg, 0.47 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (200 mg, 0.47 mmol) was reacted to give the title compound (88 mg, 39%).

HPLC $t_R$ (Agilent, acidic, 3.5 min): 1.65 min, m/z=347.2 [M+H]$^+$.

Preparation 34: 4-(5-hydroxy-2-phenoxyphenyl)-6-methyl-1,6-dihydro-7H-pyrrolo[2,3-c]pyridin-7-one

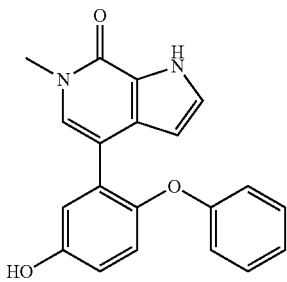 [SMILES: Cn1cc(-c2cc(O)ccc2Oc2ccccc2)c2cc[nH]c2c1=O]

Following the procedure in preparation 11, 4-(5-methoxy-2-phenoxyphenyl)-6-methyl-1,6-dihydro-7H-pyrrolo[2,3-c]pyridin-7-one (85 mg, 0.25 mmol) was reacted to give the title compound (50 mg, 58%).

HPLC $t_R$ (Agilent, acidic, 3.5 min): 1.46 min, m/z=333.2 [M+H]$^+$.

$^1$H NMR (500 MHz, DMSO-d6) δ 11.97 (s, 1H), 9.47 (s, 1H), 7.26 (dd, J=2.7, 2.7 Hz, 1H), 7.21-7.17 (m, 3H), 6.96-6.89 (m, 3H), 6.79 (dd, J=2.9, 8.7 Hz, 1H), 6.73 (d, J=7.6 Hz, 2H), 6.25-6.23 (m, 1H), 3.46 (s, 3H).

Example 7: 6-methyl-4-(1-methyl-2-oxo-5-phenoxy-1,2-dihydropyridin-4-yl)-1,6-dihydro-7H-pyrrolo[2,3-c]pyridin-7-one Preparation 35: 2-chloro-4-nitro-5-phenoxypyridine 1-oxide

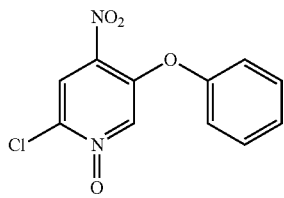 [SMILES: O=[N+]([O-])c1cc(Cl)[n+]([O-])cc1Oc1ccccc1]

To a solution of 2-chloro-5-fluoro-4-nitropyridine 1-oxide (2.00 g, 10.4 mmol) in THF (100 mL) was added K$_2$CO$_3$ (2.87 g, 20.8 mmol); phenol (1.03 g, 10.9 mmol) at 20° C., the reaction was stirred at 90° C. for 1 hour. The reaction was concentrated in vacuum and the residue was diluted with saturated NaHCO$_3$ (100 mL), the reaction mixture was extracted with DCM (100 mL×2), The combined organic phase was washed with brine (100 mL), dried with anhydrous Na$_2$SO$_4$, filtered and concentrated in vacuum. The residue was purified by column chromatography (SiO$_2$, Petroleum ether/Ethyl acetate=10/1 to 3/1) to give the title compound (950 mg, 3.56 mmol, yield=34.3%) was obtained as a yellow solid.

HPLC $t_R$ (Agilent, acidic, 3.5 min): 1.47 min, m/z=267.0 [M+H]$^+$.

Preparation 36: 2,4-dibromo-5-phenoxypyridine 1-oxide

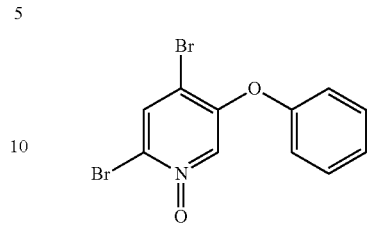

Following the procedure in preparation 26, 2-chloro-4-nitro-5-phenoxypyridine 1-oxide (950 mg, 3.56 mmol) was reacted to give the title compound (1.2 g, 98%).

HPLC $t_R$ (Agilent, acidic, 3.5 min): 1.49 min, m/z=345.9 [M+H]$^+$.

Preparation 37: 2,4-dibromo-5-phenoxypyridine

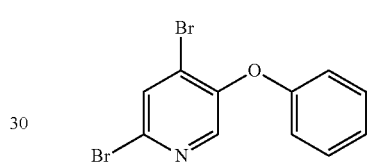

Following the procedure in preparation 27, 2,4-dibromo-5-phenoxypyridine 1-oxide (1.3 g, 3.77 mmol) was reacted to give the title compound (1.1 g, 89%).

HPLC $t_R$ (Agilent, acidic, 3.5 min): 1.91 min, m/z=330.0 [M+H]$^+$.

Preparation 38: 4-bromo-5-phenoxypyridin-2(1H)-one

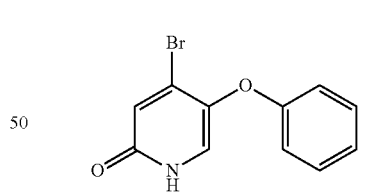

To a solution of 2,4-dibromo-5-phenoxypyridine (1.28 g, 3.9 mmol) in t-BuOH (30 mL) was added KOH (699 mg, 12.5 mmol) at 20° C., the reaction mixture was stirred at 90° C. for 12 hours. The reaction was concentrated in vacuum. The residue was diluted with H$_2$O (100 mL) and extracted with DCM (100 mL×2), the combined organic phase was washed with brine (100 mL), dried with anhydrous Na$_2$SO$_4$, filtered and concentrated in vacuum. The residue was purified by prep-HPLC (TFA condition) to give the title compound (80 mg, 0.3 mmol, yield=7.8%) as a yellow solid.

HPLC $t_R$ (Agilent, acidic, 3.5 min): 1.39 min, m/z=267.1 [M+H]$^+$.

Preparation 39: 4-bromo-1-methyl-5-phenoxypyridin-2(1H)-one

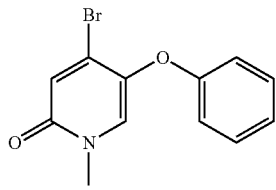 [SMILES: Cn1cc(Oc2ccccc2)c(Br)cc1=O]

To a solution of 4-bromo-5-phenoxypyridin-2(1H)-one (61 mg, 0.23 mmol) in DMF (3.0 mL) was added MeI (65.1 mg, 0.46 mmol, 2.52 mL); $Cs_2CO_3$ (224.1 mg, 0.69 mmol) at 20° C., the reaction was stirred at 20° C. for 1 hours. To this reaction was added $H_2O$ (100 mL) and extracted with DCM (100 mL×2), the combined organic phase was washed with brine (100 mL), dried with anhydrous $Na_2SO_4$, filtered and concentrated in vacuum. The residue was purified by prep-HPLC (TFA condition) to give the 4-bromo-1-methyl-5-phenoxypyridin-2(1H)-one (63 mg, 0.23 mmol, yield=98%) as a yellow solid.

HPLC $t_R$ (Agilent, acidic, 3.5 min): 1.45 min, m/z=281.0 $[M+H]^+$.

Preparation 40: 6-methyl-4-(1-methyl-2-oxo-5-phenoxy-1,2-dihydropyridin-4-yl)-1,6-dihydro-7H-pyrrolo[2,3-c]pyridin-7-one

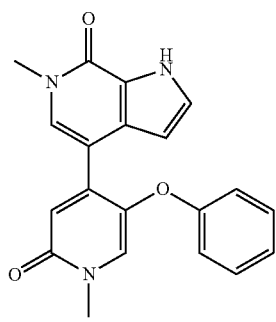 [SMILES: Cn1cc(Oc2ccccc2)c(-c2cn(C)c(=O)c3[nH]ccc23)cc1=O]

Following the procedure in preparation 10, 4-bromo-1-methyl-5-phenoxypyridin-2(1H)-one (65 mg, 0.23 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (99 mg, 0.23 mmol) was reacted to give the title compound (23 mg, 24%).

HPLC $t_R$ (Agilent, acidic, 3.5 min): 1.26 min, m/z=348.2 $[M+H]^+$.

$^1$H NMR (500 MHz, DMSO-d6) δ 12.04 (bs, 1H), 7.86 (s, 1H), 7.37 (s, 1H), 7.29 (t, J=2.8 Hz, 1H), 7.19-7.14 (m, 2H), 6.89 (t, J=7.4 Hz, 1H), 6.79-6.76 (m, 2H), 6.54 (s, 1H), 6.34 (t, J=2.4 Hz, 1H), 3.48 (s, 3H), 3.45 (s, 3H).

Example 8: 5-(5-hydroxy-2-phenoxyphenyl)-1-methyl pyridin-2(1H)-one

Preparation 41: 5-(5-methoxy-2-phenoxyphenyl)-1-methylpyridin-2(1H)-one

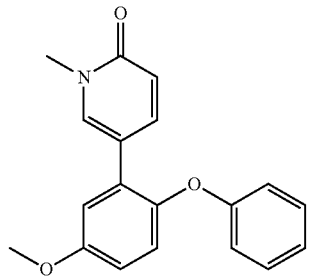 [SMILES: COc1ccc(Oc2ccccc2)c(-c2ccc(=O)n(C)c2)c1]

In a microwave tube, 2-iodo-4-methoxy-1-phenoxybenzene (90 mg, 0.28 mmol), sodium carbonate (81.6 mg, 0.77 mmol) and 1-methyl-5-(4,4,5,5-tetramethyl-1,3,2-dioxaborolan-2-yl)pyridin-2(1H)-one (84 mg, 0.36 mmol) in 1,2-Dimethoxyethane (2 mL) and Water (1 mL) was degassed by bubbling nitrogen for 10 min. $Pd(PPh_3)_4$ (14.83 mg, 0.013 mmol) was added, the tube sealed and the reaction heated at 120° C. for 30 min. Ethyl acetate (50 ml) was added and the organics washed with 2×50 ml water then 1×50 ml saturated brine solution. The organics were then separated and dried ($MgSO_4$) before concentration to dryness. The crude was then purified by flash column chromatography eluting with ethyl acetate/heptane gradient (0-100%). The desired fractions were combined and dried to give the title compound (45 mg, 48%) as a white solid.

HPLC $t_R$ (Agilent, acidic, 3.5 min): 1.58 min, m/z=308.2 $[M+H]^+$.

Preparation 42: 5-(5-hydroxy-2-phenoxyphenyl)-1-methylpyridin-2(1H)-one

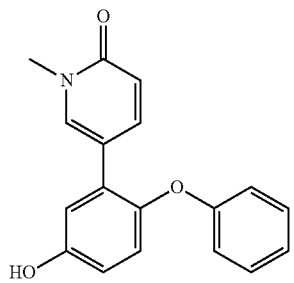 [SMILES: Cn1cc(-c2cc(O)ccc2Oc2ccccc2)ccc1=O]

Following the procedure in preparation 11, 5-(5-methoxy-2-phenoxyphenyl)-1-methylpyridin-2(1H)-one (45 mg, 0.15 mmol) was reacted to give the title compound (26 mg, 55%).

HPLC $t_R$ (Agilent, acidic, 3.5 min): 1.43 min, m/z=294.2 $[M+H]^+$.

$^1$H NMR (500 MHz, DMSO-d6) δ 9.50 (s, 1H), 7.85 (d, J=2.4 Hz, 1H), 7.55-7.53 (m, 1H), 7.29-7.25 (m, 2H), 7.00-6.90 (m, 2H), 6.85-6.76 (m, 4H), 6.33 (d, J=9.5 Hz, 1H), 3.42 (s, 3H).

Example 9: 4-(5-hydroxy-2-propoxyphenyl)-6-methyl-1,6-dihydro-7H-pyrrolo[2,3-c]pyridin-7-one Preparation 43:
1-fluoro-4-((4-methoxybenzyl)oxy)-2-nitrobenzene

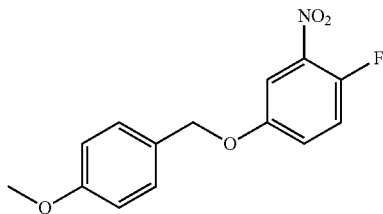 [SMILES: COc1ccc(COc2ccc(F)c([N+](=O)[O-])c2)cc1]

To a solution of 4-fluoro-3-nitrophenol (2.30 g, 14.6 mmol) in DMF (20.0 mL) was added potassium tert-butoxide (1.97 g, 17.6 mmol) at 20° C. and stirred for 15 minutes. 1-(chloromethyl)-4-methoxybenzene (2.7 mL, 19.0 mmol) was added and the reaction was stirred at 20° C. for 1.5 hours. The reaction was concentrated under vacuum. The residue was dissolved in EtOAc (2×400 mL) and washed with H$_2$O (300 mL), the combined organic phase was washed with brine (100 mL), dried with anhydrous Na$_2$SO$_4$, filtered and concentrated in vacuum to give 1-fluoro-4-((4-methoxybenzyl)oxy)-2-nitrobenzene (2.52 g, 8.64 mmol, yield=59%) as a yellow solid.

$^1$H NMR (400 MHz, CDCl$_3$) δ 7.63-7.60 (m, 1H), 7.36-7.33 (m, 2H), 7.22-7.18 (m, 2H), 6.96-6.91 (m, 2H), 5.02 (s, 2H), 3.83 (s, 3H).

Preparation 44:
4-((4-methoxybenzyl)oxy)-2-nitro-1-propoxybenzene

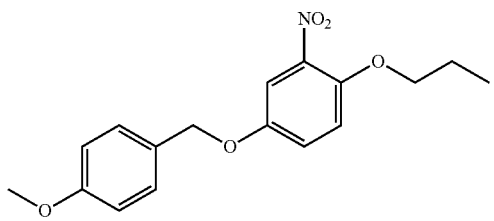 [SMILES: CCCOc1ccc(OCc2ccc(OC)cc2)cc1[N+](=O)[O-]]

To a solution of 1-fluoro-4-((4-methoxybenzyl)oxy)-2-nitrobenzene (750 mg, 2.7 mmol) in DMF (10 mL) was added sodium hydride (194 mg, 8.1 mmol) at 20° C. and stirred for 30 minutes. 1-propanol (0.6 mL, 8.1 mmol) was added and the reaction was stirred at 20° C. for 20 minutes. The reaction was concentrated under vacuum. The residue was dissolved in EtOAc (2×100 mL) and washed with H$_2$O (100 mL), the combined organic phase was washed with brine (100 mL), dried with anhydrous Na$_2$SO$_4$, filtered and concentrated in vacuum to give 4-((4-methoxybenzyl)oxy)-2-nitro-1-propoxybenzene (710 mg, 2.13 mmol, yield=79%) as a yellow solid.

$^1$H NMR (500 MHz, CDCl$_3$) δ 7.45-7.44 (m, 1H), 7.36-7.32 (m, 2H), 7.13 (dd, J=3.2, 9.2 Hz, 1H), 7.01-6.91 (m, 3H), 4.98 (s, 2H), 4.01 (t, J=6.4 Hz, 2H), 3.83 (s, 3H), 1.84 (tt, J=8.2, 8.8 Hz, 2H), 1.05 (t, J=7.6 Hz, 3H).

Preparation 45:
5-((4-methoxybenzyl)oxy)-2-propoxyaniline

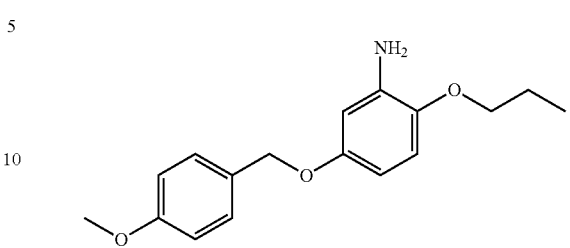

Following the procedure in preparation 8, 4-((4-methoxybenzyl)oxy)-2-nitro-1-propoxybenzene (710 mg, 2.23 mmol) was reacted to give the title compound (495 mg, 73%).

HPLC t$_R$ (Agilent, acidic, 3.5 min): 1.73 min, m/z=288.2 [M+H]$^+$.

Preparation 46:
2-iodo-4-((4-methoxybenzyl)oxy)-1-propoxybenzene

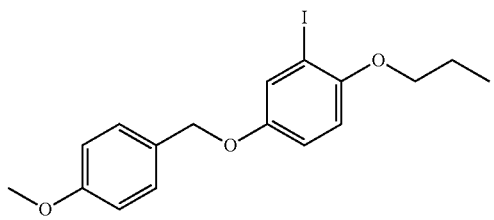 [SMILES: CCCOc1ccc(OCc2ccc(OC)cc2)cc1I]

Following the procedure in preparation 9, 5-((4-methoxybenzyl)oxy)-2-propoxyaniline (495 mg, 1.73 mmol) was reacted to give the title compound (360 mg, 50%).

$^1$H NMR (500 MHz, DMSO-d6) δ 7.41 (d, J=2.9 Hz, 1H), 7.34-7.31 (m, 2H), 6.92-6.87 (m, 3H), 6.72 (d, J=9.6 Hz, 1H), 4.91 (s, 2H), 3.90 (t, J=6.4 Hz, 2H), 3.81 (s, 3H), 1.82 (tdt, J=6.7, 6.7, 6.8 Hz, 2H), 1.07 (t, J=7.4 Hz, 3H).

Preparation 47: 4-(5-((4-methoxybenzyl)oxy)-2-propoxyphenyl)-6-methyl-1-tosyl-1,6-dihydro-7H-pyrrolo[2,3-c]pyridin-7-one

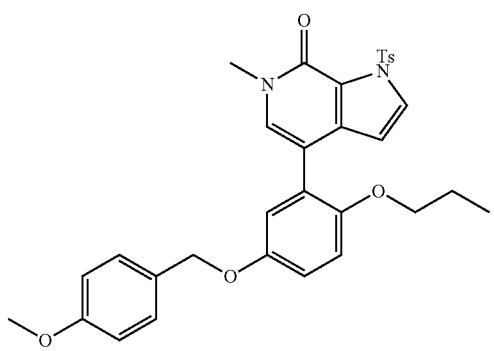 [SMILES: CCCOc1ccc(OCc2ccc(OC)cc2)cc1-c1cn(C)c(=O)c2c1ccn2S(=O)(=O)c1ccc(C)cc1]

Following the procedure in preparation 40, 2-iodo-4-((4-methoxybenzyl)oxy)-1-propoxybenzene (107 mg, 0.27 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (115 mg, 0.27 mmol) was reacted to give the title compound (93 mg, 54%).

HPLC $t_R$ (Agilent, acidic, 3.5 min): 2.07 min, m/z=573.3 [M+H]$^+$.

Preparation 48: 4-(5-hydroxy-2-propoxyphenyl)-6-methyl-1-tosyl-1,6-dihydro-7H-pyrrolo[2,3-c]pyridin-7-one

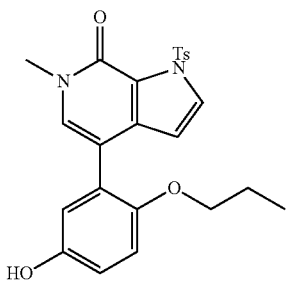 [SMILES: CCCOc1ccc(O)cc1-c1cn(C)c(=O)c2c1ccn2S(=O)(=O)c1ccc(C)cc1]

To a solution of 4-(5-((4-methoxybenzyl)oxy)-2-propoxyphenyl)-6-methyl-1-tosyl-1,6-dihydro-7H-pyrrolo[2,3-c]pyridin-7-one (90 mg, 0.16 mmol) in DCM (2 mL) was added trifluoroacetic acid (0.072 mL, 0.94 mmol) at 20° C. and stirred for 4 hours. The reaction was concentrated under vacuum. The residue was dissolved in EtOAc (2×100 mL) and washed with H$_2$O (100 mL), the combined organic phase was washed with brine (100 mL), dried with anhydrous Na$_2$SO$_4$, filtered and concentrated in vacuum to give 4-((4-methoxybenzyl)oxy)-2-nitro-1-propoxybenzene (55 mg, 0.12 mmol, yield=62%) as a yellow solid.

HPLC $t_R$ (Agilent, acidic, 3.5 min): 1.72 min, m/z=453.2 [M+H]$^+$.

Preparation 49: 4-(5-hydroxy-2-propoxyphenyl)-6-methyl-1,6-dihydro-7H-pyrrolo[2,3-c]pyridin-7-one

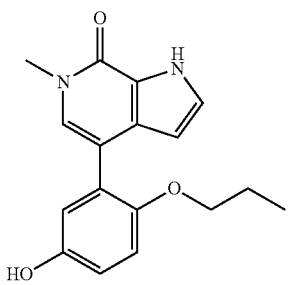 [SMILES: CCCOc1ccc(O)cc1-c1cn(C)c(=O)c2[nH]ccc12]

To a solution of 4-(5-hydroxy-2-propoxyphenyl)-6-methyl-1-tosyl-1,6-dihydro-7H-pyrrolo[2,3-c]pyridin-7-one (55 mg, 0.12 mmol) in THF (1 mL) and methanol (1 mL) was added sodium hydroxide (25.5 mg, 0.61 mmol) and the reaction mixture heated to 60° C. and stirred for 4 hours. The reaction was concentrated under vacuum. The residue was dissolved in EtOAc (2×100 mL) and washed with H$_2$O (100 mL), the combined organic phase was washed with brine (100 mL), dried with anhydrous Na$_2$SO$_4$, filtered and concentrated in vacuum. The crude material was purified by column chromatography (0-50% 20% MeOH/DCM in DCM) followed by reverse phase preparative HPLC (Gilson acidic 60-90% gradient). Fractions were concentrated on the genevac overnight to afford 4-((4-methoxybenzyl)oxy)-2-nitro-1-propoxybenzene (55 mg, 0.10 mmol, yield=62%) as a yellow solid.

HPLC $t_R$ (Agilent, acidic, 3.5 min): 1.39 min, m/z=299.2 [M+H]$^+$.

$^1$H NMR (500 MHz, CDCl$_3$) δ 10.21 (bs, 1H), 7.22 (s, 1H), 7.16 (t, J=2.8 Hz, 1H), 7.06 (s, 1H), 6.92-6.85 (m, 3H), 6.28 (t, J=2.5 Hz, 1H), 3.80 (t, J=6.5 Hz, 2H), 3.67 (s, 3H), 1.61 (dt, J=7.8, 13.9 Hz, 2H), 0.85 (t, J=7.8 Hz, 3H).

Example 10: 4-(2-cyclobutoxy-5-hydroxyphenyl)-6-methyl-1,6-dihydro-7H-pyrrolo[2,3-c]pyridin-7-one Preparation 50: 1-cyclobutoxy-4-((4-methoxybenzyl)oxy)-2-nitrobenzene

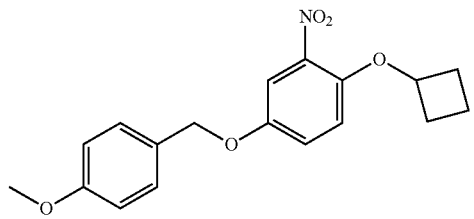 [SMILES: COc1ccc(COc2ccc(OC3CCC3)c([N+](=O)[O-])c2)cc1]

Following the procedure in preparation 44, 1-fluoro-4-((4-methoxybenzyl)oxy)-2-nitrobenzene (750 mg, 2.70 mmol) and cyclobutanol (0.64 mL, 9.2 mmol) was reacted to give the title compound (601 mg, 64%).

$^1$H NMR (400 MHz, CDCl$_3$) δ 7.44 (d, J=3.1 Hz, 1H), 7.34-7.31 (m, 2H), 7.09 (dd, J=3.2, 9.1 Hz, 1H), 6.93-6.83 (m, 3H), 4.96 (s, 2H), 4.71-4.64 (m, 1H), 3.82 (s, 3H), 2.47-2.39 (m, 2H), 2.29-2.18 (m, 2H), 1.91-1.83 (m, 1H), 1.73-1.61 (m, 1H).

Preparation 51: 2-cyclobutoxy-5-((4-methoxybenzyl)oxy)aniline

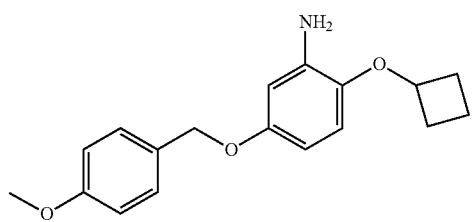 [SMILES: COc1ccc(COc2ccc(OC3CCC3)c(N)c2)cc1]

Following the procedure in preparation 44, 1-cyclobutoxy-4-((4-methoxybenzyl)oxy)-2-nitrobenzene (601 mg, 1.82 mmol) was reacted to give the title compound (375 mg, 62%).

HPLC $t_R$ (Agilent, acidic, 3.5 min): 1.76 min, m/z=300.2 [M+H]$^+$.

Preparation 52: 1-cyclobutoxy-2-iodo-4-((4-methoxybenzyl)oxy)benzene

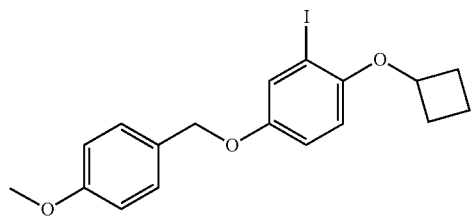 [SMILES: COc1ccc(COc2ccc(OC3CCC3)c(I)c2)cc1]

Following the procedure in preparation 45, 2-cyclobutoxy-5-((4-methoxybenzyl)oxy)aniline (375 mg, 1.25 mmol) was reacted to give the title compound (360 mg, 67%).

$^1$H NMR (400 MHz, CDCl$_3$) δ 7.40 (d, J=3.0 Hz, 1H), 7.32 (d, J=8.3 Hz, 2H), 6.92-6.84 (m, 3H), 6.60 (d, J=8.3 Hz, 1H), 4.89 (s, 2H), 4.61-4.54 (m, 1H), 3.81 (s, 3H), 2.45-2.37 (m, 2H), 2.27-2.17 (m, 2H), 1.89-1.81 (m, 1H), 1.68-1.58 (m, 1H).

Preparation 53: 4-(2-cyclobutoxy-5-((4-methoxybenzyl)oxy)phenyl)-6-methyl-1-tosyl-1,6-dihydro-7H-pyrrolo[2,3-c]pyridin-7-one

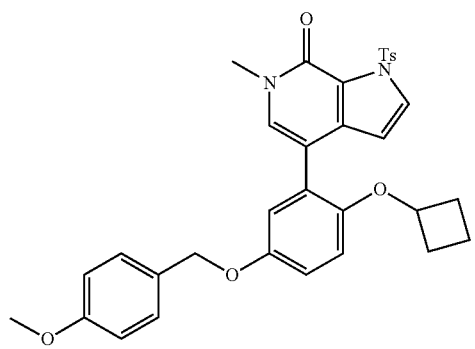 [SMILES: COc1ccc(COc2ccc(OC3CCC3)c(-c3cn(C)c(=O)c4c3ccn4S(=O)(=O)c3ccc(C)cc3)c2)cc1]

Following the procedure in preparation 40, 1-cyclobutoxy-2-iodo-4-((4-methoxybenzyl)oxy)benzene (119 mg, 0.29 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (125 mg, 0.29 mmol) was reacted to give the title compound (130 mg, 72%).

HPLC t$_R$ (Agilent, acidic, 3.5 min): 2.10 min, m/z=585.2 [M+H]$^+$.

Preparation 54: 4-(2-cyclobutoxy-5-hydroxyphenyl)-6-methyl-1-tosyl-1,6-dihydro-7H-pyrrolo[2,3-c]pyridin-7-one

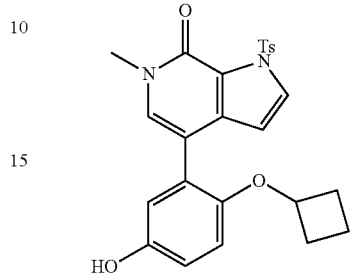

Following the procedure in preparation 48, 4-(2-cyclobutoxy-5-((4-methoxybenzyl)oxy)phenyl)-6-methyl-1-tosyl-1,6-dihydro-7H-pyrrolo[2,3-c]pyridin-7-one (130 mg, 0.22 mmol) was reacted to give the title compound (75 mg, 58%).

HPLC t$_R$ (Agilent, acidic, 3.5 min): 1.71 min, m/z=465.2 [M+H]$^+$.

Preparation 55: 4-(2-cyclobutoxy-5-hydroxyphenyl)-6-methyl-1,6-dihydro-7H-pyrrolo[2,3-c]pyridin-7-one

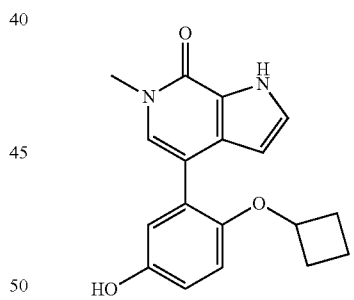

Following the procedure in preparation 49, 4-(2-cyclobutoxy-5-hydroxyphenyl)-6-methyl-1-tosyl-1,6-dihydro-7H-pyrrolo[2,3-c]pyridin-7-one (74 mg, 0.16 mmol) was reacted to give the title compound (4 mg, 7%).

HPLC t$_R$ (Agilent, acidic, 3.5 min): 1.38 min, m/z=311.2 [M+H]$^+$.

$^1$H NMR (400 MHz, DMSO) δ 11.94 (s, 1H), 8.97 (s, 1H), 7.27-7.25 (m, 1H), 7.18 (s, 1H), 6.77-6.74 (m, 1H), 6.73 (s, 1H), 6.66 (dd, J=2.9, 8.7 Hz, 1H), 6.14-6.11 (m, 1H), 4.52-4.44 (m, 1H), 3.54 (s, 3H), 2.31-2.23 (m, 2H), 1.92-1.82 (m, 2H), 1.70-1.49 (m, 2H).

Example 11: 4-(2-(cyclohexyloxy)-5-hydroxyphenyl)-6-methyl-1,6-dihydro-7H-pyrrolo[2,3-c]pyridin-7-one

Preparation 56: 1-(cyclohexyloxy)-4-((4-methoxybenzyl)oxy)-2-nitrobenzene

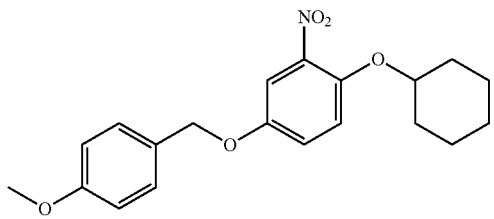

Following the procedure in preparation 44, 1-fluoro-4-((4-methoxybenzyl)oxy)-2-nitrobenzene (750 mg, 2.70 mmol) and cyclohexanol (0.87 mL, 8.2 mmol) was reacted to give the title compound (843 mg, 82%).

$^1$H NMR (400 MHz, CDCl$_3$) δ 7.40 (d, J=3.4 Hz, 1H), 7.35-7.31 (m, 2H), 7.10 (dd, J=3.1, 9.2 Hz, 1H), 7.02 (d, J=9.6 Hz, 1H), 6.95-6.90 (m, 2H), 4.97-4.96 (m, 2H), 4.28 (tt, J=4.2, 7.9 Hz, 1H), 3.82 (s, 3H), 1.95-1.88 (m, 2H), 1.81 (dd, J=10.2, 10.2 Hz, 2H), 1.68-1.50 (m, 3H), 1.38-1.26 (m, 3H).

Preparation 57: 2-(cyclohexyloxy)-5-((4-methoxybenzyl)oxy)aniline

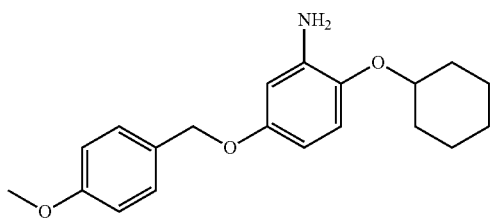 [SMILES: COc1ccc(COc2ccc(OC3CCCCC3)c([N+](=O)[O-])c2)cc1]

Following the procedure in preparation 44, 1-(cyclohexyloxy)-4-((4-methoxybenzyl)oxy)-2-nitrobenzene (843 mg, 2.35 mmol) was reacted to give the title compound (469 mg, 55%).

HPLC t$_R$ (Agilent, acidic, 3.5 min): 1.91 min, m/z=328.2 [M+H]$^+$.

Preparation 58: 1-(cyclohexyloxy)-2-iodo-4-((4-methoxybenzyl)oxy)benzene

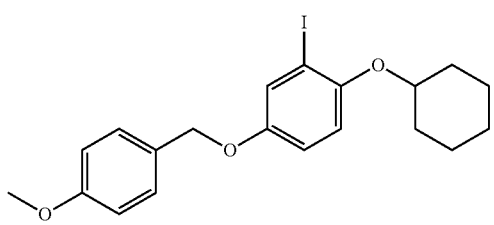 [SMILES: COc1ccc(COc2ccc(OC3CCCCC3)c(I)c2)cc1]

Following the procedure in preparation 45, 2-(cyclohexyloxy)-5-((4-methoxybenzyl)oxy)aniline (469 mg, 1.43 mmol) was reacted to give the title compound (350 mg, 52%).

$^1$H NMR (400 MHz, CDCl$_3$) δ 7.40 (d, J=2.9 Hz, 1H), 7.34-7.31 (m, 2H), 6.92-6.86 (m, 3H), 6.77 (d, J=9.4 Hz, 1H), 4.91-4.90 (m, 2H), 4.18 (tt, J=3.9, 7.7 Hz, 1H), 3.81 (s, 3H), 1.93-1.79 (m, 4H), 1.69-1.51 (m, 2H), 1.40-1.25 (m, 4H).

Preparation 59: 4-(2-(cyclohexyloxy)-5-((4-methoxybenzyl)oxy)phenyl)-6-methyl-1-tosyl-1,6-dihydro-7H-pyrrolo[2,3-c]pyridin-7-one

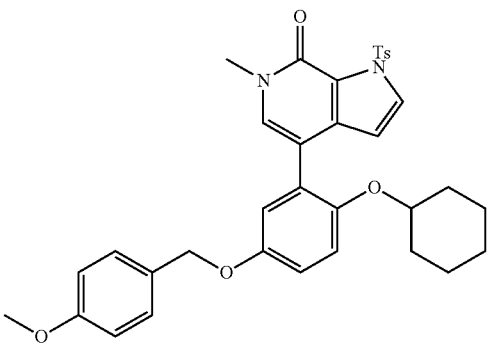 [SMILES: COc1ccc(COc2ccc(OC3CCCCC3)c(-c3cn(C)c(=O)c4c3ccn4S(=O)(=O)c3ccc(C)cc3)c2)cc1]

Following the procedure in preparation 40, 1-(cyclohexyloxy)-2-iodo-4-((4-methoxybenzyl)oxy)benzene (169 mg, 0.39 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (166 mg, 0.39 mmol) was reacted to give the title compound (107 mg, 43%).

HPLC t$_R$ (Agilent, acidic, 3.5 min): 2.21 min, m/z=613.3 [M+H]$^+$.

Preparation 60: 4-(2-(cyclohexyloxy)-5-hydroxyphenyl)-6-methyl-1-tosyl-1,6-dihydro-7H-pyrrolo[2,3-c]pyridin-7-one

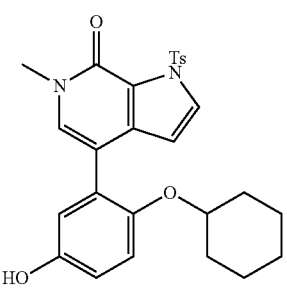 [SMILES: Cc1ccc(S(=O)(=O)n2ccc3c(-c4cc(O)ccc4OC4CCCCC4)cn(C)c(=O)c32)cc1]

Following the procedure in preparation 48, 4-(2-(cyclohexyloxy)-5-((4-methoxybenzyl)oxy)phenyl)-6-methyl-1-tosyl-1,6-dihydro-7H-pyrrolo[2,3-c]pyridin-7-one (105 mg, 0.17 mmol) was reacted to give the title compound (58 mg, 62%).

HPLC t$_R$ (Agilent, acidic, 3.5 min): 1.86 min, m/z=493.3 [M+H]$^+$.

Preparation 61: 4-(2-(cyclohexyloxy)-5-hydroxyphenyl)-6-methyl-1,6-dihydro-7H-pyrrolo[2,3-c]pyridin-7-one

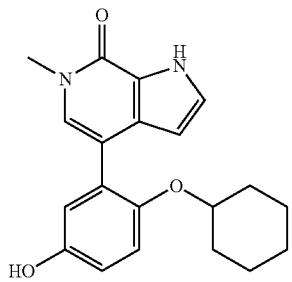 [SMILES: Cn1cc(-c2cc(O)ccc2OC2CCCCC2)c2cc[nH]c2c1=O]

Following the procedure in preparation 49, 4-(2-(cyclohexyloxy)-5-hydroxyphenyl)-6-methyl-1-tosyl-1,6-dihydro-7H-pyrrolo[2,3-c]pyridin-7-one (58 mg, 0.12 mmol) was reacted to give the title compound (12 mg, 29%).

HPLC $t_R$ (Agilent, acidic, 3.5 min): 1.51 min, m/z=339.2 [M+H]+.

$^1$H NMR (400 MHz, DMSO) δ 11.95 (s, 1H), 9.01 (s, 1H), 7.27-7.22 (m, 2H), 6.91 (d, J=8.7 Hz, 1H), 6.79 (d, J=3.0 Hz, 1H), 6.67 (dd, J=2.9, 8.7 Hz, 1H), 6.18-6.16 (m, 1H), 4.00-3.94 (m, 1H), 3.54 (s, 3H), 1.66-1.65 (m, 2H), 1.52-1.49 (m, 2H), 1.37 (s, 1H), 1.28-1.25 (m, 3H), 1.19-1.14 (m, 2H)

Example 12: 4-(5-hydroxy-2-((4-methoxycyclohexyl)oxy)phenyl)-6-methyl-1,6-dihydro-7H-pyrrolo[2,3-c]pyridin-7-one Preparation 62: 4-methoxycyclohexan-1-ol

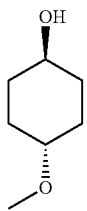

To a solution of cyclohexane-1,4-diol (4.6 g, 39.6 mmol) in DMF (15 mL) was added sodium hydride, 60% in oil (1.74 g, 43.5 mmol) at 20° C. and stirred for 30 minutes. Iodomethane (0.6 mL, 8.1 mmol) was added and the reaction was stirred at 20° C. for 16 hours. The reaction was concentrated under vacuum. The residue was dissolved in EtOAc (2×100 mL) and washed with H$_2$O (100 mL), the combined organic phase was washed with brine (100 mL), dried with anhydrous Na$_2$SO$_4$, filtered and concentrated in vacuum to give 4-((4-methoxybenzyl)oxy)-2-nitro-1-propoxybenzene (845 mg, 5.84 mmol, yield=15%) as a colourless oil.

$^1$H NMR (400 MHz, CDCl$_3$) δ 3.70-3.64 (m, 1H), 3.33 (s, 3H), 3.21-3.13 (m, 1H), 2.04-1.94 (m, 4H), 1.35-1.24 (m, 4H).

Preparation 63: 4-((4-methoxybenzyl)oxy)-1-((4-methoxycyclohexyl)oxy)-2-nitrobenzene

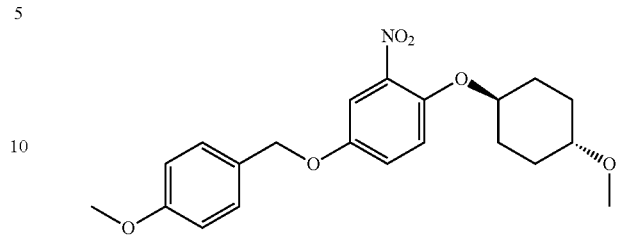

Following the procedure in preparation 44, 1-fluoro-4-((4-methoxybenzyl)oxy)-2-nitrobenzene (600 mg, 2.2 mmol) and 4-methoxycyclohexan-1-ol (845 mg, 6.5 mmol) was reacted to give the title compound (684 mg, 78%).

$^1$H NMR (400 MHz, CDCl$_3$) δ 7.44 (d, J=3.1 Hz, 1H), 7.38-7.34 (m, 2H), 7.14 (dd, J=3.1, 9.2 Hz, 1H), 7.04 (d, J=9.3 Hz, 1H), 6.96-6.93 (m, 2H), 4.99 (s, 2H), 4.43-4.36 (m, 1H), 3.85 (s, 3H), 3.40-3.33 (m, 4H), 2.07-2.01 (m, 4H), 1.72-1.63 (m, 2H), 1.57-1.47 (m, 2H).

Preparation 64: 5-((4-methoxybenzyl)oxy)-2-((4-methoxycyclohexyl)oxy)aniline

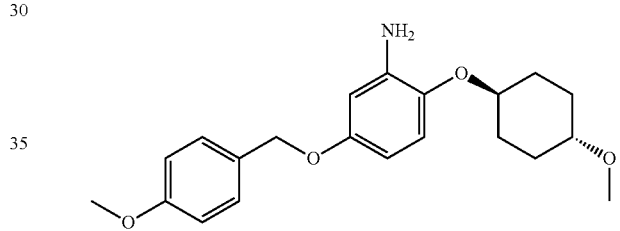

Following the procedure in preparation 44, 4-((4-methoxybenzyl)oxy)-1-((4-methoxycyclohexyl)oxy)-2-nitrobenzene (684 mg, 1.76 mmol) was reacted to give the title compound (506 mg, 76%).

HPLC $t_R$ (Agilent, acidic, 3.5 min): 1.67 min, m/z=358.2 [M+H]+.

Preparation 65: 2-iodo-4-((4-methoxybenzyl)oxy)-1-((4-methoxycyclohexyl)oxy)benzene

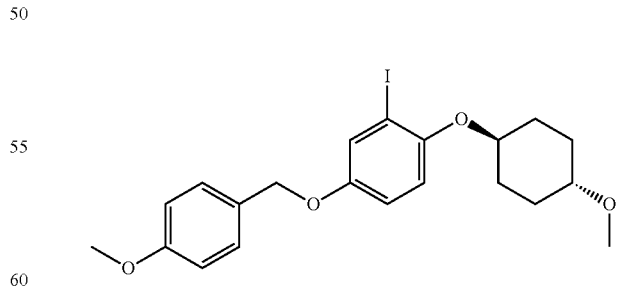

Following the procedure in preparation 45, 5-((4-methoxybenzyl)oxy)-2-((4-methoxycyclohexyl)oxy)aniline (506 mg, 1.41 mmol) was reacted to give the title compound (170 mg, 23%).

$^1$H NMR (400 MHz, CDCl$_3$) δ 7.42 (d, J=2.9 Hz, 1H), 7.35 (d, J=8.6 Hz, 2H), 6.95-6.89 (m, 3H), 6.80 (d, J=9.0 Hz,

1H), 4.93 (s, 2H), 4.30-4.24 (m, 1H), 3.84 (s, 3H), 3.37 (s, 4H), 2.12-2.01 (m, 4H), 1.71-1.44 (m, 4H).

Preparation 66: 4-(5-((4-methoxybenzyl)oxy)-2-((4-methoxycyclohexyl)oxy)phenyl)-6-methyl-1-tosyl-1,6-dihydro-7H-pyrrolo[2,3-c]pyridin-7-one

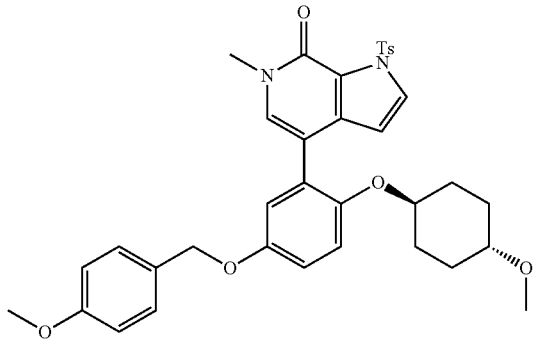

Following the procedure in preparation 40, 2-iodo-4-((4-methoxybenzyl)oxy)-1-((4-methoxycyclohexyl)oxy)benzene (169 mg, 0.36 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (155 mg, 0.36 mmol) was reacted to give the title compound (185 mg, 72%).

HPLC $t_R$ (Agilent, acidic, 3.5 min): 1.97 min, m/z=643.3 [M+H]+.

Preparation 67: 4-(5-hydroxy-2-((4-methoxycyclohexyl)oxy)phenyl)-6-methyl-1-tosyl-1,6-dihydro-7H-pyrrolo[2,3-c]pyridin-7-one

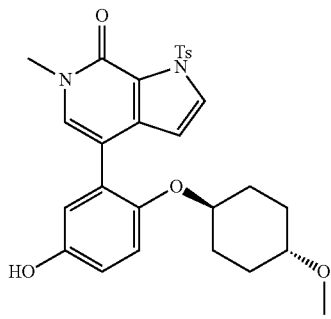 [SMILES: CO[C@H]1CC[C@H](Oc2ccc(O)cc2-c2cn(C)c(=O)c3c2ccn3S(=O)(=O)c2ccc(C)cc2)CC1]

Following the procedure in preparation 48, 4-(5-((4-methoxybenzyl)oxy)-2-((4-methoxycyclohexyl)oxy)phenyl)-6-methyl-1-tosyl-1,6-dihydro-7H-pyrrolo[2,3-c]pyridin-7-one (185 mg, 0.29 mmol) was reacted to give the title compound (97 mg, 58%). HPLC $t_R$ (Agilent, acidic, 3.5 min): 1.63 min, m/z=523.3 [M+H]+.

Preparation 68: 4-(5-hydroxy-2-((4-methoxycyclohexyl)oxy)phenyl)-6-methyl-1,6-dihydro-7H-pyrrolo[2,3-c]pyridin-7-one

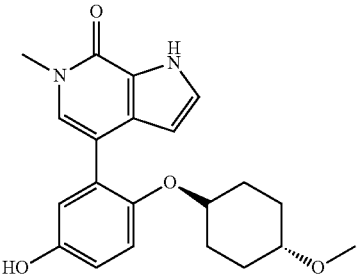

Following the procedure in preparation 49, 4-(5-hydroxy-2-((4-methoxycyclohexyl)oxy)phenyl)-6-methyl-1-tosyl-1,6-dihydro-7H-pyrrolo[2,3-c]pyridin-7-one (94 mg, 0.18 mmol) was reacted to give the title compound (21 mg, 30%).

HPLC $t_R$ (Agilent, acidic, 8 min): 2.95 min, m/z=369.2 [M+H]+.

1H NMR (400 MHz, DMSO) δ 11.92 (s, 1H), 8.99 (s, 1H), 7.29-7.23 (m, J=2.7 Hz, 1H), 7.21 (s, 1H), 6.97-6.88 (m, J=8.7 Hz, 1H), 6.80 (d, J=3.0 Hz, 1H), 6.68 (dd, J=8.8, 3.0 Hz, 1H), 6.16 (d, J=2.2 Hz, 1H), 4.10-3.91 (m, 1H), 3.55 (s, 3H), 3.16 (s, 3H), 3.12-3.02 (m, 1H), 1.87-1.65 (m, 4H), 1.32-1.11 (m, 4H).

Example 13: 4-(5-benzyl-1-methyl-2-oxo-1,2-dihydropyridin-4-yl)-6-methyl-1,6-dihydro-7H-pyrrolo[2,3-c]pyridin-7-one Preparation 69: 5-benzyl-2-chloropyridin-4-amine

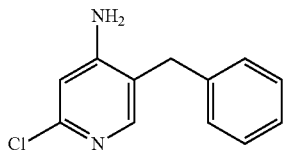 [SMILES: Nc1cc(Cl)ncc1Cc1ccccc1]

A mixture of 5-bromo-2-chloropyridin-4-amine (4.60 g, 22.17 mmol), 2-benzyl-4,4,5,5-tetramethyl-1,3,2-dioxaborolane (6.00 g, 27.51 mmol), K₃PO₄ (13.8 g, 65.0 mmol, 2.93 eq) and cataCXium A Pd-G3 (500 mg, 687 umol, 0.031 eq) in H₂O (8 mL) and dioxane (40 mL) was stirred at 75° C. for 12 hours under N₂. The mixture was poured into water (200 mL) and extracted with EtOAc (50 mL×3). The combined organic layer was washed with brine (50 mL), dried over Na₂SO₄, filtered and concentrated. The residue was purified by column chromatography (SiO₂, Petroleum ether:Ethyl acetate=10:1-5:1-3:1) (Petroleum ether:Ethyl acetate=3:1, Rf=0.5) to give the title compound (3.60 g, 16.5 mmol, 74.2% yield) as yellow solid.

1H NMR (400 MHz, CDCl₃) δ 8.09 (s, 1H), 7.34-7.32 (m, 2H), 7.31-7.30 (m, 1H), 7.25-717 (m, 2H), 6.55 (s, 1H), 4.16-4.10 (m, 2H), 3.85 (s, 2H)

Preparation 70: 5-benzyl-4-bromo-2-chloropyridine

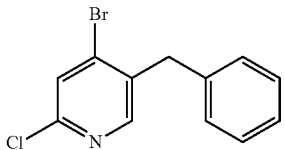 [SMILES: Clc1cc(Br)c(Cc2ccccc2)cn1]

A mixture of tert-butyl nitrite (2.70 g, 26.2 mmol) and CuBr (4.81 g, 33.5 mmol) was stirred in MeCN (10 mL) at 70° C. for 10 minutes. A solution of 5-benzyl-2-chloropyridin-4-amine (1.80 g, 8.23 mmol) in MeCN (10 mL) was added drop-wise to the reaction mixture at 70° C., and the mixture was stirred at 70° C. for 1 hour. The mixture was poured into water (80 mL) and extracted with ethyl acetate (100 mL). The combined organic layer was washed with brine (50 mL), dried over $Na_2SO_4$, filtered and concentrated to give the title compound (2.00 g, 7.08 mmol, 86.0% yield) as green oil.

$^1$H NMR (400 MHz, $CDCl_3$) δ 7.37-7.29 (m, 2H), 7.29-7.23 (m, 2H), 7.17 (d, J=7.0 Hz, 3H), 4.29 (s, 2H).

Preparation 71: 5-benzyl-4-bromo-1-methylpyridin-2(1H)-one

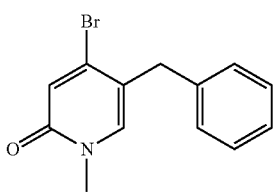 [SMILES: Cn1cc(Cc2ccccc2)c(Br)cc1=O]

5-benzyl-4-bromo-2-chloropyridine (2.00 g, 7.08 mmol) was dissolved in $CHCl_3$ (10 mL), $Me_2SO_4$ (5.35 mL, 56.4 mmol) was added and the solution heated at 70° C. for 12 hrs. Upon cooling, a mixture of TEA (15.0 g, 148 mmol), $CH_3CO_2H$ (13.7 mL, 240 mmol), and EtOH (13.7 mL, 235 mmol) was added and the reaction heated at 70° C. for a further 2 hrs. The reaction mixture diluted with $H_2O$ (50 mL) and then extracted with ethyl acetate 200 mL. The combined organic layers were washed with brine (50 mL), dried over $Na_2SO_4$, filtered and concentrated under reduced pressure to give an oil. The residue was purified by prep-HPLC (HCl condition; column: Phenomenex luna C18 250×50 mm×10 um, to give 5-benzyl-4-bromo-1-methylpyridin-2(1H)-one (859 mg, 3.09 mmol, 43.6% yield) as a yellow solid.

$^1$H NMR (400 MHz, DMSO-d6) δ 7.80 (s, 1H), 7.33-7.26 (m, 2H), 7.23-7.17 (m, 3H), 6.77 (s, 1H), 3.81 (s, 2H), 3.41 (s, 3H).

Preparation 72: 4-(5-benzyl-1-methyl-2-oxo-1,2-dihydropyridin-4-yl)-6-methyl-1,6-dihydro-7H-pyrrolo[2,3-c]pyridin-7-one

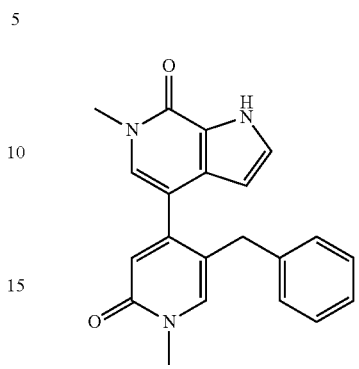

Following the procedure in preparation 10, 5-benzyl-4-bromo-1-methylpyridin-2(1H)-one (71 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (100 mg, 0.23 mmol) was reacted to give the title compound (34 mg, 39%).

HPLC $t_R$ (Agilent, acidic, 3.5 min): 1.26 min, m/z=346.2 [M+H]$^+$.

$^1$H NMR (500 MHz, $CDCl_3$) δ 10.61 (bs, 1H), 7.21 (t, J=2.4 Hz, 1H), 7.13-7.07 (m, 3H), 7.01 (s, 1H), 6.77 (d, J=6.6 Hz, 2H), 6.50 (s, 1H), 6.35 (s, 1H), 6.14 (t, J=2.4 Hz, 1H), 5.22 (s, 2H), 3.53 (s, 3H), 3.42 (s, 3H).

Example 14: 4-(1-benzyl-1H-pyrazol-5-yl)-6-methyl-1,6-dihydro-7H-pyrrolo[2,3-c]pyridin-7-one

Preparation 73: 4-(5-benzyl-1-methyl-2-oxo-1,2-dihydropyridin-4-yl)-6-methyl-1,6-dihydro-7H-pyrrolo[2,3-c]pyridin-7-one

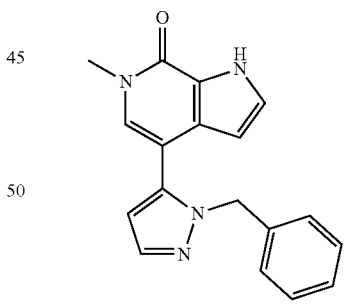

Following the procedure in preparation 10, 1-benzyl-5-bromo-1H-pyrazole (61 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (100 mg, 0.23 mmol) was reacted to give the title compound (17 mg, 23%).

HPLC $t_R$ (Agilent, acidic, 3.5 min): 1.41 min, m/z=305.2 [M+H]$^+$.

$^1$H NMR (500 MHz, $CDCl_3$) δ 9.61 (bs, 1H), 7.68 (d, J=1.8 Hz, 1H), 7.28-7.25 (m, 4H), 7.05-7.02 (m, 2H), 6.70 (s, 1H), 6.41 (d, J=1.8 Hz, 1H), 6.27 (t, J=2.6 Hz, 1H), 5.34-5.33 (m, 2H), 3.55 (s, 3H).

Example 15: 4-(1-benzyl-1H-imidazol-2-yl)-6-methyl-1,6-dihydro-7H-pyrrolo[2,3-c]pyridin-7-one Preparation 74: 1-benzyl-2-bromo-1H-imidazole

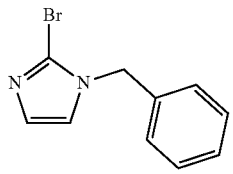 [SMILES: Brc1nccn1Cc1ccccc1]

To a solution of 2-bromo-1H-imidazole (1.0 g, 7.1 mmol) in TMF (160 mL) was added sodium hydride, 60% in oil (286 mg, 7.1 mmol) at 20° C. and stirred for 10 minutes at 70° C. (bromomethyl)benzene (0.85 mL, 8.1 mmol) was added and the reaction was stirred at 70° C. for 1 hour. The reaction mixture was added to EtOAc (100 mL) and washed with H$_2$O (100 mL), the organic phase was washed with brine (100 mL), dried with anhydrous Na$_2$SO$_4$, filtered and concentrated in vacuum to give 1-benzyl-2-bromo-1H-imidazole (920 mg, 54%).

HPLC t$_R$ (Agilent, acidic, 3.5 min): 1.29 min, m/z=238.1 [M+H]$^+$.

Preparation 75: 4-(1-benzyl-1H-imidazol-2-yl)-6-methyl-1,6-dihydro-7H-pyrrolo[2,3-c]pyridin-7-one

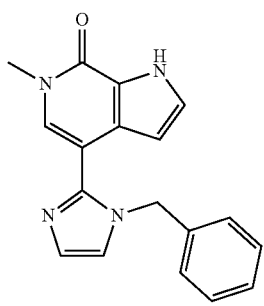 [SMILES: Cn1cc(-c2nccn2Cc2ccccc2)c2cc[nH]c2c1=O]

Following the procedure in preparation 10, 1-benzyl-2-bromo-1H-imidazole (61 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (100 mg, 0.23 mmol) was reacted to give the title compound (18 mg, 24%).

HPLC t$_R$ (Agilent, acidic, 3.5 min): 0.97 min, m/z=305.2 [M+H]$^+$.

$^1$H NMR (500 MHz, CDCl$_3$) δ 10.09 (bs, 1H), 7.36-7.33 (m, 2H), 7.31 (t, J=2.9 Hz, 2H), 7.27 (d, J=1.1 Hz, 1H), 7.12 (s, 1H), 7.06 (t, J=1.2 Hz, 1H), 7.04 (d, J=7.4 Hz, 2H), 6.41 (t, J=2.5 Hz, 1H), 5.18 (s, 2H), 3.62 (s, 3H).

Example 16: 4-(1-benzyl-1H-1,2,4-triazol-5-yl)-6-methyl-1,6-dihydro-7H-pyrrolo[2,3-c]pyridin-7-one Preparation 76: 4-(1-benzyl-1H-1,2,4-triazol-5-yl)-6-methyl-1,6-dihydro-7H-pyrrolo[2,3-c]pyridin-7-one

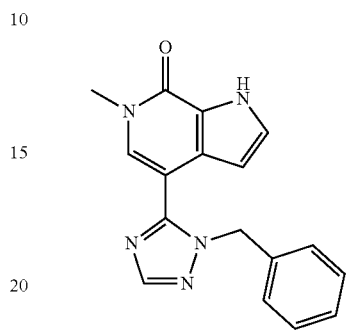

Following the procedure in preparation 10, 1-benzyl-2-bromo-1H-imidazole (61 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (100 mg, 0.23 mmol) was reacted to give the title compound (18 mg, 24%).

HPLC t$_R$ (Agilent, acidic, 3.5 min): 0.97 min, m/z=305.2 [M+H]$^+$.

$^1$H NMR (500 MHz, DMSO-d6) δ 12.22 (bs, 1H), 8.12 (s, 1H), 7.48 (s, 1H), 7.36-7.26 (m, 4H), 7.09 (d, J=7.0 Hz, 2H), 6.35 (d, J=2.4 Hz, 1H), 5.50 (s, 2H), 3.30 (s, 3H).

Example 17: 4-(4-benzylthiazol-5-yl)-6-methyl-1,6-dihydro-7H-pyrrolo[2,3-c]pyridin-7-one Preparation 77: 4-benzyl-5-bromothiazole

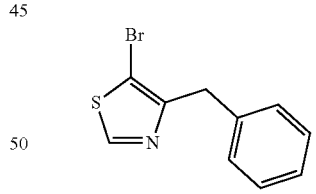

To the solution of 4-benzyl-5-bromothiazol-2-amine (16.2 g, 60.2 mmol) in DMF (160 mL) which was heated to 55° C. was added dropwise solution of tert-butyl nitrite (9.3 g, 90.2 mmol) in DMF (50 mL). The reaction mixture was stirred for 1 h at 70° C. After that it was cooled to RT water (250 mL) was added, and then water layer was extracted with EtOAc (3×100 mL). Combined organics were dried over Na$_2$SO$_4$ and concentrated under reduced pressure. The residue was purified by column chromatography (eluent Hexane:EtOAc 14:1) to give 4-benzyl-5-bromothiazole (1.1 g, 7.2% yield) $^1$H NMR (400 MHz, CDCl$_3$) δ 8.68 (s, 1H), 7.25-7.20 (m, 4H), 7.17-7.12 (m, 1H), 4.09 (s, 2H).

Preparation 78: 4-(4-benzylthiazol-5-yl)-6-methyl-1,6-dihydro-7H-pyrrolo[2,3-c]pyridin-7-one

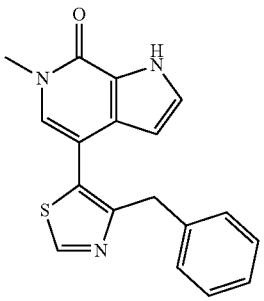

Following the procedure in preparation 10, 4-benzyl-5-bromothiazole (65 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (100 mg, 0.23 mmol) was reacted to give the title compound (5 mg, 6%).

HPLC $t_R$ (Agilent, acidic, 3.5 min): 1.43 min, m/z=322.2 [M+H]$^+$.

$^1$H NMR (500 MHz, DMSO-d6) δ 11.18 (bs, 1H), 8.86 (s, 1H), 7.34 (t, J=2.6 Hz, 1H), 7.30-7.28 (m, 2H), 7.23-7.18 (m, 3H), 6.89 (s, 1H), 6.34 (t, J=2.5 Hz, 1H), 4.18-4.17 (m, 2H), 3.66-3.65 (m, 3H).

Example 18: 1-methyl-5-(4-phenoxythiazol-5-yl)pyridin-2(1H)-one

Preparation 79: 4-(4-benzylthiazol-5-yl)-6-methyl-1,6-dihydro-7H-pyrrolo[2,3-c]pyridin-7-one

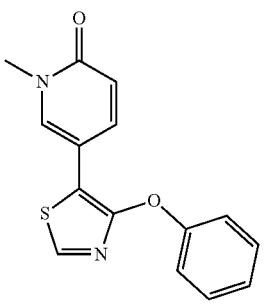 [SMILES: Cn1cc(-c2scnc2Oc2ccccc2)ccc1=O]

Following the procedure in preparation 40, 5-bromo-4-phenoxythiazole (89 mg, 0.35 mmol) was reacted to give the title compound (48 mg, 48%).

HPLC $t_R$ (Agilent, acidic, 3.5 min): 1.34 min, m/z=285.0 [M+H]$^+$.

$^1$H NMR (500 MHz, DMSO-d6) δ 8.93 (s, 1H), 8.06 (s, 1H), 7.70-7.66 (m, 1H), 7.37 (t, J=7.3 Hz, 2H), 7.12 (t, J=7.4 Hz, 1H), 7.04-7.00 (m, 2H), 6.48-6.45 (m, 1H), 3.47 (s, 3H).

Example 19: 4-(4-(2-hydroxyphenoxy)thiazol-5-yl)-6-methyl-1,6-dihydro-7H-pyrrolo[2,3-c]pyridin-7-one Preparation 80: 4-(2-methoxyphenoxy)thiazole

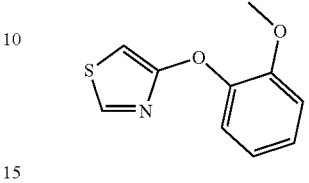

Following the procedure in preparation 22, 2-methoxyphenol (1.1 g, 8.65 mmol) was reacted to give the title compound (307 mg, 17%).

HPLC $t_R$ (Agilent, acidic, 3.5 min): 1.47 min, m/z=208.0 [M+H]$^+$.

Preparation 81: 5-bromo-4-(2-methoxyphenoxy)thiazole

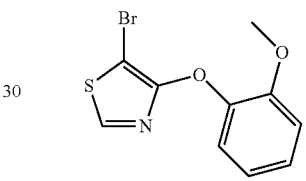

Following the procedure in preparation 23, 4-(2-methoxyphenoxy)thiazole (155 mg, 0.75 mmol) was reacted to give the title compound (170 mg, 79%).

HPLC $t_R$ (Agilent, acidic, 3.5 min): 1.65 min, m/z=287.2 [M+H]$^+$.

Preparation 82: 4-(4-(2-methoxyphenoxy)thiazol-5-yl)-6-methyl-1,6-dihydro-7H-pyrrolo[2,3-c]pyridin-7-one

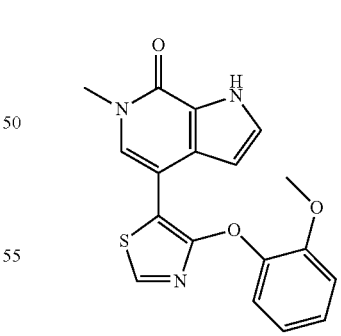

Following the procedure in preparation 10, 5-bromo-4-(2-methoxyphenoxy)thiazole (169 mg, 0.59 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (230 mg, 0.54 mmol) was reacted to give the title compound (43 mg, 23%).

HPLC $t_R$ (Agilent, acidic, 3.5 min): 1.46 min, m/z=354.2 [M+H]$^+$.

Preparation 83: 4-(4-(2-hydroxyphenoxy)thiazol-5-yl)-6-methyl-1,6-dihydro-7H-pyrrolo[2,3-c]pyridin-7-one

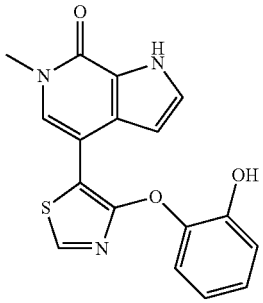 [SMILES: Cn1cc(-c2scnc2Oc2ccccc2O)c2cc[nH]c2c1=O]

Following the procedure in preparation 11, 4-(4-(2-methoxyphenoxy)thiazol-5-yl)-6-methyl-1,6-dihydro-7H-pyrrolo[2,3-c]pyridin-7-one (43 mg, 0.12 mmol) was reacted to give the title compound (9 mg, 20%).
HPLC $t_R$ (Agilent, acidic, 3.5 min): 1.36 min, m/z=340.0 [M+H]$^+$.
$^1$H NMR (500 MHz, DMSO-d6) δ 12.21 (bs, 1H), 9.48 (bs, 1H), 8.88 (s, 1H), 7.69 (s, 1H), 7.36 (t, J=2.6 Hz, 1H), 6.98-6.89 (m, 3H), 6.75-6.71 (m, 1H), 6.56 (t, J=2.1 Hz, 1H), 3.55 (s, 3H).

Example 20: 4-(4-(4-hydroxyphenoxy)thiazol-5-yl)-6-methyl-1,6-dihydro-7H-pyrrolo[2,3-c]pyridin-7-one Preparation 84: 4-(4-methoxyphenoxy)thiazole

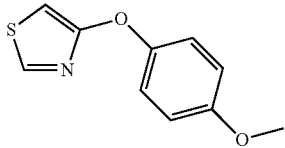

Following the procedure in preparation 22, 4-methoxyphenol (1.1 g, 8.65 mmol) was reacted to give the title compound (332 mg, 19%).
HPLC $t_R$ (Agilent, acidic, 3.5 min): 1.46 min, m/z=208.0 [M+H]$^+$.

Preparation 85: 5-bromo-4-phenoxythiazole

Following the procedure in preparation 23, 4-(2-methoxyphenoxy)thiazole (280 mg, 1.35 mmol) was reacted to give the title compound (195 mg, 50%).
HPLC $t_R$ (Agilent, acidic, 3.5 min): 1.70 min, m/z=287.2 [M+H]$^+$.

Preparation 86: 4-(4-(4-methoxyphenoxy)thiazol-5-yl)-6-methyl-1,6-dihydro-7H-pyrrolo[2,3-c]pyridin-7-one

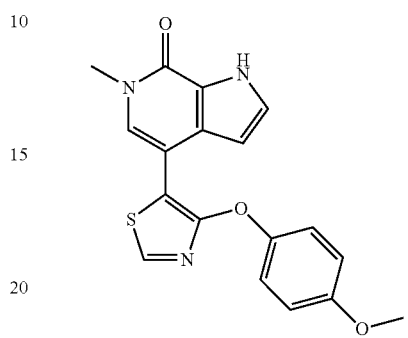

Following the procedure in preparation 10, 5-bromo-4-phenoxythiazole (162 mg, 0.57 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (220 mg, 0.51 mmol) was reacted to give the title compound (40 mg, 22%).
HPLC $t_R$ (Agilent, acidic, 3.5 min): 1.43 min, m/z=354.0 [M+H]$^+$.

Preparation 87: 4-(4-(4-hydroxyphenoxy)thiazol-5-yl)-6-methyl-1,6-dihydro-7H-pyrrolo[2,3-c]pyridin-7-one

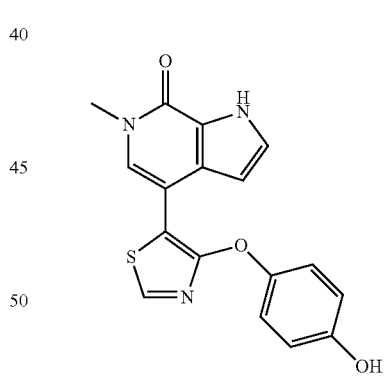

Following the procedure in preparation 11, 4-(4-(2-methoxyphenoxy)thiazol-5-yl)-6-methyl-1,6-dihydro-7H-pyrrolo[2,3-c]pyridin-7-one (40 mg, 0.11 mmol) was reacted to give the title compound (15 mg, 35%).
HPLC $t_R$ (Agilent, acidic, 3.5 min): 1.30 min, m/z=340.0 [M+H]$^+$.
$^1$H NMR (500 MHz, DMSO-d6) δ 12.19 (bs, 1H), 9.18 (bs, 1H), 8.95 (s, 1H), 7.53 (s, 1H), 7.35 (t, J=2.7 Hz, 1H), 6.86-6.83 (m, 2H), 6.71-6.69 (m, 2H), 6.44 (t, J=2.4 Hz, 1H), 3.54 (s, 3H).

Example 21: 5-(4-(2-hydroxyphenoxy)thiazol-5-yl)-1-methylpyridin-2(1H)-one

Preparation 88: 5-(4-(2-methoxyphenoxy)thiazol-5-yl)-1-methylpyridin-2(1H)-one

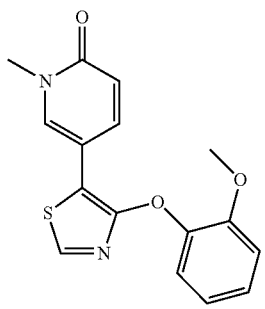 [SMILES: COc1ccccc1Oc1ncsc1-c1ccc(=O)n(C)c1]

Following the procedure in preparation 40, 5-bromo-4-(2-methoxyphenoxy)thiazole (167 mg, 0.58 mmol) was reacted to give the title compound (110 mg, 66%).

HPLC $t_R$ (Agilent, acidic, 3.5 min): 1.35 min, m/z=315.0 [M+H]$^+$.

Preparation 89: 5-(4-(2-hydroxyphenoxy)thiazol-5-yl)-1-methylpyridin-2(1H)-one

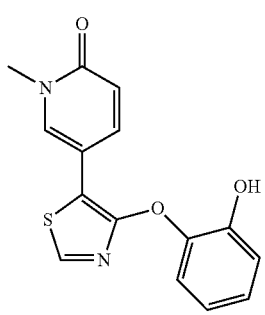 [SMILES: Cn1cc(-c2scnc2Oc2ccccc2O)ccc1=O]

Following the procedure in preparation 11, 4-(4-(2-methoxyphenoxy)thiazol-5-yl)-6-methyl-1,6-dihydro-7H-pyrrolo[2,3-c]pyridin-7-one (110 mg, 0.35 mmol) was reacted to give the title compound (53 mg, 46%).

HPLC $t_R$ (Agilent, acidic, 3.5 min): 1.26 min, m/z=301.0 [M+H]$^+$.

$^1$H NMR (500 MHz, DMSO-d6) δ 9.54 (s, 1H), 8.79 (s, 1H), 8.12 (s, 1H), 7.83-7.81 (d, J=9.7 Hz, 1H), 6.99-6.90 (m, 3H), 6.75 (t, J=7.6 Hz, 1H), 6.48 (d, J=10.4 Hz, 1H), 3.48 (s, 3H).

Example 22: 4-(5-(2-hydroxyphenoxy)-1-methyl-2-oxo-1,2-dihydropyridin-4-yl)-6-methyl-1,6-dihydro-7H-pyrrolo[2,3-c]pyridin-7-one

Preparation 90: 2-chloro-5-(2-methoxyphenoxy)-4-nitropyridine 1-oxide

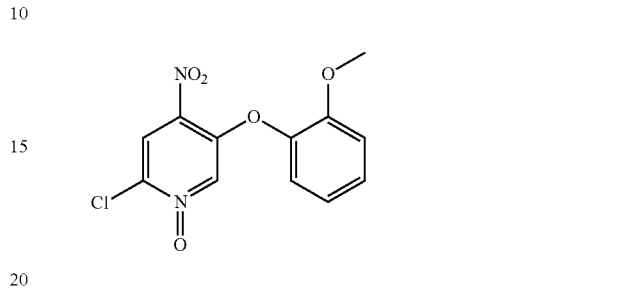

Following the procedure in preparation 35, 2-methoxyphenol (15.5 g, 125 mmol) was reacted to give the title compound (23.0 g, 75%).

HPLC $t_R$ (Shimadzu, acidic, 1.5 min): 0.92 min, m/z=297.1 [M+H]$^+$.

Preparation 91: 2,4-dibromo-5-(2-methoxyphenoxy)pyridine 1-oxide

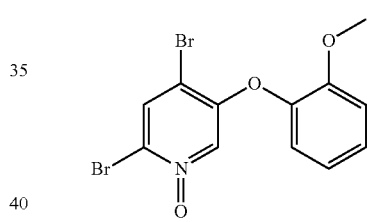

Following the procedure in preparation 26, 2-chloro-5-(2-methoxyphenoxy)-4-nitropyridine 1-oxide (6.0 g, 20.2 mmol) was reacted to give the title compound (7.0 g, 92%).

HPLC $t_R$ (Shimadzu, acidic, 1.5 min): 0.85 min, m/z=376.0 [M+H]$^+$.

Preparation 92: 2,4-dibromo-5-(2-methoxyphenoxy)pyridine

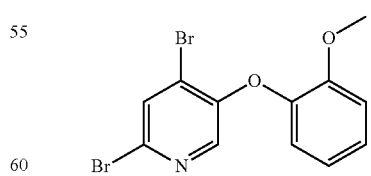

Following the procedure in preparation 27, 2,4-dibromo-5-(2-methoxyphenoxy)pyridine 1-oxide (7.0 g, 18.6 mmol) was reacted to give the title compound (6.7 g, 100%).

HPLC $t_R$ (Shimadzu, acidic, 1.5 min): 0.91 min, m/z=359.9 [M+H]$^+$.

Preparation 93: 4-bromo-5-(2-methoxyphenoxy)pyridin-2(1H)-one

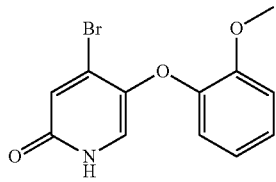 [SMILES: COc1ccccc1Oc1c[nH]c(=O)cc1Br]

Following the procedure in preparation 38, 2,4-dibromo-5-(2-methoxyphenoxy)pyridine (6.7 g, 18.6 mmol) was reacted to give the title compound (4.3 g, 77%).

HPLC $t_R$ (Shimadzu, acidic, 1.5 min): 0.81 min, m/z=298.0 [M+H]$^+$.

Preparation 94: 4-bromo-5-(2-methoxyphenoxy)-1-methylpyridin-2(1H)-one

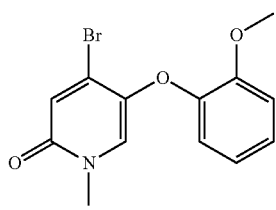 [SMILES: COc1ccccc1Oc1cn(C)c(=O)cc1Br]

Following the procedure in preparation 39, 4-bromo-5-(2-methoxyphenoxy)pyridin-2(1H)-one (4.2 g, 14.3 mmol) was reacted to give the title compound (50 mg, 1%).

$^1$H NMR (400 MHz, DMSO-d6) δ 7.78 (s, 1H), 7.13-7.02 (m, 2H), 6.90-6.84 (m, 2H), 6.80-6.76 (m, 1H), 3.82 (s, 3H), 3.37 (s, 3H)

Preparation 95: 4-(5-(2-methoxyphenoxy)-1-methyl-2-oxo-1,2-dihydropyridin-4-yl)-6-methyl-1,6-dihydro-7H-pyrrolo[2,3-c]pyridin-7-one

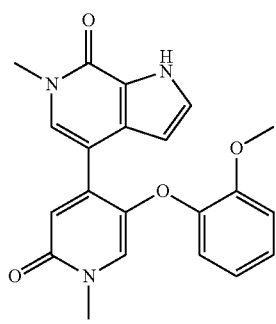 [SMILES: COc1ccccc1Oc1cn(C)c(=O)cc1-c1cn(C)c(=O)c2[nH]ccc12]

Following the procedure in preparation 10, 4-bromo-5-(2-methoxyphenoxy)-1-methylpyridin-2(1H)-one (36 mg, 0.11 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (50 mg, 0.11 mmol) was reacted to give the title compound (8 mg, 18%).

HPLC $t_R$ (Agilent, acidic, 3.5 min): 1.25 min, m/z=378.1 [M+H]$^+$.

Preparation 96: 4-(5-(2-hydroxyphenoxy)-1-methyl-2-oxo-1,2-dihydropyridin-4-yl)-6-methyl-1,6-dihydro-7H-pyrrolo[2,3-c]pyridin-7-one

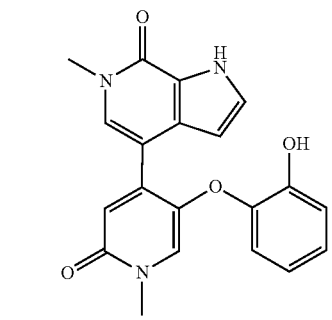 [SMILES: Cn1cc(Oc2ccccc2O)c(-c2cn(C)c(=O)c3[nH]ccc23)cc1=O]

Following the procedure in preparation 11, 4-(5-(2-methoxyphenoxy)-1-methyl-2-oxo-1,2-dihydropyridin-4-yl)-6-methyl-1,6-dihydro-7H-pyrrolo[2,3-c]pyridin-7-one (24 mg, 0.06 mmol) was reacted to give the title compound (13 mg, 50%).

HPLC $t_R$ (Agilent, acidic, 3.5 min): 1.17 min, m/z=364.0 [M+H]$^+$.

$^1$H NMR (500 MHz, CDCl$_3$) δ 9.56 (bs, 1H), 7.06 (s, 1H), 7.00 (s, 1H), 6.81-6.81 (m, 1H), 6.69-6.62 (m, 2H), 6.56 (s, 1H), 6.50-6.47 (m, 2H), 6.26 (t, J=2.5 Hz, 1H), 5.55 (bs, 1H), 3.36 (s, 3H), 3.32 (s, 3H).

Example 23: 4-(5-(3-methoxyphenoxy)-1-methyl-2-oxo-1,2-dihydropyridin-4-yl)-6-methyl-1,6-dihydro-7H-pyrrolo[2,3-c]pyridin-7-one

Preparation 97: 2-chloro-5-(3-methoxyphenoxy)-4-nitropyridine 1-oxide

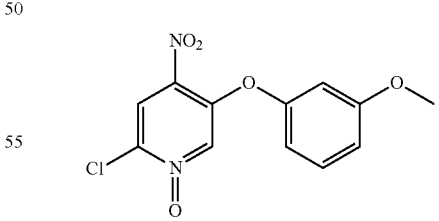

Following the procedure in preparation 35, 3-methoxyphenol (15.5 g, 125 mmol) was reacted to give the title compound (24.0 g, 78%).

HPLC $t_R$ (Shimadzu, acidic, 1.5 min): 0.94 min, m/z=297.1 [M+H]$^+$.

Preparation 98: 2,4-dibromo-5-(3-methoxyphenoxy)pyridine 1-oxide

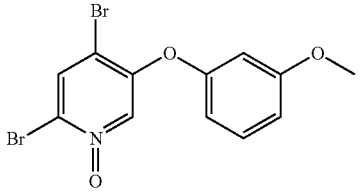 [SMILES: COc1cccc(Oc2c[n+]([O-])c(Br)cc2Br)c1]

Following the procedure in preparation 26, 2-chloro-5-(3-methoxyphenoxy)-4-nitropyridine 1-oxide (6.5 g, 21.9 mmol) was reacted to give the title compound (7.0 g, 85%).
HPLC $t_R$ (Shimadzu, acidic, 1.5 min): 0.83 min, m/z=376.0 [M+H]$^+$.

Preparation 99: 2,4-dibromo-5-(3-methoxyphenoxy)pyridine

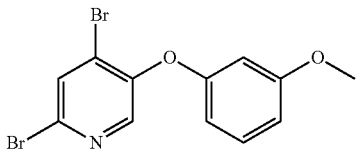 [SMILES: COc1cccc(Oc2cnc(Br)cc2Br)c1]

Following the procedure in preparation 27, 2,4-dibromo-5-(3-methoxyphenoxy)pyridine 1-oxide (15 g, 40.0 mmol) was reacted to give the title compound (2.0 g, 14%).
HPLC $t_R$ (Shimadzu, acidic, 1.5 min): 1.00 min, m/z=359.9 [M+H]$^+$.

Preparation 100: 4-bromo-5-(3-methoxyphenoxy)pyridin-2(1H)-one

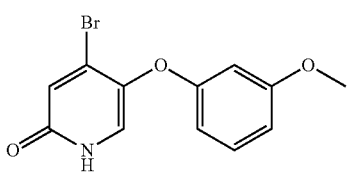 [SMILES: COc1cccc(Oc2c[nH]c(=O)cc2Br)c1]

Following the procedure in preparation 38, 2,4-dibromo-5-(3-methoxyphenoxy)pyridine (1.1 g, 3.06 mmol) was reacted to give the title compound (900 mg, 90%).
HPLC $t_R$ (Agilent, acidic, 1.5 min): 0.82 min, m/z=297.1 [M+H]$^+$.

Preparation 101: 4-bromo-5-(3-methoxyphenoxy)-1-methylpyridin-2(1H)-one

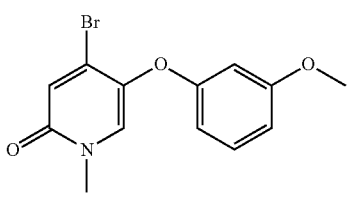 [SMILES: COc1cccc(Oc2cn(C)c(=O)cc2Br)c1]

Following the procedure in preparation 39, 4-bromo-5-(3-methoxyphenoxy)pyridin-2(1H)-one (450 mg, 3.56 mmol) was reacted to give the title compound (0.25 g, 53%).
HPLC $t_R$ (Shimadzu, acidic, 1.5 min): 0.66 min, m/z=309.8 [M+H]$^+$.

Preparation 102: 4-(5-(3-methoxyphenoxy)-1-methyl-2-oxo-1,2-dihydropyridin-4-yl)-6-methyl-1,6-dihydro-7H-pyrrolo[2,3-c]pyridin-7-one

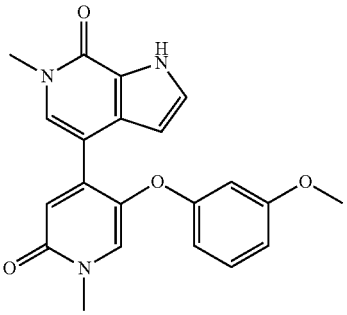 [SMILES: COc1cccc(Oc2cn(C)c(=O)cc2-c2cn(C)c(=O)c3[nH]ccc23)c1]

Following the procedure in preparation 10, 4-bromo-5-(3-methoxyphenoxy)-1-methylpyridin-2(1H)-one (80 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (110 mg, 0.26 mmol) was reacted to give the title compound (42 mg, 40%).
HPLC $t_R$ (Agilent, acidic, 3.5 min): 1.25 min, m/z=378.1 [M+H]$^+$.
$^1$H NMR (500 MHz, CDCl$_3$) δ 9.63 (bs, 1H), 7.28-7.25 (m, 2H), 7.17-7.16 (m, 1H), 7.08 (t, J=8.2 Hz, 1H), 6.86-6.86 (m, 1H), 6.55 (t, J=2.9 Hz, 1H), 6.51 (dd, J=2.6, 8.4 Hz, 1H), 6.36 (dd, J=2.1, 8.3 Hz, 1H), 6.32 (t, J=2.3 Hz, 1H), 3.70-3.69 (m, 3H), 3.61 (s, 3H), 3.58 (s, 3H).

Example 24: 4-(5-(3-hydroxyphenoxy)-1-methyl-2-oxo-1,2-dihydropyridin-4-yl)-6-methyl-1,6-dihydro-7H-pyrrolo[2,3-c]pyridin-7-one

Preparation 103: 4-(5-(3-hydroxyphenoxy)-1-methyl-2-oxo-1,2-dihydropyridin-4-yl)-6-methyl-1,6-dihydro-7H-pyrrolo[2,3-c]pyridin-7-one

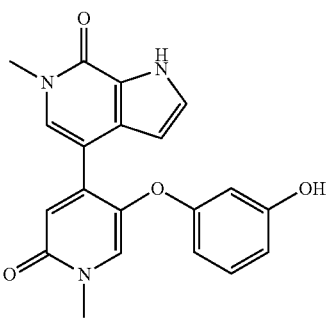 [SMILES: Cn1cc(Oc2cccc(O)c2)c(-c2cn(C)c(=O)c3[nH]ccc23)cc1=O]

Following the procedure in preparation 11, 4-(5-(3-methoxyphenoxy)-1-methyl-2-oxo-1,2-dihydropyridin-4-yl)-6-methyl-1,6-dihydro-7H-pyrrolo[2,3-c]pyridin-7-one (37 mg, 0.10 mmol) was reacted to give the title compound (22 mg, 58%).

HPLC $t_R$ (Agilent, acidic, 3.5 min): 1.13 min, m/z=364.0 [M+H]⁺.

¹H NMR (500 MHz, DMSO) δ 12.05 (bs, 1H), 9.37 (s, 1H), 7.85 (s, 1H), 7.38 (s, 1H), 7.31 (t, J=2.7 Hz, 1H), 6.94 (t, J=8.0 Hz, 1H), 6.55-6.54 (m, 1H), 6.34 (t, J=2.3 Hz, 1H), 6.30 (dd, J=1.9, 8.0 Hz, 1H), 6.20 (dd, J=2.2, 8.1 Hz, 1H), 6.17 (d, J=2.4 Hz, 1H), 3.48 (s, 6H).

Example 25: 4-(5-(4-methoxyphenoxy)-1-methyl-2-oxo-1,2-dihydropyridin-4-yl)-6-methyl-1,6-dihydro-7H-pyrrolo[2,3-c]pyridin-7-one Preparation 104:
2-chloro-5-(4-methoxyphenoxy)-4-nitropyridine 1-oxide

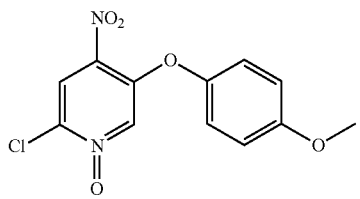 [SMILES: COc1ccc(Oc2c[n+]([O-])c(Cl)cc2[N+](=O)[O-])cc1]

Following the procedure in preparation 35, 4-methoxyphenol (4.6 g, 37.4 mmol) was reacted to give the title compound (6.0 g, 65%).

¹H NMR (400 MHz, DMSO-d6) δ 8.69 (s, 1H), 8.11 (s, 1H), 7.21 (d, J=9.2 Hz, 2H), 7.01 (d, J=9.2 Hz, 2H), 3.77 (s, 3H)

Preparation 105:
2,4-dibromo-5-(4-methoxyphenoxy)pyridine 1-oxide

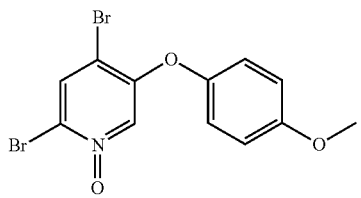

Following the procedure in preparation 26, 2-chloro-5-(4-methoxyphenoxy)-4-nitropyridine 1-oxide (6.0 g, 20.2 mmol) was reacted to give the title compound (7.60 g, 98%).

HPLC $t_R$ (Shimadzu, acidic, 1.5 min): 0.85 min, m/z=376.0 [M+H]⁺.

Preparation 106:
2,4-dibromo-5-(4-methoxyphenoxy)pyridine

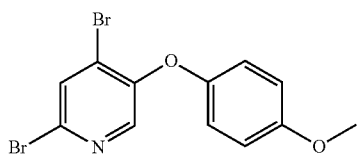 [SMILES: COc1ccc(Oc2cnc(Br)cc2Br)cc1]

Following the procedure in preparation 27, 2,4-dibromo-5-(4-methoxyphenoxy)pyridine 1-oxide (7.6 g, 20.3 mmol) was reacted to give the title compound (7.3 g, 99%).

HPLC $t_R$ (Shimadzu, acidic, 1.5 min): 1.02 min, m/z=359.9 [M+H]⁺.

Preparation 107:
4-bromo-5-(4-methoxyphenoxy)pyridin-2(1H)-one

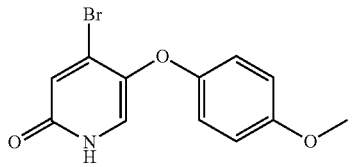 [SMILES: COc1ccc(Oc2c[nH]c(=O)cc2Br)cc1]

Following the procedure in preparation 38, 2,4-dibromo-5-(4-methoxyphenoxy)pyridine 7.3 g, 20.3 mmol) was reacted to give the title compound (4.0 g, 59%).

¹H NMR (400 MHz, DMSO-d6) δ 7.49 (s, 1H), 6.92-6.88 (m, 4H), 6.85 (s, 1H), 3.71 (s, 3H)

Preparation 108: 4-bromo-5-(4-methoxyphenoxy)-1-methylpyridin-2(1H)-one

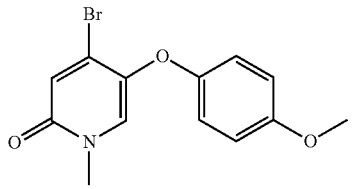 [SMILES: COc1ccc(Oc2cn(C)c(=O)cc2Br)cc1]

Following the procedure in preparation 39, 4-bromo-5-(4-methoxyphenoxy)pyridin-2(1H)-one (4.0 g, 13.5 mmol) was reacted to give the title compound (0.7 g, 16%).

¹H NMR (400 MHz, DMSO-d6) δ 7.90 (s, 1H), 6.92-6.87 (m, 5H), 3.71 (s, 3H), 3.39 (s, 3H)

Preparation 109: 4-(5-(4-methoxyphenoxy)-1-methyl-2-oxo-1,2-dihydropyridin-4-yl)-6-methyl-1,6-dihydro-7H-pyrrolo[2,3-c]pyridin-7-one

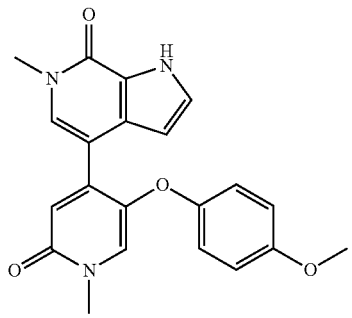 [SMILES: COc1ccc(Oc2cn(C)c(=O)cc2-c2cn(C)c(=O)c3[nH]ccc23)cc1]

Following the procedure in preparation 10, 4-bromo-5-(4-methoxyphenoxy)-1-methylpyridin-2(1H)-one (80 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (110 mg, 0.26 mmol) was reacted to give the title compound (50 mg, 47%).

HPLC $t_R$ (Agilent, acidic, 3.5 min): 1.23 min, m/z=378.1 [M+H]⁺.

¹H NMR (500 MHz, CDCl₃) δ 10.94 (bs, 1H), 7.22 (t, J=2.7 Hz, 1H), 7.09 (s, 1H), 7.04 (s, 1H), 6.76 (s, 1H), 6.64 (s, 4H), 6.43 (t, J=2.3 Hz, 1H), 3.64 (s, 3H), 3.53 (s, 3H), 3.49 (s, 3H).

Example 26: 4-(5-(4-hydroxyphenoxy)-1-methyl-2-oxo-1,2-dihydropyridin-4-yl)-6-methyl-1,6-dihydro-7H-pyrrolo[2,3-c]pyridin-7-one Preparation 110: 4-(5-(4-hydroxyphenoxy)-1-methyl-2-oxo-1,2-dihydropyridin-4-yl)-6-methyl-1,6-dihydro-7H-pyrrolo[2,3-c]pyridin-7-one

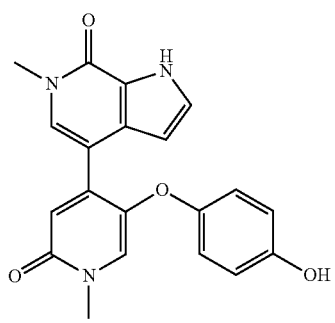 [SMILES: Cn1cc(Oc2ccc(O)cc2)c(-c2cn(C)c(=O)c3[nH]ccc23)cc1=O]

Following the procedure in preparation 11, 4-(5-(4-methoxyphenoxy)-1-methyl-2-oxo-1,2-dihydropyridin-4-yl)-6-methyl-1,6-dihydro-7H-pyrrolo[2,3-c]pyridin-7-one (46 mg, 0.12 mmol) was reacted to give the title compound (27 mg, 59%).

HPLC t$_R$ (Agilent, acidic, 3.5 min): 1.13 min, m/z=364.0 [M+H]⁺.

¹H NMR (500 MHz, DMSO) δ 12.03 (bs, 1H), 9.02 (s, 1H), 7.66 (s, 1H), 7.37-7.36 (m, 1H), 7.30 (t, J=2.7 Hz, 1H), 6.65-6.62 (m, 2H), 6.58-6.55 (m, 2H), 6.49 (d, J=13.6 Hz, 1H), 6.32 (t, J=2.3 Hz, 1H), 3.49 (s, 3H), 3.45 (s, 3H).

Example 27: 5'-(4-methoxyphenoxy)-1,1'-dimethyl-[3,4'-bipyridine]-2',6(1H,1'H)-dione Preparation 111: 5'-(4-methoxyphenoxy)-1,1'-dimethyl-[3,4'-bipyridine]-2',6(1H,1'H)-dione

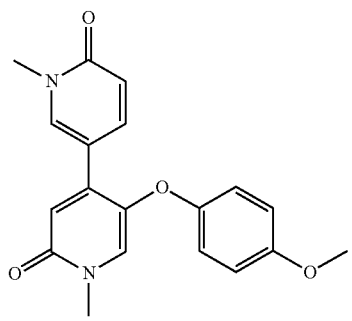

Following the procedure in preparation 40, 4-bromo-5-(4-methoxyphenoxy)-1-methylpyridin-2(1H)-one (50 mg, 0.16 mmol) was reacted to give the title compound (31 mg, 53%).

HPLC t$_R$ (Agilent, acidic, 3.5 min): 1.22 min, m/z=339.0 [M+H]⁺.

¹H NMR (400 MHz, CDCl₃) δ 7.67 (d, J=2.6 Hz, 1H), 7.56 (dd, J=2.7, 9.5 Hz, 1H), 7.06 (s, 1H), 6.82-6.81 (m, 4H), 6.60-6.54 (m, 2H), 3.79-3.78 (m, 3H), 3.53 (s, 6H).

Example 28: 5'-(3-hydroxyphenoxy)-1,1'-dimethyl-[3,4'-bipyridine]-2',6(1H,1'H)-dione Preparation 112: 5'-(3-hydroxyphenoxy)-1,1'-dimethyl-[3,4'-bipyridine]-2',6(1H,1'H)-dione

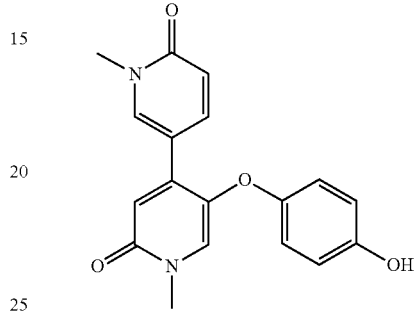

Following the procedure in preparation 11, 5'-(4-methoxyphenoxy)-1,1'-dimethyl-[3,4'-bipyridine]-2',6(1H,1'H)-dione (25 mg, 0.07 mmol) was reacted to give the title compound (12 mg, 49%).

HPLC t$_R$ (Agilent, acidic, 3.5 min): 1.08 min, m/z=325.0 [M+H]⁺.

¹H NMR (500 MHz, DMSO-d6) δ 9.10 (bs, 1H), 8.04 (d, J=2.6 Hz, 1H), 7.66-7.61 (m, 2H), 6.75-6.72 (m, 2H), 6.67-6.64 (m, 2H), 6.51 (s, 1H), 6.35 (d, J=9.5 Hz, 1H), 3.42 (s, 3H), 3.41 (s, 3H).

Example 29: 5'-(3-hydroxyphenoxy)-1,1'-dimethyl-[3,4'-bipyridine]-2',6(1H,1'H)-dione Preparation 113: 5'-(3-methoxyphenoxy)-1,1'-dimethyl-[3,4'-bipyridine]-2', 6(1H,1'H)-dione

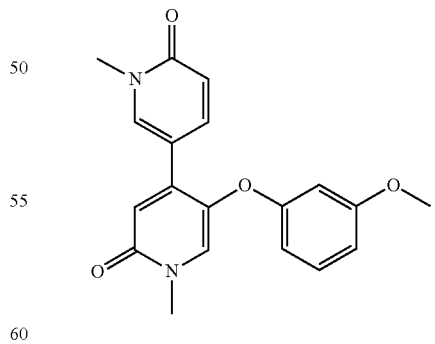

Following the procedure in preparation 40, 4-bromo-5-(3-methoxyphenoxy)-1-methylpyridin-2(1H)-one (50 mg, 0.16 mmol) was reacted to give the title compound (29 mg, 48%).

HPLC t$_R$ (Agilent, acidic, 3.5 min): 1.23 min, m/z=339.0 [M+H]⁺.

Preparation 114: 5'-(3-hydroxyphenoxy)-1,1'-dimethyl-[3,4'-bipyridine]-2', 6(1H,1'H)-dione

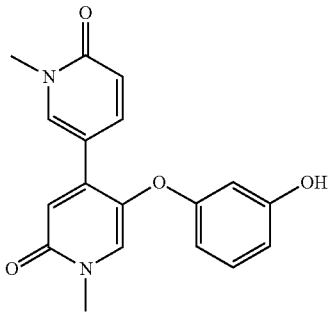 [SMILES: Cn1cc(-c2cc(=O)n(C)cc2Oc2cccc(O)c2)ccc1=O]

Following the procedure in preparation 11, 5'-(4-methoxyphenoxy)-1,1'-dimethyl-[3,4'-bipyridine]-2',6(1H, 1'H)-dione (23 mg, 0.07 mmol) was reacted to give the title compound (13 mg, 53%).

HPLC $t_R$ (Agilent, acidic, 3.5 min): 1.08 min, m/z=325.0 [M+H]$^+$.

$^1$H NMR (500 MHz, DMSO-d6) δ 9.48 (bs, 1H), 8.06-8.05 (m, 1H), 7.83-7.82 (m, 1H), 7.62-7.59 (m, 1H), 7.04 (t, J=8.2 Hz, 1H), 6.54 (s, 1H), 6.40-6.25 (m, 4H), 3.44 (s, 3H), 3.41 (s, 3H).

Example 30: 4-(3-(2-methoxyphenoxy)-1-methyl-2-oxo-1,2-dihydropyridin-4-yl)-6-methyl-1,6-dihydro-7H-pyrrolo[2,3-c]pyridin-7-one

Preparation 115: 2-chloro-3-(2-methoxyphenoxy)-4-nitropyridine 1-oxide

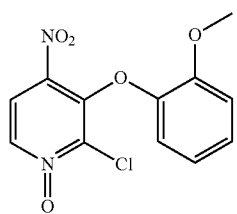 [SMILES: COc1ccccc1Oc1c([N+](=O)[O-])cc[n+]([O-])c1Cl]

Following the procedure in preparation 35, 2-methoxyphenol (6.45 g, 51.9 mmol) and 2-chloro-3-fluoro-4-nitropyridine 1-oxide (10.0 g, 51.9 mmol) was reacted to give the title compound (12.0 g, 78%).

$^1$H NMR (400 MHz, DMSO-d6) δ 8.59 (d, J=7.6 Hz, 1H), 8.20 (d, J=7.6 Hz, 1H), 7.17-7.10 (m, 2H), 6.94-6.82 (m, 2H), 3.83 (s, 3H).

Preparation 116: 2,4-dibromo-3-(2-methoxyphenoxy)pyridine 1-oxide

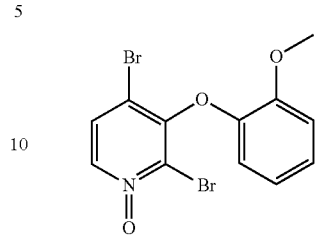

Following the procedure in preparation 26, 2-chloro-3-(2-methoxyphenoxy)-4-nitropyridine 1-oxide (12.0 g, 40.5 mmol) was reacted to give the title compound (11.8 g, 82%).

HPLC $t_R$ (Shimadzu, acidic, 1.5 min): 0.83 min, m/z=376.1 [M+H]$^+$.

Preparation 117: 2,4-dibromo-3-(2-methoxyphenoxy)pyridine

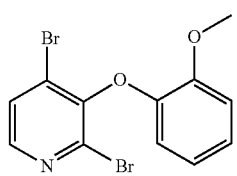 [SMILES: COc1ccccc1Oc1c(Br)ccnc1Br]

Following the procedure in preparation 27, 2,4-dibromo-3-(2-methoxyphenoxy)pyridine 1-oxide (18.0 g, 48.0 mmol) was reacted to give the title compound (14.0 g, 68%).

HPLC $t_R$ (Shimadzu, acidic, 1.5 min): 0.94 min, m/z=360.1 [M+H]$^+$.

Preparation 118: 4-bromo-3-(2-methoxyphenoxy)pyridin-2(1H)-one

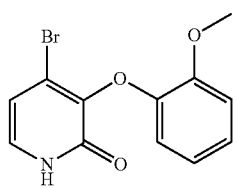 [SMILES: COc1ccccc1Oc1c(Br)cc[nH]c1=O]

Following the procedure in preparation 38, 2,4-dibromo-3-(2-methoxyphenoxy)pyridine (14.0 g, 39.0 mmol) was reacted to give the title compound (2.5 g, 20%).

$^1$H NMR (400 MHz, DMSO-d6) δ 12.1 (brs, 1H), 7.26 (d, J=6.8 Hz, 1H), 7.06-7.04 (m, 1H), 6.99-6.78 (m, 2H), 6.53-6.50 (m, 2H), 3.82 (s, 3H).

Preparation 119: 4-bromo-3-(2-methoxyphenoxy)-1-methylpyridin-2(1H)-one

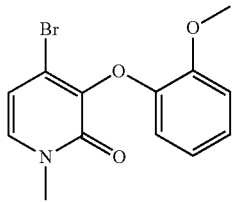 [SMILES: COc1ccccc1Oc1c(Br)ccn(C)c1=O]

Following the procedure in preparation 39, 4-bromo-3-(2-methoxyphenoxy)pyridin-2(1H)-one (2.4 g, 8.1 mmol) was reacted to give the title compound (1.2 g, 46%).

$^1$H NMR (400 MHz, DMSO-d6) δ 7.62 (d, J=7.2 Hz, 1H), 7.08-7.03 (m, 1H), 7.01-6.94 (m, 1H), 6.81-6.74 (m, 1H), 6.58 (d, J=7.2 Hz, 1H), 6.54-6.48 (m, 1H), 3.82 (s, 3H), 3.43 (s, 3H).

Preparation 120: 4-(3-(2-methoxyphenoxy)-1-methyl-2-oxo-1,2-dihydropyridin-4-yl)-6-methyl-1,6-dihydro-7H-pyrrolo[2,3-c]pyridin-7-one

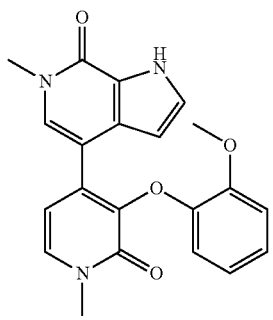 [SMILES: COc1ccccc1Oc1c(-c2cn(C)c(=O)c3[nH]ccc23)ccn(C)c1=O]

Following the procedure in preparation 10, 4-bromo-3-(2-methoxyphenoxy)-1-methylpyridin-2(1H)-one (30 mg, 0.10 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (41 mg, 0.10 mmol) was reacted to give the title compound (13 mg, 33%).

HPLC $t_R$ (Agilent, acidic, 3.5 min): 1.20 min, m/z=378.1 [M+H]$^+$.

$^1$H NMR (400 MHz, DMSO-d6) δ 12.08 (bs, 1H), 7.68 (d, J=7.2 Hz, 1H), 7.41 (s, 1H), 7.29 (t, J=2.7 Hz, 1H), 6.95 (dd, J=1.5, 8.1 Hz, 1H), 6.87-6.82 (m, 1H), 6.71-6.66 (m, 1H), 6.50-6.41 (m, 2H), 6.31 (t, J=2.3 Hz, 1H), 3.76 (s, 3H), 3.51 (s, 3H), 3.45 (s, 3H).

Example 31: 4-(3-(2-hydroxyphenoxy)-1-methyl-2-oxo-1,2-dihydropyridin-4-yl)-6-methyl-1,6-dihydro-7H-pyrrolo[2,3-c]pyridin-7-one

Preparation 121: 4-(3-(2-hydroxyphenoxy)-1-methyl-2-oxo-1,2-dihydropyridin-4-yl)-6-methyl-1,6-dihydro-7H-pyrrolo[2,3-c]pyridin-7-one

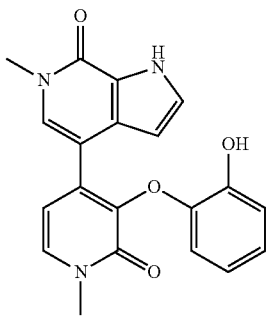 [SMILES: Cn1ccc(-c2cn(C)c(=O)c3[nH]ccc23)c(Oc2ccccc2O)c1=O]

Following the procedure in preparation 11, 4-(3-(2-methoxyphenoxy)-1-methyl-2-oxo-1,2-dihydropyridin-4-yl)-6-methyl-1,6-dihydro-7H-pyrrolo[2,3-c]pyridin-7-one (66 mg, 0.18 mmol) was reacted to give the title compound (17 mg, 26%).

HPLC $t_R$ (Agilent, acidic, 3.5 min): 1.16 min, m/z=364.1 [M+H]$^+$.

$^1$H NMR (500 MHz, DMSO-d6) δ 12.17 (bs, 1H), 9.38 (s, 1H), 7.72 (d, J=7.2 Hz, 1H), 7.64 (s, 1H), 7.32 (t, J=2.8 Hz, 1H), 6.78-6.72 (m, 2H), 6.53-6.47 (m, 2H), 6.38-6.35 (m, 2H), 3.54 (s, 3H), 3.17 (s, 3H).

Example 32: 4-(3-(3-methoxyphenoxy)-1-methyl-2-oxo-1,2-dihydropyridin-4-yl)-6-methyl-1,6-dihydro-7H-pyrrolo[2,3-c]pyridin-7-one

Preparation 122: 2-chloro-3-(3-methoxyphenoxy)-4-nitropyridine 1-oxide

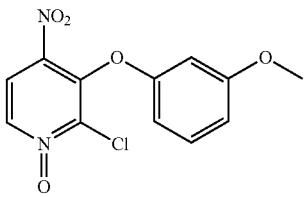 [SMILES: COc1cccc(Oc2c([N+](=O)[O-])cc[n+]([O-])c2Cl)c1]

Following the procedure in preparation 35, 3-methoxyphenol (6.45 g, 51.9 mmol) and 2-chloro-3-fluoro-4-nitropyridine 1-oxide (10.0 g, 51.9 mmol) was reacted to give the title compound (9.0 g, 58%).

$^1$H NMR (400 MHz, DMSO-d6) δ 8.61 (d, J=7.6 Hz, 1H), 8.22 (d, J=7.2 Hz, 1H), 7.27-7.23 (m, 1H), 6.74-6.61 (m, 3H), 3.74 (s, 3H).

Preparation 123: 2,4-dibromo-3-(3-methoxyphenoxy)pyridine 1-oxide

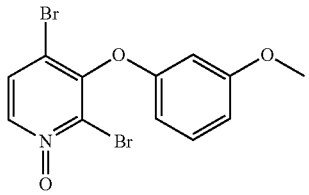 [SMILES: COc1cccc(Oc2c(Br)cc[n+]([O-])c2Br)c1]

Following the procedure in preparation 26, 2-chloro-3-(3-methoxyphenoxy)-4-nitropyridine 1-oxide (9.0 g, 30.3 mmol) was reacted to give the title compound (11.0 g, 97%).
HPLC $t_R$ (Shimadzu, acidic, 1.5 min): 0.85 min, m/z=376.0 [M]+.

Preparation 124: 2,4-dibromo-3-(3-methoxyphenoxy)pyridine

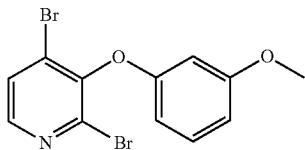 [SMILES: COc1cccc(Oc2c(Br)ccnc2Br)c1]

Following the procedure in preparation 27, 2,4-dibromo-3-(3-methoxyphenoxy)pyridine 1-oxide (11.0 g, 29.3 mmol) was reacted to give the title compound (10.1 g, 96%).
HPLC $t_R$ (Agilent, acidic, 1.5 min): 0.97 min, m/z=359.8 [M+H]+.

Preparation 125: 4-bromo-3-(3-methoxyphenoxy)pyridin-2(1H)-one

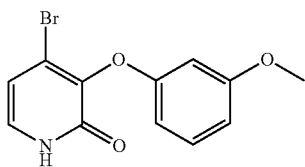 [SMILES: COc1cccc(Oc2c(Br)cc[nH]c2=O)c1]

Following the procedure in preparation 38, 2,4-dibromo-3-(3-methoxyphenoxy)pyridine (10.0 g, 27.9 mmol) was reacted to give the title compound (1.0 g, 12%).
$^1$H NMR (400 MHz, DMSO-d6) δ 7.34 (d, J=5.6 Hz, 1H), 7.13-7.09 (m, 1H), 6.52-6.21 (m, 4H), 3.70 (s, 3H).

Preparation 126: 4-bromo-3-(3-methoxyphenoxy)-1-methylpyridin-2(1H)-one

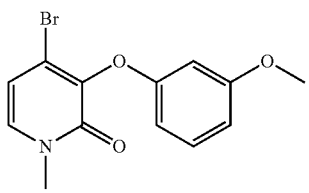 [SMILES: COc1cccc(Oc2c(Br)ccn(C)c2=O)c1]

Following the procedure in preparation 39, 4-bromo-3-(3-methoxyphenoxy)pyridin-2(1H)-one (1.0 g, 3.38 mmol) was reacted to give the title compound (0.7 g, 66%).
$^1$H NMR (400 MHz, DMSO-d6) δ 7.65 (d, J=7.2 Hz, 1H), 7.17 (t, J=8.4 Hz, 1H), 6.64-6.58 (m, 2H), 6.43 (t, J=2.4 Hz, 1H), 6.38-6.34 (m, 1H), 3.72 (s, 3H), 3.45 (s, 3H).

Preparation 127: 4-(3-(3-methoxyphenoxy)-1-methyl-2-oxo-1,2-dihydropyridin-4-yl)-6-methyl-1,6-dihydro-7H-pyrrolo[2,3-c]pyridin-7-one

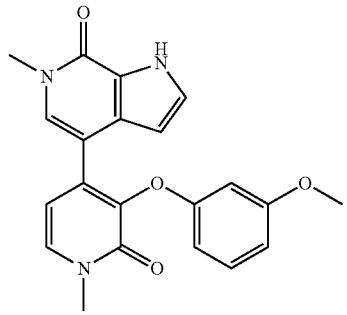

Following the procedure in preparation 10, 4-bromo-3-(3-methoxyphenoxy)-1-methylpyridin-2(1H)-one (30 mg, 0.10 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (39 mg, 0.092 mmol) was reacted to give the title compound (12 mg, 30%).
HPLC $t_R$ (Agilent, acidic, 3.5 min): 1.19 min, m/z=378.1 [M+H]+.
$^1$H NMR (400 MHz, DMSO-d6) δ 12.07 (s, 1H), 7.71 (d, J=7.1 Hz, 1H), 7.36 (s, 1H), 7.32 (t, J=2.7 Hz, 1H), 7.06 (t, J=8.1 Hz, 1H), 6.48 (dd, J=2.0, 7.9 Hz, 1H), 6.40 (d, J=7.1 Hz, 1H), 6.32-6.25 (m, 3H), 3.64 (s, 3H), 3.52 (s, 3H), 3.47 (s, 3H).

Example 33: 4-(3-(3-hydroxyphenoxy)-1-methyl-2-oxo-1,2-dihydropyridin-4-yl)-6-methyl-1,6-dihydro-7H-pyrrolo[2,3-c]pyridin-7-one

Preparation 128: 4-(3-(3-hydroxyphenoxy)-1-methyl-2-oxo-1,2-dihydropyridin-4-yl)-6-methyl-1,6-dihydro-7H-pyrrolo[2,3-c]pyridin-7-one

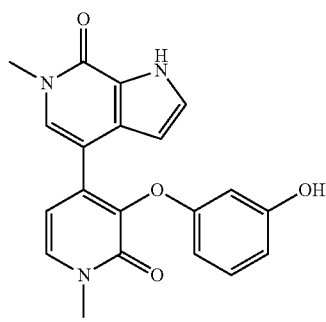 [SMILES: Cn1ccc(-c2cn(C)c(=O)c3[nH]ccc23)c(Oc2cccc(O)c2)c1=O]

Following the procedure in preparation 11, 4-(3-(3-methoxyphenoxy)-1-methyl-2-oxo-1,2-dihydropyridin-4-yl)-6-methyl-1,6-dihydro-7H-pyrrolo[2,3-c]pyridin-7-one (66 mg, 0.18 mmol) was reacted to give the title compound (15 mg, 23%).

HPLC t_R (Agilent, acidic, 3.5 min): 1.12 min, m/z=364.1 [M+H]⁺.
¹H NMR (500 MHz, DMSO-d6) δ 12.15 (bs, 1H), 9.34 (s, 1H), 7.71 (d, J=7.0 Hz, 1H), 7.37-7.31 (m, 2H), 6.93 (t, J=8.1 Hz, 1H), 6.41 (d, J=7.0 Hz, 1H), 6.32-6.28 (m, 2H), 6.16-6.09 (m, 2H), 3.52 (s, 3H), 3.47 (s, 3H).

Example 34: 4-(3-(4-methoxyphenoxy)-1-methyl-2-oxo-1,2-dihydropyridin-4-yl)-6-methyl-1,6-dihydro-7H-pyrrolo[2,3-c]pyridin-7-one Preparation 129:
2-chloro-3-(4-methoxyphenoxy)-4-nitropyridine 1-oxide

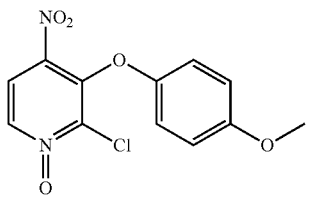 [SMILES: COc1ccc(Oc2c([N+](=O)[O-])cc[n+]([O-])c2Cl)cc1]

Following the procedure in preparation 35, 4-methoxyphenol (6.5 g, 52.4 mmol) and 2-chloro-3-fluoro-4-nitropyridine 1-oxide (10.0 g, 51.9 mmol) was reacted to give the title compound (12.0 g, 78%).
¹H NMR (400 MHz, DMSO-d6) δ 8.60 (d, J=7.6 Hz, 1H), 8.20 (d, J=7.2 Hz, 1H), 7.05-6.99 (m, 2H), 6.92-6.87 (m, 2H), 3.73 (s, 3H).

Preparation 130:
2,4-dibromo-3-(4-methoxyphenoxy)pyridine 1-oxide

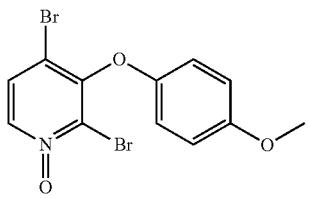 [SMILES: COc1ccc(Oc2c(Br)cc[n+]([O-])c2Br)cc1]

Following the procedure in preparation 26, 2-chloro-3-(4-methoxyphenoxy)-4-nitropyridine 1-oxide (12.0 g, 40.5 mmol) was reacted to give the title compound (12.1 g, 79%).
HPLC t_R (Shimadzu, acidic, 1.5 min): 0.85 min, m/z=375.9 [M+H]⁺.

Preparation 131:
2,4-dibromo-3-(4-methoxyphenoxy)pyridine

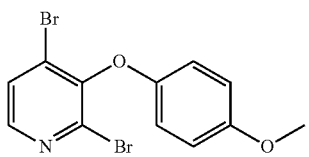 [SMILES: COc1ccc(Oc2c(Br)ccnc2Br)cc1]

Following the procedure in preparation 27, 2,4-dibromo-3-(4-methoxyphenoxy)pyridine 1-oxide (18.0 g, 48.0 mmol) was reacted to give the title compound (14.0 g, 75%).

HPLC t_R (Shimadzu, acidic, 1.5 min): 0.97 min, m/z=360.1 [M+H]⁺.

Preparation 132:
4-bromo-3-(4-methoxyphenoxy)pyridin-2(1H)-one

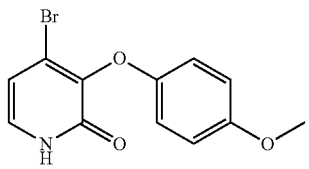 [SMILES: COc1ccc(Oc2c(Br)cc[nH]c2=O)cc1]

Following the procedure in preparation 38, 2,4-dibromo-3-(4-methoxyphenoxy)pyridine (14.0 g, 39.0 mmol) was reacted to give the title compound (2.0 g, 17%).
¹H NMR (400 MHz, DMSO-d6) δ 7.28 (d, J=6.8 Hz, 1H), 6.86-6.81 (m, 2H), 6.80-6.75 (m, 2H), 6.46 (d, J=6.8 Hz, 1H), 3.70 (s, 3H).

Preparation 133: 4-bromo-3-(4-methoxyphenoxy)-1-methylpyridin-2(1H)-one

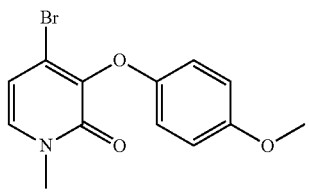 [SMILES: COc1ccc(Oc2c(Br)ccn(C)c2=O)cc1]

Following the procedure in preparation 39, 4-bromo-3-(4-methoxyphenoxy)pyridin-2(1H)-one (2.0 g, 6.8 mmol) was reacted to give the title compound (1.8 g, 82%).
¹H NMR (400 MHz, DMSO-d6) δ 7.62 (d, J=7.6 Hz, 1H), 6.86-6.82 (m, 2H), 6.81-6.75 (m, 2H), 6.57 (d, J=7.2 Hz, 1H), 3.70 (s, 3H), 3.44 (s, 3H)

Preparation 134: 4-(3-(4-methoxyphenoxy)-1-methyl-2-oxo-1,2-dihydropyridin-4-yl)-6-methyl-1,6-dihydro-7H-pyrrolo[2,3-c]pyridin-7-one

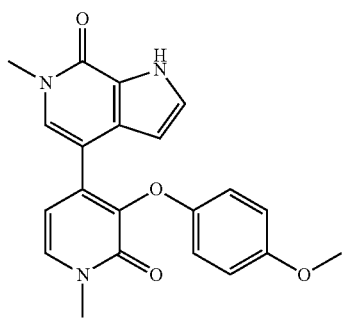

Following the procedure in preparation 10, 4-bromo-3-(4-methoxyphenoxy)-1-methylpyridin-2(1H)-one (30 mg, 0.10 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (39 mg, 0.092 mmol) was reacted to give the title compound (8 mg, 20%).

HPLC $t_R$ (Agilent, acidic, 3.5 min): 1.17 min, m/z=378.1 [M+H]$^+$.

$^1$H NMR (400 MHz, DMSO-d6) δ 12.08 (s, 1H), 7.68 (d, J=7.2 Hz, 1H), 7.36-7.30 (m, 2H), 6.75-6.62 (m, 4H), 6.39 (d, J=7.1 Hz, 1H), 6.30 (t, J=2.3 Hz, 1H), 3.64 (s, 3H), 3.51 (s, 3H), 3.48 (s, 3H).

Example 35: 4-(3-(4-hydroxyphenoxy)-1-methyl-2-oxo-1,2-dihydropyridin-4-yl)-6-methyl-1,6-dihydro-7H-pyrrolo[2,3-c]pyridin-7-one Preparation 135: 4-(3-(4-hydroxyphenoxy)-1-methyl-2-oxo-1,2-dihydropyridin-4-yl)-6-methyl-1,6-dihydro-7H-pyrrolo[2,3-c]pyridin-7-one

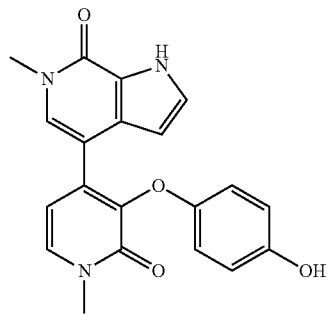 [SMILES: Cn1ccc(-c2cn(C)c(=O)c3[nH]ccc23)c(Oc2ccc(O)cc2)c1=O]

Following the procedure in preparation 11, 4-(3-(4-methoxyphenoxy)-1-methyl-2-oxo-1,2-dihydropyridin-4-yl)-6-methyl-1,6-dihydro-7H-pyrrolo[2,3-c]pyridin-7-one (63 mg, 0.17 mmol) was reacted to give the title compound (17 mg, 27%).

HPLC $t_R$ (Agilent, acidic, 3.5 min): 1.06 min, m/z=364.0 [M+H]$^+$.

$^1$H NMR (500 MHz, DMSO-d6) δ 12.12 (bs, 1H), 8.93 (s, 1H), 7.68 (d, J=7.2 Hz, 1H), 7.35 (s, 1H), 7.32 (t, J=2.7 Hz, 1H), 6.54-6.52 (m, 4H), 6.38 (d, J=7.0 Hz, 1H), 6.29 (t, J=2.2 Hz, 1H), 3.51 (s, 3H), 3.47 (s, 3H).

Example 36: 3'-(2-hydroxyphenoxy)-1,1'-dimethyl-[3,4'-bipyridine]-2',6(1H,1'H)-dione Preparation 136: 3'-(2-methoxyphenoxy)-1,1'-dimethyl-[3,4'-bipyridine]-2',6(1H,1'H)-dione

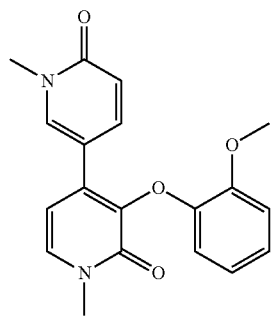

Following the procedure in preparation 40, 4-bromo-3-(2-methoxyphenoxy)-1-methylpyridin-2(1H)-one (100 mg, 0.32 mmol) was reacted to give the title compound (37 mg, 34%).

HPLC $t_R$ (Agilent, acidic, 3.5 min): 1.15 min, m/z=339.0 [M+H]$^+$.

Preparation 137: 5'-(2-hydroxyphenoxy)-1,1'-dimethyl-[3,4'-bipyridine]-2',6(1H,1'H)-dione

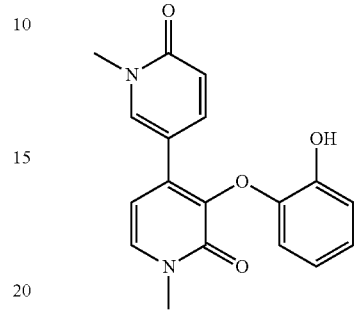

Following the procedure in preparation 11, 3'-(2-methoxyphenoxy)-1,1'-dimethyl-[3,4'-bipyridine]-2',6(1H,1'H)-dione (37 mg, 0.11 mmol) was reacted to give the title compound (21 mg, 53%).

HPLC $t_R$ (Agilent, acidic, 3.5 min): 1.10 min, m/z=325.0 [M+H]$^+$.

$^1$H NMR (500 MHz, DMSO-d6) δ 9.38 (s, 1H), 8.24 (d, J=2.4 Hz, 1H), 7.76 (dd, J=2.6, 10.0 Hz, 1H), 7.71 (d, J=7.2 Hz, 1H), 6.84-6.77 (m, 2H), 6.60-6.56 (m, 1H), 6.46 (d, J=6.9 Hz, 1H), 6.42-6.37 (m, 2H), 3.50 (s, 3H), 3.46 (s, 3H).

Example 37: 3'-(3-hydroxyphenoxy)-1,1'-dimethyl-[3,4'-bipyridine]-2',6(1H,1'H)-dione Preparation 138: 3'-(3-methoxyphenoxy)-1,1'-dimethyl-[3,4'-bipyridine]-2',6(1H,1'H)-dione

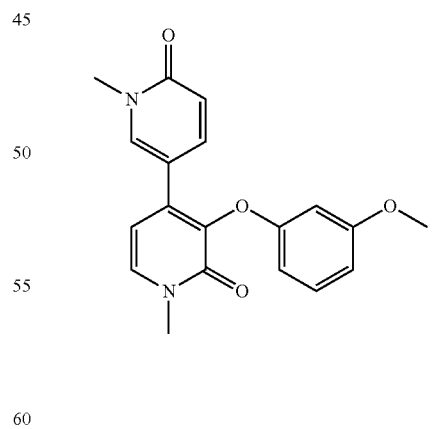

Following the procedure in preparation 40, 4-bromo-3-(3-methoxyphenoxy)-1-methylpyridin-2(1H)-one (100 mg, 0.32 mmol) was reacted to give the title compound (58 mg, 53%).

HPLC $t_R$ (Agilent, acidic, 3.5 min): 1.17 min, m/z=339.0 [M+H]$^+$.

Preparation 139: 5'-(3-hydroxyphenoxy)-1,1'-dimethyl-[3,4'-bipyridine]-2',6(1H,1'H)-dione

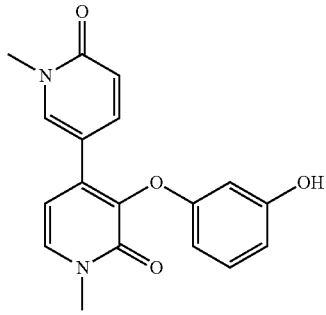 [SMILES: Cn1cc(-c2ccn(C)c(=O)c2Oc2cccc(O)c2)ccc1=O]

Following the procedure in preparation 11, 3'-(3-methoxyphenoxy)-1,1'-dimethyl-[3,4'-bipyridine]-2',6(1H,1'H)-dione (58 mg, 0.17 mmol) was reacted to give the title compound (23 mg, 40%).

HPLC $t_R$ (Agilent, acidic, 3.5 min): 1.05 min, m/z=325.0 [M+H]$^+$.

$^1$H NMR (500 MHz, DMSO-d6) δ 9.43 (s, 1H), 8.10 (d, J=2.6 Hz, 1H), 7.71 (d, J=7.2 Hz, 1H), 7.63 (dd, J=2.7, 9.5 Hz, 1H), 7.02 (t, J=8.2 Hz, 1H), 6.43 (d, J=7.2 Hz, 1H), 6.40-6.37 (m, 2H), 6.24 (dd, J=2.3, 8.1 Hz, 1H), 6.17 (t, J=2.2 Hz, 1H), 3.48 (s, 3H), 3.45 (s, 3H).

Example 38: 3'-(4-hydroxyphenoxy)-1,1'-dimethyl-[3,4'-bipyridine]-2',6(1H,1'H)-dione

Preparation 140: 3'-(4-methoxyphenoxy)-1,1'-dimethyl-[3,4'-bipyridine]-2',6(1H,1'H)-dione

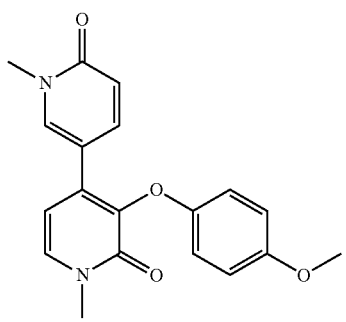

Following the procedure in preparation 40, 4-bromo-3-(4-methoxyphenoxy)-1-methylpyridin-2(1H)-one (100 mg, 0.32 mmol) was reacted to give the title compound (50 mg, 46%).

HPLC $t_R$ (Agilent, acidic, 3.5 min): 1.15 min, m/z=339.0 [M+H]$^+$.

Preparation 141: 5'-(4-hydroxyphenoxy)-1,1'-dimethyl-[3,4'-bipyridine]-2',6(1H,1'H)-dione

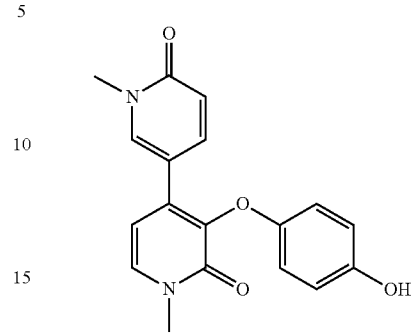

Following the procedure in preparation 11, 3'-(4-methoxyphenoxy)-1,1'-dimethyl-[3,4'-bipyridine]-2',6(1H,1'H)-dione (50 mg, 0.15 mmol) was reacted to give the title compound (18 mg, 34%).

HPLC $t_R$ (Agilent, acidic, 3.5 min): 1.00 min, m/z=325.0 [M+H]$^+$.

$^1$H NMR (500 MHz, DMSO-d6) δ 9.02 (m, 1H), 8.08 (d, J=2.6 Hz, 1H), 7.69-7.62 (m, 2H), 6.62-6.61 (m, 4H), 6.39 (dd, J=8.4, 10.9 Hz, 2H), 3.46 (s, 3H), 3.45 (s, 3H).

Example 39: 3'-(4-fluoro-2,6-dimethylphenoxy)-1,1'-dimethyl-[3,4'-bipyridine]-2',6(1H,1'H)-dione

Preparation 142: 2-chloro-3-(4-fluoro-2,6-dimethylphenoxy)-4-nitropyridine 1-oxide

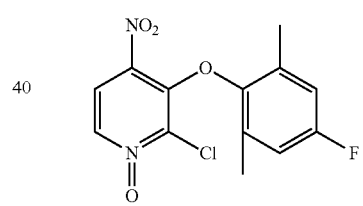

Following the procedure in preparation 35, 4-fluoro-2,6-dimethylphenol (14.0 g, 99.9 mmol) and 2-chloro-3-fluoro-4-nitropyridine 1-oxide (10.0 g, 51.9 mmol) was reacted to give the title compound (11.0 g, 47%).

HPLC $t_R$ (Shimadzu, acidic, 1.5 min): 0.94 min, m/z=313.2 [M+H]$^+$.

Preparation 143: 2,4-dibromo-3-(4-fluoro-2,6-dimethylphenoxy)pyridine 1-oxide

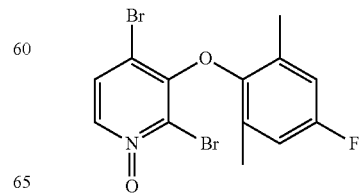

Following the procedure in preparation 26, 2-chloro-3-(4-fluoro-2,6-dimethylphenoxy)-4-nitropyridine 1-oxide (10.0 g, 31.9 mmol) was reacted to give the title compound (11.6 g, 93%).

HPLC $t_R$ (Shimadzu, acidic, 1.5 min): 0.92 min, m/z=392.0 [M+H]$^+$.

Preparation 144: 2,4-dibromo-3-(4-fluoro-2,6-dimethylphenoxy)pyridine

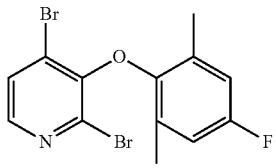 [SMILES: Cc1cc(F)cc(C)c1Oc1c(Br)ccnc1Br]

Following the procedure in preparation 27, 2,4-dibromo-3-(4-fluoro-2,6-dimethylphenoxy)pyridine 1-oxide (15.0 mg, 38.4 mmol) was reacted to give the title compound (12.2 g, 85%).

HPLC $t_R$ (Shimadzu, acidic, 1.5 min): 1.15 min, m/z=376.1 [M+H]$^+$.

Preparation 145: 4-bromo-3-(4-fluoro-2,6-dimethylphenoxy)pyridin-2(1H)-one

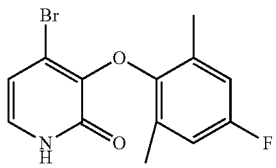 [SMILES: Cc1cc(F)cc(C)c1Oc1c(Br)cc[nH]c1=O]

Following the procedure in preparation 38, 2,4-dibromo-3-(4-fluoro-2,6-dimethylphenoxy)pyridine (11.6 g, 30.9 mmol) was reacted to give the title compound (8.0 g, 83%).

HPLC $t_R$ (Shimadzu, acidic, 1.5 min): 0.88 min, m/z=313.8 [M+H]$^+$.

Preparation 146: 4-bromo-3-(4-fluoro-2,6-dimethylphenoxy)pyridin-2(1H)-one

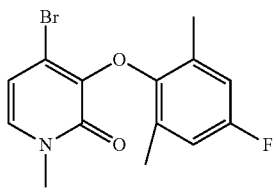 [SMILES: Cc1cc(F)cc(C)c1Oc1c(Br)ccn(C)c1=O]

Following the procedure in preparation 39, 4-bromo-3-(4-fluoro-2,6-dimethylphenoxy)pyridin-2(1H)-one (7.5 g, 24.0 mmol) was reacted to give the title compound (1.0 g, 13%).

$^1$H NMR (400 MHz, DMSO-d6) δ 7.46 (d, J=7.2 Hz, 1H), 6.83 (d, J=9.2 Hz, 2H), 6.55 (d, J=7.2 Hz, 1H), 3.35 (s, 3H), 2.09 (s, 6H)

Preparation 147: 3'-(4-fluoro-2,6-dimethylphenoxy)-1,1'-dimethyl-[3,4'-bipyridine]-2',6(1H,1'H)-dione

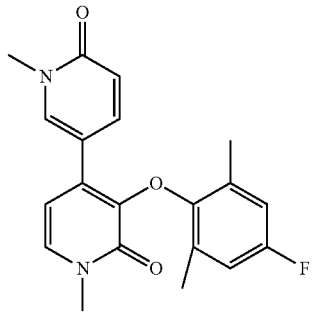 [SMILES: Cc1cc(F)cc(C)c1Oc1c(-c2ccc(=O)n(C)c2)ccn(C)c1=O]

Following the procedure in preparation 40, 4-bromo-3-(4-fluoro-2,6-dimethylphenoxy)pyridin-2(1H)-one (100 mg, 0.31 mmol) was reacted to give the title compound (73 mg, 60%).

HPLC $t_R$ (Agilent, acidic, 3.5 min): 1.34 min, m/z=355.0 [M+H]$^+$.

$^1$H NMR (500 MHz, DMSO-d6) δ 8.11-8.09 (m, 1H), 7.80 (dd, J=2.7, 9.5 Hz, 1H), 7.53 (d, J=7.2 Hz, 1H), 6.78-6.75 (m, 2H), 6.45 (d, J=9.5 Hz, 1H), 6.36 (d, J=7.2 Hz, 1H), 3.51-3.50 (m, 3H), 3.40 (s, 3H), 2.04-2.03 (m, 6H).

Example 40: 4-(3-(4-fluoro-2,6-dimethylphenoxy)-1-methyl-2-oxo-1,2-dihydropyridin-4-yl)-6-methyl-1,6-dihydro-7H-pyrrolo[2,3-c]pyridin-7-one Preparation 148: 4-(3-(4-fluoro-2,6-dimethylphenoxy)-1-methyl-2-oxo-1,2-dihydropyridin-4-34)-6-methyl-1,6-dihydro-7H-pyrrolo[2,3-c]pyridin-7-one

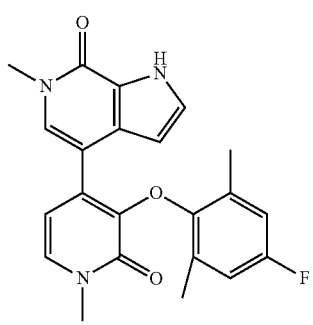 [SMILES: Cc1cc(F)cc(C)c1Oc1c(-c2cn(C)c(=O)c3[nH]ccc23)ccn(C)c1=O]

Following the procedure in preparation 10, 4-bromo-3-(4-fluoro-2,6-dimethylphenoxy)pyridin-2(1H)-one (100 mg, 0.31 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (124 mg, 0.29 mmol) was reacted to give the title compound (50 mg, 40%).

HPLC $t_R$ (Agilent, acidic, 3.5 min): 1.36 min, m/z=395.1 [M+H]$^+$.

$^1$H NMR (500 MHz, DMSO-d6) δ 12.07 (s, 1H), 7.54 (d, J=7.0 Hz, 1H), 7.36 (s, 1H), 7.31 (t, J=2.7 Hz, 1H), 6.69-6.66 (m, 2H), 6.32-6.26 (m, 2H), 3.55 (s, 3H), 3.44 (s, 3H), 2.01-2.00 (m, 6H).

Example 41: N-ethyl-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide

Preparation 149: ethyl 4-bromo-6-methyl-7-oxo-1-tosyl-6,7-dihydro-1H-pyrrolo[2,3-c]pyridine-2-carboxylate

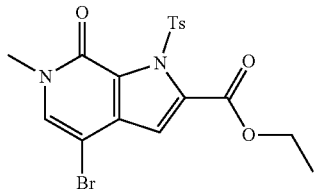 [SMILES: CCOC(=O)c1cc2c(Br)cn(C)c(=O)c2n1S(=O)(=O)c1ccc(C)cc1]

4-bromo-6-methyl-1-tosyl-1,6-dihydro-7H-pyrrolo[2,3-c]pyridin-7-one (1.3 g, 3.4 mmol), in THF (100 mL) was cooled to −78° C. LDA (2.03 mL, 4.06 mmol) was added dropwise and the resulting solution stirred at this temperature for 30 minutes. Ethyl carbonochloridate (0.39 mL, 4.06 mmol) was added and the reaction stirred for 1 hour at −78° C. Ethyl acetate (500 ml) was added and the organics washed with 2×500 ml water then 1×500 ml saturated brine solution. The organics were then separated and dried (MgSO$_4$) before concentration to dryness. The crude was then purified by flash column chromatography eluting with ethyl acetate/heptane gradient (0-100%). The desired fractions were combined and dried to afford was reacted to give the title compound (770 mg, 50%).

HPLC $t_R$ (Agilent, acidic, 3.5 min): 1.85 min, m/z=454.8 [M+H]$^+$.

Preparation 150: ethyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate

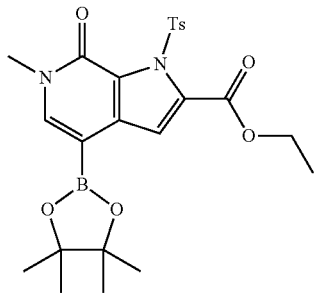 [SMILES: CCOC(=O)c1cc2c(B3OC(C)(C)C(C)(C)O3)cn(C)c(=O)c2n1S(=O)(=O)c1ccc(C)cc1]

Following the procedure in preparation 6, ethyl 4-bromo-6-methyl-7-oxo-1-tosyl-6,7-dihydro-1H-pyrrolo[2,3-c]pyridine-2-carboxylate (710 mg, 1.6 mmol) was reacted to give the title compound (437 mg, 56%).

HPLC $t_R$ (Agilent, acidic, 3.5 min): 2.10 min, m/z=501.1 [M+H]$^+$.

Preparation 151: 4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxylic acid

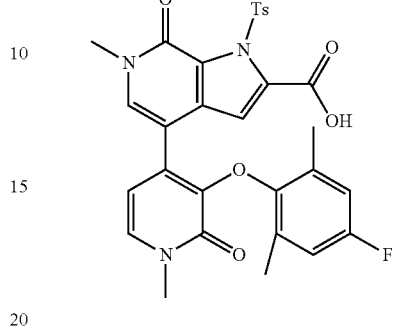

Following the procedure in preparation 10, 4-bromo-3-(4-fluoro-2,6-dimethylphenoxy)pyridin-2(1H)-one (285 mg, 0.87 mmol) and ethyl 6-methyl-7-oxo-4-(4,4,5,5-tetramethyl-1,3,2-dioxaborolan-2-yl)-1-tosyl-6,7-dihydro-1H-pyrrolo[2,3-c]pyridine-2-carboxylate (436 mg, 0.87 mmol) was reacted to give the title compound (112 mg, 29%).

HPLC $t_R$ (Agilent, acidic, 3.5 min): 1.17 min, m/z=378.1 [M+H]$^+$.

Preparation 152: N-ethyl-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide

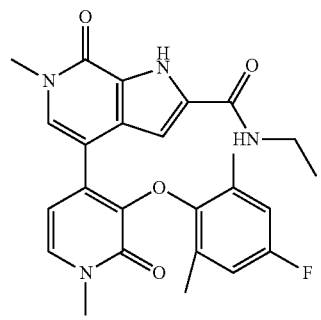 [SMILES: CCNC(=O)c1cc2c(-c3ccn(C)c(=O)c3Oc3c(C)cc(F)cc3C)cn(C)c(=O)c2[nH]1]

To a solution of 4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxylic acid J25 mg, 0.06 mmol) in DCM (1 mL) was added oxalyl chloride (0.1 mL, 0.11 mmol) and DMF (0.01 mL). Reaction was stirred for 1 h at room temperature. Solvent removed under reduced pressure and THF (1 mL) added. 30% ethylamine solution (0.11 mL, 0.23 mmol) in THF was added and the resulting solution stirred for 2 h at room temperature. Ethyl acetate (50 ml) was added and the organics washed with 2×50 ml water then 1×50 ml saturated brine solution. The organics were then separated and dried (MgSO$_4$) before concentration to dryness. The crude was then purified by flash column chromatography eluting with ethyl acetate/heptane gradient (0-100%). The desired fractions were combined and dried to afford was reacted to give the title compound (12 mg, 42%).

HPLC $t_R$ (Agilent, acidic, 3.5 min): 1.52 min, m/z=465.2 [M+H]$^+$.

$^1$H NMR (500 MHz, DMSO-d6) δ 12.25 (bs, 1H), 8.34 (t, J=5.3 Hz, 1H), 7.57 (d, J=7.2 Hz, 1H), 7.41 (s, 1H), 6.90 (s, 1H), 6.70-6.67 (m, 2H), 6.33-6.31 (m, 1H), 3.56 (s, 3H), 3.45 (s, 3H), 3.28-3.30 (m, 2H), 2.00 (s, 6H), 1.14 (t, J=7.2 Hz, 3H).

Example 42: N-(tert-butyl)-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide Preparation 153: N-(tert-butyl)-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide

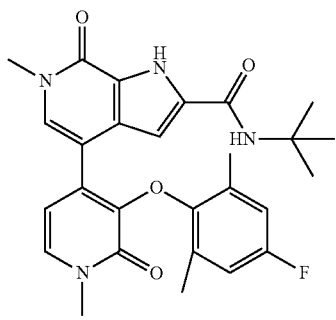 [SMILES: Cc1cc(F)cc(C)c1Oc1c(-c2cn(C)c(=O)c3[nH]c(C(=O)NC(C)(C)C)cc23)ccn(C)c1=O]

Following the procedure in preparation 152, 4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxylic acid (15.6 mg, 0.04 mmol) and 2-amino-2-methylpropane (0.015 mL, 0.14 mmol) was reacted to give the title compound (3 mg, 16%).

HPLC $t_R$ (Agilent, acidic, 3.5 min): 1.54 min, m/z=493.2 [M+H]$^+$.

$^1$H NMR (400 MHz, DMSO-d6) δ 12.36 (bs, 1H), 7.84 (s, 1H), 7.56 (d, J=7.2 Hz, 1H), 7.43 (s, 1H), 6.89 (d, J=1.1 Hz, 1H), 6.71-6.67 (m, 2H), 6.33 (d, J=7.0 Hz, 1H), 3.57 (s, 3H), 3.45 (s, 3H), 2.01-2.00 (m, 6H), 1.39 (s, 9H).

Example 43: N-(tert-butyl)-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide Preparation 154: N-(tert-butyl)-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide Following the procedure in preparation 152, 4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxylic acid (15.6 mg, 0.04 mmol) and 1,1,1-trifluoro-2-methylpropan-2-amine (18.3 mg, 0.14 mmol) was reacted to give the title compound (5 mg, 23%).

HPLC $t_R$ (Agilent, acidic, 3.5 min): 1.60 min, m/z=547.1 [M+H]$^+$.

$^1$H NMR (400 MHz, DMSO-d6) δ 12.49 (bs, 1H), 8.06 (s, 1H), 7.57 (d, J=7.1 Hz, 1H), 7.44 (s, 1H), 7.00 (d, J=2.2 Hz, 1H), 6.70-6.67 (m, 2H), 6.33 (d, J=7.1 Hz, 1H), 3.57 (s, 3H), 3.45 (s, 3H), 2.01 (s, 6H), 1.63 (s, 6H).

Example 44: N-(2,2-difluoro-1-methylcyclopropyl)-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide Preparation 155: N-(2,2-difluoro-1-methylcyclopropyl)-4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3-c]pyridine-2-carboxamide

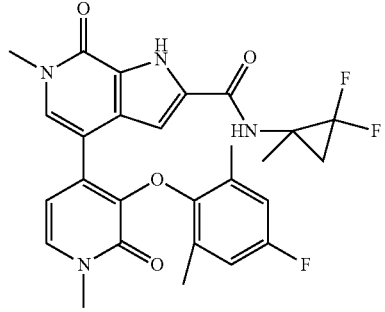 [SMILES: Cc1cc(F)cc(C)c1Oc1c(-c2cn(C)c(=O)c3[nH]c(C(=O)NC4(C)CC4(F)F)cc23)ccn(C)c1=O]

Following the procedure in preparation 152, 4-(3-(4-fluoro-2,6-dimethylphenoxy)-1-methyl-2-oxo-1,2-dihydropyridin-4-yl)-6-methyl-7-oxo-6,7-dihydro-1H-pyrrolo[2,3- c]pyridine-2-carboxylic acid_(15.6 mg, 0.04 mmol) and 2,2-difluoro-1-methylcyclopropan-1-amine hydrochloride (20.5 mg, 0.14 mmol) and DIPEA (0.019 mL, 0.14 mmol) was reacted to give the title compound (3 mg, 14%).

HPLC $t_R$ (Agilent, acidic, 3.5 min): 1.49 min, m/z=527.2 [M+H]$^+$.

$^1$H NMR (400 MHz, DMSO-d6) δ 12.35 (s, 1H), 8.79 (s, 1H), 7.57 (d, J=7.1 Hz, 1H), 7.43 (s, 1H), 6.96 (d, J=2.2 Hz, 1H), 6.70-6.66 (m, 2H), 6.33 (d, J=7.1 Hz, 1H), 3.55 (s, 3H), 3.45 (s, 3H), 2.00 (s, 6H), 1.71-1.62 (m, 2H), 1.48 (s, 3H).

Example 45: 4-(4-cyclobutoxythiazol-5-yl)-6-methyl-1,6-dihydro-7H-pyrrolo[2,3-c]pyridin-7-one Preparation 156: 4-cyclobutoxythiazole

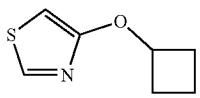

NaH (183 mg, 4.5 mmol) was added to cyclobutanol (1.29 mL, 16.5 mmol) at room temperature and then the resulting solution heated to 60° C. for 1 hour. 4-bromo-thiazole (300 mg, 1.83 mmol) was added and the resulting solution heated to 150° C. for 1 hour. Ethyl acetate (50 ml) was added and the organics washed with 2×50 ml water then 1×50 ml saturated brine solution. The organics were then separated and dried (MgSO$_4$) before concentration to dryness. The crude was then purified by flash column chromatography eluting with ethyl acetate/heptane gradient (0-100%). The desired fractions were combined and dried to afford was reacted to give the title compound (124 mg, 44%).

$^1$H NMR (500 MHz, DMSO-d6) δ 8.52 (s, 1H), 6.04 (s, 1H), 4.80-4.73 (m, 1H), 2.47-2.16 (m, 4H), 1.90-1.81 (m, 1H), 1.70-1.61 (m, 1H).

Preparation 157: 5-bromo-4-cyclobutoxythiazole

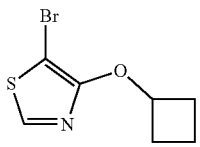 [SMILES: Brc1scnc1OC1CCC1]

Following the procedure in preparation 23, 4-cyclobutoxythiazole (485 mg, 3.1 mmol) was reacted to give the title compound (453 mg, 62%).

$^1$H NMR (400 MHz, DMSO-d6) δ 8.42 (s, 1H), 5.03-4.90 (m, 1H), 2.37-2.27 (m, 2H) 2.15-2.05 (m, 2H) 1.79-1.67 (m, 1H), 1.58-1.45 (m, 1H).

Preparation 158: 4-(4-cyclobutoxythiazol-5-yl)-6-methyl-1,6-dihydro-7H-pyrrolo[2,3-c]pyridin-7-one

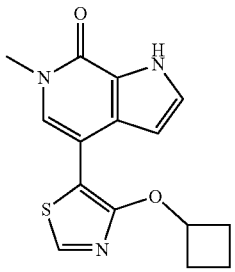 [SMILES: Cn1cc(-c2scnc2OC2CCC2)c2cc[nH]c2c1=O]

Following the procedure in preparation 10, 5-bromo-4-cyclobutoxythiazole (66 mg, 0.28 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (110 mg, 0.026 mmol) was reacted to give the title compound (7 mg, 8%).

HPLC $t_R$ (Agilent, acidic, 3.5 min): 1.51 min, m/z=302.1 [M+H]$^+$.

$^1$H NMR (400 MHz, DMSO-d6) δ 12.17 (bs, 1H), 8.85 (s, 1H), 7.56 (s, 1H), 7.36 (t, J=2.8 Hz, 1H), 6.44 (t, J=2.4 Hz, 1H), 5.12-5.05 (m, 1H), 3.58 (s, 3H), 2.40-2.32 (m, 2H), 2.15-2.05 (m, 2H), 1.81-1.72 (m, 1H), 1.66-1.56 (m, 1H).

Example 46: 6-methyl-4-(4-propoxythiazol-5-yl)-1,6-dihydro-7H-pyrrolo[2,3-c]pyridin-7-one Preparation 159: 4-propoxythiazole

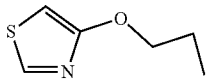

Following the procedure in preparation 156, 1-propanol (3.6 mL, 54.9 mmol) was reacted to give the title compound (150 mg, 28%).

$^1$H NMR (500 MHz, CDCl$_3$) δ 8.56 (d, J=2.1 Hz, 1H), 6.14 (d, J=2.3 Hz, 1H), 4.13-4.09 (m, 2H), 1.89-1.82 (m, 2H), 1.07 (t, J=7.5 Hz, 3H).

Preparation 160: 5-bromo-4-propoxythiazole

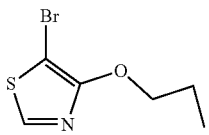

Following the procedure in preparation 23, 4-propoxythiazole_(610 mg, 4.3 mmol) was reacted to give the title compound (592 mg, 62%).

$^1$H NMR (500 MHz, CDCl$_3$) δ 8.53 (s, 1H), 4.33-4.29 (m, 2H), 1.82-1.74 (m, 2H), 1.04-1.00 (m, 3H).

Preparation 161: 6-methyl-4-(4-propoxythiazol-5-yl)-1,6-dihydro-7H-pyrrolo[2,3-c]pyridin-7-one

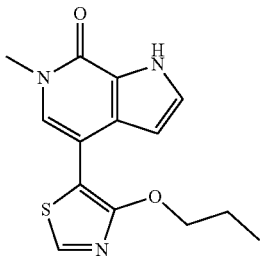 [SMILES: CCCOc1ncsc1-c1cn(C)c(=O)c2[nH]ccc12]

Following the procedure in preparation 10, 5-bromo-4-propoxythiazole (57 mg, 0.26 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (100 mg, 0.023 mmol) was reacted to give the title compound (17 mg, 23%).

HPLC $t_R$ (Agilent, acidic, 3.5 min): 1.52 min, m/z=290.1 [M+H]$^+$.

$^1$H NMR (400 MHz, DMSO-d6) δ 12.19 (bs, 1H), 8.87 (s, 1H), 7.56 (s, 1H), 7.35 (t, J=2.8 Hz, 1H), 6.44 (t, J=2.4 Hz, 1H), 4.31 (t, J=6.5 Hz, 2H), 3.29 (s, 3H), 1.76-1.69 (m, 2H), 0.96 (t, J=7.4 Hz, 3H).

Example 47: 4-(3-(4-fluoro-2,6-dimethylphenoxy)-1-methyl-2-oxo-1,2-dihydropyridin-4-yl)-6-methyl-1,6-dihydro-7H-pyrrolo[2,3-c]pyridin-7-one Preparation 162: 2-chloro-5-(4-fluoro-2, 6-dimethylphenoxy)-4-nitropyridine 1-oxide

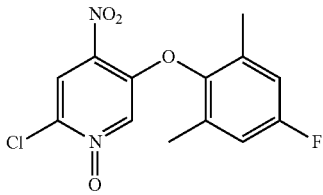 [SMILES: C/C(Oc1c(C)cc(F)cc1C)=C(\C=C(\Cl)N=O)[N+](=O)[O-]]

Following the procedure in preparation 35, 4-fluoro-2,6-dimethylphenol (15.0 g, 77.9 mmol) was reacted to give the title compound (16.0 g, 64%).

$^1$H NMR (400 MHz, CDCl$_3$) δ 8.25 (s, 1H), 7.69 (s, 1H), 6.88 (d, J=8.4 Hz, 2H), 2.183 (s, 6H).

Preparation 163: 2,4-dibromo-5-(4-fluoro-2,6-dimethylphenoxy)pyridine 1-oxide

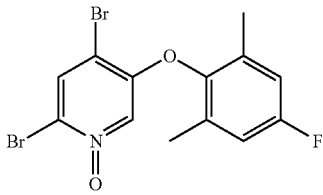

Following the procedure in preparation 26, 2-chloro-5-(4-fluoro-2,6-dimethylphenoxy)-4-nitropyridine 1-oxide (11.0 g, 35.1 mmol) was reacted to give the title compound (11.9 g, 78%).

HPLC $t_R$ (Shimadzu, acidic, 1.5 min): 0.93 min, m/z=391.8 [M+H]$^+$.

Preparation 164: 2,4-dibromo-5-(4-fluoro-2,6-dimethylphenoxy)pyridine

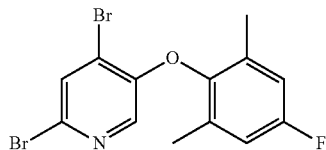 [SMILES: Cc1cc(F)cc(C)c1Oc1cnc(Br)cc1Br]

Following the procedure in preparation 27, 2,4-dibromo-5-(4-fluoro-2,6-dimethylphenoxy)pyridine 1-oxide (17.7 g, 42.5 mmol) was reacted to give the title compound (16.5 g, 65%).

HPLC $t_R$ (Shimadzu, acidic, 1.5 min): 1.08 min, m/z=375.8 [M+H]$^+$.

Preparation 165: 4-bromo-5-(4-fluoro-2,6-dimethylphenoxy)pyridin-2(1H)-one

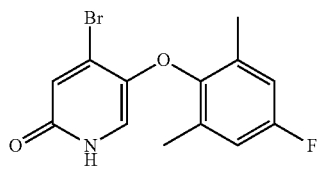 [SMILES: Cc1cc(F)cc(C)c1Oc1c[nH]c(=O)cc1Br]

Following the procedure in preparation 38, 2,4-dibromo-5-(4-fluoro-2,6-dimethylphenoxy)pyridine (7.5 g, 20.0 mmol) was reacted to give the title compound (6.2 g, 99%).

HPLC $t_R$ (Shimadzu, acidic, 1.5 min): 0.90 min, m/z=312.0 [M+H]$^+$.

Preparation 166: 4-bromo-5-(4-fluoro-2,6-dimethylphenoxy)-1-methylpyridin-2(1H)-one

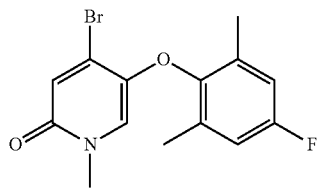 [SMILES: Cc1cc(F)cc(C)c1Oc1cn(C)c(=O)cc1Br]

Following the procedure in preparation 39, 4-bromo-5-(4-fluoro-2,6-dimethylphenoxy)pyridin-2(1H)-one (6.24 g, 20.0 mmol) was reacted to give the title compound (1.42 g, 22%).

$^1$H NMR (500 MHz, DMSO-d6) δ 7.04 (d, J=8.8 Hz, 2H), 6.92 (s, 1H), 6.82 (s, 1H), 3.27 (s, 3H), 2.12 (s, 6H)

Preparation 167: 4-(3-(4-fluoro-2,6-dimethylphenoxy)-1-methyl-2-oxo-1,2-dihydropyridin-4-yl)-6-methyl-1,6-dihydro-7H-pyrrolo[2,3-c]pyridin-7-one

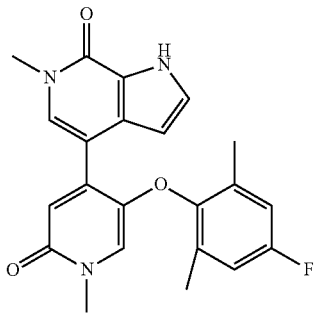 [SMILES: Cc1cc(F)cc(C)c1Oc1cn(C)c(=O)cc1-c1cn(C)c(=O)c2[nH]ccc12]

Following the procedure in preparation 10, 4-bromo-3-(4-fluoro-2,6-dimethylphenoxy)pyridin-2(1H)-one (152 mg, 0.47 mmol) and 6-methyl-4-(4,4,5,5-tetramethyl-1,3,2-dioxaborolan-2-yl)-1-tosyl-1,6-dihydro-7H-pyrrolo[2,3-c]pyridin-7-one (200 mg, 0.47 mmol) was reacted to give the title compound (77 mg, 42%).

HPLC $t_R$ (Agilent, acidic, 3.5 min): 1.36 min, m/z=394.1 [M+H]$^+$.

$^1$H NMR (400 MHz, DMSO-d6) δ 12.17 (bs, 1H), 7.46 (s, 1H), 7.36-7.33 (m, 1H), 7.00-6.96 (m, 2H), 6.72 (s, 1H), 6.51-6.50 (m, 1H), 6.34 (t, J=2.3 Hz, 1H), 3.58 (s, 3H), 3.34 (s, 3H), 2.09 (s, 6H).

Primary Activity

The dissociation constant ($K_d$) of Examples 1 to 47 of the compounds described herein, from BRD4 BD1 and BD2 were determined. BRD4 is a representative example of the BET family, as to date highly isoform selective compounds do not exist. Dissociation constants were determined as described below and are represented in Table 1.

Bromodomain Assay Procedure

T7 phage strains displaying bromodomains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 min). The lysates were centrifuged (5,000×g) and filtered (0.2 μm) to remove cell debris. Streptavidin-coated magnetic beads were treated with biotinylated small molecule or acetylated peptide ligands for 30 min at RT to generate affinity resins for bromodomain assays. The ligated beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining bromodomains, ligated affinity beads, and test compounds in 1× binding buffer (16% SeaBlock, 0.32×PBS, 0.02% BSA, 0.04% Tween 20, 0.004% Sodium azide, 7.9 mM DTT). Test compounds were prepared as 1000× stocks in 100% DMSO and subsequently diluted 1:25 in MEG. The compounds were then diluted directly into the assays such that the final concentrations of DMSO and MEG were 0.1% and 2.4%, respectively. All reactions were performed in polypropylene 384-well plates in a final volume of 0.02 ml. The assay plates were incubated at RT with shaking for 1 hr and the affinity beads were washed with wash buffer (1×PBS, 0.05% Tween 20). The beads were then re-suspended in elution buffer (1×PBS, 0.05% Tween 20, 2 μM non-biotinylated affinity ligand) and incubated at RT with shaking for 30 min. The bromodomain concentration in the eluates was measured by quantitative polymerase chain reaction (qPCR).

An 11-point 3-fold serial dilution of each test compound was prepared in 100% DMSO at 1000× final test concentration. All compounds were distributed by acoustic transfer (non-contact dispensing) in 100% DMSO. The compounds were then diluted directly into the assays such that the final concentration of DMSO was 0.09%. Most dissociation constants were determined using a compound top concentration=10,000 nM. If the initial dissociation constant determined was <0.169 nM (the lowest concentration tested), the measurement was repeated with a serial dilution starting at a lower top concentration.

TABLE 1

Dissociation constants of exemplified compounds from BRD4 BD1 and BD2

| Example | BRD4 BD1 $K_d$ | BRD4 BD2 $K_d$ |
|---|---|---|
| 1 | ++++ | ++++ |
| 2 | +++ | |
| 3 | +++ | ++++ |
| 4 | +++ | ++++ |
| 5 | +++ | ++++ |
| 6 | ++++ | |
| 7 | +++ | ++++ |
| 8 | +++ | |
| 9 | +++ | |
| 10 | ++++ | |
| 11 | ++++ | |
| 12 | ++++ | |
| 13 | ++ | |
| 14 | ++ | |
| 15 | ++ | |
| 16 | ++ | |
| 17 | +++ | |
| 18 | ++ | |
| 19 | ++ | |
| 20 | +++ | |
| 21 | ++ | |
| 22 | ++ | |
| 23 | +++ | |
| 24 | +++ | |
| 25 | +++ | |
| 26 | +++ | |
| 27 | ++ | |
| 28 | ++ | |
| 29 | +++ | |
| 30 | +++ | |
| 31 | +++ | |
| 32 | +++ | |
| 33 | ++++ | |
| 34 | +++ | |
| 35 | +++ | |
| 36 | ++ | |
| 37 | ++ | |
| 38 | ++ | |
| 39 | + | ++ |
| 40 | ++ | +++ |
| 41 | + | ++++ |
| 42 | + | ++++ |
| 43 | + | +++ |
| 44 | + | +++ |
| 45 | ++ | +++ |
| 46 | ++ | +++ |
| 47 | +++ | ++++ |

Key
+ Kd > 1 μM
++ Kd > 0.1 μM and ≤ 1 μM
+++ Kd > 0.01 μM and ≤ 0.1 μM
++++ Kd ≤ 0.01 μM Preferably, BET protein inhibitors exhibit a $K_d$ of <0.1 μM for BRD4 BD2 or BD1 and BD2. BET protein inhibitors with a $K_d$ of <0.1 µM selective for BRD4 BD2 are promising oral drug candidates, whilst BET protein inhibitors with a $K_d$ of <0.1 µM selective for BRD4 BD1 and BD2 are promising topical drug candidates.

BET Selectivity

The selectivity of Examples 1 and 41 of the current invention, against BRD2,3,4 and T BD1 and BD2 were determined as described below and are represented in Table 2.

Bromodomain Assay Procedure

The same bromodomain assay procedure as that outlined above was used. Example compounds were screened at 30 times their $K_d$, and results for primary screen binding interactions are reported as '% Ctrl', where lower numbers indicate stronger hits in the matrix.

$$\% \ Ctrl = \frac{\text{test compound signal} - \text{positive control signal}}{\text{negative control signal} - \text{positive control signal}} \times 100$$

Test compound=A compound of formula (I), such as example 1

Negative control=DMSO (100% Ctrl)

Positive control=control compound (0% Ctrl)

TABLE 2

Single point concentration binding interactions of exemplified compounds

| Example | BRD2(1) % Ctrl | BRD3(1) % Ctrl | BRD4(1) % Ctrl | BRDT(1) % Ctrl |
|---|---|---|---|---|
| 1 | 0 | 0 | 0 | 0 |
| 41 | 100 | 85 | 90 | 100 |

| Example | BRD2(2) % Ctrl | BRD3(2) % Ctrl | BRD4(2) % Ctrl | BRDT(2) % Ctrl |
|---|---|---|---|---|
| 1 | 0.6 | 0.05 | 2.6 | 3.8 |
| 41 | 0.1 | 2.3 | 8.7 | 13 |

Preferably, BET protein inhibitors exhibit a % Ctrl of <10 for BRD 2,3,4 and T BD2 or T BD1 and BD2. BET protein inhibitors with % Ctrl of <10 for BRD 2,3,4 and T BD2 are promising oral drug candidates, whilst BET protein inhibitors with % Ctrl of <10 for BRD 2,3,4 and T BD1 and BD2 are promising topical drug candidates. The data of Table 2 show that Example 41 is a promising oral drug candidate, whilst Example 1 is a promising topical drug candidate.

BET Selectivity Dose Response

The dissociation constants ($K_d$) of Example 41 of the current invention, from BRD2,3,4 and T BD1 and BD2 was determined as described below and tabulated in Table 3.

Bromodomain Assay Procedure

The same bromodomain assay procedure as that outlined above was used.

TABLE 3

Dose response binding interactions of exemplified compounds

| Example | BRD2(1) Kd (nM) | BRD3(1) Kd (nM) | BRD4(1) Kd (nM) | BRDT(1) Kd (nM) |
|---|---|---|---|---|
| 41 | >3000 | >3000 | >3000 | >3000 |

TABLE 3-continued

Dose response binding interactions of exemplified compounds

| Example | BRD2(2) Kd (nM) | BRD3(2) Kd (nM) | BRD4(2) Kd (nM) | BRDT(2) Kd (nM) |
|---|---|---|---|---|
| 41 | <10 | <10 | <10 | <10 |

BET protein inhibitors with a $K_d$ of <10 nM for BRD 2,3,4 and selectively T BD2 are promising oral drug candidates. Example 41 exhibits a $K_d$ of <10 nM for BRD4(2) and a $K_d$ of >3000 nM for BRD4(1). Thus, Example 41 is a promising oral drug candidate.

Cellular Activity—Broad Panel

The EC50 values of Example compounds 1 and 3 of the invention in the reduction of GM-CSF, IL-1a, IL-6, IL-8, CCL2, TNF-α, TSLP, CCL27, CCL20 and CXCL9 levels in primary keratinocytes stimulated by polyinosinic:polycytidylic acid were determined.

EC50s were determined as described below and are represented in Table 4.

Assay Procedure

1. Seed Primary Human Keratinocytes cells (PHK) at 9000 cells/well in a flat bottom 96 well plate.
2. Before treatment, cells must reach a confluence of 90-100% then medium is replaced with fresh medium that does not contain hydrocortisone.
3. Cells are cultured for 24 hr prior to TLR ligand stimulation (polyinosinic:polycytidylic acid).
4. Cells are treated with 20 µg/mL polyinosinic:polycytidylic acid for 48 hrs in 180 µL of media and treated for different compounds or controls.
5. Supernatant is collected and Chemokine and Cytokines analysis is performed by Magpix-Luminex.

Immunoassay Procedure

Day 1

1. Add 200 µL of Assay Buffer per well. Shake 10 min, RT. Decant.
2. Add 25 µL of Standard or Control to the appropriate wells.
3. Add 25 µL of Assay Buffer to background and sample wells.
4. Add 25 µL of cell media to background, standard and control wells.
5. Add 25 µL neat samples to sample wells.
6. Add 25 µL of Beads to each well.
7. Incubate overnight (16-18 hr) at 4° C.

Day 2

8. Remove well contents and wash 2× with 200 µL Wash buffer.
9. Add 25 µL of Detection Antibodies per well.
10. Incubate 1 hr at RT (20-25° C.).
11. Add 25 µL of Streptavidin-Phycoerytrin per well (do not aspirate).
12. Incubate for 30 min at RT.
13. Remove well contents and wash 2× with 200 µL Wash buffer.
14. Add 150 µL of Wash Buffer per well. Resuspend the beads on a plate shaker for 5 min.
15. Read on Luminex 100 µl (50 beads per bead set).

TABLE 4

EC50 values of exemplified compounds of the invention. The measured drug respons is the reduction of GM-CSF, IL-1a, IL-6, IL-8, CCL2, TNF-a, TSLP, CCL27, CCL20 and CXCL9 levels in primary keratinocytes stimulated by polyinosinic:polycytidylic acid.

| Example | GM-CSF | IL-6 | IL-8 | TSLP | IL-1a |
|---|---|---|---|---|---|
| 1 | ++++ | +++ | ++++ | +++ | ++++ |
| 3 | ++++ | +++ | ++++ | ++++ | ++++ |

| Example | TNF-a | CCL2 | CCL20 | CCL27 | CXCL9 |
|---|---|---|---|---|---|
| 1 | ++++ | +++ | +++ | +++ | ++++ |
| 3 | ++++ | ++++ | ++++ | +++ | ++++ |

Key
+ EC50 > 1 µM
++ EC50 > 0.1 µM and ≤ 1 µM
+++ EC50 > 0.01 µM and ≤ 0.1 µM
++++ EC50 ≤ 0.01 µM Preferably, BET protein inhibitors exhibit cellular EC50 values of <0.1 µM for one or more of the disease relevant markers in stimulated human primary keratinocytes. Examples 1 and 3 exhibit cellular EC50 values of <0.1 µM in stimulated human primary keratinocytes.

Cellular Activity—IL-4

The EC50 values of specific Example compounds of the invention in the reduction of IL-4 levels produced by CD4+ T-cells activated with CD2, CD3 and CD28 antibodies were determined as described below and tabulated in Table 5.

Assay Procedure
1. CD4+ T-cells are isolated from cryopreserved human peripheral blood mononuclear cells (PBMCs) using EasySep™ Kit (Cat. No. 17952, Stemcell Technologies).
2. CD2, CD3 and CD28 antibodies coated beads from T cell Activation/Expansion Kit (Cat. No. 130-091-441, Miltenyi Biotec) are added to the CD4+ T-cells at a bead-to-cell ratio of 1:2.
3. CD4+ T-cells along with the beads are seeded at 2×10$^5$ cells/well in a round bottom 96-well plate and treated with different compounds and controls in a total volume of 200 µl.
4. The cells are cultured for 48 hrs at 37° C., 5% $CO_2$.
5. Supernatant is collected and IL-4 is analysed by ELISA.

TABLE 5

EC50 values of exemplified compounds of the invention. The measured drug response is the reduction of IL-4 levels in CD4+T-cells stimulated by CD2, CD3 and CD28 antibodies

| Example | IL-4 |
|---|---|
| 1 | ++++ |
| 3 | +++ |
| 4 | +++ |
| 5 | ++++ |
| 6 | +++ |
| 7 | +++ |
| 8 | ++ |
| 10 | +++ |
| 18 | + |
| 20 | +++ |
| 24 | ++ |
| 39 | + |
| 40 | ++ |
| 41 | +++ |
| 42 | ++ |
| 43 | ++ |
| 44 | ++ |
| 46 | +++ |
| 47 | ++ |

+ EC50 > 1 µM
++ EC50 > 0.1 µM and ≤ 1 µM
+++ EC50 > 0.01 µM and ≤ 0.1 µM
++++ EC50 ≤ 0.01 µM Preferably, BET protein inhibitors exhibit cellular EC50 values of <0.1 µM for the reduction of IL-4 levels Examples 1, 3, 4, 5, 6, 7, 10, 20, 41, and 46 exhibit cellular EC50 values of <0.1 µM in CD4+ T-cells stimulated by CD2, CD3 and CD28 antibodies coated beads from T cell Activation/Expansion Kit.

Human Tissue Data—Th2 and Th17 Stimulation of Human Skin Explants

The % reduction of Example compounds at 2.5 µM listed below of the invention in IL-4 or IL-17A mRNA in healthy human skin stimulated by a Th2 or Th17 biasing cocktail were determined as described below and tabulated in Table 6.

Assay Procedure
1. Freshly excised healthy human skin tissue from abdominoplasties is defatted, cleaned and sectioned into 7 mm biopsies.
2. The biopsies are placed in Transwell® inserts with the epidermis apical and exposed to air and the dermis submerged in media in the basal chamber.
3. The biopsies are pre-treated overnight at 37° C., 5% $CO_2$ with different compounds and controls added to the media in the basal chamber.
4. The next day, contents of the basal chamber is replaced with fresh media containing the test compound and a stimulation cocktail for either Th2 inflammation (proprietary Medpharm cocktail) or Th17 inflammation (mix of antibodies against CD3, CD28, IL-4, IFNγ and recombinant IL-1β, IL-6, IL-21, TGF-β).
5. The biopsies are incubated at 37° C., 5% $CO_2$ for a further 24 hrs.
6. After harvesting, the biopsies are cut in half, and one half is homogenized and used for RNA extraction by standard methods. IL-4 or IL-17A is assessed by RT-qPCR.

TABLE 6

% reduction in IL-4 and IL-17A mRNA of compounds 1 and 41 of the invention at 2.5 μM. The measured drug response is the reduction of IL-4 or IL-17A mRNA levels in healthy human skin stimulated by a Th2 or Th17 biasing cocktail.

| Example | IL-17 | IL-4 |
|---|---|---|
| 1 | +++ | +++ |
| 41 | +++ | ++ |

Key
+ > 25% reduction
++ > 50% reduction
+++ > 75% reduction

Preferably, BET protein inhibitors exhibit >50% reduction of IL-4 or IL-17 levels, Examples 1 and 41 exhibit >50% reduction in healthy human skin stimulated by a Th2 or Th17 biasing cocktail.

Intrinsic Clearance in Human Liver Hepatocytes

BET protein inhibitors with a rapid rate of clearance in human liver hepatocytes are promising topical drug candidates. Some of the exemplary compounds of the current invention have rapid clearance in human liver hepatocytes, the rate of which is expressed as a % of liver blood flow. The experimental methods and results (Table 7) are provided hereinafter.

Assay Procedure

Vials of human cryopreserved hepatocytes, supplied by Life Technologies, were thawed according to manufacturer's instructions and cells re-suspended in Williams Medium E (WME) containing cell maintenance supplement pack (CM4000, Life Technologies). Hepatocytes were incubated in suspension (0.5 million cells/mL) in 48 well non-collagen coated cell culture plates for 10 min at 37° C., 5% $CO_2$. Upon addition of an equal volume of supplemented WME containing 1 μM test compound, an aliquot of incubation solution was removed to acetonitrile containing internal standard (final concentration 0.5 μM test compound and a cell density of 0.25 million cells/mL). Similarly, aliquots were removed at 3, 6, 9, 15, 30, 45, 60, 90 and 120 min. 100 μL of 80:20 water:acetonitrile was added to all samples and the analysis plate was centrifuged for 10 min at RT prior to injection and analysis of samples by UPLC-MS/MS. The response (area ratio of test compound to internal standard) was plotted against time using an exponential decay model from which rate of disappearance was calculated.

TABLE 7

Intrinsic clearance (%) of exemplary compounds 1 to 3 in human liver hepatocytes.

| Example | % Liver Blood Flow |
|---|---|
| 1 | 83 |
| 2 | 88 |
| 3 | 86 |
| 4 | 80 |
| 5 | <34 |
| 6 | 94 |
| 7 | <34 |
| 8 | 95 |
| 9 | 95 |
| 10 | 93 |
| 11 | 97 |
| 12 | 82 |
| 13 | 34 |
| 18 | 69 |

TABLE 7-continued

Intrinsic clearance (%) of exemplary compounds 1 to 3 in human liver hepatocytes.

| Example | % Liver Blood Flow |
|---|---|
| 22 | <34 |
| 23 | 38 |
| 24 | 45 |
| 25 | 38 |
| 26 | <34 |
| 27 | <34 |
| 28 | <34 |
| 29 | <34 |
| 30 | <34 |
| 31 | <34 |
| 32 | <34 |
| 33 | <34 |
| 34 | <34 |
| 40 | <34 |
| 41 | <34 |
| 42 | <34 |
| 43 | 38 |
| 44 | 34 |
| 45 | 86 |
| 46 | 89 |

Preferably, BET protein inhibitors for use as topical drugs exhibit intrinsic clearance rates >75% in human liver hepatocytes. Exemplary compounds 1 to 4, 6, 8 to 12, 45 and 46 exhibit intrinsic clearance rates of >75%.

Solubility in Topical Formulations

Examples 1 to 3 and 6 of the current invention have been shown to have desirable solubility in a range of simple topical formulations. The solubility is expressed in mg/mL. The experimental methods and results are provided hereinafter.

Assay Procedure

The solubilities of solid exemplary compounds were determined in a selection of solvents and solvent combinations (Transcutol, 50:50 Transcutol:water, Labrasol, propylene glycol and 1:5:4 ethanol:propylene glycol:water), after equilibration. An appropriate volume of each combination was added to a manual weighing of solid compound to provide a 20 mg/mL concentration. The resulting suspension was shaken at 1000 rpm for 5 hr at 32° C. before centrifugation at 13,000×g for 10 min to pellet any precipitate. The supernatant solution was removed and inserted into a HPLC vial and quantified by HPLC-UV against a calibration of a known concentration of the compound in DMSO.

TABLE 8

The solubilities of exemplary compounds of the invention in various solvents and solvent combinations. TC is Transcutol; LB is Labrasol; PG is Propylene glycol; EtOH is Ethanol.

| Example | TC | TC:water 1:1 | LB |
|---|---|---|---|
| 1 | +++ | ++ | ++ |
| 2 | +++ | ++ | ++ |
| 3 | +++ | +++ | +++ |
| 6 | +++ | ++ | +++ |

| Example | PG | EtOH:PG:water 1:5:4 |
|---|---|---|
| 1 | ++ | ++ |
| 2 | ++ | − |

TABLE 8-continued

The solubilities of exemplary compounds of the invention in various solvents and solvent combinations. TC is Transcutol; LB is Labrasol; PG is Propylene glycol; EtOH is Ethanol.

| | | |
|---|---|---|
| 3 | +++ | ++ |
| 6 | +++ | ++ |

Key
+ > 0.1 mg/mL and ≤ 1 mg/mL
++ > 1 mg/mL and ≤ 10mg/mL
+++ > 10mg/mL

Preferably, BET protein inhibitors for use in topical formulations exhibit solubilities of >1 mg/mL of formulation. Exemplary compounds 1 to 3 and 6 exhibit solubilities of >1 mg/mL and in some instances >10 mg/mL of the formulations described.

Stability in Human Skin S9 Fraction

Exemplary compounds 1 to 3 and 6 have desirable stabilities in human skin S9 fractions. Such fractions model human skin and stability is expressed as the time it takes for the concentration of the compound to decrease by a half (half-life). The experimental methods and some results (Table 9) are provided hereinafter.

Assay Procedure

An incubation mixture was prepared containing 50 mM potassium phosphate buffer, pH 7.4), 0.3 mg/mL human skin S9 (Sekisui Xenotech), NADPH (final conc 0.8 mg/mL), UDPGA (final conc 0.16 mg/mL) and warmed to 37° C. for 5 min. The reaction was initiated upon addition of test compound (final concentration 0.5 μM). Immediately, at time zero, then at 3, 6, 15, 30, 60, 120 and 180 min, an aliquot (50 μL) of the incubation mixture was removed and mixed with acetonitrile (100 μL) to terminate the reaction. Internal standard was added to all samples, the samples centrifuged to sediment precipitated protein and the plates then sealed prior to UPLC-MS/MS analysis using a Quattro Premier XE (Waters corporation, USA).

Grafit (Erithacus Ltd) was used to calculate the exponential decay and consequently the rate constant (k) from the ratio of peak area of test compound to internal standard at each timepoint. The half life ($T_{1/2}$) of each test compound was determined using the following equation:

$$T_{1/2} = 0.693/k$$

TABLE 7

$T_{1/2}$ of exemplary compounds in human skin S9 fractions.

| Example | $T_{1/2}$ (min) |
|---|---|
| 1 | >120 |
| 2 | >120 |
| 3 | >120 |
| 6 | >120 |

Preferably, BET protein inhibitors for use in topical formulations exhibit >120 minute $T_{1/2}$ value in human skin. Exemplary compounds 1 to 3 and 6 exhibit $T_{1/2}$ values in human skin S9 fractions of >120 min.

Hydrolytic Stability at a Range of pHs

Exemplary compounds 1 to 3 of the invention are stable under conditions designed to promote hydrolytic degradation. Stability is expressed as a % decrease after 6 days. The experimental methods and results (Table 8) are provided hereinafter.

Assay Procedure

To test the hydrolytic stability a 1 mg/mL solution of test materials was made in DMSO (0.1% solution). To 300 μL of each solution in a HPLC vials was added 1200 μL of one of the following:

pH 4.0 buffer—left at 60° C. for 5 days. Samples taken t=0 hr and 6 days pH 5.5 buffer—left at 60° C. for 5 days. Samples taken t=0 hr and 6 days pH 7.4 buffer—left at 60° C. for 5 days. Samples taken t=0 hr and 6 days A 100 μL aliquot was taken at each time point and added to 900 μL of DMSO. This sample was used to determine % decomposition.

% decomposition was measured with a Bruker MicrO-TOF II focus ESI Mass Spectrometer connected in parallel to Dionex Ultimate 3000 RSLC system with diode array detector.

TABLE 8

The hydrolytic stability of exemplary compounds of the invention under conditions designed to promote hydrolytic degradation, measured at specific pH values and given as % decomposition.

| Example | pH 4.0 % decomposition | pH 5.5 % decomposition | pH 7.4 % decomposition |
|---|---|---|---|
| 1 | 0 | 0 | 0 |
| 2 | 15 | 30 | 0 |
| 3 | 0 | 0 | 0 |

Preferably, BET protein inhibitors exhibit <5% decomposition in conditions designed to promote hydrolytic cleavage. Exemplary compounds 1 to 3 exhibit decompositions of <5% when tested at a pH value of 7.4. Compounds 1 and 3 exhibit decompositions of <5% at all pH values tested.

Skin Penetration (Franz Cell)

Examples 1 of the invention has desirable skin penetration properties in human skin. Epidermal skin concentrations were determined as described below; the experimental methods and some results (Table 9) are provided hereinafter.

Assay Procedure

A dosing solution was prepared for each test compound at a saturated concentration in an appropriate formulation mixture. The positive control, caffeine (final concentration 10 mg/mL), was prepared in 50:50 transcutol/water. Warm, degassed phosphate buffered saline (PBS) was applied to the receiving chambers of each jacketed Franz cell (1 cm containing a magnetic stirring bar). Pig/Human skin was removed from −80° C. storage and cut to size (~2 cm$^2$) using a scalpel. The skin was then allowed to thaw at RT before being placed into warmed PBS for 10 min. Each skin piece was then dried before being placed onto the orifice of the Franz cell, removing any bubbles that occurred. The donor chamber was placed onto the skin and clamped in place. 10 μL of dosing solution was then placed onto the skin and parafilm was placed onto the donor chamber to provide occlusion. Using a 1 mL syringe, 200 μL of receiver solution was removed via the sampling arm to a 96 deepwell plate, this was the first time point (To). 200 μL of fresh warmed buffer was added to replace the volume removed. A further 200 μL was removed as described at defined time points over a 24 hr period. 100 μL of each sample was then removed to 100 μL of acetonitrile containing Internal Standard (IS, Donepezil, 4 ng/mL).

After completion, the skin surface was swabbed with a cotton bud to remove any remaining compound. The cotton bud tips were then submerged in DMSO for compound extraction. The skin was removed from the Franz cell and 30 tape strips applied to remove the stratum corneum, which were placed into a vial containing a known volume of DMSO. The skin was then placed surface down onto a heater block at 70° C. for 1 minute after which the epidermis was gradually teased from the dermis using a scalpel. The remaining dermis was cut from the compressed tissue such that only the exposed tissue was left, both pieces of tissue were weighed prior to being placed into individual glass vials and a known volume of DMSO was added.

All skin extraction and wash samples were placed on a shaker for 24 hrs at RT after which, samples were removed to Eppendorfs (where applicable) and centrifuged. Supernatant was removed and diluted appropriately (eg. 1 in 10, 100, 500 and 1000).

A calibration line was prepared in PBS (5000 ng/mL-0.2 ng/mL). 100 µL of each was added to 100 µL of acetonitrile containing IS. All samples were quantified using UPLC-MS/MS (Waters Xevo TQ-S).

The concentration of compound present at each time point was corrected for the addition of fresh buffer. By plotting the concentration of compound vs time, the J flux and T lag could be calculated (values for caffeine should be approximately J Flux: 0.9-1.1 µg/cm/hr, $T_{lag}$: 244-257 min, ~20% of dose present in receiving chamber after 24 hrs, mass balance 70-90%).

Skin extraction samples were corrected for dilution factor and volume of extraction solution. The quantity of dose measured in skin layers and time point samples were used to measure the mass balance of the experiment.

The exemplary compound did not penetrate through the skin (so a J flux and T lag value is not given). Rather, the exemplary compound was present in high concentrations in the skin (see Table 9). The mass balance was calculated to be 94%.

TABLE 9

Concentration of exemplary compounds of the invention in the epidermis of pig/human skin after 24 hour exposure of the surface of the skin with the corresponding compound.

| Example | Epidermal concentration (µM) |
|---|---|
| 1 | 27 |

Primary Keratinocyte Cell Viability

The EC50 of exemplary compounds 1 and 3 of the invention in human primary keratinocytes, stimulated by polyinosinic:polycytidylic acid, were determined. EC50s were determined as described below and are represented in Table 10, in which the compound numbers correspond to the numbers in the examples.

Assay Procedure
1. Seed Primary Human Keratinocytes cells (PHK) at 9000 cells/well in a flat bottom 96 well plate.
2. Before treatment, cells must reach a confluence of 90-100% then medium is replaced with fresh medium that does not contain hydrocortisone.
3. Cells are cultured for 24 hr prior to TLR ligand stimulation (polyinosinic:polycytidylic acid).
4. Cells are treated with 20 µg/ml polyinosinic:polycytidylic acid for 48 hrs in 180 µl of media and treated for different compounds or controls.
5. 20 µL of Cell titre blue reagent together with 100 µL of fresh media is added directly to each well and incubated at 37° C. (cellular incubator) until blue colour turns slightly pink (usually 1 hr). 7. Fluorescence is measured using Citation 3 device. Excitation: 560 nm. Emission: 590 nm.

TABLE 10

The EC50 values of exemplary compounds of the invention in human primary keratinocytes.

| Example | Viability (EC50 µM) |
|---|---|
| 1 | >10 |
| 3 | >10 |

Preferably, BET protein inhibitors exhibit a cell viability, EC50 value, of >1 µM. Exemplary compounds 1 and 3 exhibit a cell viability, EC50 value, of >1 µM in human primary keratinocytes.

The invention claimed is:
1. A compound of Formula (II),

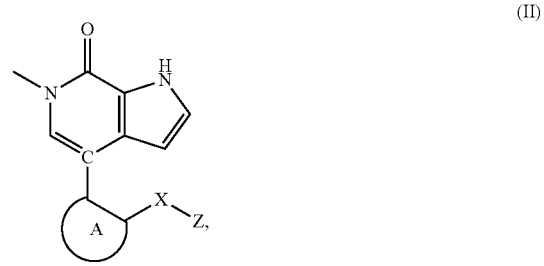

or a stereoisomer thereof or a pharmaceutically acceptable salt thereof, wherein:
the C-A-X moiety of Formula (II) is of Formulae (Ia), (Ib), (Ic), or (Id):

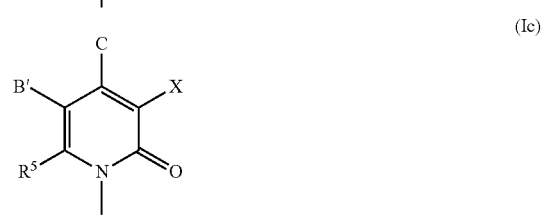

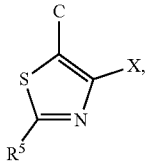

wherein:
$A_1$ is $CR^1$ or N, $A_2$ is $CR^2$ or N, $A_3$ is $CR^3$ or N, and $A_4$ is $CR^4$;
$R^1$ is H or hydroxy;
$R^2$ is selected from H, hydroxy, $C_1$-$C_6$alkyl, $C_3$-$C_6$cycloalkyl, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $C_1$-$C_5$alkyloxy, and $C_1$-$C_5$alkylamino;
$R^3$ and $R^4$ are independently selected from H, hydroxy, $C_1$-$C_6$alkyl, $C_3$-$C_6$cycloalkyl, halo, $C_1$-$C_5$alkyloxy, and $C_1$-$C_5$alkylamino;
with the proviso that one or more of $R^1$, $R^2$, $R^3$, or $R^4$ is hydroxy;
B' is H or hydroxy;
$R^5$ is
selected from hydrogen, hydroxy, $C_1$-$C_6$alkyl, $C_3$-$C_6$cycloalkyl, $C_1$-$C_6$alkylol, halo, $SO_2C_1$-$C_4$alkyl, $NHSO_2C_1$-$C_4$alkyl, $SO_2C_3$-$C_6$cycloalkyl, $NHSO_2C_3$-$C_6$cycloalkyl, $SO_2C_1$-$C_4$alkylol, $NHSO_2C_1$-$C_4$alkylol, $C_1$-$C_5$alkyloxy, $C_1$-$C_5$alkylamino, $SO_2NH_2$, $CONH_2$, $CONHC_1$-$C_4$alkyl, $NHCOC_1$-$C_4$alkyl, $NHSO_2N(C_1$-$C_4$alkyl) 2, $C_1$-$C_6$fluoroalkyl, $SO_2C_1$-$C_4$fluoroalkyl, $NHSO_2C_1$-$C_4$fluoroalkyl, $C_1$-$C_5$fluoroalkyloxy, and $C_1$-$C_5$fluoroalkylamino;
X is O, C(R) 2, NR' or S, wherein each R is independently selected from H, $C_1$-$C_4$alkyl, and halo, and R' is $C_1$-$C_4$alkyl or H;
Z is selected from a 5- or 6-membered aromatic or heteroaromatic ring, $C_1$-$C_6$alkyl, $C_3$-$C_6$cycloalkyl, $CR^AR^BR^C$, $C_2$-$C_5$oxacycloalkyl, $C_2$-$C_5$azacycloalkyl, and morpholinyl, each of which is optionally substituted with one or more second substituents;
wherein $R^A$ is a $C_3$-$C_5$cycloalkyl, $R^B$ is a $C_3$-$C_5$cycloalkyl, methyl or ethyl, and $R^C$ is OH; and
each second substituent is independently selected from hydroxy, $C_1$-$C_6$alkyl, $C_3$-$C_6$cycloalkyl, halo, $C_1$-$C_5$alkyloxy, $C_1$-$C_5$alkylamino, oxo, cyano, $C_1$-$C_6$fluoroalkyl, $C_1$-$C_5$fluoroalkyloxy, and $C_1$-$C_5$fluoroalkylamino.

2. The compound, stereoisomer thereof, or pharmaceutically acceptable salt thereof of claim 1, wherein $R^5$ is selected from H, hydroxy, methyl, and halo.

3. The compound, stereoisomer thereof, or pharmaceutically acceptable salt thereof of claim 1, wherein each R is independently selected from H, methyl, and fluoro.

4. The compound, stereoisomer thereof, or pharmaceutically acceptable salt thereof of claim 3, wherein R' is methyl.

5. The compound, stereoisomer thereof, or pharmaceutically acceptable salt thereof of claim 1, wherein X is O.

6. The compound, stereoisomer thereof, or pharmaceutically acceptable salt thereof of claim 1, wherein Z is selected from a 5- or 6-membered heteroaromatic ring, $C_1$-$C_6$alkyl, and $C_3$-$C_6$cycloalkyl, each of which is optionally substituted with one or more second substituents.

7. The compound, stereoisomer thereof, or pharmaceutically acceptable salt thereof of claim 1, wherein Z is selected from a 6-membered aromatic ring, $C_1$-$C_6$alkyl, and $C_3$-$C_6$cycloalkyl, each of which is optionally substituted with one or more second substituents.

8. The compound, stereoisomer thereof, or pharmaceutically acceptable salt thereof of claim 1, wherein Z is a phenyl or pyridyl ring, each of which is optionally substituted with one or more second substituents.

9. The compound, stereoisomer thereof, or pharmaceutically acceptable salt thereof of claim 1, wherein each second substituent is independently selected from hydroxy, $C_1$-$C_4$alkyl, and halo.

10. The compound, stereoisomer thereof, or pharmaceutically acceptable salt thereof of claim 1, wherein each second substituent is independently selected from hydroxy, methyl, and fluoro.

11. The compound, stereoisomer thereof, or pharmaceutically acceptable salt thereof of claim 1, wherein
$R^2$ is selected from H, $C_1$-$C_3$alkyl, halo, $SO_2C_1$-$C_4$alkyl, and $NHSO_2C_1$-$C_4$alkyl.

12. The compound, stereoisomer thereof, or pharmaceutically acceptable salt thereof of claim 11, wherein $R^3$ and $R^4$ are independently selected from H, hydroxy, $C_1$-$C_3$alkyl, and halo.

13. The compound, stereoisomer thereof, or pharmaceutically acceptable salt thereof of claim 1, wherein the C-A-X moiety of Formula (II) is of Formula (Ia), and Z is a phenyl ring, a $C_1$-$C_6$ alkyl, or a $C_3$-$C_6$ cycloalkyl, each of which is optionally substituted with one or more second substituents.

14. The compound, stereoisomer thereof, or pharmaceutically acceptable salt thereof of claim 13, wherein the C-A-X moiety of Formula (II) is of Formula (Ia), and Z is a phenyl ring optionally substituted with one or more second substituents.

15. The compound, stereoisomer thereof, or pharmaceutically acceptable salt thereof of claim 14, wherein the C-A-X moiety of Formula (II) is of Formula (Ia), and Z is a phenyl ring.

16. The compound, stereoisomer thereof, or pharmaceutically acceptable salt thereof of claim 1, wherein the C-A-X moiety of Formula (II) is of Formulae (Ib), (Ic), or (Id), and Z is a phenyl or pyridyl ring, a $C_1$-$C_6$ alkyl, or a $C_3$-$C_6$ cycloalkyl, each of which is optionally substituted with one or more second substituents.

17. The compound, stereoisomer thereof, or pharmaceutically acceptable salt thereof of claim 16, wherein the C-A-X moiety of Formula (II) is of Formula (Ib).

18. The compound, stereoisomer thereof, or pharmaceutically acceptable salt thereof of claim 16, wherein the C-A-X moiety of Formula (II) is of Formula (Id).

19. The compound, stereoisomer thereof, or pharmaceutically acceptable salt thereof of claim 16, wherein the C-A-X moiety of Formula (II) is of Formulae (Ib) or (Ic), and Z is a phenyl or a pyridyl ring, each of which is optionally substituted with one or more hydroxy, methyl, fluoro, or chloro.

20. The compound, stereoisomer thereof, or pharmaceutically acceptable salt thereof of claim 16, wherein the C-A-X moiety of Formula (II) is of Formula (Ic).

21. The compound, stereoisomer thereof, or pharmaceutically acceptable salt thereof of claim 1, wherein the compound is selected from Formulae (Ie) to (IIi):

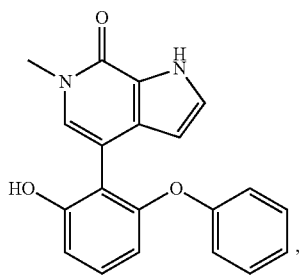
(Ie)
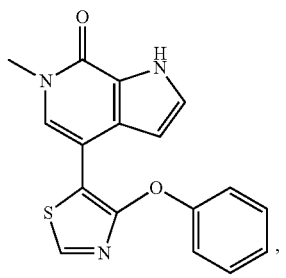
(Ij)
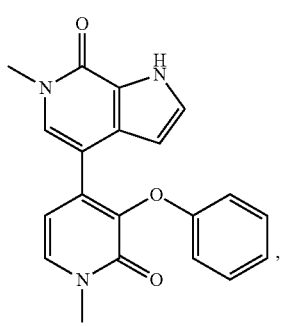
(If)
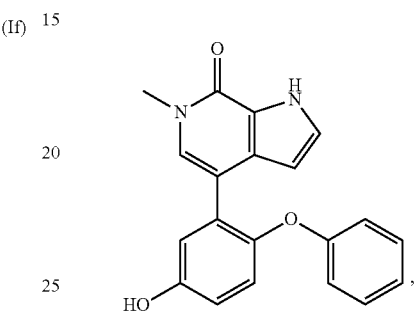
(Ik)
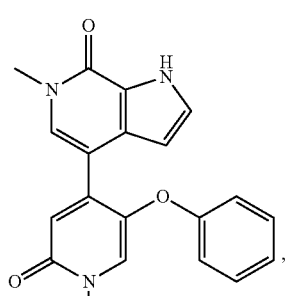
(Ig)
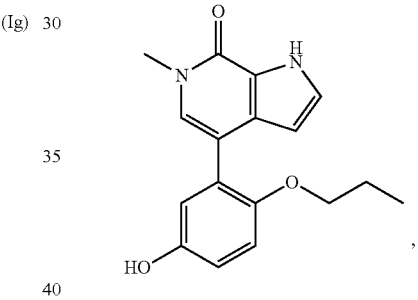
(Il)
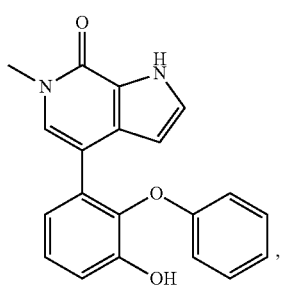
(Ih)
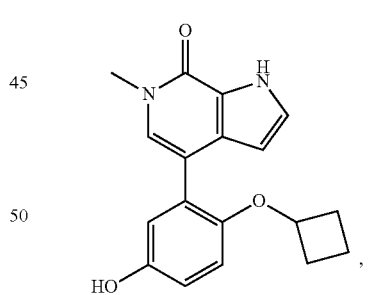
(Im)
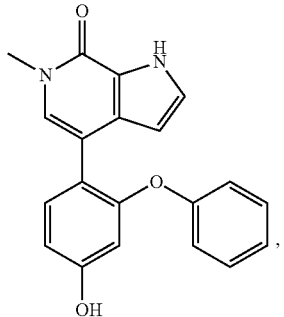
(Ii)
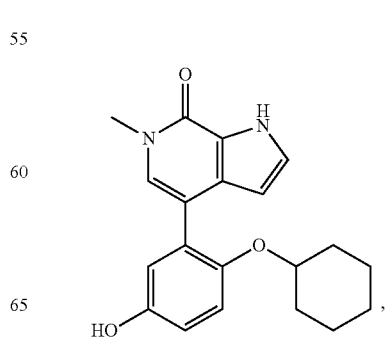
(In)

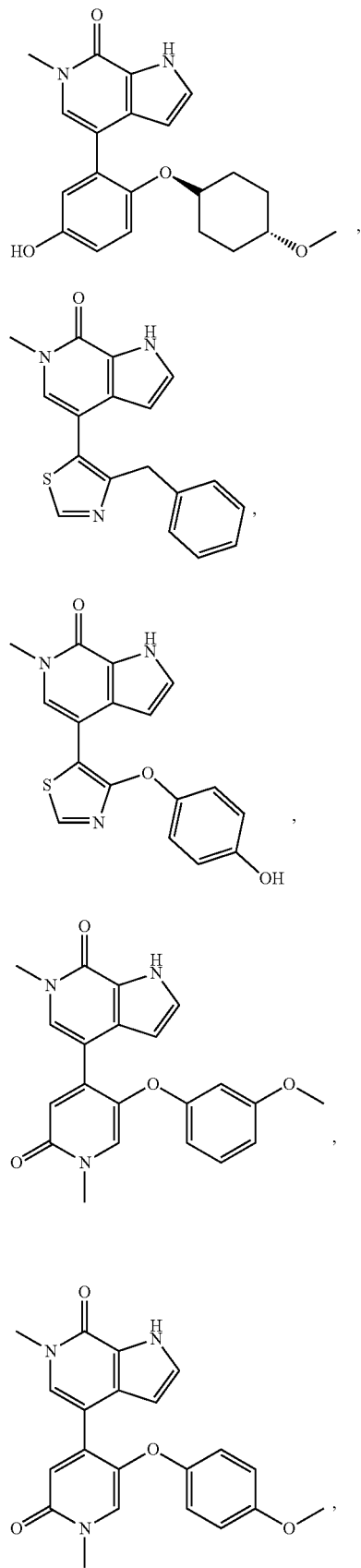
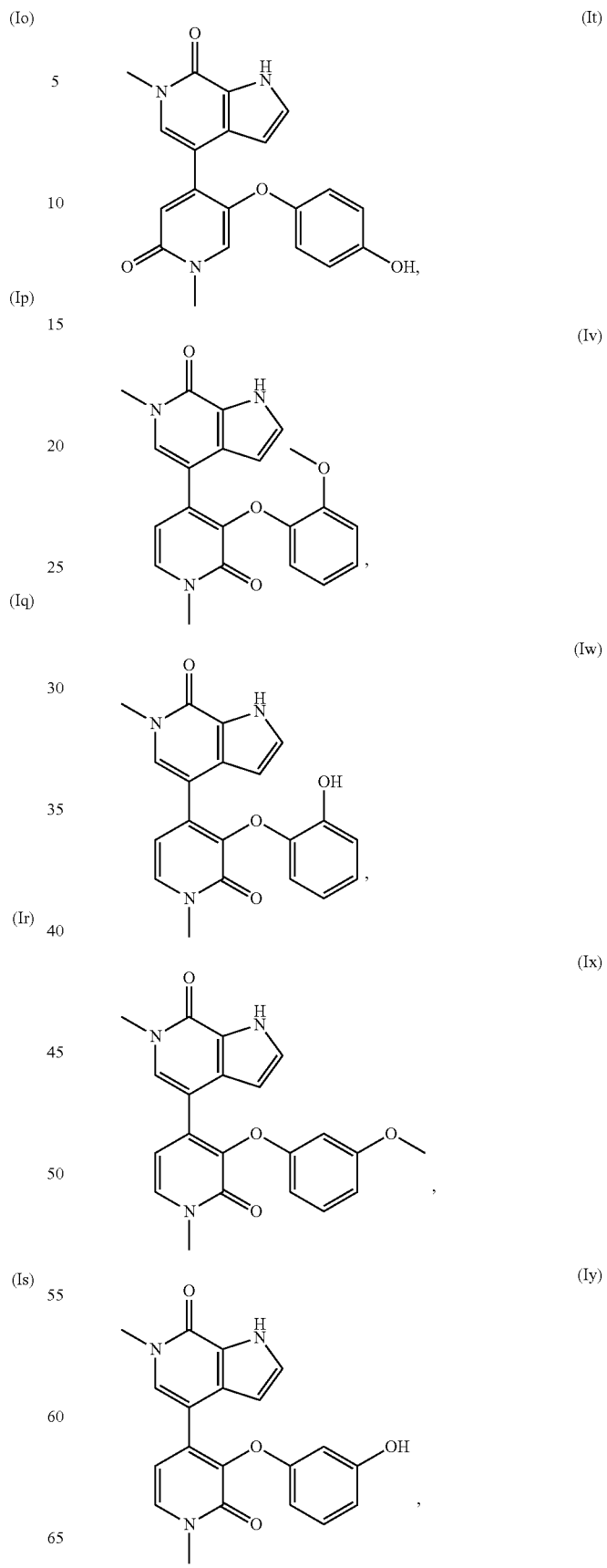

(Iz)
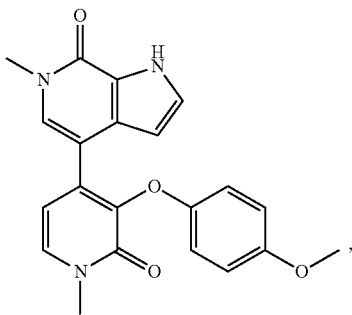

(IIa)
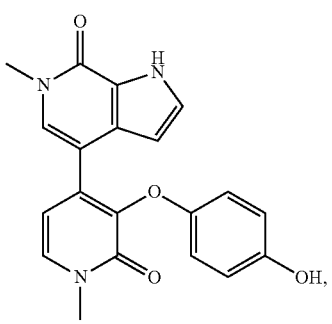

(IIc)
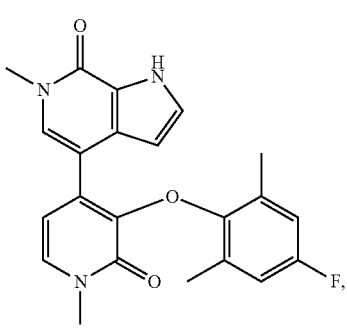

(IIg)
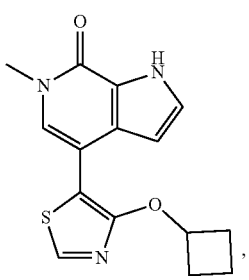

(IIh)
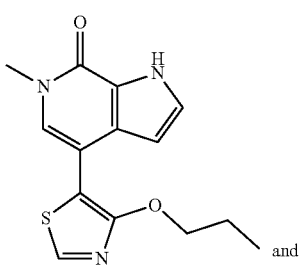

and (IIi)
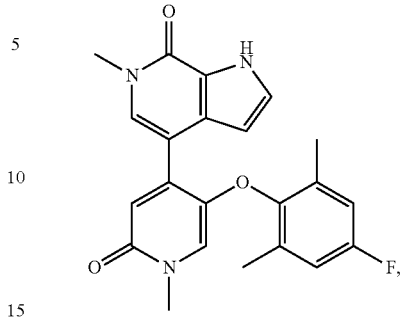

or a stereoisomer thereof, or a pharmaceutically acceptable salt thereof.

22. A pharmaceutical composition comprising a compound of claim 1, a stereoisomer thereof, or a pharmaceutically acceptable salt thereof, and a pharmaceutically acceptable carrier.

23. A method of treating an inflammatory disorder or disease comprising administering to a subject the pharmaceutical composition of claim 22.

24. A method of treating an inflammatory disorder or disease comprising administering to a subject the compound of claim 1, stereoisomer thereof, or pharmaceutically acceptable salt thereof.

25. The method of claim 24, wherein the inflammatory disorder is an inflammatory skin disorder.

26. The method of claim 24, wherein the inflammatory disease is an autoimmune disease.

27. The method of claim 24, wherein the method comprises topical or oral administration of the compound, stereoisomer thereof, or pharmaceutically acceptable salt thereof.

28. The method of claim 24, wherein the method comprises administration by injection of the compound, stereoisomer thereof, or pharmaceutically acceptable salt thereof.

29. The method of claim 24, wherein the method comprises topical administration of the compound, stereoisomer thereof, or pharmaceutically acceptable salt thereof to the skin.

30. A method of inhibiting Bromodomain and Extra-Terminal proteins comprising administering to a subject the compound, stereoisomer thereof, or pharmaceutically acceptable salt thereof of claim 1, wherein the subject has a disease or condition associated with the activity of the Bromodomain and Extra-Terminal protein.

31. The compound, stereoisomer thereof, or pharmaceutically acceptable salt thereof of claim 1, wherein the C-A-X moiety of Formula (II) is of Formula (Ia); $A_1$ is $CR^1$; $A_2$ is $CR^2$; $A_3$ is $CR^3$; and $A_4$ is $CR^4$.

32. The compound, stereoisomer thereof, or pharmaceutically acceptable salt thereof of claim 31, wherein at least one of $R^1$, $R^3$, and $R^4$ is hydroxy.

33. A compound of Formula (Ih):

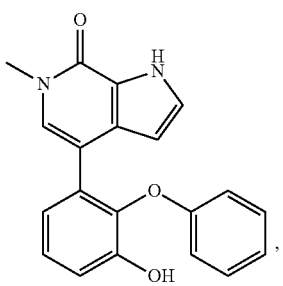

(Ih)

or a pharmaceutically acceptable salt thereof.

34. A pharmaceutical composition comprising the compound of claim 33, or a pharmaceutically acceptable salt thereof, and a pharmaceutically acceptable carrier.

35. A method of treating an inflammatory disorder or disease comprising administering to a subject the pharmaceutical composition of claim 34.

36. The method of claim 35, wherein the inflammatory disorder is an inflammatory skin disorder.

37. The method of claim 35, wherein the inflammatory disease is an autoimmune disease.

38. The method of claim 35, wherein the method comprises topical administration of the pharmaceutical composition.

39. The method of claim 35, wherein the method comprises oral administration of the pharmaceutical composition.

40. The method of claim 35, wherein the method comprises administration by injection of the pharmaceutical composition.

41. The method of claim 35, wherein the method comprises topical administration of the pharmaceutical composition to the skin.

42. A compound of Formula (Ih):

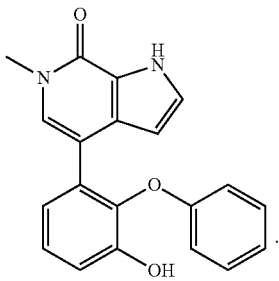

(Ih)

43. A pharmaceutical composition comprising the compound of claim 42, and a pharmaceutically acceptable carrier.

44. A method of treating an inflammatory disorder or disease comprising administering to a subject a compound of Formula (Ih):

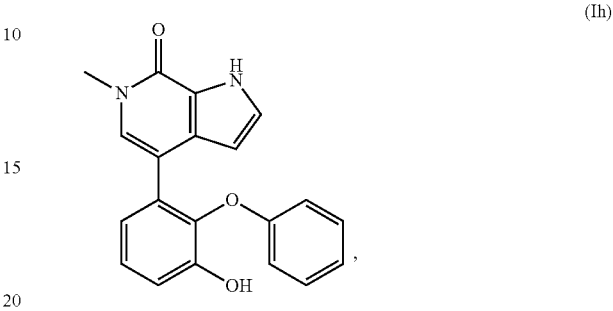

(Ih)

or a pharmaceutically acceptable salt thereof.

45. The method of claim 44, wherein the inflammatory disorder is an inflammatory skin disorder.

46. The method of claim 44, wherein the inflammatory disease is an autoimmune disease.

47. The method of claim 44, wherein the method comprises topical administration of the compound.

48. The method of claim 44, wherein the method comprises oral administration of the compound.

49. The method of claim 44, wherein the method comprises administration by injection of the compound.

50. The method of claim 44, wherein the method comprises topical administration of the compound to the skin.

51. The method of claim 44, comprising administering to a subject a compound of Formula (Ih):

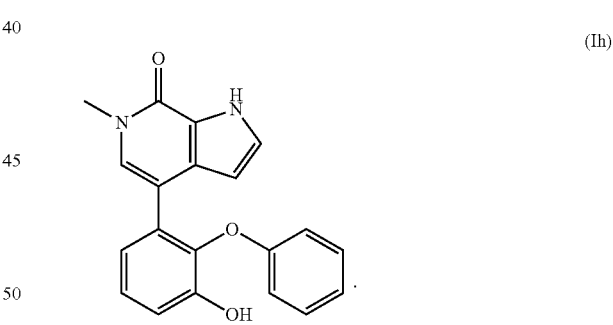

(Ih)

\* \* \* \* \*